(12) United States Patent
Moore et al.

(10) Patent No.: US 10,779,543 B2
(45) Date of Patent: Sep. 22, 2020

(54) BIOPESTICIDE

(71) Applicants: RHODES UNIVERSITY, Grahamstown (ZA); CITRUS RESEARCH INTERNATIONAL (PTY) LTD, Stellenbosch (ZA); RIVER BIOSCIENCE (PTY) LTD, Port Elizabeth (ZA)

(72) Inventors: Sean Moore, Port Elizabeth (ZA); Martin Hill, Grahamstown (ZA); Caroline Knox, Grahamstown (ZA); Tamryn Marsberg, Grahamstown (ZA); Michael Jukes, Grahamstown (ZA); Boguslaw Szewczyk, Gdansk (PL); Lukasz Rabalski, Gdansk (PL); Craig Chambers, Kirkwood (ZA)

(73) Assignees: RHODES UNIVERSITY, Grahamstown (ZA); CITRUS RESEARCH INTERNATIONAL (PTY) LTD, Stellenbosch (ZA); RIVER BIOSCIENCE (PTY) LTD, Port Elizabeth (ZA)

( * ) Notice: Subject to any disclaimer, the term of this patent is extended or adjusted under 35 U.S.C. 154(b) by 0 days.

(21) Appl. No.: 16/320,890

(22) PCT Filed: Jul. 26, 2017

(86) PCT No.: PCT/IB2017/054543
§ 371 (c)(1),
(2) Date: Jan. 25, 2019

(87) PCT Pub. No.: WO2018/020441
PCT Pub. Date: Feb. 1, 2018

(65) Prior Publication Data
US 2019/0159464 A1    May 30, 2019

(30) Foreign Application Priority Data
Jul. 26, 2016    (ZA) ................................ 2016/05197

(51) Int. Cl.
| | |
|---|---|
| *A01N 63/00* | (2020.01) |
| *A01N 63/40* | (2020.01) |
| *C12N 7/00* | (2006.01) |
| *A01N 63/10* | (2020.01) |
| *C12N 15/86* | (2006.01) |

(52) U.S. Cl.
CPC ............ *A01N 63/10* (2020.01); *A01N 63/00* (2013.01); *C12N 7/00* (2013.01); *C12N 15/86* (2013.01); *C12N 2710/14121* (2013.01); *C12N 2710/14122* (2013.01); *C12N 2710/14132* (2013.01); *C12N 2710/14143* (2013.01)

(58) Field of Classification Search
None
See application file for complete search history.

(56) References Cited

PUBLICATIONS

Marsberg et al. Morphological, genetic and biological characterisation of a novel alphabaculovirus isolated from Cryptophlebia peltastica (Lepidoptera:Tortricidae). Journal of Invertebrate Pathology 157 (2018) 90-99.*
Takatsuka. Characterization of a nucleopolyhedrovirus of Epinotia granitalis (Lepidoptera: Tortricidae). Journal of Invertebrate Pathology 96 (2007) 265-269.*
Moore et al. The Cryptophlebia Leucotreta Granulovirus—10 Years of Commercial Field Use. Viruses 2015, 7: 1284-1312.*
Haase et al. Baculovirus Insecticides in Latin America: Historical Overview, Current Status and Future Perspectives. Viruses 2015, 7: 2230-2267.*
Abdulkadir, Fatima, et al. "Genetic and biological characterisation of a novel Plutella xylostella granulovirus, PlxyGV-SA", Biocontrol, Mar. 20, 2015, pp. 507-515, vol. 60, No. 4.
Guarino, Linda "Baculoviruses", Encyclopedia of Life Sciences, Nov. 15, 2011, John Wiley & Sons, Ltd, Chichester, pp. 1-15.
Jehle, J.A., et al. "Molecular identification and phylogenetic analysis of baculoviruses from Lepidoptera", Virology, Mar. 1, 2006, pp. 180-193 vol. 346, No. 1.
Sciocco, A., et al. "Nucleopolyhedrovirus from the Western Avocado Leafroller, Amorbia cuneana: Isolation and characterization of a potential viral control agent", Biological Control, May 1, 2009, pp. 154-159, vol. 49, No. 2.
Takatsuka, Jun "Characterization of a nucleopolyhedrovirus of Epinotia granitalis (Lepidoptera: Tortricidae)", Journal of Invertebrate Pathology, Oct. 19, 2007, pp. 265-269, vol. 96, No. 3.
International Search Report and Written Opinion dated Oct. 12, 2017, prepared in International Application No. PCT/IB2017/054543.
Marsberg, et al., 'Genetic and biological characterisation of a novel alphabaculovirus for the microbial control of Cryptophlebia peltastica' 49th Annual Meeting of the Society for Invertebrate Pathology, poster abstract VI-14STU of p. 125, [retrieved from the internet Oct. 6, 2017]. Published Jul. 24, 2016.

* cited by examiner

*Primary Examiner* — Nianxiang Zou
(74) *Attorney, Agent, or Firm* — Brinks Gilson & Lione; John C. Freeman

(57) ABSTRACT

A nucleopolyhedrovirus (NPV), a composition comprising the NPV, and a method comprising the use of the NPV is provided. The NPV was isolated from *Cryptophlebia peltastica* and has insecticidal activity against several species of moths within the tortricid tribe, Grapholitini. The NPV or composition may be suitable for use in controlling insect populations, particularly populations of insects that infest plants.

20 Claims, 5 Drawing Sheets
Specification includes a Sequence Listing.

| C. peltastica NPV | Sma1 | | | C. peltastica NPV In silico |
|---|---|---|---|---|
| | A | Band Size | B | |
| | 80 494 | 1 | 116 646 | |

FIGURE 6

BIOPESTICIDE

CROSS-REFERENCE TO RELATED APPLICATIONS

This application is a National Stage application of International Application No. PCT/162017/054543, filed 26 Jul. 2017. This application also claims priority under 35 U.S.C. § 119 to South African provisional patent application number 2016/05197 filed on 26 Jul. 2016, which is incorporated by reference herein.

FIELD OF THE INVENTION

This invention relates to a biopesticide, more particularly a nucleopolyhedrovirus (NPV), for use in controlling insect populations.

BACKGROUND TO THE INVENTION

Chemical pesticides are the most commonly used agents for controlling insect pests in agriculture and forestry. Chemical insecticides may have adverse impacts not only on their target organisms but also on beneficial insects, such as bees and other pollinators. Accumulation of chemical pesticides through the food chain of an ecosystem has also been shown to have an adverse effect on birds and other insect predators. Furthermore, residues of chemical pesticides on fruit, vegetables and nuts may cause health problems among the human population.

Concerns over the use of chemical pesticides have led to an increased interest in biological pesticides. Insect baculoviruses are one group of insect biopesticides that have been promoted as an alternative control agent to chemical pesticides. These viruses, which can be isolated from a variety of insect species, exhibit relatively narrow host ranges and have almost no adverse environmental impact due to their host specificity. The absence of chemical residues means that long-term environmental hazards and health concerns are reduced with biopesticides. However, there are several disadvantages to biopesticides, including cost of production, efficacy and stability.

Nucleopolyhedrovirus (NPV) or alphabaculovirus is a genus of baculoviruses that infect insects, mostly moths and butterflies. NPVs have been known to be useful as biopesticides for insect-infested crops. NPVs have a high species specificity and while this enhances their utility as biopesticides, it may limit their effectiveness in cases of multiple pest infestation. Furthermore, there are isolated incidents of species of moth pests developing resistance to commercially-available strains of baculoviruses.

*Cryptophlebia peltastica* (also known as *litchi* moth) is a species of moth that is an important pest of *litchi* trees (*Litchi chinensis*) in Southern Africa, Mauritius and elsewhere. *C. peltastica* larvae are known to damage up to 20% of fruits in commercial orchards. This moth is also a pest of macadamia and a variety of other commercially significant trees and plants. There are currently no known biopesticides that specifically target *C. peltastica* and to date, no NPVs have been isolated from *C. peltastica* or from any other species within the same genus or the lepidopteran tribe Grapholitini.

There is therefore a need for a biopesticide which is active against *Cryptophlebia peltastica* and/or other insect pests.

SUMMARY OF THE INVENTION

In accordance with a first aspect of the invention, there is provided a nucleopolyhedrovirus (NPV) for use in controlling insect populations, the NPV having a genome sequence with at least 85% sequence identity to SEQ ID NO: 2.

The NPV may have a polyhedrin gene with more than 93% sequence identity to SEQ ID NO: 1.

The NPV may be an isolate or genotype of the species whose genome sequence is represented by SEQ ID NO: 2.

The NPV may have a virulence host range comprising the Grapholitini tribe of the lepidopteran family, Tortricidae, and the host range may include *Cryptophlebia peltastica*, *Thaumatotibia leucotreta*, *Cydia pomonella*, *Grapholita molesta*, and *Thaumatotibia batracopa*.

The insects may be selected from the tribe Grapholitini, particularly the larvae of *Cryptophlebia peltastica*, *Thaumatotibia* (*Cryptophlebia*) *leucotreta* and *Cydia pomonella*.

The NPV may be used in combination with one or more additional biopesticides, and the one or more additional biopesticide may be a *Cryptophlebia leucotreta* granulovirus, a *Cydia pomonella* granulovirus, a *Cryptophlebia batracopa* granulovirus or a *Grapholita molesta* granulovirus.

The NPV genome sequence may contain only one recognition site for the restriction enzyme Sma1.

In accordance with a second aspect of the invention, there is provided a biopesticidal composition comprising an NPV as described above and one or more agronomically acceptable adjuvants and/or diluents.

The composition may comprise an additional biopesticide, which may be a *Cryptophlebia leucotreta* granulovirus, a *Cydia pomonella* granulovirus, a *Cryptophlebia batracopa* granulovirus or a *Grapholita molesta* granulovirus. The composition may further comprise a feeding stimulant, a mineral oil and a UV protectant.

In accordance with a third aspect of the invention, there is provided a method of controlling insect populations, the method comprising applying to the insects and/or their locus an insecticidally effective amount of an NPV as described above or a biopesticidal composition as described above.

The method may comprise simultaneously or sequentially applying, in addition to the NPV or biopesticidal composition, at least one additional biopesticide to the insects and/or their locus.

In accordance with a fourth aspect of the invention, there is provided a method of treating or preventing insect infestations on plants or fruit, the method comprising applying an insecticidally effective amount of an NPV as described above or a biopesticidal composition as described above to the plants or fruit.

In accordance with a fifth aspect of the invention, there is provided an NPV isolated from *Cryptophlebia peltastica*, which has a genome sequence with at least 85% sequence identity to SEQ ID NO: 2.

The NPV may have a polyhedrin gene with more than 93% sequence identity to SEQ ID NO: 1.

BRIEF DESCRIPTION OF THE FIGURES

FIG. 6 is a Sma1 restriction profile comparing an in silico digest of *C. peltastica* NPV and a REN digest of *C. peltastica* NPV.

DETAILED DESCRIPTION OF THE INVENTION

Figure 1:
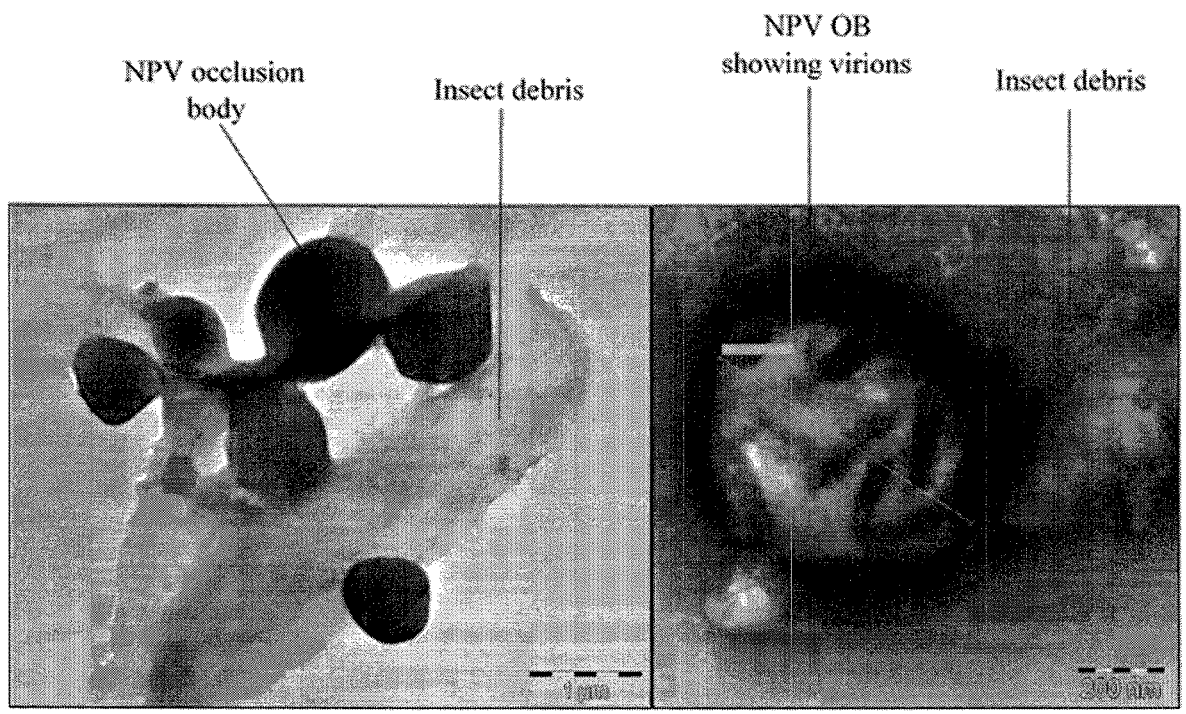
FIG. 1 illustrates transmission electron micrographs of NPV occlusion bodies (OBs) isolated from symptomatic *C. peltastica* larvae.

The invention provides a nucleopolyhedrovirus (NPV), also known as an alphabaculovirus, a biopesticidal composition comprising the NPV, and a method of controlling insect populations and infestations.

Throughout the specification, the term 'plant' is used in a general sense and is understood to refer to trees, shrubs and bushes, as well as the fruit, seeds and nuts of such trees, shrubs and bushes.

Moreover, the word 'comprise' or variations such as 'comprises' or 'comprising' is understood to imply the inclusion of a stated integer or group of integers but not the exclusion of any other integer or group of integers.

Furthermore, 'insecticidally effective amount' is understood to refer to those quantities of virus which will result in a significant mortality rate in a treated group of insect pests as compared to an untreated group.

The definition of a baculovirus species as herein described is understood to refer to all isolates and genotypes that have a K-2-P distance between single and/or concatenated polh, lef-8 and lef-9 nucleotide sequences which is smaller than 0.015. K-2-P is the Kimura 2-parameter distance (K), which is determined by the Kimura two parameter model according to the following formula:

$$K = -\frac{1}{2}\ln\!\left((1-2p-q)\sqrt{1-2q}\right)$$

where p is the proportion of nucleotide sites that show transitional differences and q is the proportion of nucleotide sites that show transversional differences. Transitions refer to substitutions between nucleotide bases of the same type (purine for purine or pyrimidine for pyrimidine), whereas transversions refer to substitutions of a purine for a pyrimidine or a pyrimidine for a purine. Furthermore, two viruses are considered to be different virus species if the K-2-P distance between single and/or concatenated sequences is larger than 0.050. For distances between 0.015 and 0.050, complementary information is needed to determine whether two viruses are the same or different species. This definition is explained in further detail in Jehle et al Virology 346 (2006) 180-193.

The NPV was isolated from larvae of the *Cryptophlebia peltastica* moth in which it proliferates and to which it is pathogenic. The virus produces polyhedrin proteins that form occlusion bodies (OBs or polyhedra), which are globular structures that protect the virus particles from the outside environment until they are ingested by an insect host. The NPV is characterized by its genome sequence which has at least 85% sequence identity to SEQ ID NO: 2. The NPV has a characteristic polyhedrin gene that has a nucleotide sequence with at least 75% sequence identity to SEQ ID NO: 1, with the proviso that SEQ ID NO: 1 does not encode the *Epinotia granitalis* baculovirus polyhedrin gene.

In some embodiments the NPV can be characterized by its genome sequence which can have at at least 90%, 91%, 92%, 93%, 94%, 95%, 96%, 97%, 98%, 99% or 100% sequence identity with SEQ ID NO: 2.

In further embodiments, the virus can have a polyhedrin gene with a sequence that has at least 80% sequence identity to SEQ ID NO: 1, and in further embodiments the virus can have a polyhedrin gene with at least 85%, 90%, 91%, 92%, 93%, 94%, 95%, 96%, 97%, 98%, 99% or 100% sequence identity with SEQ ID NO: 1. In some embodiments, the virus has a polyhedrin gene with a nucleotide sequence that has more than 93% sequence identity to SEQ ID NO: 1.

The NPV can be characterised in that it is an isolate or genotype of the NPV species whose genome sequence is represented by SEQ ID NO: 2.

The NPV may have a virulence host range that comprises the Grapholitini tribe of the lepidopteran family, Tortricidae. In particular, the NPV can have a virulence host range that includes members of the Grapholitini tribe selected from *Cryptophlebia peltastica*, *Thaumatotibia leucotreta*, *Cydia pomonella*, *Grapholita molesta* (oriental fruit moth), and *Thaumatotibia batracopa* (macadamia nut borer).

The nucleotide sequence of the NPV genome can have a characteristic single recognition site for the restriction enzyme, Sma1. This allows the NPV to be identified from other viruses that have more than one Sma1 recognition site.

The NPV can be applied in combination with one or more additional biopesticides, simultaneously, sequentially, or in a combined composition, in order to increase the spectrum of activity and to reduce the possibility of insect pests developing resistance to the virus. In particular, the NPV can be co-administered with another NPV or a betabaculovirus, also referred to as a granulovirus (GV), such as a *Cryptophlebia leucotreta* granulovirus, a *Cydia pomonella* granulovirus, a *Cryptophlebia batracopa* granulovirus or a *Grapholita molesta* granulovirus.

The NPV can be combined with one or more agronomically acceptable components, including adjuvants, diluents, surfactants, dispersing agents, emulsifiers, spreading agents and/or wetting agents to form a biopesticidal composition. The NPV can also be formulated to improve the stability or maintain the activity of the virus.

In particular, a composition comprising the NPV may additionally contain:
  (i) one or more of the GVs referred to above;
  (ii) one or more feeding stimulant selected from molasses, sugar, syrup, alcohol sugars (such as mannitol and xylitol) and Stevia leaf extract; and
  (iii) one or more UV protectant.

In a preferred embodiment, the composition can be formulated to comprise molasses, mineral oil, and one or more of the UV protectant Break-Thru® OE446, Uvinil and clove oil. In this and other embodiments, the formulation can further comprise glycerine and distilled water.

The minimum effective concentration of the virus is 1 OB, which can be sufficient to kill 50% of first instar larvae in a treated sample.

The biopesticidal composition can be formulated to have a concentration of the NPV of from about $1 \times 10^3$ to about $1 \times 10^{15}$ viral occlusion bodies/ml. In some embodiments, the biopesticidal composition can have a concentration of the NPV of about $1 \times 10^{10}$ viral OBs/ml.

A solution of the NPV can be produced on a commercial scale according to the following method. Jars containing cooked larval diet are placed into a biohazard chamber and sheets containing *C. peltastica* eggs each containing approximately 400 eggs are sterilized with formalin before being placed onto the diet in the rearing jars. The jars are then sealed. Approximately 80% of the rearing bottles containing $4^{th}$ and $5^{th}$ instar larvae are removed. The remaining 20% of the rearing bottles have their lids replaced with a cotton wool plug under the biohazard chamber and are left for a further ±8 d for the larvae to move out of the diet and begin pupation in the cotton wool substrate.

The pupated larvae are then removed from the jars and placed into containers containing approximately 10 mm of larval diet. Once the larvae cover the surface of the diet they are inoculated by spraying the surface of the diet with viral inoculum. The jars are then closed with a breathable lid and monitored. The diet and infected larvae are then harvested from the container after 7-8 days. The diet and harvested larvae are then homogenized in 4 litres of water per kilogram of diet and infected larvae (at pH 5.0), until the mixture appears uniformly smooth (approximately 20 min at 2400 rpm). The resulting liquid is sieved through a 100 micron nylon mesh into a clean container and re-homogenized after dilution with fresh water. The re-homogenized mixture is re-sieved and stored in cooling vats at 4° C. Storage bottles containing glycerol and distilled water are prepared before being filled with the virus suspension. The final product is stored at 4° C.

The biopesticidal composition can include one or more additional biopesticides, such as another NPV or GV. In some embodiments, the additional biopesticide is a *Cryptophlebia leucotreta* granulovirus, a *Cydia pomonella* granulovirus, a *Cryptophlebia batracopa* granulovirus or a *Grapholita molesta* granulovirus.

The NPV or composition is suitable for use as a biopesticide for controlling insect populations, particularly populations of moth and butterfly larvae of the tribe Grapholitini. Although isolated from *C. peltastica*, the virus also has activity against a range of other insect pests and can be used as a biopesticide for controlling *Thaumatotibia leucotreta* (false codling moth) and *Cydia pomonella* (codling moth) species. *Thaumatotibia leucotreta* is sometimes referred to as *Cryptophlebia leucotreta* and the two names can be used interchangeably. Furthermore, the virus can have activity against at least some strains of codling moth larvae that are resistant to *Cydia pomonella* granulovirus.

The NPV or composition can be applied to trees or plants as a biopesticide for treating or preventing insect infestations. Suitable examples include citrus (all varieties), grape (all varieties), peaches, plums, nectarines, apples, pears, walnuts, quinces, hazelnuts, pecans, macadamia, avocado, litchis, lychees, peppers, ornamentals, cotton, karalla, olives, grape vines, pepper bushes, pomegranates and persimmons.

The NPV or composition can be applied to the insects themselves and/or to the locus of the insects. For example, the NPV can be applied to the fruit, leaves, flowers and/or bark of the trees or plants which may be occupied or anticipated to be occupied by insect pests. In some embodiments, the NPV can be applied by spraying, although any suitable application method can be used.

The insecticidal activity or effectiveness of the NPV arises when an occlusion body (OB) of the virus is ingested by an insect host during feeding. Once inside the insect gut, the polyhedrin sac of the OB is solubilised by action of the alkaline digestive juices (pH 9.5 to 11.5) and by enzymatic degradation, which releases viral particles. Primary infection occurs in cells in the gut, followed by other cell types including haemocytes, tracheal cells, and fat cells. In advanced stages of viral infection, the cells contain multiple viral particles which are present in the nucleus. Eventually the nucleus and the cell rupture, liberating a plurality of viral OBs. The external appearance of infected larvae changes during viral infection. The larvae become sluggish and their growth is stunted. As infection progresses, the integument of the larvae may change colour. Eventually the integument ruptures and a greyish-white fluid is released containing multiple viral OBs. When healthy larvae feed on plant parts that have been contaminated with this fluid, they ingest the viral OBs and become infected themselves, leading to further propagation of the virus.

The invention will now be described in more detail by way of the following non-limiting examples.

Examples

Methods and Materials

A laboratory culture of *C. peltastica* was established at Rhodes University, Waainek research facility, South Africa. During rearing, larvae showing symptoms of 'wilting' disease were collected in microtubes and placed at −25° C. for future use. These symptoms were associated with colour change: milky pink appearance (early stage) and black/brown appearance (late stage).

In an attempt to isolate a baculovirus from the symptomatic larvae, a protocol for a granulovirus (GV) crude extract was adapted from Parnell et al. (2002). However, no virus was observed using this method and therefore an NPV protocol adapted from Grzywacz et al. (2007) was used instead. Insect cadavers were homogenised in 1 ml of 0.1% SDS in a microtube to disrupt the cuticle. The microtube was then vortexed for approximately 2 minutes. The homogenate was then centrifuged at 100×g for 10 to 20 seconds to remove insect debris. The supernatant was collected and placed into a separate microtube. The pellet was re-suspended in 1 ml 0.1% SDS and again centrifuged at 100×g for 10 to 20 seconds. The supernatant was pooled and the pellet discarded. The pooled supernatant was centrifuged at 2 500×g for 5 minutes to pellet the virus. The supernatant was discarded and the pellet was re-suspended in 1 ml ddH$_2$O and centrifuged at 2 500×g for 5 minutes. The supernatant was again discarded and the pellet re-suspended in approximately 100 to 200 µl ddH$_2$O.

Purification of Virus Occlusion Bodies by Glycerol Gradient Centrifugation

To distinguish the morphology of the baculovirus, occlusion bodies (OBs) were purified using a glycerol gradient. A 50 to 60% glycerol gradient was prepared in a microtube, following a method adapted from Grzywacz et al (2007), by placing 500 µl of 60% glycerol into a 2 ml tube overlaid with 500 µl of 50% glycerol. The pellet from a crude extract was re-suspended in 500 µl of 20% glycerol. 100 µl of this sample was then placed on top of the gradient and centrifuged at maximum speed for 15 minutes. Both the band and pellet were collected and re-suspended in 1 ml ddH$_2$O and centrifuged at maximum (12 100×g) speed for 15 minutes. The supernatant was discarded and the pellet was re-suspended and centrifuged again as described above. The final pellet was re-suspended in ddH$_2$O.

Transmission Electron Microscopy (TEM)

A drop of the prepared sample (±2 μl) was placed on a Forvar carbon coated grid for 30 seconds. Filter paper was used to drain off the excess sample. A drop of uranyl acetate was then placed on the grid and left for 20 seconds. Filter paper was used to remove the excess stain and the grid was left overnight. The grid was observed using a Zeiss Libra 120 transmission electron microscope at 80 000 kV. The images were analysed using Mega View (G2) Olympus analyses software. The size, width and diameter of the OBs was determined by measuring 100 OBs from the images taken.

CTAB DNA Extraction

A CTAB DNA extraction protocol was adapted from Aspinall et al. (2002). Using 200 μl of crude/purified occlusion bodies extracted, 90 μl of 1M sodium carbonate ($Na_2CO_3$) was added and incubated at 37° C. for 30 minutes. 120 μl Tris-HCl (1M, pH 6.8), 90 μl of 10% SDS and 50 μl proteinase K (25 mg/ml) were added and samples incubated for a further 30 minutes at 37° C. 10 μl RNAse A (10 mg/ml) was then added and incubated for another 30 minutes at 37° C. The solution was then centrifuged at 12 100×g for 3 minutes. The supernatant was transferred to a new 1.5 ml tube and the pellet was discarded. 400 μl of warm CTAB buffer was then added to the supernatant and incubated at 70° C. for 60 minutes. 400 μl of 4° C. chloroform was added and the sample centrifuged at 6 500×g for 10 minutes. The upper phase was transferred into a new 1.5 ml tube and 400 μl of −25° C. isopropanol was added. The sample was then left overnight at −25° C. The sample was then centrifuged at 12 100×g for 20 minutes and the supernatant discarded. 1 ml of cold 70% ethanol was added to the pellet and the sample centrifuged at 12 100×g for 5 minutes. The supernatant was discarded and the pellet was incubated at 50° C., until dry. The pellet was re-suspended in 20 μl 10 mM Tris-HCl (pH 8.0).

Polymerase Chain Reaction (PCR)

Degenerate oligonucleotide primers, prPH-1 and prPH-2 designed by Lange et al. (2004) were used to genetically characterise the isolated NPV (Table 1). The primers were used to amplify the polyhedrin gene using DNA extracted from the purified OBs.

TABLE 1

Degenerate oligonucleotide primers for the partial amplification of the polH/gran gene region (Lange et al. 2004).

| Oligonucleotide name | Sequence (5' to 3') |
| --- | --- |
| Polh/gran (prPH-1) | TGTAAAACGACGGCCAGTNRCNGARGAYCCNTT SEQ ID NO: 3 |
| (Polh/gran (prPH-2) | CAGGAAACAGCTATGACCDGGNGCRAAYTCYTT SEQ ID NO: 4 |

*N = C, A, T or G; R = A or G; Y = C or T; D = A, G or T

PCR reactions were set up for a positive control, negative control and *C. peltastica* NPV. The positive control consisted of DNA extracted from CrleGV (*Cryptophlebia leucotreta* granulovirus) to ensure correct amplification with the degenerate primers and the negative control contained no DNA to determine the presence of contamination. The DNA concentration for *C. peltastica* NPV was determined using a Nanodrop spectrophotometer (Thermo Scientific®) to be approximately 84 ng/μl. This was considered when mixing the reagents.

PCR parameters used for the amplification of the polyhedrin gene were adapted from Lange et al. (2004) in order to obtain a PCR product of the 507 to 510 nucleotides for analysis. The PCR amplification was performed in a thermocycler (BIO-RAD®). The PCR products were analysed by 1% AGE and band sizes estimated using GeneRuler 1 Kbp DNA Ladder (Thermo Scienticfic®) to confirm the presence and size of the virus gene.

Sequencing

The PCR products obtained were sequenced by Inqaba Biotechnology Industries (Pty) Ltd (South Africa). FinchTV® version 1.4.0 (Geospiza Inc. 2004-2006) was used to view the chromatograms in order to clean-up ambiguous nucleotides. Following the clean-up, sequences were subjected to NCBI BLAST to determine a closely matched baculovirus sequence. Sequences were analysed in MEGA® 6 (Tamura et al. 2013) to determine single nucleotide polymorphisms (SNPs). Once SNPs were determined, the sequences were translated to determine if the SNPs resulted in amino acid changes.

Results

Symptomology

Collection of symptomatic larvae from the culture began once the culture reached high densities. Symptomatic larvae were found randomly during rearing, in medium to low densities depending on how crowded the larvae were and the time the infected larvae were found. Symptomatic larvae were found on the surface of the diet, within the diet and hanging from the sides of the containers. Early symptoms of the virus were observed by a colour change in the insects, commonly from milky pink to brown-black. Once larvae had reached the brown/black stage they were prone to rupturing as the cuticle became soft and liquefied. Caution was therefore taken when these larvae were collected to avoid rupturing the cuticle.

Crude Baculovirus Extraction and Transmission Electron Microscopy

Transmission electron microscopy of a crude extract confirmed the presence of a baculovirus. The OBs were observed as amorphous black structures clumped together. The images of the OBs show the characteristic features of a NPV (FIG. 1). The OBs varied in size between 421 nm to 1263.2 nm. The mean size of 100 NPV OBs was found to be 731.09±15.13 nm.

Purification of Virus Occlusion Bodies by Glycerol Gradient Centrifugation

Glycerol gradient centrifugation was used to purify OBs from the crude extract. A band forming on top of the gradient and the pellet were collected and placed in separate microtubes. TEM was then completed on both samples. Very few to no OBs were observed in the band, with numerous pure OBs found in the pelleted sample.

Figure 2:
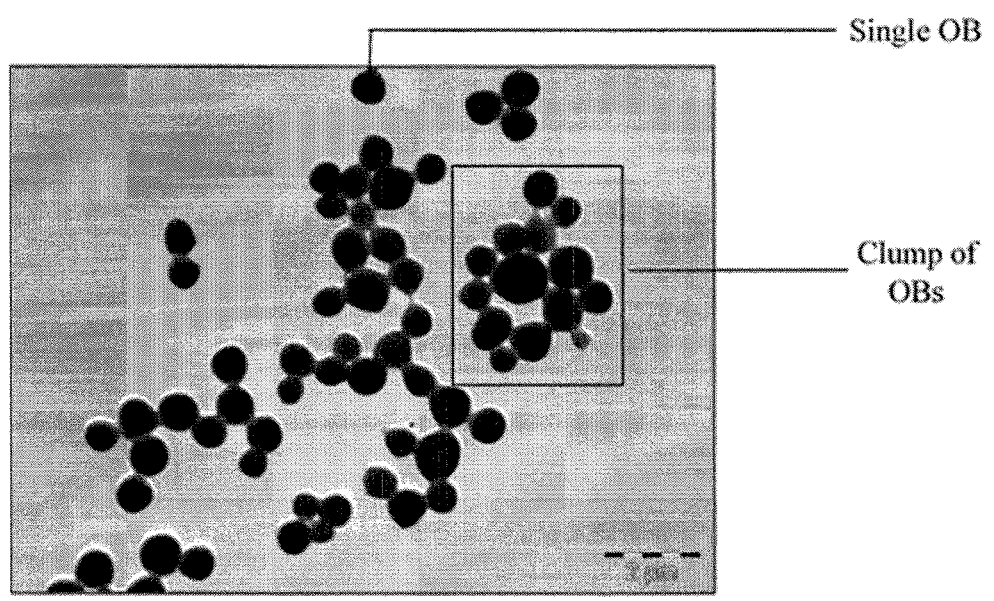
FIG. 2 illustrates a transmission electron micrograph of purified *C. peltastica* NPV OBs.
Figure 3:
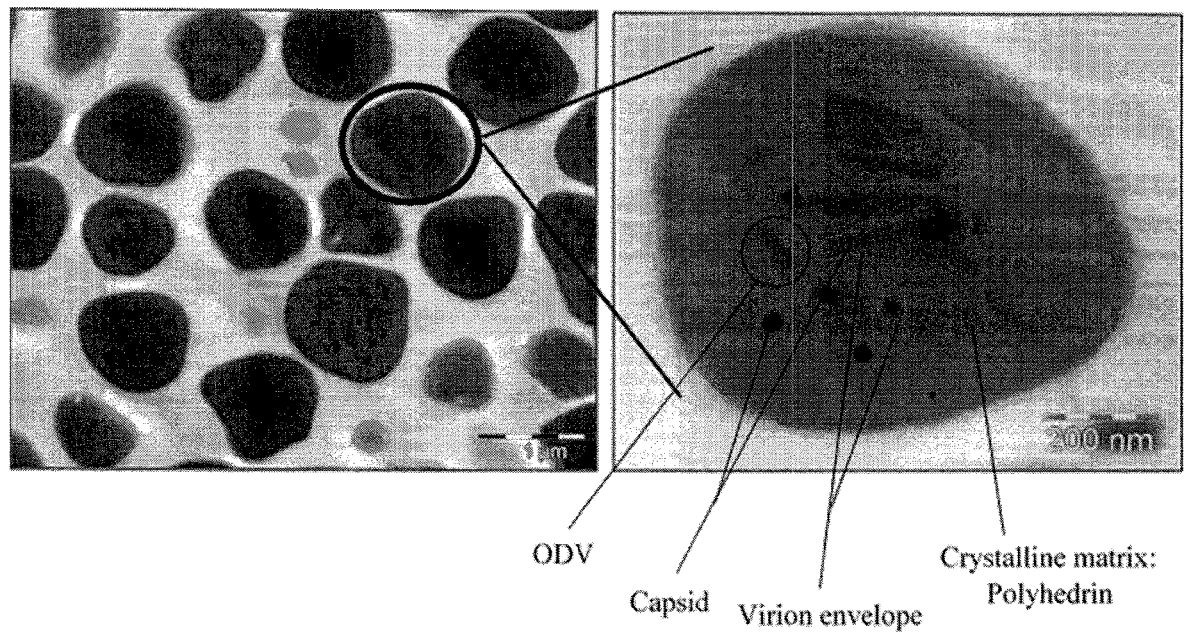
FIG. 3 illustrates transmission electron micrographs of OBs after sectioning of resin-embedded samples.

The pelleted sample contained the majority of the NPV OBs. Even though the sample was found in the pellet where the insect debris is usually found, the sample was pure. OBs were observed and could be morphological characterised. As shown in FIG. 2 the varying sizes, circular shapes and clumping together of the NPV can be observed.

DNA Extraction Using NPV Genomic DNA

Figure 4:
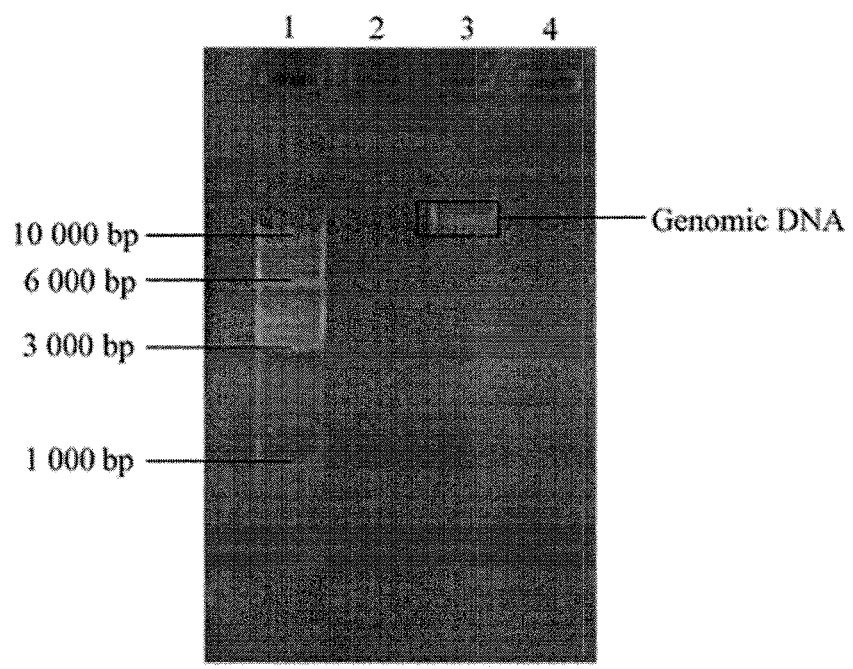
FIG. 4 illustrates a 0.7% agarose gel electrophoresis used to observe genomic DNA of *C. peltastica* NPV. Lane 1: GeneRuler 1 Kbp DNA Ladder (Thermo Scientific®), Lane 3: NPV genomic DNA.

Genomic DNA was successfully extracted from *C. peltastica* NPV crude extract of OBs. The DNA was analysed on 0.7% agarose gel electrophoresis and found to be of high molecular weight (>10 000 bp) (FIG. 4).

PCR Amplification of the Polyhedrin Gene Using Degenerate Primers

Figure 5:
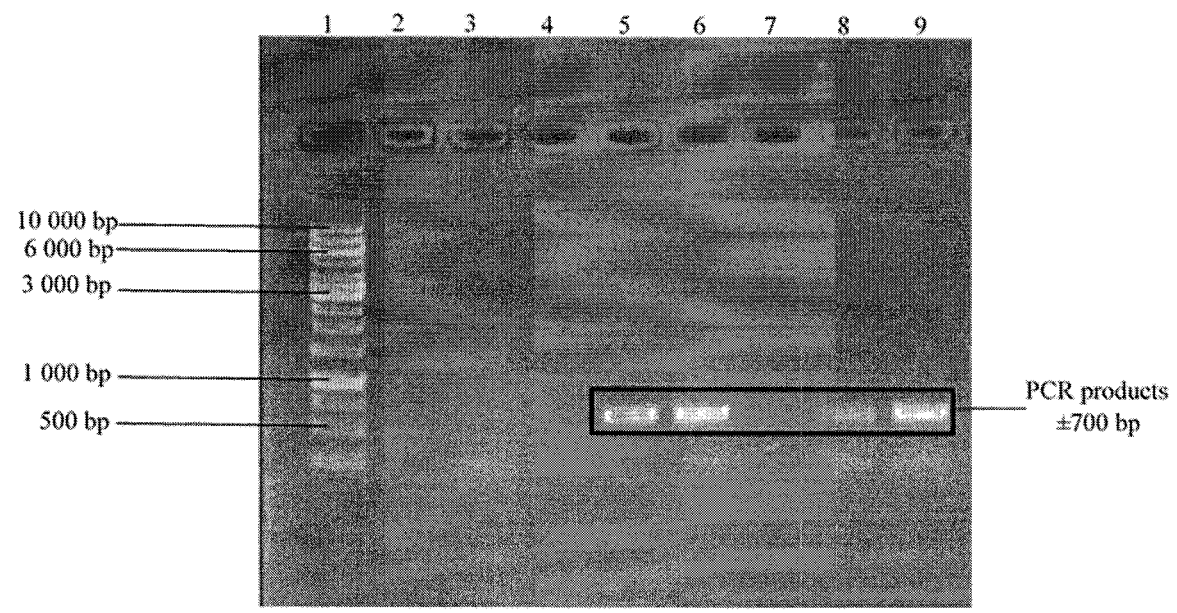
FIG. 5 illustrates a 1% agarose gel electrophoresis showing PCR amplification of the polyhedrin gene of *C. peltastica* NPV. Lane 1: GeneRuler 1 Kbp DNA Ladder (Thermo Scientific®), Lane 3: negative control and Lane 5: ±700 bp positive control PCR product of concentrated CrleGV DNA, Lane 6: ±700 bp PCR product of 1:10 dilution of CrleGV DNA, Lane 8: concentrate DNA of *C. peltastica* NPV and Lane 9: 1:10 dilution of *C. peltastica* NPV DNA.

Genomic DNA obtained was used to amplify the polyhedrin gene using degenerate primers. The amplified product was analysed on 1% agarose gel electrophoresis, illustrated in FIG. 5. There was no evidence of contamination as no band was present in the negative control (Lane 3). The positive control of CrleGV was successful as a ±700 base pair product was amplified (Lane 5 & 6). The polyhedrin gene of C. peltastica was successfully amplified, as evidenced by the obtained PCR product of approximately 700 base pairs (Lane 8 & 9). All products were of good quality, producing pure, tight bands.

Sequencing Analysis

Sequences obtained were subjected to a BLAST, using a blastn analysis where a closest match of 93% was observed with a partial sequence of Epinotia granitalis baculovirus polyhedrin gene region (501 nucleotides). After sequence clean-up the sequence for C. peltastica NPV polH was found to be 507 nucleotides in length (SEQ ID NO:1). Following translation and alignment between the two sequences, several SNPs were observed. Five of these SNPs resulted in amino acid changes: Isoleucine to Valine, Phenylalanine to Tyrosine, Serine to Alanine, Valine to Isoleucine and Glutamic acid to Aspartic acid. The remaining SNPs were minor and did not result in any changes.

E. granitalis, the cypress bark moth, is native to Japan and is a pest of Japanese cedar and Japanese cypress (Takatsuka 2007). There is limited research on E. granitalis baculovirus and only a partial polh/gran sequence is available for comparison. The reasons as to why the polyhedrin gene sequences of these viruses are so closely matched are unknown because they infect different insect species that are not found in the same geographic region and they do not share the same hosts.

This is the first identification of a NPV infecting C. peltastica and further characterisation through whole genome sequencing and REN analysis of genomic DNA was conducted to investigate the novel status of this virus.

Genomic Analysis of *Cryptophlebia Peltastica* Nucleopolyhedrovirus

Further genetic characterisation of the isolated NPV was carried out using restriction endonuclease (REN) analysis and sequencing of the full genome. REN analysis is a technique used extensively in molecular biology for genetic engineering, genome mapping and DNA sequence analysis (Roberts 1979; Bikandi et al. 2004). REN analysis is also an important technique that can be used to compare the genotypes of different virus isolates for biological control purposes.

Restriction endonuclease analysis is used to create a genetic 'fingerprint' for isolated viruses. In order to produce this 'fingerprint' viral DNA is digested with the use of restriction enzymes. These enzymes cut the DNA strands at certain nucleotide sequences, resulting in several pieces of DNA strands. The fragments are then analysed by agarose gel electrophoresis, which separates them according to size creating a DNA profile. It is from these 'fingerprints' that viral isolates can be characterised in terms of genotype.

Restriction Endonuclease Analysis

Genomic DNA was extracted and used to create REN profiles, using the following fast digest restriction enzymes BamH1, EcoR1, Hind111, Kpn1, Pst1, Sal1, Sma1, Xba1 and Xho1 (Thermo Scientific®, USA). A 30 µl reaction was set up, comprising of 200 ng/µl of template DNA, 3 µl fast digest restriction enzyme, 3 µl fast digest buffer and the remaining volume made up with ddH$_2$O. The reaction was incubated at 37° C. for 15 minutes. REN profiles were visualised using 0.6% agarose gel electrophoresis, which were electrophoresed at 30 volts for 16 hours in 1× TAE buffer and stained with ethidium bromide. Images of the REN profiles were captured using UVIpro chemi (UVItec) UV trans-illuminator. To determine the band sizes two DNA ladders were used, a GeneRuler high range ladder (Thermo Scientific®, USA) and GeneRuler 1 Kb DNA ladder (Thermo Scientific®, USA). UviBand software (UVItec) was used to estimate the band and genome sizes.

Restriction Endonuclease Analysis Profiles

None of the REN profiles of BamH1, EcoR1, Hind111, Kpn1, Pst1, Sal1, Xba1 and Xho1 produced a characteristic profile that could be used to easily distinguish CrpeNPV from similar baculoviruses. However, the REN profile produced by Sma1 digestion produced a characteristic profile containing a single band in the agarose gel electrophoresis gel (FIG. 6). This indicates that there is only one recognition site in the CrpeNPV genome for Sma1, which can be used as a simple means of analysis and identification of virus isolates.

As no other profiles of known CrpeNPV analogues were available for comparison, REN analysis could not be used to accurately characterise CrpeNPV. Therefore the whole genome was sequenced for a more accurate method of genetic characterisation.

Genome Sequencing

The full genome (SEQ ID NO:2) of CrpeNPV, using approximately 100 ng of DNA extracted from purified OBs, was sequenced by Inqaba Biotechnical Industries (Pty) Ltd (South Africa) using a MiSeq Desktop Sequencer (Illumina). The Illumina sequencing of the full genome of CrpeNPV produced a total of 3 871 946 paired reads. Geneious (New Zealand) version R7 (Kearse et al. 2012) was used to complete a de novo assembly. In order to produce a de novo assembly, the ends of the paired reads were trimmed using the soft trimming function in Geneious. Once the paired reads were trimmed a de novo assembly was run using 20% of the data and numerous contigs were produced. The longest contig was selected and a consensus sequence was generated to create a full genome sequence for CrpeNPV.

Analysis of the CrpeNPV Genome

A total of 3 871 946 paired reads were produced from the Illumina sequencing. Of these reads 760 297 were used to complete a de novo assembly, which produced 104 532 contigs. The largest contig, contig 1, was used to create a consensus sequence of 116 646 bp. The consensus sequence had a coverage of 731.6±390.8 (Mean±StDev) and a GC content of 37.1%. The full genome of CrpeNPV (SEQ ID NO: 2) was annotated using a database of 18 NPV full genome reference sequences. A total of 105 genes with complete coding regions (stop to start condons) were identified in the genome. The 105 genes were labelled according to ORF numbers, ORF1 starting at the polyhedrin gene.

The majority of the 31 core genes identified in all baculovirus genome were recognised in the CrpeNPV genome with the exception of gp64, p6.9, odvp-6e, p95, vp80/97, gp67, p87, lef-6, ptp-2, ptp-2, arif, vef, pcna, ie-2, lef-7, pe38 and lef-3. The gp64 gene is a distinguishing feature for NPVs, as NPVs are divided into two groups, group 1 and group 2. Group 1 NPVs express the gp64 gene and fusion protein, whereas group 2 NPVs lack the gp64 gene but contain the fusion protein. Therefore the CrpeNPV is a group 2 NPV since it lacks the gp64 gene.

The results of the BLAST search revealed that there are no known polyhedrin genes having a nucleotide sequence greater than 93% sequence identity to SEQ ID NO: 1 (the CrpeNPV polyhedrin gene sequence).

Biological Activity

The bioassays were used to determine the virulence of CrpeNPV against *C. peltastica, T. leucotreta* and *C. pomo-*

*nella* using a surface dose bioassay method. The first objective of the bioassay study was to determine the concentration of the viral product required to cause 50% ($LC_{50}$) and 90% ($LC_{90}$) mortality by using a range of doses against all three species. The second objective was to determine the speed to kill 50% ($LT_{50}$) and 90% ($LT_{90}$) of the population using the $LC_{90}$ value obtained from the dose-response assays.

Surface Dose-Response Bioassays with *C. peltastica* Neonate Larvae

Surface dose bioassays were conducted in glass vials. Each glass vial was filled with 2 g of false codling moth (FCM) artificial diet and 2 ml of distilled water, the diet autoclaved at 121° C. for 13 minutes. Six five-fold dilutions of purified OBs of CrpeNPV in sterilised distilled water were used for doses and sterile distilled water as a control. Forty eight larvae were treated per dose (48 glass vials per dose) and assays were replicated three times. A volume of 100 μl of each viral dilution and control was pipetted onto the centre of the diet surface. The fluid was spread evenly over the diet surface by rotating the vial at an angle. Inoculated glass vials were left for ±30 mins, until the diet had dried. One neonate larva was placed into each vial. All larvae were from the same batch of eggs, hatching at the same time. Vials were then closed with a lid and left upside down for approximately twelve hours to prevent larvae from escaping. Vials were kept in a CE room at 27° C. and a relative humidity of 60-80%. Vials were then turned upright. Approximately 24 hours later, lids were replaced with cotton wool.

After 7 days, vials were opened and diet was inspected. Larvae were recorded as dead or alive. The dose-response curve was calculated using PROBAN (Van Ark 1995) software used for probit analysis (Finney 1971). Mortality of control larvae were taken into consideration by PROBAN and corrected using Abbott's formula (Abbott 1925). From the analysis, $LC_{50}$ and $LC_{90}$ were calculated for each replicate. An average $LC_{50}$ and $LC_{90}$ were obtained from the means from the three assays.

Surface Dose-Response Bioassays with FCM Neonate Larvae

Surface dose bioassays were conducted in 24 well plates. Diet was prepared by adding 250 g of FCM artificial diet to a pyrex dish, 300 ml of $dH_2O$ was added to the diet. The diet was sterilised in an oven at 180° C. for 30 mins. Diet plugs were then cut out using a glass vial. Diet plugs were then pressed into the wells of the plate using a sterile glass rod. Six five-fold dilutions of purified OBs of CrpeNPV in sterilised distilled water were used for doses and sterile distilled water as a control. Forty eight larvae were treated per dose (two 24 well plates per dose) and assays were replicated three times. A volume of 50 μl of each viral dilution and control was pipetted onto the centre of the diet surface. The fluid was spread evenly over the diet surface by rotating the plates.

Inoculated plates were left for ±30 mins, until diet had dried. One neonate larva was placed into each well. All larvae were from the same batch of eggs, hatching at the same time. Assay plates were sealed with parafilm and kept in a CE room at 27° C. and a relative humidity of 60-80%.

After 7 days, plates were opened and diet was inspected. Larvae were recorded as dead or alive. The dose-response curve was calculated using PROBAN (Van Ark 1995) software used for probit analysis (Finney 1971). Mortality of control larvae were taken into consideration by PROBAN and corrected using Abbott's formula (Abbott 1925). From the analysis, $LC_{50}$ and $LC_{90}$ were calculated for each replicate. An average $LC_{50}$ and $LC_{90}$ were obtained from the means from the three assays.

Surface Dose-Response Bioassays with Codling Moth Neonate Larvae

Surface dose bioassays were conducted in 24 well plates. Diet was prepared by autoclaving 13 g of agar in 400 ml of distilled water. 235.27 g of pre-mixed bollworm diet was sterilised in an oven at 180° C. for 10 mins. A 1527 μl of propionic acid and 154 μl of phosphoric acid was mixed into the sterilised diet. Agar was then added to the diet, 200 to 400 ml of boiling water was added and mixed to form a uniform paste. Diet was then piped into the 24 well plates. Five five-fold dilutions of purified OBs of CrpeNPV in sterilised distilled water was used for doses and sterile distilled water as a control. Forty eight larvae were treated per dose (two 24 well plates per dose) and assays were replicated three times. A volume of 50 μl of each viral dilution and control was pipetted onto the centre of the diet surface. The fluid was spread evenly over the diet surface by rotating the plates. Inoculated plates were left for ±30 mins, until diet had dried. One neonate larva was placed into each well. All larvae were from the same batch of eggs, hatching at the same time. Wells were sealed with parafilm and kept in a CE room at 27° C. and a relative humidity of 60-80%.

After 7 days, plates were opened and diet was inspected. Larvae were recorded as dead or alive. The dose-response curve was calculated using PROBAN (Van Ark 1995) software used for probit analysis (Finney 1971). Mortality of control larvae were taken into consideration by PROBAN and corrected using Abbott's formula (Abbott 1925). From the analysis, $LC_{50}$ and $LC_{90}$ were calculated for each replicate. An average $LC_{50}$ and $LC_{90}$ were obtained from the means from the three assays.

Time-Response Bioassays

Time response bioassays were conducted in glass vials. Fifty glass vials were inoculated with 100 μl of sterile distilled water and 50 vials were inoculated with the $LC_{90}$ (calculated from the dose-response bioassays) solution of purified CrpeNPV. The diet was left for ±30 mins, until it had dried adequately. One neonate larva was placed into each vial. Vials were sealed with a lid and the same process repeated as above and kept in a CE room at 27° C. and a relative humidity of 60-80%. Bioassays were replicated three times. After 16 hours, the vials were inspected for dead larvae. Subsequently, vials were checked every 8 hours until mortality had ceased. Diet was then dissected to determine whether the remaining vials contained dead or alive larvae. Time-response was analysed using a logit regression in STATISTICA version V12 (StatSoft 2013). From the results obtained, the $LT_{50}$ and $LT_{90}$ were calculated.

Results of Surface Dose-Response Bioassays

The dose response curves for $LC_{50}$ and $LC_{90}$ were determined for each species and isolate. The results are presented in Table 2 below.

TABLE 2

Comparison of the mean $LC_{50}$ and $LC_{90}$ values for *C. peltastica*, *T. leucotreta* and *C. pomonella* (South African) and *C. pomonella* (European, with isolates CpS and CpRR1 being susceptible and resistant, respectively, to CpGV).

DOSE RESPONSE (OBs/ml)

| | | CrpeNPV | CrleGV | CpGV |
|---|---|---|---|---|
| *C. peltastica* | $LC_{50}$ | $8.19 \times 10^3$ | — | — |
| (Litchi Moth) | $LC_{90}$ | $3.33 \times 10^5$ | — | — |

TABLE 2-continued

Comparison of the mean $LC_{50}$ and $LC_{90}$ values for C. peltastica, T. leucotreta and C. pomonella (South African) and C. pomonella (European, with isolates CpS and CpRR1 being susceptible and resistant, respectively, to CpGV).
DOSE RESPONSE (OBs/ml)

|  |  | CrpeNPV | CrleGV | CpGV |
|---|---|---|---|---|
| T. leucotreta | $LC_{50}$ | $2.29 \times 10^3$ | $4.095 \times 10^3$ | — |
| (False Codling Moth) | $LC_{90}$ | $9.97 \times 10^4$ | $1.185 \times 10^5$ | — |
| C. pomonella | $LC_{50}$ | $1.43 \times 10^3$ | — | $1.632 \times 10^3$ |
| (South African Codling Moth) | $LC_{90}$ | $1.26 \times 10^4$ | — | $1.163 \times 10^5$ |
| CpS | $LC_{50}$ | $2.70 \times 10^3$ |  |  |
|  | $LC_{90}$ | $2.86 \times 10^4$ |  |  |
| CpRR1 | $LC_{50}$ | $3.64 \times 10^3$ |  |  |
|  | $LC_{90}$ | $3.24 \times 10^4$ |  |  |

The virulence of CrpeNPV against T. leucotreta and C. pomonella was slightly more fatal than that of their homologous baculoviruses, CrleGV and CpGV-SA. The $LC_{50}$ and $LC_{90}$ for CrleGV against its homologous host, T. leucotreta was found to be $4.095 \times 10^3$ OBs/ml and $1.185 \times 10^5$ OBs/ml respectively (Moore et al. 2011). The $LC_{50}$ and $LC_{90}$ for CpGV-SA against its homologous host, C. pomonella was found to be $1.632 \times 10^3$ OBs/ml and $1.163 \times 10^5$ OBs/ml respectively (Motsoeneng 2016).

TABLE 3

Comparison of $LC_{50}$ values for European C. pomonella isolates CpS, CpRR1 and Cp5M against isolates of CpGV. The CpS, CpRR1 and Cp5M isolates are susceptible, resistant, and more resistant, respectively, to CpGV.
$LC_{50}$ (OBs/ml) for 14 days

| CpGV Isolates | Cps | CpRR1 | Cp5M |
|---|---|---|---|
| M | $1.34 \times 10^2$ | $4.46 \times 10^7$ | $1.88 \times 10^8$ |
| V015 | $9.94 \times 10^2$ | $8.82 \times 10^2$ |  |
| I07R | $1.58 \times 10^3$ | $6.97 \times 10^2$ | $1.46 \times 10^7$ |
| I12 | $8.90 \times 10^2$ | $1.40 \times 10^3$ | $7.76 \times 10^6$ |
| S | $2.50 \times 10^3$ | $7.20 \times 10^2$ |  |
| E2 | $9.50 \times 10^2$ | $2.80 \times 10^2$ |  |
| Madex Plus |  | $5.26 \times 10^2$ | $6.32 \times 10^6$ |
| CrpeNPV | $8.39 \times 10^2$ | $1.39 \times 10^3$ |  |

The results illustrated in Table 3 demonstrate comparable activity of CrpeNPV against CpGV-sensitive and CpGV-resistant European codling moth isolates. M is a Mexican strain of CpGV; V015 is a resistance overcoming Mexican isolate of CpGV; I07R and I12 are Iranian isolates of CpGV; S is an isolate of CpGV isolated from the commercial product, Virosoft; E2 is an English isolate of CpGV; Madex Plus is a laboratory selected isolate from CpGV-resistant codling moth.

Results of Time-Response Bioassays

Speed to kill values $LT_{50}$ and $LT_{90}$ were determined for each species and are illustrated in Table 4 below.

C. peltastica had an $LT_{50}$ of 73.44 hours and $LT_{90}$ of 89.21 hours.

T. leucotreta had a $LT_{50}$ of 80.69 hours and $LT_{90}$ of 96.37 hours.

C. pomonella had a $LT_{50}$ of 106.09 and $LT_{90}$ of 125.52 hours.

TABLE 4

Comparison of the mean $LT_{50}$ and $LT_{90}$ values for C. peltastica, T. leucotreta and C. pomonella.
TIME RESPONSE (at $LC_{90}$ dose)

|  |  | CrpeNPV | CrleGV | CpGV |
|---|---|---|---|---|
| C. peltastica | $LT_{50}$ | 73.44 hours | — | — |
| (Litchi Moth) | $LT_{90}$ | 89.21 hours | — | — |
| T. leucotreta | $LT_{50}$ | 80.69 hours | 118 hours | — |
| (False Codling Moth) | $LT_{90}$ | 96.37 hours | 176 hours | — |
| C. pomonella | $LT_{50}$ | 106.09 hours | — | 135 hours |
| (Codling Moth) | $LT_{90}$ | 125.52 hours | — | — |

Speed to kill values $LT_{50}$ and $LT_{90}$ were also determined for two Cydia pomonella cultures and against four viral isolates, as illustrated in Table 5 below.

TABLE 5

Comparison of LT50 and LT90 values for two Cydia pomonella cultures; CpS (susceptible) and Cp5M (resistant) against four viral isolates; CpGV-S, CpGV-E2, CpGV-M and CrpeNPV.

|  | CpS | | CpR5M | |
|---|---|---|---|---|
|  | $LT_{50}$ | $LT_{90}$ | $LT_{50}$ | $LT_{90}$ |
| CpGV-S | 139.28 | 183.55 | — | — |
| CpGV-E2 | 107.68 | 132.07 | 126.89 | 156.48 |
| CpGV-M | 115.58 | 148.74 | 200.00 | — |
| CrpeNPV | 120.34 | 147.49 | 110.92 | 135.18 |

The speed of kill for CrpeNPV against the heterologous hosts was greater than that of their homologous granuloviruses (Table 4). As the $LT_{50}$ and $LT_{90}$ for CrleGV against T. leucotreta was observed to be 118 hours and 176 hours (Moore et al. 2011) and a $LT_{50}$ of 135 hours for CpGV-SA against C. pomonella (Motsoeneng 2016).

From the above results it was established that CrpeNPV was more virulent against the neonate T. leucotreta and C. pomonella larvae, specifically with a significantly faster speed of kill for both species. The mean LC and LT values were slightly less than for their own homologous baculovirus, CrleGV and CpGV-SA.

Test for Infectivity

Figure 7:
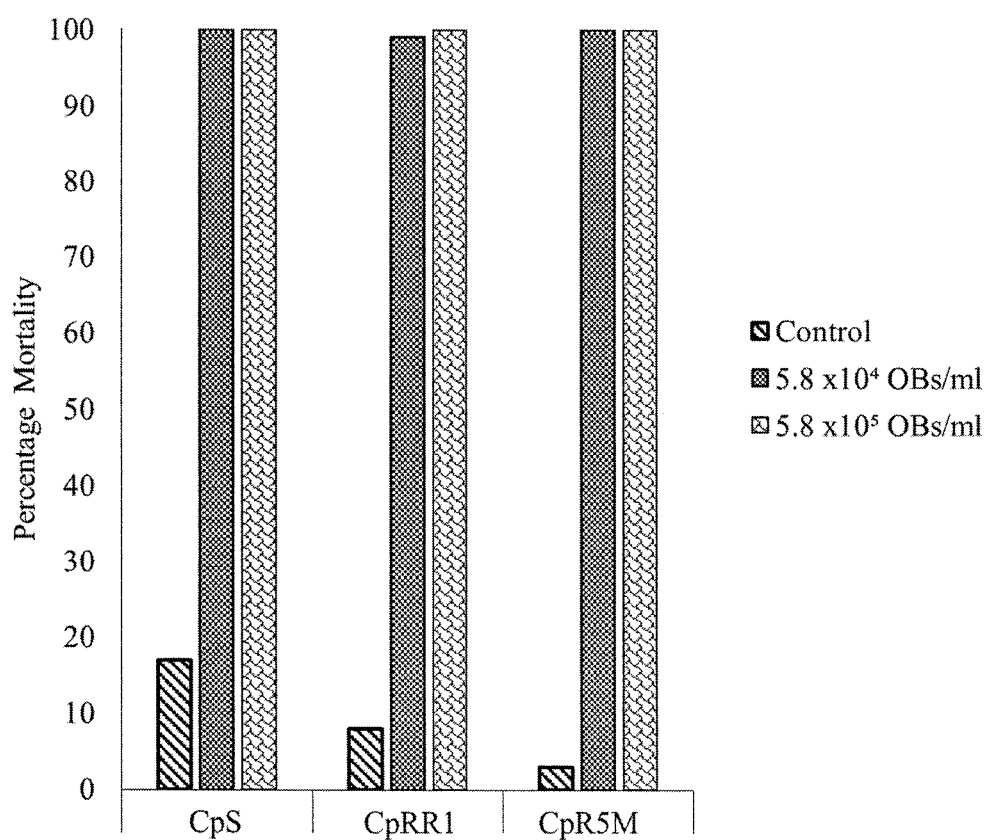
FIG. 7 is a graph illustrating the infectivity of *C. peltastica* NPV against three European codling moth cultures with varying degrees of resistance to *Cydia pomonella* granulovirus (CpGV): CpS (susceptible), CpRR1 (resistant) and Cp5M (more resistant).

Two discriminating virus concentrations ($5.8 \times 10^4$ and $5.8 \times 10^5$ OBs/ml) were used to test the infectivity of CrpeNPV against three European codling moth (C. pomonella) cultures with varying susceptibilities to Cydia pomonella granulosis virus (CpGV): CpS (susceptible), CpRR1 (resistant) and Cp5M (more resistant). CrpeNPV caused 100% mortality for all three cultures at $5.8 \times 10^4$ and $5.8 \times 10^5$ OBs/ml (see FIG. 7). Assays were also performed to determine the LC50 and LC90 values after seven and fourteen days incubation time and the results are presented in Tables 6 and 7 below.

TABLE 6

Comparison of the LC50 and LC90 values for the three European codling moth cultures: CpS, CpRR1 and CpR5M after seven days

|  |  | Dose (OBs/ml) |
|---|---|---|
| CpS | $LC_{50}$ | $2.70 \times 10^3$ |
|  | $LC_{90}$ | $2.86 \times 10^4$ |
| CpRR1 | $LC_{50}$ | $3.64 \times 10^3$ |
|  | $LC_{90}$ | $3.24 \times 10^4$ |

TABLE 6-continued

Comparison of the LC50 and LC90 values for the three European codling moth cultures: CpS, CpRR1 and CpR5M after seven days

| | | Dose (OBs/ml) |
|---|---|---|
| Cp5M | $LC_{50}$ | $2.19 \times 10^3$ |
| | $LC_{90}$ | $2.32 \times 10^4$ |

TABLE 7

Comparison of the LC50 and LC90 values for the three European codling moth cultures: CpS, CpRR1 and CpR5M after fourteen days

| | | Dose (OBs/ml) |
|---|---|---|
| CpS | $LC_{50}$ | $8.39 \times 10^2$ |
| | $LC_{90}$ | $7.98 \times 10^3$ |
| CpRR1 | $LC_{50}$ | $1.39 \times 10^3$ |
| | $LC_{90}$ | $1.69 \times 10^4$ |
| Cp5M | $LC_{50}$ | $7.02 \times 10^2$ |
| | $LC_{90}$ | $4.68 \times 10^3$ |

These results indicate that CrpeNPV has activity against a wide host range including CpGV-resistant species of moth pests. This could be useful when multiple lepidopterans infest the same host because not only will the primary pest be controlled but also the secondary pests. The secondary pests are usually only observed once the primary pest has been suppressed.

The biological activity of CrpeNPV was found to be more virulent against the heterologous hosts including CpGV-resistant codling moth species with a faster speed of kill.

These results indicate that CrpeNPV has the potential to be commercially developed into a biopesticide for controlling insect populations of *C. peltastica*, *T. leucotreta* and *C. pomonella* in trees and plants, particularly in fruit (e.g. *litchi*, citrus, apple and pear) and nut (e.g. macadamia and walnut) trees. Additionally, CrpeNPV could also be used to control other lepidopteran pests in the Tortricidae family.

TABLE 8

Nucleotide sequence of *C. peltastica* NPV polyhedrin gene (polH) (SEQ ID NO: 1)

ACTTACTTTGTTTAAAGAAATCCGTAGCGTTAAGCCCGACACAATGAAAC

TAGTTGTTAATTGGAGCGGTAAAGAGTTTTTGAGGGAAACTTGGACTCGT

TTCATGGAGGACAGCTTTCCCATTGTAAACGACCAAGAAATTATGGATGT

TTTCCTAGTAGTTAACATGCGCCCGACTAGACCTAACCGTTGCTACAAGT

TCTTGGCTCAACACGCTCTTCGTTGCGACCCAGACTATGTGCCTCACGAA

GTAATTAGAATAGTTGAGCCGTCATGGGTGGGAAGCAACAACGAGTACCG

TATTAGTCTGGCCAAGCGCGGCGGCGGATGTCCAGTGATGAATCTGCATG

CTGAGTACACCAACTCGTTTGAAGAGTTCATTAACAGAGTCATTTGGGAA

AACTTCTACAAGCCCATTGTGTACATTGGTACCGACTCTGCTGAGGAAGA

GGAAATTCTAATGGAAGTTTCCCTGGTGTTCAAAGTAAAGGATTTCGCCC

CGGGGCCATACCTGTTTTTCGG

TABLE 9

Nucleotide sequence of the *C. peltastica* NPV genome (SEQ ID NO: 2)

ATGTATACGCGTTACAGTTATAACCCATCTTTGGGTCGTACGTATGTTTATGACAACAAGTATTACAAAAACCTCGGCTCAGTA

ATCAAAAACGCCAAACGTAAGCGCCACCTACTCGAGCATGAAATCGAGGAACGTAATTTGGACCCCCTAGATAATTATCTGGTC

GCCGAGGATCCTTTCCTGGGACCCGGCAAAAACCAGAAACTTACTTTGTTTAAAGAAATCCGTAGCGTTAAGCCCGACACAATG

AAACTAGTTGTTAATTGGAGCGGTAAAGAGTTTTTGAGGGAAACTTGGACTCGTTTCATGGAGGACAGCTTTCCCATTGTAAAC

GACCAAGAAATTATGGATGTTTTCCTAGTAGTTAACATGCGCCCGACTAGACCTAACCGTTGCTACAAGTTCTTGGCTCAACAC

GCTCTTCGTTGCGACCCAGACTATGTGCCTCACGAAGTAATTAGAATAGTTGAGCCGTCATGGGTGGGAAGCAACAACGAGTAC

CGTATTAGTCTGGCCAAGCGCGGCGGCGGATGTCCAGTGATGAATCTGCATGCTGAGTACACCAACTCGTTTGAAGAGTTCATT

AACAGAGTCATTTGGGAAAACTTCTACAAGCCCATTGTGTACATTGGTACCGACTCTGCTGAGGAAGAGGAAATTCTAATGGAA

GTTTCCCTGGTGTTCAAAGTAAAGGAGTTTGCTCCTGATGCTCCTTTGTACACCGGACCAGCGTATTAAACAATAGATTGCGCA

GGTTTCATAATTTTCAATAGTCTTTGCTGTAGTTGAAGCAAAGGTGCCGAAGCGGGTTTCGCTTGTAAAGCCTTGTTGATAAAA

TCCATAGCATTTTGATATTTCTCGTGTAAAATTATGAATTTTACTTCCCTAAGAAATTGGGCTTCGTTTTCGTTATATAAATTT

GTGGTGCTCGGAGTTTGGTTTTCTAAGATATTAATATTTTTAGTCTTTTAACAATCGAATTAATAATTTCGTCTGCCGAATTT

AAATTTTGCTCGTTTTCGTACGGAATATTGATTAAACGACTCGCTTCGGAGATTTCGTTAGCAAAACTATTATCGCTAATTTCT

GTTAATATTACTAATTTTGAGGCTAGCGCATTCTTTCTATCCCGGTACTCTGTTTTATCATCATCGTCCCACTCATCGTTAGTC

GTGTTTTCGTTTTCGGAAGCCGTACTAACAGGTTCTAAGGCTATACGTCTACTCATAATTTGAGCGACATGTTCGATACCTTTT

GTTTCTTTTAGAGGTTCTTTTTCTATTTCAACCTTTTTCAATGTAGGTCTTTTCTTAATAGCCTCTAATAGGGCGCTTCTGGGG

TCTACTGTAGTTTCAGGTTTAGGTGGGGTAGAACGTTCTGCGGCAGATTTTAATGCTGGCCTAGATCTTATTTGTTCCATTAGT

TTACTAGGGTCTAAAGGCGATTCGGAAGGTTTTGGAGGAGACGGTGTCGATGTTTCTAAACCCGACATTGGCGGAGCAGGCGGT

GCCTCGCTAGCTGTGGGCATAGGCGGTGGGGGCGGAGGACCAAAATCTGAAGCCATCGGCGGAGGCGGAGGAGGAACAAAATCT

TABLE 9-continued

| Nucleotide sequence of the *C. peltastica* NPV genome (SEQ ID NO: 2) |
|---|
| GAAACCATCGGCGGAGGCGGAGGCGGCGGTGGTGGTATGCTCGTTTCTAGCTCTTTCATAGGAGGCGGCGGAGGTATGTTTGTA |
| ATAGGTTCAGGAGGCGGCGGAGGCGGCGGTGGCATGAAAGGTTCAACTATTTTATCGTTTACCGTAGATATAAAATCGTTGGAT |
| GTAAGTAGAATGTCTTCCACACGTTTAACTAACTCACCATAGTTTTGATCGGGAATAACAGTTTTAATGTTTTGATCATCAGTT |
| TCGTTCGAAACAATTGGTGCTACTATCGTTTCCCTGTTCAAACTTTTGTCGGCGCCTTTTGTGGCGATATCATCCAACGAAACT |
| ATATCATTGAGAATGCTATCGATCTTTTCGGTGTCCTTTTGAATCTTTTGGTTGTGATCGTGTAAATATTTTTTATACACGACA |
| AAAAATTGTTTATAGTTATCTTCTACGTTTGTTTCATTTTGAATTTCGTCAATTATCGAAAGTAGCAATGATTTATTTTCATCG |
| TTGTCGTCTACTTTTCTGGCAATGTTTATTAAAATTTTGACTTTATTATCAACCGATTTAACTATGGGCAACGTCGTTTCTGTT |
| TCTACATGACTTACCCTTTCCTGCTCATAAATTATGGCAGTGTTATTGTAAATATCATTGGCAAGTTGAATCAATTCTAACGAC |
| TCTGCTAAAGTAAGTTTCAGCAGTTCGTTTTTGGGAGTAGCAAAAACTTTACGTTTCAGTTTATTTATTTGGGGACTTTTGATC |
| ATATGCATTAATTTGATAGGTTCAATTAAAGATTCATGTATAAAATAATCTCTGGCGGATTGTATGTCAGTTCGGTCTAGTCTT |
| TTCTCAAACATGGACATTGTGGTTGACGATTTAGACGAGTTTAAACAAAATTTAACTCTAGAAAAAAATATTAAACTTATAAAT |
| GGAAAATTTGGCAAAGTGTCCGTGTGGCGCCACGAGCCCACTAAAAAACTATTTTTACTGAAGCAAATAACTCATGGTTATAAT |
| GAAATCGAACCTATGATTCATTATTTGATGAAAAAAAACAAGTACTTTTTAAATCTTTACTACTCTGTCAATTCGCCAACTACT |
| AATATACTTATTATGGACTACATCGCCGATGGTGACCTGTTTGATCTTCTGCGCCGCGAGTCCCGCTTGCCCGAACCCGAAGTC |
| CGCAGCATTATTTTACAGCTAGTCGACGCTCTACAAGCCCTACATAAAAACTTCATTATACATAACGATGTCAAGCTGGAAAAT |
| GTTTTGTACCATAGAAAGAGACAAATTTATTTGTGTGACTATGGACTCTGCCGCATAGTCGGAGTCAAGTCTTGCCAAGACGGC |
| ACTTTAGATTATTTCTCACCCGAAAAAATCATGGGAAGAAACTATGACTTTGGATTTGACTGGTGGTCAGTCGGTGTTCTAACC |
| TACGAGCTAATCACAGGAACCCATCCATACAAATTTGATCCGGACGAAGACCTCACTACAAATGTTCTGCAGCGAAGGCAGCAA |
| AGAAAACTTGAATTTAAACCTAGCGTGTCTATAGCTGCTCAGTCTTTTATTGAAAAATTACTGTTTTATAATATTAACTATAGA |
| TTAACTAGTGGTGATGAAATAAAATTAAACAAGTTTTTGCAATAAAAAAATTTATTTCATTTATAACTATAGTACCCTATACAA |
| AATACTAGAGAATACAGGTTATTAATACTAATACTATGCTAAGTTTATACAATAAATGCTTAAATGTTAGTACACTTAAATTTT |
| TTGTCGTGTTCCGTATGAATATGATTAACAATGATATCTGACATGCAATCTGTATTTAACAATTTGTGGGACACATTTGACAAA |
| AATATGTTACGTTTTTTAAGTTCCTGAAACTTTTGTTTAACAATTTCATCGTTAGTTTTATATAAAACTTGCCGCTGGTTACAA |
| ATTTGCTGCGGCTTAGGCATAGGATCAGCACTGACAATGATGACATCATCATCGTCGTCATCATTGTCAGCCACATTAATAACT |
| TTAACCGATTCGTCAATTACTTCAACGTCCTCATCGGGTTCTTTTTTAATTATAGGCTCGTTATCTTGAACTATGGCAGAAATT |
| ACAAAAGGTTCGTCATCAGCGGGCTCGGTTTTAATTACGCGCGAAGTTGACATTGTAGTTATTAAATCGGAAATGTCAGCTGTC |
| TTATGTGACTTATGTGATTTAGATTTGCGCGATTTTGACTTTTTAGTTTTCTCTGGCAGCGGCTCGGGCGCCAATATGTGGTTA |
| CGGTCTAAATTCTGGTCTAAAATCAGGTTCTCCACAGCCGCTGCGGTAGAATCATCAAACTGAGCTAAAACGTCTTCAAAGTTA |
| ATAATAGGTATAGCGGGATTGTTAGAATCAAATATGTATGATTCCTCTGGTTCGCGAACCGAAGCCGGCTCGTTTTTCATAATA |
| TATATTTTGTTATTTTTCTCAAAGTATTTGACCCCATTGTGTATTATTTCTTGCGCCTCACTGACAAAATCTGTTAGATTTTTA |
| CCTCTAATCGCGTCAGACCTATCAATTGCCGGGGCCGGTTGGTCACCAAGAATTTGTTCCAATTCTTGGGCAGGTTGTTCACCG |
| AGAATTAGTTCTAATTGTTTTTCTTGCTCCAGAATAGCCTGCCTTTCTCTTTCACACTTGTTTATTTTTTTTTGAAGCTCGATA |
| ATGGCGGCTTCATTGTCGGTGTTAGATGTACGAATCACACTACGGCTACGATCAGTATTAGCGACTTTTACCTTTAATCCTTTT |
| TTAGGTTTTCTGTTACGGCTGCGGCTGCGTCTTTCATGGACAACGGCGGGGCTGTAAGGTTCATTTTGTCGCTCAGATCGAGCG |
| GGGCTGAGGCTTTGCTGAGGTTGGTCGGGACTAGGGCTACGGCGGCTGAAGGTAGGACTGGGGCTGCGGTGGTTGGCAGGGCTG |
| GGGCTGCGGCGGGTTGCGGCTGAATGCTGGCTGAAGGCGGGGCTAGGCGTGCGCTCGTTCGAACCAAAACGATGTCCGACACAA |
| GGACTCGGAGTTCTGGTTCTGTCATTGCGGGCAGGGGTCGGGTCCCTGCTTAAAGCGGGACTCGGAGTTCTGGTACGGTCGCCA |
| TTGCGTGACCCGCTCTGGCTGCGAGAGCGAGATCTGCTTTTGCGCTCACTAGATTGGCTGCGGGAACGGCTTCTACACGTTTCG |
| CTCGATTGGCTGCGGGAACGGTCGCTGTCGTCAGCGACGGAACGCTGGCCAGAAGTGGACCGGCGACTTTTACGAATAGAAACG |

TABLE 9-continued

| Nucleotide sequence of the *C. peltastica* NPV genome (SEQ ID NO: 2) |
|---|
| GACCGGGATCGGTCTGATGTCTCGCTGCCGGAAGGACTTGAAGATCGGGTTCGGTTGCCATGGTTAATAATATCGCTTTGGTCG |
| CTTTCGTGTGAACTGTTACTATAACTACGTTTACTGACACGACTATCGGTACGGTTTAACGCGGGCTTCTTTTTTCCTTTTTTT |
| AGAATTACATTATCTTTAAGGCCTCGCGAAATGGCAATGGCTTCGGCCACTTCAAATGGGGTTTCTTCGCGTTTATAGTTACAT |
| TTAATACACGCGCCTCTCTGATAACTTTCAATGAAACAATCGCTGCACAATTTATGTTCGCAGTTTTTGTAAAAGCTTCTAATA |
| AAAGATTTTTTACACGCCTCGCATATTATAGTTTGCAATTCTTTATTACCGTTACATTGACTGATTATTTCAGAACTGATTTTA |
| ATTTTAACTAAATTATTAATTTTATTGATAAGATCTTTCCGAAGATTTTCAATGGCAGTGAGGCCACATTTGTCCATAATCCTA |
| ATATGTTCTCGAATTTCATAGGTCGCGCCTATGTTACGCAAGTTTTTAGGAACGTGTTGAATCTGTTCGTAAAAAAACTCGCTA |
| GAAGCAATAAAGTCGTGTTTAGACCCATTGGACATCTCCAACAATACGTTATGGACCGTGCCGAAAGCGCTGTTATTATCTCCT |
| AAAGTGGGATAGTAATGATTGTAAAAGGCTCCATAACACAGTCTGAGATGAATCAAAACATCAAACTGAGTCAGACACGTCAGT |
| AAAGTTTGTAAGTCTTTTTTTACTTGGAGGTTAGGCGATTCTATAATGTAATTATAGATGTTTTCATAGTTTCGTGTCAGTAAA |
| TTACGATTTTTAAAGGTAATACCCATAAATTTAAACGTATTAGTATTAGTGTAGTCTAAAAAGGCGACCTTTTTTTTCCCGGCT |
| TGAAATTCAAGATAGAAATAAAGCCTGCCCTCAGGTTTATTATTAACCATTTGCAACTTTTTGTACGAGTTCTGAAAATAAAGG |
| AAAAAACTTAGAGTTTGTCACTCTAAAAAAAAAAAACACAAAATTATTTACAAGTCCAAAAATGGGAAACATAAAAAAACACTG |
| TTACTCACATCAAGTAGACGGCTCATCCTGTGCACTTCACTGGACTTTGCAGGGAGAAGAGGTGTTGCGTGTTCGAAGCTCGAA |
| ACGAAACTGAATCCAAGTTTCGCTACCAAGGCTTATATACCCTGGCTGGCGACCTTGTGGGCGTAATCAGTCACGCGGCTGCGG |
| GCGTAAACAAAGTCAGTCACGTACGCCCTGACCTCCAGACGAACGGAACAAACAACCTAATCAGCAGCGCTTATCGGCGCATGA |
| CCGGAGATTGTTATCCGGTCACGTAGGCGCTCGTTTGTCACGTAGGCGCTTGTTTGTCACGTACGCCAGGAAGGTGATAAGCAG |
| TTTTTTGCTCTACAAAAAAGGACCTAAAATCGTAGTATATTGGGAGCATATTGTACAGTGTAGACTATTATAGTAAAATAGTCT |
| ACGATATGAAATATTCCACTGTATATTAGCTGTAAGGACTTAAGTAACTTTTTTGCACTGCAAAAAAATGACCTTTCGATTCTG |
| GACTAGTCGTGCTTGATTAGATTAGGTTTCGTATAAAAGGCCTGACAAATTGAACACGAATCATACTTTCGTACGGAGCCCTAC |
| ATACCAACAGATAACCGGCCGTAGCATCATGAACAAAGTGAGTATTCTTGTGTATTATTTTTGTGCATATCCTGTCAGACATAG |
| TTTGTTCGTTTTATTTATTTTGTTTTTTGTTTCAGATCGACAAAAAATCTGTTACCAAAATCGAATTATTTAAACCTACTATTT |
| ACAGCCTGAGAAAAAATAACAAAGATTTTGTCCATCACACCGAATTTACTAACCTCATGTTCAATAATTTAATTCGTCAGTATA |
| AAATTTCTGAAAAAGAAACTGGCGACGCAAAAAAATTACGCCAAATAGATGCTTTTAATTTTTGTCGTTACATCCAAAATTACT |
| ACGAATTTAACACAGATCAAAGTTCTTTTTATTTGTATAATATCAGAACTGCCGTTATTAAATATGATTTGATTTTAAGGATGG |
| AAAAGTTTAAAAAATTTGTTAAAAGGCGCTACTTCAAAGAACATGGCGTACGTATGCATCAGGATAAAGTTATGTGTCCTGACA |
| AACATTACGTGGACATTTACAAACCTAAACTTACAAAAATTCACCTCACAAGTAAAGAAGAAAAATATTCGGACGACTCTGATC |
| TGGACAGCTCGGAGGATGAAGGCTTCGGAGGACTACGCCAGCGACCTCGGTCTCCTATTAGGTTTAGGATTGTAAATAACACGA |
| GAGTAATGTCGCGTTACTATCCTCAGTATTAATTATAACAGTATTTTATAGTATTACAGTATTATATAGTATTCAATAAACATT |
| ATTATGGTATTTTTTGTTTCAATTATCTCGCCATAGGTTCTAGAGGTTTGGTTAACAATTGTTTAAAAATAAAAATGCCAATGG |
| CAAGCATAATTAATAAACCCCCTACCAACATGATTAAAGGCAAAAGTTTTTCTCCCAAACTTTTACTTTTATTCATGGATTTGT |
| TAACCAGACCTTCTTCTCCGAGCAAATGATCTAGACCTAAATCTCCTATCAGATCTCCTAAATTGTAGGGTTCTATACATTGGA |
| TAGTTTGGCCGACAGACAAATCAGAAATGTCAACATACTGAGGTGACTCTGGGTCGGCATTAGGATCGCTAGCTCTACAAACTG |
| TCTGTTCTGTTTCGTAATTAAACCCCCTGCAAAGTTCCAGCAGCTCTTGCTCATTCGAAATTAGCGGGTCGAATTCGCATAAAA |
| CTACTCTGTCCATTGCGTCCGCATTCAGCTGACAGGTTCTGTGTCTGAGCATACAAACAGTCATATCATCGCCTCCGTTAAAAC |
| CCACATAAAAATAGCTACCGCCAGTGTTATTCAATGCATTGATTATGTCCTGAATTAAGCTAGCGGTGCTAAATGCCAAATATA |
| CACCCGTACCGATGAGAGCTGTAACGCCTGCAAGTTTTAAATTTTCTAAGTATGTGCGCAAACGAGGCTGTTGAGTAAGCACAG |
| TTTCCACACCGTTTGCGTTTCGTGTGTTTGTAGACGGATAGTTTTGTTTAACCGCATTTTTACGCAAATTAATGGAATGTAAAT |
| TAGCATCGGGAACATTGTCTATACGGCGTAAAGATCCTAAAGAATTTAACTGGCCGTTAGTTGCGTCGGGAAACATGGTTCGTA |

TABLE 9-continued

| Nucleotide sequence of the *C. peltastica* NPV genome (SEQ ID NO: 2) |
|---|
| AGTTTGTACTGTCATTATTGCGCATAAATCGATTCATGTCAGCGACACTAACAAAATCATTGTTTCTGACCAAATAACCTGGCA |
| TGTACATGTCATTGTTTAGGTTTCGAAAACTTGAAGACGAAAAAACGTTTTGAAAACCAGCAGGGGAGGAGTTGACGACATTTA |
| AATTGTCTACATTAAGAAATTGATTAGGGTTATTATAAACTTTATTAACTCTACGCAATGAGGTAAAGAAACTCATTTTTCCTT |
| ATTTACTTTTTAGGCTTAGTTCTACGCGTTTCAGGCGTAGGTTCAGGCTCGGGCTCCGGTTCTGGCTCAGGTTCCGGCTCTGGC |
| TCAGGTTCGGGCTCCGGCTCTGGGTCGAGATCAGGATTAAGAGTTTCATCAATTTTATCTACGGTAGTTTGGATAGTTTGTAGA |
| GTCTCTGACTGAGCCTGCAGTGCCTCATTAATTTCGGACACATCTGGCAGATTGGCTCTGATGTCTTGCACCGATGCCTGTAGC |
| GCCGCGACTTTAGTGTCCACGGCTTTAATATCGGATCGAATCAAAACCAAAATATTTTGGGACATGATTATTTAATATACAAAT |
| GATTATGTATTATAACTTATTAACGGCCCGTCAAACCTCACCCTGTCAATTTCGTATTCACCCTCTGATAAAGTTATAACAATT |
| TCGTGGTCGTTATAAAAAACATTAATATTTCTGGGCAAATCTCGATACGTATTTTTATTTTGATCAACAGTTAACGCATACCTT |
| TTGAGCATGAAACTAGAATCGCCAACGTACGGCAATTGTTTTGTACCATACACGGACATACCTTGCAAAAATTTATGGAACGAA |
| ACAGATTTATCAAAGTTCATTTGACCGGACACTAATTTCTCGGGACGTATGCCCGTTATAGGAAAAATGACCAGGCCGTTTTTA |
| TAGTCATTGTGACGACAAGTAATTACTGAAATTAGTCGATTTTCTCTAAAAACGGGCGCGCCCAAGTAAATTTTGTTTGCCAGA |
| CTAAAATCAGTGAGTGCAAACGCATACATTTGACCATAAATTAACCTTTGTTTGTGGATATGAAAATTTGCATACACACGATCC |
| ACCGTAAAACTAGCCAGATCGCCGTTATTTAACAAAACATCTAACGCGGAATTGTTCGATACTTTAGGGAACACAATATTGCTC |
| GCTACGCCGGGAAATTGGTGCAGCAGACCATATTCCTCGTCGTGTACACGGCTCATGGGCGCTATGATTTTAATAAACGATTCT |
| TGCCCGTCAACTTTTGTTATTGTAACAGTCTTTTTTAGCTCGTTTTTTTCATAGTTAACATTATTAATTTCTAAATTTTGACCG |
| TTTCTGATACAGAGCAATAGCAATAACAAAAATGTCATTGTCCTTTTTATAATCATATCTTATTAGTTCTTTAACCTTTGATAA |
| AAATTACTATATAATTGTCTCGTTTCTCGAGATGAATCACAGAATCACACAGCATCTTAAGATATATCCATCATCATGCCGGTT |
| ACAAAATGCAAGCAAATACCCGCCTACCAGTTTATTCAAAAACTCAATTCATTGCTACGCAACATTAGTTCTGTGGAAAAACGG |
| ATCGATCATTGGAAGAGAATTAAACGGATTACAAAGGATAAACGAGAACTCATCGAAATAGATTGTATGCTGGCAAAAATGGAT |
| GCTGAACTTAGATCACTAAGAAACGATGTATTGGTTTTAAACAGTAAATAAAATAAAATATTTTTATAAATTGTATTTTATTCA |
| ATATCATCTTCACAAACTTCCACATCAATTATAGATCCATTTTCGTACCAATCTTCATCCACGTTTTCGCTAGTTTCCACCGCT |
| GCAGGCGTTTTCTCCGGTATTTTGACTCGATGCCGATTATTATGAAATCCGTTTCTAACCAAATAGCATTTAAAAGGTTCACCA |
| CTGGGCCAGTAAACACGCCGGTTCACATTCAACAAGCGGTTAGCCGTATAGCGGCAATGTAGTATTAATTTTTTGCGCGTACAG |
| GAATCCCAGTCAATATCGAGCCTACCGCCGCAAACATGGTTAAGAAACTCTTTGGTGAACCTTTTGGCATAGTTGGTACCGTTA |
| ATGTGAAATATGTACATTTTTAATCGGTTTGCTCGATATTGAAAAATATCATAGGTTTGATGGCCAACGAGTATGTTTTCTCTT |
| GGTACTTCTTATTGTTAACACTTTCCAACGTAGTTTCGTTCTTACTCTGCTTGAATCCCTCAATTATAGCGCCCATATACAGAT |
| CCACTTCTTGAGAGGGCTGTGCTTGTTCTCCGCCTTCTTGTTGGAACGCGAATAAATCGTTGTAACGTTCCACGGTAAATGGCT |
| CACACACAACGCTTTTGACCAAGTCTCCTGTGCTATAAACGGTCTCGTTGCTGTGCTGCTTTATATCATAAAATTTTCGCACAA |
| ACGAGATCTTACCCGGGTTATTTTCATCGGGCGCGTTTATTATGGAACAGTCTTGCAATTTTATTTGGTCCTCTTTGAAATATT |
| GTGACATGATGTTGGAATAGATCATATTATGCCGATTGATATTGGACCAGCGCAGAATAAAGAACTCACCAAAAGTACTTTTGT |
| AGCGCTTCATTTTCACCGTATCGAAAAAATAAAACGGTATAGCTCCTCCTTTGACATGATAACCCACGTTGTACACCACTCTAG |
| GCGCTTTAGGGGTTTCTATGGTGATCTTGTCATCGATCTTTGGATACAAACGGCTTTCCCATCGAGAAAAGTTGTTGCACGTTT |
| CCAAAAATCCTAGCGCCGTTTCCAATTGATTCTGATTAAACTCTGTCTGGCAATTAACCACCGTGATGTTCTTGCCCTTGGCCA |
| AATTGTGTATCATTTTTTCGACCCATGTCATGGCACGCGTCTCTTCACGATTTTTAAAAATGCAAATCAACTTATCGTTAGCGT |
| CATATTCCACTTCGGTTTTGTAAATGTCCAAACTATCGCAGCTTTTTTTGGACACCGACATACCGTCCGAGGAATCGCTTGATC |
| TACGCTTGGTAGCCATTATTAAAATAATGTTGCACTTAATTTAAGGTTACTATTTATACTATGGAACCGTTTACCACCGATGAA |
| CTACTCTTCGAAATTACCCTTTAAATTTTCTCAATACATTGATATATTAAATTTAACCAAAGGTGTTATATCCAAAAACATTTT |
| GCCATGTTTTATTAACGAACTCAACAAAATCCCCCGAATCGATTTGGATCCCGACACACGTTTCATAAAAAACGCTTTCGATTA |

TABLE 9-continued

| Nucleotide sequence of the *C. peltastica* NPV genome (SEQ ID NO: 2) |
|---|
| CAATTATTACATCAAGGAAAATGACATTTCCAAGATTTATGTAGTCGATGCCGAAACAAAAGTGTGTATTTCTCAAATTACAGT |
| AGCAATGGTTGACGAAAATTGCATTAAACTGTTTGTAGACCTAGTATAAATTTTGGAACCACGGCACCTCGCCAATCTCGTCGG |
| TCAAAGATCGCATAGTCAAAAAATATTTAAACGAATCTTCGAAAAACATGTACATTCCTATGAGTAAAAATATCACGAAAAACA |
| CAATAACGTTTTCAGTGTGCGGCAAAAAATAAATAATCAGAGCGCTCGCAAACCACAAATATGCCAAGTTTTTATGGCCACTTT |
| CGTGGTACAAAATATTATTGTGTCGTTCTGTGTAGAGCATAAATTCTAGCCGCGAATACATAGAACTCGAAGCTAAAACGCTAC |
| CAACCAAAGTTACTTCGTCAAAATCGTCGATAACTTTACTGTCTTCAAAATTCAAAAGCTGACCATTGGAATTTACTTCCAACG |
| CAGACACGTAATCTAAAATATAAAACAATGAATCGAACATGGCCTCGTCATCTTCCTCAATTAAATCATCAAAAAACTCCGGCA |
| AAAACTCAATCATGTCCCGCGTTTCTCCCATCGACTCGAAATAAGCGCTCAAAAACGACCGCGACATATCGTCGGGAAATTCAC |
| GAGGAAACATGTTGCTATAGCCGAACGGGTCCCACAGCATGAGCACCAGATCAGTTATGGTTAGTAGAATTAACAGAATGCCTA |
| CCACCGATGCAGCTTTGATGGCAATTTTGGTCATGGCTTTAGCCACTGCAGAAATAGTTTTAATAGCGATACGGTTGAAAGAAT |
| GAACGATTGCCGCTTTGTAGGTTTCGCCCAATAATTTTACCGTTACTTGTTTAGACGAAGTTAGCAAAACTCTTTTCAATAATG |
| GTATTAAAGAACTATTAATTTTCTTTAACATAGCTTTAAGTTGATCGAAAACGACATCGAAACCTATGCTAGTGAGAATGCCAA |
| ACAAAAACGCGTGATCCTCCAAAAACTGGGAAATTATCTCGTCCAATGTAGCGTTGTCAATTTCGTTAGTAAGCGGTACGAAAC |
| CGGATTCGCCAAGTTTAATACGTTCCTCAATTATTCGTTTCGAAATAGATTCTTTAGAAAAACCATTTTGAGCGCGGTAAATCA |
| ATTTAACGTTTTCGTTTATACCCAAATCTGACAACGTTTCAAAGTTGACCATGTCAATTTCTCTTTCCAAGTCCACAAAAGAAT |
| CTCGCTGATTTAGCCAAGAGTCTAGTACGTGAGCAGAGTTCGCGGCCGGTTTCGTGGGCAATTCGGGCGATGGACGCGTGTAGT |
| CAAAGTGTCTCAGTTCGCTAAAAATATTATTAGCCATAAGCTTGAAAGTGACATAGATAGTATCGCCTAACACAAAACCTATTA |
| AGCTTTCCCACCATCGCAACGAGCATCCGCCGTTGATGAGCTCGCGTCCAAATCGGCGGCAATAAGCCTCGTTGAATTCGCCTT |
| TGAACATTTCGGGAAACAACGGATCATCACTGGGCGTTACATTGAAGCCCGGCACATCGTCGACACCCTGAATCAAATGTTCGT |
| CGGTACGCAAGTACGGCGAATTCATGTACATTTTTGACAAAGTGTCTACCAAAATACATTTATTACCGTTTTCAATGTACCTCA |
| ATTCTGGCGATTGAACTTCGTTTTCGGCTCCTTCTCGTGTGGCCATTGCCCGGTCAAGATTGTAACATGCGGGCTGGGCATAAC |
| CGACGGCCACATCAGACGTTTGAGTATAACCAAAGGGTGTCGCGTAATCCGCCGGGCCGGTTTCATGAAACGGATAGCAAGACA |
| TACTCTCGCAACCGACTTTACTAAATTTTAGGCTAACGGCGATGGCGCGTTCGGCTAGTTTGGGCGGCACATAATAGTCGTCAT |
| TGTTGGCCGGTCGAATTTCATAGTCAACAAATATGTGGGGAAATTTGGTTCTCCAACGTGGTATGAAATTCAGGCGGTGCATGT |
| GTGTCGCATAGCGAGAAGCGTTGGTCAAATCTAGAATCGTTAAACTTGTCATAGTAATTTTTACTTATGATTTCGTGTATAAAC |
| GAAACTAGAATTTGAGTAAAATCTTACTCATATTCAAGTTTCGTTGATATATATTTTTACTAGTCTTTTGTGAAACAACGAAAT |
| TAGAATATGAGTAAGATCCTACTCATATCCAAGTTTCGTTTATTTCCATACAATGAAATTTAGATTCGAGTAAGATCCTACCCC |
| AATTCAGATTTCGATGGTTAGGTGTAAAAAAAACAAGAATTATTTACTCATACCATATTTTAATATACAATATACATCGCATTT |
| TTCACAAGTATTGTCTTTTAGATGATTACATATAACAAAACATTTACCCAAACATTCATCGGTACAATAAAGTTCTCGCATGTA |
| CACGCTGCGACCTAATCGCGAAGTCGATTTTCTGCATTTCGTGCACACCATAGTTTGAACGGCATTATCAAAATACGGACTCAA |
| CATGGTTTTACTGATCGTGTTAATGAACAACATATCGATCAAAGTTTTGGGCAAAAAGCACTTTGAAATAAACGCCTCTAAACG |
| GGTATCCAATTCGAGTACGGGCATAATTTTTTTTCCCTCAGTAATTTCGCCGCTAAGTTTGTTCAAACACAAATTAACCAAACT |
| GCGAGGAGTCTTGTGCCATTCGTTTACTCTTCGAACGATATTTTCATAGACATCTTCTAATCGTTCATACTGCTTCAAGTCTAC |
| ATTTATGTCATAGTTGTAACAGCGCAACAAACGCTCTTCGTTTTCCACCAAAACTGCGGGGCAAGTTTTATAGAACATTCGGCC |
| CTTTAATTCTTTGTAGCGTTTGTTCAACAAATTATATGGTCGTATGTCGAAATTATCATCGTAACATTTGTCTACATGGGTGTA |
| AAACGAACCCAGACGGGCAAAGTTCGTTTCATATTTCGTCCACAGGATGGATACAGAATGTGTCGAAGAGCAATATTTTTGTAT |
| TTTTTGAGAAAAACTCAACTTTTCATTGTAAGAATCGACACGGTCCAAATTTATAACTATTATAGACGTCATGTTCACACAATT |
| TTAACATGATAACTGTCGAAACTTGGATATGGGTAAAATCTTACTCATATTCTAGTTTCGTTCAAGAGAATATATAAAGTTATT |
| AATTAATTATGACTATCATTATTTTTAAAGCACTCATCATGGCACAAGTGAAAATCGGTCAATTCAAATTCGGCGAGGACCTGT |

TABLE 9-continued

| Nucleotide sequence of the *C. peltastica* NPV genome (SEQ ID NO: 2) |
|---|
| TCAACCTGCGGTACGTGCTGGATCAAAATCAGCAAGTAAAATTTGTGGCCAAAGACATCGCGAATAAATTAAATTATTTAGATA |
| CTAAAAAAGCTGTGAAAGACCACGTTGACGAAAAATATAAATGTAAGTTCGAGCAGGGGGGGCGATTTGTCGCCCCTGCCTCCG |
| ACAGCGTAGCCAAGAGGGGTGACCCGTTGTATTTACAACCACATACTGTACTCATCAGTAAGGAAGGCGTCATCCAGCTTATTA |
| TGAAGAGCAAACTGCCTTACGCCGTGGAACTGCAAGCGTGGCTGTTGGAAGAAGTGATTCCGCAGGTGCTATGCACGGGCAAAT |
| ACGACCCGGCTTTAAAACAGCAACAAGAGGAAAACAAGCAGCTGGTAACCAAACTAATAGCGACATTCACCGAACACACTAACG |
| AGCTACAGAAACAACTAGTGAAAAAACAAGAGTTTATTGAGCATGTCGTCGCTATGAAAGACAAACAAATCGAAGCAAAGGACA |
| AGCAGGTGATGCGCGTGATGACCGATCTAAACCGCATGTACACCGGATTCCAGGAAACCATGCAGCGCAAAGATGAGTTGTTGC |
| AAACTAAAGATGAGCAAGTTAGCGAACTTGTTAACAAAATAATGGACCTATCGGATCGTGCGGTGCAGTACCCAGCGGACGAGC |
| GCAAGCACCCGGTCCTGTGCGTGGCGCGCGACGGTACCACCTTTACGGCCATCGCCGGGCAAAAATCCTATGTGCACAACCAAA |
| AACAAAAACGCAACATTGATGAGGACAACATCGTGGTCGAAACGAGGCGGCCCAATCCCACCGTGGACTGGAACAACGCGACGG |
| AGCAAGTTTCGATGCCGGCCAAAAAAAGCAGACGGTCCATTAGTTTCGACTCGCCGGAGGACGCCCAGCAGTTCGAAGATCAGA |
| TCAAACAATTGATGAACAAATAAATTTTAAAATGAACCAAATTCTTTTATTTCATACAACGAAACTCGAATATGGGTAAGATTT |
| TACTCTTAAATGTATAGCATCATATTCGAGTTTCGTTTTGAGCAAGTCTAAACTTGTCTAGATGATGTCATGTGGATGGGTGAC |
| CTAATGGGTCGGTCTGCTCAAATAGAAATTTCGCATGTGAGTATGTTTGAAACGATCTTTTGGGATGGGTGAGTAAATCTCATA |
| TGTAGTTTTGTATTTGTCAACATGATGTTATGTAGTGTGTAATCATACATCCGTTTGCGTAAACAACGGATGTATGAGATCATC |
| GGTATGAGATCATCGAATGAATAAAAAAAATATTTCACAACAACAGTTTTTATTTCACAATCATTTCACAGCAATTTTCTTAAA |
| CTCTGTTAAATCATAATACAACAAGCTACCTAAAATCCGTTTCTTCATTTTAACACACAGTTTATAGTAATCAATCTTGGAAAT |
| GTCAATTTTGTTAATGAAATACCACGGATTTGTAAATCCACAGTACACACAGTAAAGAATCAAATTATTCTTGTACATCTTTCC |
| GCGGCACTTTTCGCATTCCAACTTTATACAAGGCAAAGCAAAAAATGCGGTATAATCAAAATTAGTATTGTAAACTTTGCGATG |
| CACCACATAATAGTATGTTAGATTCAAGTGAGTATGCCCGTTGACGAACTTCAGAATGTTACTTTCTTCGGGCACGACTCTGAT |
| CAAACCGTCCTCTATTTCATGCTTGCGAGCCGAAAACTCGTCGAGATTTTTTTGCAAAAAAAATCTGTTGGCCGATTCTGACAC |
| CAATGTTTTCTCCAGAGTGCAAATATCCACGCTTATAATTTGTTCGTTTGCCTTCTTGGCGTCCACTATAGATTTGAAAAATTC |
| ATACACGTTTTCGTGGGTTTCTTTCACGGTATTTTTAACAATTTTGTGGCTCAGATCCACGGGAAACAAATAGCGGTTGACGAA |
| GCGAAGTTCGCACAACTTTTCCACCACATCGAGATACAATCGAGGAAACAGTTCGTAAAAATCGTAATTGGAATCGAATTGATT |
| GCTCAAATAACAATCAAAACAGTTCATTTTGAACTTTTCCATAGCAGTTTGGGGTGTAGTAATATCGATACTTTTGTCGCTTCT |
| CACATATAATTTTCTAGATTGAGACCCGGAAAACGGCTCGCGACATAGATCGCAAAAAGTTGACACCACCACGTCCCGATTGTT |
| GTGGCGCAAACAATCCATGAGATTTTTGTTGGTCACAAAATATCTGCCCTGTATGTACTCGTTGGCGAATTGAAGGACGGAGCA |
| CATTAAATAATAGTTTTGGTTAGACAAAAATCGCCATCGCAAGTCCTTGCGAAGCGTGGCGCGCGGTGCGGGCACGGGAGTCGT |
| CATTATTATGTGGAGGAAACTTCAACGAAATGTTGGCTTATATCATGTATTTTGAGTTCATAATTCGGTCTCATCTCAATTATT |
| TAAATTCGTTTCCGGCGCACTTCCTTCTCCTACCACGCCGTTGGGGTCTATATAAGTTCTGTTGACAAAAATTCGATGACAGTT |
| TTGTGGTATCCACAATGGATTACACCATCTCTAATAACACAATGGAAGCTGACAGCGAGTCCTCCACGCACTTTTGCAATATGG |
| GCGAGGATTTTTTCAAAGAGGTAATACTAAAGTTTATATTTTCTAACCACTACAAACCCACTTTACCTTTGAATCCCAAACAAC |
| AACACGAACTCAGATTGGCAGCATTCGATATCGTTAACAAAATGTTTCTTCAAATGTACAACGAACCGATTCCGCCCCTGTTAA |
| TGTTTCGCGAAGTTGACGATGAAATTTTATTGTCGAAAGAGCGGTGTTCTCATCACTTGATCGAGACCATTGCCAAAGTTTGCG |
| CCGCGATTAACCAACTCAAGAGCATGCCCAAATATAAACACCAAATTTTTATTTTCCTTCCTTACTTGAAACAGTTAAAAACTA |
| TTTTGTCTTGTTTTGTCAACGATTATTGCTGCGGAAAGATCGTTAATAAAACCCTAAAAAATTTAACCACACTGATAGACACCG |
| GACAAAGTTCTCTTGAAACTATCAAAACACTTTTCGAGCGTGTGCAAGTGATGAACGTGTTTCGCGACGACATTCATTTATATC |
| AATGTAATATTTGCCACGAAACTTCGGCTGAGAGCCATTTCCTTAAACCTAATGAATGTTGCGGCTACAAAATTTGCCAGGCGT |
| GTTACGCGAACCTTTGGAAATTTAGCAATCTGTATCCCGTGTGTCCCGTGTGTAAACAGAGTTTTAAAAAATCCAGCAGCGGCA |

TABLE 9-continued

| Nucleotide sequence of the *C. peltastica* NPV genome (SEQ ID NO: 2) |
| --- |
| AATAGACGATTGTTTTGTGGTAGTTTTTATTATTAAGTATGAATTCGTTACACAGTCTAGAAGAGAGACAATATAAATTTTTGT |
| TTCTAGCCAGTTACTTTAATCTCAACGATTATGATCACTTGCAAACGGACAGCAAACCGTTCATCGGCGAATATTTAAAAAACA |
| ACTTTGCCAATTTGAACGAGGAAAGTTTATTGTCATACATTGATTATTTACATTCCATCAACCTAAAGTTTTTAATCGCCGATC |
| GTACCACGGACGTTTTCAAATATATCAAACCCCAGTTCAAGTTTAAATGTATCAAAAATAATATTGATATTTTGGAGTTTGACA |
| ACAAAACCTACATCCAACCTAACACGGCCATTTACGCCACCAATTTTTTTGTAAAAGATCCGAAAGATTTTCGATTGCTCATGT |
| ATCAGCAATTTTCTCAGGTGTTTAGCGACAGGCATTTTGTTAGTAACGGAGAAAACTATTGTTTAATGAACGGAAACGTCGGGT |
| ACATTTTCGAAGACTCGTACTTGGATTGGTGCGGCGCGCGCATGTGTAGCGTGCCAAGAATAGAGGAAACGTTTCATCCCTTTC |
| GTTTGTATTTGATCGGCGACGAAATGGCCCACCATTTTATCGTTAATAACATCGCTTTTGATAAAAGCAACATGTGGATTTTTA |
| AAAATTTTCATAAAGGTTTGCCACTATTTAAAACCAACTATCGGCTCATAAACTCTAAAAAATTTCAAACTAAAAAACCTAATG |
| AACTTTTCAATGAAATGAGACAAGAGTTGGATCGTACCGAATACATTAAGTTTATCCAACGAGATTATATTTACGATGCCAACT |
| TCCCCGAAGATTTGCTCGAGGAACTCAACGAGTACATGAGCAAAACAGCCATTTACAAGTTTATTACCAAATTTATAGAACCGC |
| ATGAACGTATGTCCAATTTTTACTCTGAAATTATTGTGGACAGATATGCGATAAATAAGTACCGCAAATTAAATATAAAAATTG |
| AACCGTCCACGCTCTTTCCATCTTTGCGAATTAACGATCCTTCATATATTTTTGTACGACCCGACATAATTCAAATCAAAGGCA |
| CTCTGAACGCGTTTTACGTACCCAAAGAAAAACTGTTTGCTATTTTGGCGAGCAACAGTTTGTTCGGTTCCACCGAACTTTTGC |
| ATTTCGACATCAGATTAATTCCCTACAAACAGAGTTCGCCTCCAAAACGGTTGGAACTCGAAACTTTCATAGTAAACAAACAAC |
| AAAAACTATATTTGACTAAATTTATTTTCGGTAACAGGATCCCTGCATATCTTTTAATAAGAGGTGATTACGAAAGTTCATTTA |
| AAACTTTGGATCATTTAAAAAATCCTTGGGTAGAGAACACGCTTCTTAAGTTGTTAAACACACCTATTCGCGCATAAAATGGAA |
| GATTTGAGAAGTCCCGCGGGCGGTGTAGGTGGCCGTTTTGGCTCGTTTTTCAATCCTAGCGTCCTTATGACGGTGTTAATTTTT |
| CTTGTGATTATCATTCTTATGATCATGCTTTTCCAGTCTAGTAGCAGCGGTGGTAACAACAGTAGTTCTCCCGCGCAAGGTGCC |
| ACAACAACATATACCAATCCTTTGAACGCAACAATGAGAGCCAATCCTTTTATTAACTCTCCCCAACGCCTATAATCTAAGTGA |
| AATTCTTAAACTGTAACACGATGAAACGATTCAAATGTCAAACTCCTAAAGTTAGGACCGTCACTGAAATTATTCACAGTGACG |
| AAAGGTTAAAAAAAGAATATGATATGGCAGAATTCGATGCCAAAAATCTCAACAGTCTGGAAGGGTTTAACGCTGTTCGCATTA |
| AAATGATTATAGTCAAGTACATGGCCATGTTGAACACCCTAGATTTGAGTCAGCCTCTCTTAACGATTTTTCGCGATCGCAACG |
| CCACTGTTGACATAACAAAAATTATTATCGGTTCTTTGGGGTATGTTCATAGGCGGGTGAATCCTTTAGTCACGAATTTCGAGG |
| GCAGAATGGAAACGGTCATTATCGAAAATCCCCAACATAGCATCGCGGGTGAACCCATTTATTTTACGGAAACCGAAAAAGGCG |
| ACATTCGTTGCCATATTGACCGTGTCAGTATCGTTCGTATGTTGGAACGCCATTACGATATGGACGTTAAGATAAACGATTCGC |
| CTCTCAACCAAAATAAACTAAAGTTAATGCAAGCGCTAACATTGAGCGGGAGTAGCAAGCGTAGAAGAAGCCACGATACTTCCC |
| GATACGATTTGCAATTGACAGAAGTCGAGTGCACCCGCTACCTAACTCTACTGTTAATAATCGAGCATGCCTATTGTCACTATG |
| TTATCCTTAAAACTTTCGACACGTACAATTATGTCAAATCGCTGTTAGACCATTCGTTGTTTGCTCACAAGTGCCGCCCCGGTG |
| TCAACATGAACTTGTCAAGTTTACTTTTAAGTAAATTTAAATTTACTGTAGAAGAATTTGATCCGAACAAAAGTAGCAATAAAA |
| ATTTGGGCATACTAAACTATAAGTCGTAATGTGGCTTATGCTAGCCTTTTTTATCATAGTAAAACTGTTGGTATTTCACAAACT |
| ACAAAAAATGCACCTCGACATGCACGTTGCTAAAATTTGCCCTAACGGTTTCCACGGACTCGCCCCCGATCCTTTCGATTGCTC |
| CAGCTACTATTTGTGTCCGCAATCGATTCAAATGTTTTGCACCGAAAATACCCAATTTGATCTGGAAACGAATTCGTGTGTGCC |
| ACAATCGTTTGAGAGCGGCTGTCTCGGTAGATTGTATAAAAATTTGTTAATTTAATCGCACACAATTCTTACCGGGTCGTTTTT |
| GGTTTTAATATTTCGCCACATGTGTGTCACGATTTCAAAGTTTTTTTCATGTGAAATCGGCTTTGACAATATTGAAATAAAGTT |
| AGCCGGCACATTTCCAGTAACCGCGATCAATTCTTTTTTGATGAATACATCTCGGCCGTTTTCGTCTACCAAGTTTACGCCTTT |
| AATTTTTTTTGTCGAAAGTAACTCGGTTTTTCGTCGGACGGAGAATATGTGCCAAACTTGATCTTCCGTTTTCGATGTCATCAC |
| AACTAACGAAAGCGGCGTAGTAAAATATTCATTAAAAATTAGTTTCGAATAAATGTACGGCAAACGAACACAGCTCACAACGAA |
| GCCGTCTTTAAACTTTTTCATGTCAATTTCGTTTAAAATATCTAAAACGACATGCACTTTTCGTTTTGGTGTATTTTCGTAGCC |

TABLE 9-continued

Nucleotide sequence of the *C. peltastica* NPV genome (SEQ ID NO: 2)

GCTAACCAATTTGGTACTAATAACTTCGTCTTTATCATCCTTTTCTGTGTCGTCACAAAACAAAACAATATTAAATCCGTTTAT
CGAAGTAGGACAGACGAATGTGATAATGCTGTTATCGTATGTGGGTCGGTATAAATGGACCTTCATTTTTTATTTGGTTTCAGT
ATACGATCAACGTTGCCGAGTTCGATCAACTACTTACAATGAAGAACCAAGCTAGCAACATGCCCTGCTTGGACAGAAACGTTT
CACCTTATGTAAGTTTTGAAAAAACACCACACAGGGAAGACATTCGCAACGAGTCTCCTGAGCCGCCAAGCGCCGATATAGATA
CTTTAATGAAAACGGTCAACGAGATCGTGGAAACTATGGAGCAGGGAACTTCGGCGGCAACGACACCGATTAACGTCACACCGC
CTACCATGCCGATTGGTAAAAAACAAATTTCTTTTAAAAGAAGCCATAGCAAAAGTGATGACATGAAAAGTAGCAAGAAAAAAC
GTCCCACTTTGACAGATTTGGCTAAAACTGATATTCATGAAGAAACAGAAAAAGAAAAGCAAAAAAAAAGTTCAGTCGCCAAGA
TTCGCGGACCGTACCGCAAACTAAAAATCGACAAGGCTGTGCCTATTACGCACCATATCAAGCAGGTGACTTTTGAACAGCAAA
ACCAAATTATTAACAGTGCCACCGACTTGATTAGGGAAAATACAAGCCAGATCAACGAGCTATACGGAAACCAATATACAGACG
ACCGCCGATTTACCGATTGTATCAGTAGTACGTATTACTACATGTTTATTGTGTGCGAAGACAATAACAATGGTAATGTTTACA
AAATTCATTATGTGAATTGTGTGGCTAGGGTTACCGTAGAGTATGCTGCTCGTTACAGTTGCATTGATAATTATGTGATGGTAG
TTTCCATTAACAATCACAGATTCATGATTTCGTATAATCTGTTGAAAAAATTAAACGTTAAAATCCCCAAATCGGAAGATTTTA
ACGAATCTTCCAAAAACAAAAATAAATGTCAGTTTAACGAAGTTAAAGATATCGATTTCATGGCCACATTGATTAACATGTTTC
ACTTAGATATTTGTTATGTTCAGTCGAACATGATGTTAATGTTGGCGGCGCTAGGTCCGAGCAAAGCGCCTTTCATAGCCGACC
GGTTGTATTACATGATCAACCAGTCTGTAATATTTAATTTACCCATCAATTTGGCCATTAAAGAGAGTCAGTCTACGGAAAATG
TGGACGATATTTCTGCCTATGTGCAGGAAATTATGAAGTATTCAGCAAAGGCCAAGTTTGAAACTCTTAAACATGGCGAAATCG
GTATGGACAAGATTGTAAAACATGTCGACATGTGGTTTAACAACAAAAAAGATAAAACCTGGCCTTTCTTTTTTACTTACAAAT
ACGGTAGCGTAGTGAGAATTTTTTACAACAAAAACGATGATAGTTTCAACAAATTGTTGAAGGTTAAAAACCGAAAGGAAAACA
ATGGTGTTAATTTGATTGAGACATATTTAAATTCTAGCGTAAATTCTGACACTTCCGAAAATTTCATTTTGATTAACGTGAAAG
CCGACGAGCGCATTACGATTATAAAAAAGGGAAAAAAATATGTCTGGATCAGCACCGTGTGCAAGGAAATTAACGTTTTAGACA
TTATTTCAAAGTTTAGACGCTTCAGGCACCATATTTTCGATGTAAGCTGCGTTGCTCGCAAAGAGCTCAATAATACGCACAACG
CCATGATCACTTTGGCCAGTTTCTATGTAAAGAATGTTATCAGTAGCAAACAGGCCGAGGAGATTGCCTCGCAAAAGTTTAACG
TCAAATACAGGTCTAAAAATTATGAGTAAATATTGTGTAAATAGTTTAAGCCTTTTTATTATAGTTTTAAGCCTTTTTATATTA
CCCTATGAGATTATTATGTGTTTATTTTAAATAAATTTTTTAAAAATAAATTTTTGTTTATCCTTCATCCTCATCACCCACATC
CATACTTTGAATGTTTGCCTGGTCGACATCATCGGCAACATTGTGGCCGTAATAGGTTAGCAATTCTTTGAGACTGGAAAAGCC
GGTCAAATCTCTAAGTAGAATTTGAGCATTCGCTTTCCAAAACTCCAAGCTCAGATAGGTGTAGTACAGCTCAATAAAACTAAT
GATGCCCATTTCGCTGTTGAGAAATTCAATGTATTCTTCATAATTTTCCTTTTCGTTTTTAGTAAAAATATACTTTTTGTGAAA
ATCACAGCGGGTCTGATCATTGCGATGGTAACATAGTCGACAGTGTTCAAACTTCTCGGTCTGTAACGCGTTTAGATAGTCTCT
CGTCTCGTCGGACACTTCTAAAACGACTTTTATATCGAAATTATCATCCTTTTTCCTTTGCAACAACAAACCGTGCGCCCCCAA
ATACTGAACCACATCGCCCAACTTAGAGTCGGGATTGACGGGACAGTCTTTGGTTATGGTAGCGGTCAGCTTTTTAAGATCGCG
CCTAAAATCATTCATTCTTATAAGAGTGAGAATTCATAATGCAGATTTTTGTAAAAACTCTAACGGGTAAAACTATTACCTTAG
AAGTGGAATCAGCGGACACGATAGAAATTATCAAACAAAAATTGCCGAAAAAGAAGGCATTCCGCCCGACCAGCAGAGATTAA
TTTTTGCCGGCAAGCAATTGGAGGATAGTAGGACAATAAGTGATTACAACATACAAAAAGAATCTACGCTACACTTGGTATTAA
GACTCAGGGGTGGCTGAAAAAAATGGGTGGATAATATAAAGAAACAAAAAAAATTTTTTTTTACATTTTTATTTATTTCAAAAT
ACATCTATTCGGACATTTGACTATCTTCAAAAGTGTCATTACTCATTACAAATTCTGTCTTTTTAACACGCTTGCTAGTGGTGT
TGGATTTGACAGAGTCTTTTGTATTTTTCCTTTTTCGTACAGGGGCAGGAACGACGTCGGTTGGAGTTGATGAATGGCTCGTAT
TCCTCTTCTTGTACAGTACTTTGACAAAAGTTTTTAGAGGGTTTTGGATTTTTGAACTGTTCAATTTTTCATTGTTCACAGTGT
ACGCATAAAAGGGATCATCTATAGGAGCGTGTAAATTTTCAGAGTCCAGTGTGTGCGTAAGCAGACGATAAAATTGTTCATAAA
TAACATTTCGTTTCGCGTTGATAATTTCGTGTTTCTTGGTTTCTTCGTTTTCATTCGTAACTTCAATAGATTTGCCCAGTTTTT

TABLE 9-continued

| Nucleotide sequence of the *C. peltastica* NPV genome (SEQ ID NO: 2) |
|---|
| CCACAAAGTCGAACAGATTGATAAAATCTGCTGATTCTGTCTTCATCAAGTTCCACATGTCACAGCTGCTGGGATACCACTCTT |
| TTTTGATGCTGTGATACCAACTATTAAAAAGAATATATTTATTGTTGCTGATGATCTTTTTGCTGCGTTTAATGTTCTTCTTTT |
| CGTCCCCGTAAACCGGCACCACCTGCAGTACATAAGGCATTTTTTTCTTTTCGCACAAGCTAATGTTCTGTCCTAGAAAATCAT |
| TTTTAGTCTTGTTATACACGCTTTGTTCACTCTTGTTGATGATTTCTGCGAGTGTTTGAGGCGCCATTGTATCTTGAGGAGGAT |
| CGCTTGTATTCAGTGAATAAATCAGTGTTTAAATTAAACACGTTTTCTATACGTTTGTGGTGCGACACTAAACGCTTGCGATTC |
| TGGCTACAGTCCGCAATTACAAAGGCGCTTTTTAGATTATCCCTTATATACTTCATTTGCGTTTCAAATGCCTCTTCGAAAATG |
| TGAGCGCAAACTCCAGTGTAATCGCCTGAATGTTTTCTCTTGTTTATCACTTCTCTAACAAGCGCGTAAATTTCGCTGCGGGTC |
| ACGCAAGATTCATCAAATTTTTCAATTCCGTTTTTGCTAAAGCCGAAATCTTTTTGCGTTTTTGTTGACATGTCGGTGTTTGCC |
| GCTGGTAAATGTCTAGTTTTAACGACAGCAAAAAAAATTCATTTAAAGAACCGTAATCAAATTTTTTTTAATGGTTTTCACAA |
| AGTCAAAAAATTCCAAATAATTGCTCGAATCGTAAGTGAAAAGTTGCTTTTCGTTCATGTACTGGAAATAATCATCGAGCGGCA |
| GAATATATAGGTTGCGTTGAATTTCGTTGTTGTATCGGCGAGTTTCAATGTTAATTTTGTAATCGTTGGGACGAAACAGTCTCA |
| GCTTGACACAAAAAGTGTTGGGCTCTTGCGGAATGCTTTGCAACGGACCGTTCAAAATGCCAATGTAAATGGCATACTTGTACG |
| TCACACCACAGTCATTCCACTGTAGCACAAAAGGACTTTTGTAAACATGGGCGCTTTCGAAAAAAGTGCCCGTTTCTTCGATAA |
| ACTCTCTGATGGCAGTTTCGTAATCAAATATGTCCTGTCCGTCGCGCTTACCGCGCGGTATGGATATTTTTTCTAGGAATGTTA |
| TAGCGTTGTTGGTGTTGAAGGCGGCATTGTACGCGCGTCGAGCCCTCAAAAGCACGGCGCGGTTATGGTCCATTATCATGAAAA |
| GACCGGCACACTTCATGCCTCAAGTAAATAATAACACTACTGTTATAAATATGACGTGTATTTTTATTATATATCAACATATTT |
| AACTTATTATGAACAATTACATTTGGAACAGCTATGACATTGGCACAAACGTTTCATTTACAATTGAACAATTCGGTGACTGTA |
| ATGAGTGCCCGTTTTTATTCGTTTTCCCTTAATGAAATCGATTTTAATTTCATTGTTATTTTGCACAACTCTAGATTGAGCGGC |
| CGATCTTTTTATAGAGTTCAATCTACGCGTGGACAATTCCAGCGGATTATACAACAAAGATTTTTCCAGCGTAAAGGAATTTAA |
| GTGCCCACCATTGTGCCACTCCAACGAAATTATCATATTCAACAAGAAAATTATTTCAGAGTCTCTTTTTTCAAACACAAACTT |
| ATTTTGCAAACAATAATAGTACAGTTTTAAGGAATTATACAAATAAAACATGTAATTGTTAGTTTTATAATAATGATCCACATC |
| GGTCACGAACAGCACATTGATGATCTTGTCCTGGATGAGTTGGCTAAACTTTAATAAATACTGCATGGAATTTTTGTCGTCGTC |
| AATACAAATCGCACACACGTTTTTCAGATAGACGTTTTCGATCACCACAAATTGATTGTTAACAAAAAGTTCTTTGAGGTTTTC |
| GTTGTAATCATTGGCAAGTTCGAGCACTATGTATTTTTTGGCACATCGGTGCCGCTTGATCACGTCCGAAATCGAAGCGATGGA |
| CGAGAGAAACTTTTCAAAATACTTATCGTTTTTCCAGCCTCTAGCGCCGATCGTTTTGCGCGGATCGTCGTTATTCTGATGTTT |
| GAAATCCAAACCACTTTGTATAAGTTTGGTGGTGATGCGAATGCTCAATTGCTGACCCAAGGTATAATTATTTTCATATCCACG |
| TTCCCACATAACGTTACAAGCGAACGCTATCAAATCGGCTACGTCGTTTTGCTTTAACATTTTATGCAATCTATCAAAGTCACC |
| CTTGTACCAACGATCTCGCGCCATCAACTTTAGCATATTTTTATCGTGCTCGTTTAACGATTTTCGACTCACGTCAATGTATTG |
| GTCGATTTGGTCGGGCTTGCTGCTCCTCAAGCACGCCATGTCGAACACAACTACTTTTCTGTGTAGAGTGATAAAATTTTCATC |
| GTCAACATCAATACTTTCCCACAAAATATGCTTTGACGTTTTCGGTGGCATGCCTTGCAAATGTAACAAATAATTGCCGATGGG |
| ATCGGCAAGGTACTTGCAGCATTGCGGCAAACGTTGCGTGGAAGTTTTGTAGTAGATAGCAAACATTGTGACGCCCGCCATACA |
| AATGATATCACATATCTTGTCTGCATATATATAGCCCGTCATTTCGATAAAAGTTTTAGTTTATGTTCAACACCAGCAGCATAA |
| TGAATAGCAAGTATCATTTCAATCCTGCGAAACTGGAGATTATGGCTAAAATGTCGTTGGACAACAACGTGGCAGTGTCTAAAT |
| TTTTGCCAAAACATCTTGCCATGCAATTTCAATTTTGCCTGAGGTGTAACATTACTACTGTAGAAAAAAGCTTTAATAGGATCT |
| CCTATTGCTACGACTGCGGTTCCAAGTGCCAACACTGTGACAAGCCTGGCAGAGTTCGCCGGCTGGAAACGTTACACGGATGGA |
| CCACGGACATGGAGTCGTTGGAACGACATTTCAACATTCGATTGAAAGATGTCATGACGGTCCGCCGGCAGACTCACATGCAAT |
| ATTACGATAATTACATATTTAATAATGTTGCATACAAAATTTTATGCTCAGATTGCAAGTACAATTTTTGCGCACTGTGCAAGG |
| CAGAGATGCCCGAAAATGAAATGGTCAAGATCGGAGTAAGTTCCGGTACCCTGGAAATGACCCATGCGTTTTGCTGTAAAGAAT |
| GCGTGTTACATTGCAAGTGTGTAGAGTGTCGGCGTACCATTAGCTTAGAGAACGTTTTAGAGTTTGAAAATAGCACGGCCGAAA |

TABLE 9-continued

| Nucleotide sequence of the *C. peltastica* NPV genome (SEQ ID NO: 2) |
|---|
| TAATTTTTGGTGTGTATGGTTATTCTTACGTGTTGATTTGCTTTAACCACACTCATACAGTGACCGCTTGCAACGAGTGTACAT |
| CTTGGCAATTTAACAATGTATGTGAAACATGTGAAATTGAAGGAAACAATAGGGAGTACATACACAATCATCAAACGTTTAATA |
| ATCAAAACGTTACAGTTTGTGATGAGAACGAAGCAGTAATAAAAATGCTATGTCAAATCGATAATAGGCAAGTGCTTTTTAATT |
| GTATTCAATCTGTGTCTGAACAATTATTCTATCCCATTTCTTTCGACACAGCCGTAGGGTACATAGAAAGAGGCATGCTTAACT |
| TGGGTCGTAAGGAAGTGATAGAGCTGATTATTTACGCGATTGTTTCAAGAAAACGCGAGACTATAGTTAGCTTTTACGACCAAA |
| CAGGCATACCGTGGTATACGTATAACAAGGAAATTTGTCCCGATTGTGAAGATAGGGAAAACATGTGTGTCTCTCGTAATAAAC |
| CAAGGAATTTGTACCATACAGCTATGTATGATACTCAGTGCTGCAACACCACTAAATGTAAAGTGTATTCCGAAGATGACGATA |
| TTTCTGATGTGTTTTTAAATGAATATAATTATTGTGAAAAATGTTTAAAACCTTTGTTTGAAATTATGGATGTACAATTCGATT |
| CAGATTTTGTTTGCACTAACCAAGAATCTCTTGAATATTGCTAAGTTTTTAATAAACCTGTTTAATAAACCTGTTATATATTCG |
| AAATCTGCCTGTTATTTATTATTCCCTAACTCACCATGCCAAAGTTAGGATCTACGGTAACGATAATTGATCGTTGCGCTTTTG |
| AAGAGCGATTAAATCATGTAAAGTTTTTTGTGCAACTAATGAATGTTGTAATATGTGAAATGATCGCTTCGCACGAAATCACCA |
| AAGCAGAAGGCGCGTCGTTGTGTTTAGCCGACGATACGGCCGCCTGGATTTGCGGACGCATTTCCGATTGCAACTTTGTCACTT |
| TCCGTGTGAAAAGTTTATCATTTAACAAAATACAAAGTAAAATATTAAAGAAAAAATACAACTTTGAAGAAACTTACGAACAGC |
| AACTATTGGGAAACGAGTGGCAATACCTAATTTACATAAACCGCACGTTCAAACAGGTAGCTATCAAATTGATTGTGGTCAGAG |
| AGGACGTGCCCATGATTTATTCGAACCCGTACATAAAACTTTCGTATTTCATCAAATTGCAAGATTTGAACGTGAGCACTCTGG |
| ACTGCGATTGTGGCAACGACAACGACGACCTACAGTGGTGTAACGAGATGGACCATTATCACCGTTCGCTTGCTGTACAAGCAG |
| ACTTGTGTGAGGATAATCACAACGAAAATATTATTAGTTTAGTGTGTTTTTGTAAAAATAAAGTATATTATTAAGTTAACAAGA |
| TGGTTATTATCTATTGGATTGTGTTAATAGCCGTGATCGTTTTTATTTTTTTGTATGTAACGTGGTCAGAAGAAGCGGCACCAT |
| CCCCTAGCCCGCCTCCTAGTCCTCCAATAATAATAATAAACAATGAACTAAAAGACTTTGAGTATTATTTCGTTGAAACTTTAC |
| CCGTATATTTTAGTCGCAAAGCTGAAAAAATTGCAAATCCCACTAGACAATGGAGTTCTAGTAGCGGTTTTGTCGGTTTAGACC |
| CATGGACAAGTACTGTCGATTTTGGTACTTTTTGTCACACCATGATAGGTTATGCCGTTAACTTTGTGGACAAAAATAGTAACC |
| AATATTACGATGAACAAATCGGTTATAATTTGTTGATGTGCCTTCGTCTTCTCTCTCATCATCTACCCGACACGCCGCCCGTTC |
| AAAACGCGCCTTGGGGACCCGTGGCGGATTGGTATCACTTCTCAATTACCATGCCCGAAGTTTACATGACGGTAACTTGCGTTT |
| TAAAAGATACAATTTATTATGAAACCGCCGCAGAGTTAACAAAAACTACGTTATCGAAGTACTTGCCCACCGCCACAACGTCTT |
| TGGGATGGGTGAGAACGGCGGGCAACGCGATGCGCATGGGCGTGCCGTATGTTTATTCTCAATTGCTTAAAGGTTTCAACATTA |
| GCCAAATACGAATGCAGGATTCTGTACAAGACGTGCTCAAAATTATTAGCTTTCCGTTTGTAACCGAAGGCAACGGATTGCACA |
| TAGACTCAATTTACATAGATCATATTGATGTGAGGGCTTACGGATATTTGATTAATTCCTTCTTTACATTCGGTTACTACATGT |
| GGTTCTTTGGTTCAGATGTCATTAATCACTACGGGCTAACCAAATCGATATTGAACGTTTCCTCCCCAGAAGGAATAGTAAACC |
| CGGCAGTCATGTCGAGACAGGGCACTATGTTTTCCAATGTCATTGGAAACTTTGTCGATTATAAAATCGCCGTTCATTCTGCCG |
| ATGTGAGTAAAGTGCTAACGAAATTAACAAACAAATATTACGGGTGCTGTGTGGGATACACTACCAAACTGGCATATTACGAAG |
| CTGACCCGACCAACTTTAATCACGCACCTTTGTGGGCTATGAACCGCCGATTGTGGCGGCGAGATTATCCCATAATAAATTACA |
| CACCCGAAACGGTCGGTTTTGAATCTGGCGTGCTTTTGCAAGACTTGAGCGGCCGATGGCCCGTGCCGTCCACGACCACCTCGA |
| CACAATCGTTTAGACCTGTCATGGCCAAAACCGCCGTTGTGAAAAACGAAACTCTCGGCGCAATGTTAGGGTACGCAAAAATAA |
| AAGAATTAAACGATTTAGAGTTTTATTCGTGTACGGTTTATTATGAAACGGGCATGGTACAACTTTATTACAACATGAAAATTC |
| CAGTAGATACTTTGTCCATTAATCCTCGAATGGTTATTTTGACCAAACCTGTGATCGACCAATCGACCAACTGGAGTACATCAA |
| ACAGCTTCAACACTGCCACATTCAATGGCGTAACTTGCCACCATGTCAATATAATCAATTTAGCAGGTTTAGCAAACTACGTGT |
| ATAGACAAGTTAATGCCGTTGAAAATATTGAACAAATTATAGCAAGATCGGTTTTAGAAGAAGGCATGGGGATGTCATGTTACA |
| AACTAACCGTGACCGAAACTAATGACAGCGTCACCGTTACTAACAATTCAAAATACAATAATTTCACTGTAAACATACCGAATG |
| AGGGAATTTTTATATTTTATTTTCCATATTTAGCACTGTACGACGACAATCAGTTAATAATTTCAAACGCTGACGAGGACAATG |

TABLE 9-continued

| Nucleotide sequence of the *C. peltastica* NPV genome (SEQ ID NO: 2) |
|---|
| AAATACCAAAAATGATAGTAGATAGTTTCATATACCAATTCGATATACAAGCCGATATGGAACCTTTCAATTGTGTCCTAATCA |
| ATGACTTTTACCGAATATTTACCGACGAATACAGTTTTATTTTTAATAAGCTCTCCTAAACATGAATATCAACAGGTACACTAG |
| TTGTTTTTTGTGCAACGAAATTGTTTATAGTTTTCGTCAATACAGCAATAAATCCTCAGACTTCTTTTTTAACAAACACAGATC |
| TGTTTGTAAAAGTTCTGTGTATTTTTGTTTAAAGTGCTACAGAGATCTTTACGTGAAAAAGGTTGTAAAACTAAAAAATTTTAC |
| AATCCCTAACCGTTTATTTAGTAAATAAAACACACAGAGAAAATTTTGTTTTTTTTTTATTGAATAATTGTATTGTTACAATGA |
| AGCAAACTCAGCATGACGTTGTATTCGCCACTGTTATCGGGCAAATTAGAACTGCCCTTGACGCACTGCAAACTCTCCGTCCAA |
| CGGTTGCCTGCAAACGACTGGTTATGGTCCATTGATCTAGCCGAGTTCCTTCCACTTTTTCGTGGCCGGTATGGTTGATTTTT |
| ATAAACTCTTTAAATATGTTGTCTGGCGTGTTATTGAAAAGCATGTACGGAATGTTGAAAATAGGATATCGCTTGGCGTTTGGA |
| TTGTTAAAATCGCCTCCTCTCACCACATATTTTACTTCGACGTCCTCGAAATTAGATTGGCGAGAAAGATACGAAATGGGCGAC |
| AAACATATTTGCGCGCAAGTCCCGTCTTCTGCGATCCACTCGGTCAAATCTTCGGCGCCGTTTATGACTCCTTTCTGGCCATGA |
| ATACCGCATATTTTGATGCCTTCCAGATCGTCGGTTGAAGTTATCGTAACCAACTTTATGTACACTGTATCGTTAAAAATAGTA |
| ATGATGGTGTCGATTTTATTGATCGCTTGGTTTTTTATTTGCCTCAGATACAGGTAAATCTTGAAAACGAAAAAGTTTTTGTTT |
| TTGCACGCTTCAATTTTATATTTTTTACCGTCGTAAATCCAACCGATCTTTACGTTGGAAACAACGGTTCCCGCGATATGCAAC |
| AAATTTCCACCTTCCACCGCCACACAATTGTTTTCTGGCGGAGGTTTAATCAACTTTACTACGGGAGTTTCGTTTTTAGTGTAA |
| ATCATTTTTCCTTTTAGTTTGTTAATTTTATTATTGTATAGTCGAATGGGCAATTTGATGTCAGCGATGTAAGGATCCTCAGCC |
| GTCATAAGTTTACTGTCACGCACAATCGTCCATAATTTGAACATTTTGTTGTTAAGTTTGATCTCCGGCTTGACAGCGACGCAA |
| TTGCCAAACGGTAGCGTGTCCAAAAAAGTTTCATCGGTTTCACTGCTGGACAAAATCGGCATGGCATTTTTCAAGTTAGTTAAA |
| GATACAATCAATTTGGGCGTCGGAATGGTGCTGTAGATTTTTAAAAAATTATTGTAATAATATTGAACCAACTTTGACATGAGA |
| CAATCAACGCTGTCGTTTTCCATAATGATCCCCACGTCGGTAGTGCTGTTTAAGATAGAATGGCTGTTGTGGTATTCGTATGGA |
| GTTAACAGCGTGGCGATAGTTGCCTGGTCGTTTACCTTCACTGTTCGTTTAATACAAATCATACCTTCGTGATGATTGATAAAT |
| AAAATTCCGTTGGACATTTTCATCTCCACGGGCGTCATGCCCCGTTTAAATTCGTAAAAAATTTTGTACAAATCTGCTCGCTGA |
| CAATAAAAAACGGTCGGACGATCGTTGAAAGTTAGCCACAAAGTTTTCGAATCCGCGTTAGAATTAAAAACATGGGTATCATTT |
| TCGTCGATCATTTTAGTTATTAATTTTTGTTCAATTAATCTATTGAACTTTTCACGGACCATTTCATAATCCACGGTCGGTAGA |
| CGAACGTTGCGGCATAAGAAAAATTTTTTACCCGCCACCGTCATTTCGCCGTGGAAAAAACTGTCCACGAACTTGACAAAGTCA |
| TCTTTCTGCATCAACATGTCTTGGCGCATTGTGTCATTGGTGATCCTGACCACTTCGTTGCCGATGCGATATTTCAAGTGTGGC |
| GGTGTTATTTCAATGTTATTGTTGCTACTATTGTCCTGATAATTTATGAAATTCTTTCTTTGCTTGCTAAAAGTTTTTGAAACG |
| CTGTAAATCAGTTTTCCGTTGACGATAGTGTCCACGATTTTTTTGCTATCTTTGGGATACAAAATGGTTTGCATTTTCTTACGC |
| TTTGTACTTTCACGGTTAAGTCCGTTGGATATCAAAGTTTTGTAATTATTTAGCACGGGACTGTAGATCAGCTCCAGCAGATAA |
| ACGTGTTTGTATATAATTTTGTTGGCCAAACTGTCGATGGAATAATTGATGCCGGCTTTCATGATTTTCTTGATTTGTTCCACC |
| AGCGTCTTGCTCTGGCACGGTTCGTATTCGAAAATATCGTTGAGAGGTTTCCATTTTCCGCTGTTTTTTAAATAGATGCCGAGA |
| ATCGCGTTCAAATCCTCGGACACGACATAGTCACTTGCGTACACGTCTCTAGCGAATAAAACGTCCTCGTTGTTATCGTACACC |
| AATTGTATGGCTCTATTGATTTTTTTCTCTTCGTCCACGTTACCGTAAAGAAACATGCGTTTGCAACTTTTGGAGTAGAGTTTG |
| TCATAAAAATTGTGAATCAGAATATTGTTATTCATCATTATGTTGGGGAAACTGAGATTACGACCATCGATCATAAAAGTGCCA |
| TCGAAATTGCAACTTTTGTTTGTGTCGTTTTTTCTAAATATATGATCGAGCCAAGTGCCGAAAATCACCACGACACATTTGTGA |
| AGCACACACCGGTTTAAATTGTCGACGGCGCAGCAAAAGTATGATTTTCTTTCCAGCAAAAATTTGATCGTGCAATGATTTACG |
| TTCTTTTCGTTGCAATTCAGGTAAAACGACAAACCGTAATTGTTTTTTAAATTATCATATAAGTTGTTAAAATCGTTAATAACA |
| TCAGTCATAATGGAAACTAACAAAGCAACTGAATTTACCGAAGCGAATGATAACAATGACCCATCGGAACGTATGATATATACT |
| AAAAGAATTCATGAGGGAAGAAAACGAAAATCATTGAATCCCATCACCACCAACCCCCGCAAAATTATTAGAGTTAGTAAAAGA |
| AGATTTGAATATGAGAGCAATGAATTTCACCCTGATAATTTGAGATATGTGGATTTTTACACATTTTTAGATGTCGATTTTAAA |

TABLE 9-continued

Nucleotide sequence of the *C. peltastica* NPV genome (SEQ ID NO: 2)

AATTATAATCTAAATGATGTTTTAGCAAAAATTAAAAGTAAATATGAAACATTGAAAAATATACACTTTAATTCAGAATATTTC
GAAGATACTTTAATTTTCATTAAATTTGTAAATCAAGTATTTAAAAATGAAGACGCGTTATCAGAATATAATACAACAACTATA
CCAGTTTTAAATTTTTTAGAACTTGTAAATAAAATAAATGAATTTAAAAATTTCCTCGATGTGGTCAACGAAAAAATTAATGGG
TCGAACATTCAAATGGAAAATAGACTAAATTTAAAAATAGTACCACGAAACACTAAAACTAACAGAGCTTTGATCACATGGGAT
GTTCACCCGAATAACGTTAACAACGAAAACATCAATATTGAAAGTATTATTGCACATTTCAGTATTTATGGTGAAATAATAGGA
GGGGTAATGTGTGAAAATAAACAAGGTTGTGCTGTTTTAGAATTTGCTTTATTGGATGATATGTTGAAAGCAATAAATAGGGAA
CAAATGTACCGTGTTTCAGACTACACGGAAAATGAAATAGTAAAAATTCGCTCAGACACAATAACCAACTTAAAAGAACAGTTA
CAAAATATACGATCCCAGATTGTTTGAATCGATTTCATAAGTATGCCTTTAATAATAGTCGTTATAACAAAAAATAAAAAATGG
TTTAAAAGTACAAAACGGCGAGCCGTTAAACGATATACACAAAAGTCTCTATCAAAACTTGTAAAACGAAATATATTGAATTC
CGAGAAACTTGGATATGAGTAAAAATAAACTCGAATATAATTTTCGAATGGATCTCATTCAATGAAACTTGGATATGAGTAAAA
ATAAACTCATATCCAAGTTTCGATTTAAACCTGTCGAGACTTGTCGGCATAATTATGGTGCAATAATTAAATGATGTCACGACG
GCGTCCAACAGGTTGTGACCGGTTAGATCGAAACTGGAATATGAGTAAAATCATACTCACATTGAAAAATATACACTTTAATTC
AGAATATTTCGAAGATACTTTAATTTTCATTAAATTTGTAAATCAAGTATTTAAAAATGAAGACGCGTTATCAGAATATAATAC
AACAACTATACCAGTTTTAAATTTTTTAGAACTTGTAAATAAAATAAATGAATTTAAAAATTTCCTCGATGTGGTCAACGAAAA
AATTAATGGGTCGAACATTCAAATGGAAAATAGACTAAATTTAAAAATAGTACCACGAAACACTAAAACTAACAGAGCTTTGAT
CACATGGGATGTTCACCCGAATAACGTTAACAACGAAAACATCAATATTGAAAGTATCATTGCACATTTCAGTATTTATGGTGA
AATAATAGGAGGGGTAATGTGTGAAAATAAACAAGGTTGTGCTGTTTTAGAATTTGCTTTATTGGATGATATGTTGAAAGCAAT
AAATAGGGAACAAATGTACCGTGTTTCAGACTACACGGAAAATGAAATAGTAAAAATTCGCTCAGACACAATAACCAACTTAAA
AGAACAGTTACAAAATATACGATCCCAGATTGTTTGAATCGATTTCATAAGTATGCCTTTAATAATAGTCGTTATAACAAAAAA
TAAAAAATGGTTTAAAAGTACAAAACGGCGAGCCGTTAAACGATATACACAAAAGTCTCTATCAAAACTTGTAAAACGAAAATA
TATTGAATTCTGAGAAACTTGGATATGAGTAAAAATAAACTCGAATATAATTTTCGAATGGATCTCATTCAATGAAACTTGGAT
ATGAGTAAAAATAAACTCATATCCAAGTTTCGATTTAAACCTGTCGAGACTTGTCGGCATAATTATGGTGCAATAATTAAATGA
TGTCACGATGGCGTCCAACAGGTTGTGACCGGTTAGATCGAAACTGGAATATGAGTAAAATCATACTCATATTCCAGTTTCGTT
TTCTTTATAAAAGAGTAGTAAAAAATTTATAAACAAACTTTGAATTTGAGTAAAATCCTACTCATATTCCAGTTTCGTTGTTTT
ATAAAATAGTAGTAAAAAATTTATAAACGAACTTTGATTTGGAGTAGGATCTTACTCATATTCCAGTTTCGTTTTCTTTATAAA
CGAACTTTGAATTGGAGTAAGATTTTACTCATATTCCAGTTTCGTATATACAAATAAAATTGAAACAACAGATTGTTTTCAAAT
GTAGTTTATTTGAAATAAAGGGAACAAACATCTTCGACAAAAAAGATCATAATTAAATTTCTTGGTTACTAATTCGCTATCACT
AACACATGATTCACATTGCAAACATTGTTCGATATCAACTTTGTAAATTTTGTCGTGGGTTTCGTGTAAGGTCCATGCCATTTT
TACTCGCGCGTTCCACACTGTGTAATCGTTTTCAGACACCTCATGCATGTTCATTTCCCAGTAACACACGCTCAGCAAACAGTA
CATTGAAAATTCCTTGTCCGTTTTTAGTATGCACACGGGAAACAGGCAATTTTTACACAGCTCCGTTCCACTGTTGTCGGTGAA
ACAATAATCGCAAACCGAAACGGCGCATGAAGATTGTCTCATAAACGGTTCTTTAAAGCTTGCCAACCGTTCATTACATTGGTC
GAAAAATTGAGTTCTCACAGTGGGATCTGTAAGTTTTTTGTATAATTTTGAGTATTTAATAAAAGGCTCAATTAAATTCATGAT
TAACGTTTAACCCTGATGAGTTGTGAATAAGTAATAACATGCTATTGATAATTAATTTACAGGATAAATCTGATTTCCTGTTTA
GATCGTTTATCAAACTGTGGAAAGATACGTTTGTCGAGTGCCAAATTTGTTACGAAAAAATCGAAATGACGGCGAAGTCGCCA
TCACTGATAACGGCTCGATCAATTTAGAAAAAATGTTTCATTCAAAATGCATAACACGCTGGAGACTTGAAAACACTAGGGATC
CTTTTAATCGCAACGTTAAGTTTTGGTTTAACTTTCCGCCTAAAAACCAAGCAGAGTGTAGCGCGCTGGTAAATCAGATTAAAA
AATTCATTGGTGATAATGAAACCGACAAAAAATACGGCGCGGAATTTAAAAGAGTCAATGAAGAATCGTGTATAGATGTGGACA
TTGACTTTACTAATTTATTACATTATTGAAGTTCAACGTGGTCTTTTGCACAATTACAACCACTTTAATATGATCGATCATGTT
TTCTTTCTTAACTTTTAACGTTTTAATATTGTTAACATCGTTGTCATTAGTGTATTTGTAATAAACATTATTATGTATTCGAGA

TABLE 9-continued

Nucleotide sequence of the *C. peltastica* NPV genome (SEQ ID NO: 2)

CAACACATGGTTAATTTTTTTCGTTAATATATTTTGATTGATGTGAACTTTTGATTGAAAACGTATGGGTACATTCATTTCCTC

GTTCGGTTTAGTCACTTGCGCTTTCAAAAACCTTCTCAACATATTGATGGCTAAATTATTTACAACGCCACAAATTAACAACGA

AATGTTGGTTTTGTTATGAGTGTAATTGACGTTAATTAAAATTGGCACGATATTTTCTATGTTATCCAGTAAACTATAGTAATA

TTTAAAAATTAGCTCACTCATTTTTGAATAATTTCGTGCGTTTATATCGTATTTGCCAAAATTAGACATGATATCTTCGTACAA

AATTTTATTTGATAACTTCGATGTAAGTTTAAGTATCTTCTCTAATTTTACGAACAGTTCGAAGTTCAGGTATGTTATTAAAAC

GTTAAAGCCGTTTTGAATAGATTCTATATTTTCATGTACGATAGGCATCATTAACGGTTTGATTTGTATTATTTTTTGTCTATA

TTCTATTATTTCGGCTGCGGTTTCGTTTGGATCGGGGTTATTTTCGGAATCATTATTATTATCTTGATATATAATATCATAATC

AGGTATATCTTTGTTCGCCATACTTAAATTATACTTAATAAACTATTATTTGATAATCAGTATAATCATTTATAGTTTCTTTTT

CTTCAAAAGTGCGAATAACTTTTTCTTCCAAAACATCATAATAATGAATTGATCCGTCGGCATTATAGGACATGGTTTTAAAAC

GATTCAATTTATTAAATTCATTATAAGTAACTAGTTTTACTTTCGCATCATCAAATATGTCTTTTCTGTTATCGGAATCGGACG

CCATAATAAAAATATTCTAAAAAACAACCTCGAATTAATCGATGATACTTATATTATTTTAAATGTCATCGAAAACGACGAAA

GTGGCAACGCCCAGATTCAACCAATGTGTATCGGAGAAATTAATTCCTTTCAAACCGATCAAATTACCTCAGACTCAATGTCCC

TATCATCCTCTACGAGCGAATTGCCGACTGATCAAACCATGTGACCGATACGACCGAGAAGAAGATGCCGGCAAACACGTTACG

GTTTTACAAGCTGCCACCGGCATCAATTATAACCTGCAGCCGTATTACATGTGCCTTTTAGACGACGCTGAACTGCGTGGCTAC

AGTATGAACGCAAACGAATTTTTTGGCCATGTCCAGTTGAACAAACTAGATAATGACGAAGAATTTTTTGGTATAGACGCTGCC

GGAGAAAAAAATATGGGAACTATAAAAATGGTAATCAAAAGTATTATGGACAGTTTCGCAACATGTGAAAATTATTACATTTTG

ATGATTGACGAACTTCAACTCGATCTATTGTTTTCCATGTTCAGATCGATAATTTTACCTCAAAGAATGGTATCTATTCACAAA

AACAATTTTGTGACCGACGATGTTTATTTTAAACTTTTCTCTGTACCCGTAACCGACGAATCGGATCAGTCGCAACAAATTTAC

CGCACCTTTTTGATGTATAACACCGTGTTAACTATGATACTCAAACAGCCTAATCCTTTCAATGACGCTAGAAAAAACATTTCG

GTGATTTTCAGAAGTCTGGGCGATGTCCGAACAATAAAGAAAGAGTTAAATGTTGCGATTTAGCCTATGGCGGTAACGCGCCG

AATCATGTAATGTGTCCTCCCCGCGAAATGGTCAAAAGAGTTTTCCATTACGCTAAATGGTCGCGCACGCCCAATAACTACAAA

AGATACTACGAAAAAATTACCAACAAAATTGATGATTCAAGAAACGATCAAAGTTCATTATCAAAATATGCGCTATTGACGTTA

GATTGGTACAATTTTATAGAAGATTTTCGTACATACTTTGGAGTCTGATGGCAAAATGCCCAAAGTTGACCTATTTAAACGTTG

CGCATGTCCTATTTTTATTTATTAAACGAATTGAACTTTTATCAGAAGGAGGATCGGACGCGAAAAAAATGGACATCAATTTTA

AGCTGAAAGAAATAATAAACACTACCGTGGATAACAAATATGGAGAAAAAAGCACCAAAATTTCCTTGGCCGATTTTTATAAGA

AACATCAAGAAGACATTGCGTGCGTCGGAAAAAGCACCACATACAACTGTACCGGCAAACGTGACTACGAAAACACCTAAGCG

ACAAAAAATACAAATTCTAATGGACCGGCGAGTGGATGAAACTGACCAAGTGATTCGGTGTGCGCACTGCTTGTTTGTTGCTCC

AATATCATTAAGTTATGAAGAATATCAATATTTACACAGGGTCTATAATAATTTGTTATGCCAAGATTGTTTTGCAAGTAACCC

TTTCATGTCAACAACAGAATTGGATCCAACCACTAAGTTGGATGAAGTTTCTTGATGGATTGTTTTGTTTACCCAAATAGTTTG

CCAGTTTTCCAATAAACAATTTAATAGAACTACACCAGCCTTTCATTATGTCTACCTTAACGCCGCTCCATATAAACGACGAAC

ATTGCTTCGATAGTTTAGTTCGATTCGCAATGGCTACCAATATGAGCGCGCGCTTCTTGGAGTTTGAAGAAGTGTGTATTGATC

TTAGAAATGTACACTTTAGTTTTGACCAGGACCATCAAAGTAACAATAAAACATTCATAATATTTATGAACGTGAAGCAAGCTT

TTTATTCAAATTTCAAAATAAAAACGGATTTGTCACTTGAAACTTTGACATATTACATATATCAGCACTGTTTATGTACTGTGG

AAGACACCGTTTTACCTATATTCCGGCGTTTCGACCAATTCATCTTTAATGAAAACGATAAATGTAAATCCATTATCATTCAGC

TGCATCGGCGCGCCCGTGTCATTGTGGCTGAATGTATACGCGAGAACGAATATTACCATTCGGATGTGAGTGGTTACATTGATT

TTGAAAACCGGCACACTAGATTACCGCTTTCGCTGAGCGAAGAGGAAAGATCGAAAATAAACCGAGAGGCACAATTAAAACTAC

TGGAAACGACCTAAAATCTTTGAGAAGAGGTCTCGATGTAATCTTCGTCATCGGCGTCGTCATCGGTTTCGTCGTCATCGTCGT

CGTGGTAGTGACGTTGTGTGGTATTGGCGGTAGTGTTATTGTTAGCGTTAATGTCATCATCATATTCATATTCGTCCTCGTCTT

CATCGTAATCTAAGTCATTGTAAGAAAGGTGACTAGCTGTGTGAGGCGCATTAGCAGGCGCACTGGTAGATTCATCCTCGCTGT

TABLE 9-continued

| Nucleotide sequence of the *C. peltastica* NPV genome (SEQ ID NO: 2) |
|---|
| CGTAAATGTCGTGCCGTACAATGTGTTCAGCGGCAACCTTAGGAATCCACATGTTATTTAATTTTACATAATTACGTTCAATAG |
| CCTTTCTAGCCATGTGCAGTGCCACGTCTTCGTTGGCGCTATCTAATTTATGATATTTATTAAAAGTGTCTTTAAAAAGTTTTT |
| TTGCTTTAGCGGGAAGCTCCTCTTGGTAGTATGCGTCGGTTAGATGAAACATTTTATTATACCCTTACAATTACTCTGTATCGT |
| AGTCGTCGTTTTCAGTGTCGGTGGTGTCAAAATCGTTGTCATTTGTATAAGCTAACCATCTGTAATTTTTCTTGTAATATTTTC |
| TTTTAACCGCCGACCACGCTATACTATTGGCCGACACTTTTGATTTGTAATTTTTGTATGCACGATTAAAAAATTTCATGTATA |
| TTCTACGACCATTGTAAGGAAGCCGTTTTACAGCGGAAGGTAACTCTGATATGCTGTCATACATTGTATTCTTAATAAATATAT |
| TAAAAAAAAATTGTTTCATTAATTTTATTTTTCCTAAACTACAAAAATCAGATCCATTTTATGAGATTCAACAAATAATCACAA |
| CCATTTAACGGGCATAAAATTATTGCCTGCAAGTCATATTAAATTAGATTCGGCACTGTCCAAACTATCAAACGACACACGTTT |
| GGCCTTTACTAGCAATTCATGAATGTCGTTTTCGTTTTTAACAATATGCACAGTACTTCTGTCTGTTTTGCGAGCCATCACGCC |
| GTTTTTACACAAACTTACATATTTGTAGTGAGGCAAAAGAGCGTCGCGAGTTTTCTTTAGGAGATTTTTGTGTTCCAAAGATGC |
| GGCTACAAAAATTTTAACAGGCCCGTCATAATTTATGTTTAAATCGTAATTTTTGATTCTGATTTCACGCGACCGGTTTTGCCA |
| CTCTCGAGCTGTGGCAGCATCCGTCAAATGAACTACGATATGATTTTTTTCGTAATCGTTTTCAATTACTTGTTTCAAATCTAG |
| TTTTAAAAGAGAGCATATTTTTTTAATGTAATTTAGCCGGATTTTTTTGTTAGTCAGGCGTTTGTCGTGAATACCGTAAATTTC |
| CACGCTGTCGTTTAGATTGATTATTTCTAATTTCTTAAGTTTTTCATTTAATTCGTTAACATTGCGGTCAATTTCGCGTTTAAT |
| TAAAGTTTGTAAAATCGGCACGTTTATCAAGCTGTCGGCTTCCATGATGTTGGCAAGAATGTTTAAATCCGAAATACCCTCTTA |
| TTAATAATTCAAACTCTGTTGTTAATTTCAGTCGCTATTATGGAGCACGACGCGCAAACACCCAAAATCAATTTTGTTGAGAAA |
| AGTCCCGCTGTTTTTTCGATACTCACCAATCCCGATCAAATTAAGAATGTGTTTTTCATTAAAATTAACAAATTTAGATCGTTT |
| TTAAAAAATTTTTTGGCGGATCTAAAAAAGGTTAAAATAAACTTTTTCAACAGCCTGATCGAACAGTTGATATCCGTTTACACG |
| GAAAACAATGTGAGAAACGAGCACACCGAAACTCTCGTTAAAATAATCAACGCTACAACTATTGTCATTACCGACTTGCCGTCC |
| AATGTGTTTTTGAAAAAACTTAAAACTAACAAGTTTACAGACACAATCGATTATCTTATCCTTCCTAATTTCATATTGTGGGAT |
| CACAACTTTATAATTTTTTTGAACAAAGCTTTCAATTCGAAACACGAAAACGGTCTCGTGGACATTTCCGGAGCCATACAAAAG |
| ATTAAATTAACACACGGTGTTATCAAAGACCAATTGCAAAGCAAAAATGGTTACGCTGGCCAATTTTTATATTCTACTTTCCTA |
| AACACGGCATCGTTCTACGCCAATGTCCAATGTTTAAACGGCGTCAACGAAATTATCCCTCCGAAAGCGAGCATTAAACGCTAT |
| TACGGCCGAGACGTTAAGAACGTTCGCGCATGGACCACTCGCCATCCCAACATTTCGCAATTGAGCACACAAATTTCAGATGTT |
| CATCAACCAAAGGAATATACCGATTGGAACGTTAAAGTGGGCCTAGGAATATTCACCGGTGCAAACACAGATTGTGACGGTGAC |
| AAAAAAGTAATTACTTTTCTACCTCAACCGAATTCGTTAATCGACTTGGAATGTTTGTTGTACGGAGACCCGAGATACAATTTT |
| ATTTGTTTTGACAAGAATCGTCTGTCTTTTGTGTCTCAACAAATATATTATCTCTATAAAAACAGGAAAAATATAGAAGTGATT |
| TTAAACACTATGCCTATGTTAAAAACGGTATGGCAAACATACGGCGATAGAAAGTTTTCCACCAAACTTGATATGCTGCTGCGG |
| GATTGTGCATTATTATTGAGCTCAAATTGTAGTTATTTACTGTTTAAAGAATTAACAAACCTAATTGACGAAGAAGAAATGGTT |
| TGCGGTGAAGAGGAAATATTCGAATTTAAAGGAATATTTAACGATGTGATCGACAGCGGAGCCAAAGGAAGTTACGACCTGATA |
| AAAAGTACTAAAATTTACAAGGAAACCAGCTTCAAAGACATTGAAACCGTATCACAGCGAGCAATTAATAGTTTAAACAATTAC |
| ATTTCGTCGCATAATCGTGTCAAGGTGGGCGGAGGCGATATTTACCACAATACCACAGTCTTACAAAACATTTATTTAAAAAAC |
| AATAAAATTTGTTACAAAAGTGACTTTAGACAAATTGGCGATATTTGTACCTTGCCTTCGGAATTTTTATTTCCCGAACATTTG |
| CTTGACACCTTTCTATGTTAACGATGTAAACAGAACCCGAATGCTGCCGAACAAGCACCGCTACAACATTGATCGTTTCGATTA |
| CAGTTTCGTCCGGTCTCAACACACGCCATTGCATAGGCGACACATGCCATCAAAATTATTAATGTAGTTTTTAAACGCATTTTG |
| ATTAAAACTTTATATAAACTTATGTTTAAAACTCATAGTGTGTACGGTCGAAAACGACATCGGCACAATTGTAGAACCCTTCGC |
| CGGCCGGATCGTTTCTTTGCCAACGCACATACAATAAAAATGGGTTTTTTCTGAAAGGAACGTTTACGGGTATAGTGTAGACAA |
| AATCCGAATTACAAAGTTTGTCATGTGGATACGAAACTAAATTTGATCCGTCGCCGCCGATTAGTTCGAGATCGTCCCACAACA |
| AGTGATGTTTACGATTCCAGTTTTCTTTAGTAATATAAACTTCAAAGTAACTCGGCTCATGAATTGCGGTGGGACAGAATCTAA |

TABLE 9-continued

| Nucleotide sequence of the *C. peltastica* NPV genome (SEQ ID NO: 2) |
|---|
| TCAAAGTTGGCGAAACGTCTTTTGATATAGTCGTAAGTTGCCAATTCGTAAAAGGTTCGTCCATACCGCTTTTGTCGCCAAAAA |
| CTGCGCGGCTATCATTGGCTCCCGCGCCGCATAGTGTGTGGGGAACGACATTGGTCTTGATATGTTCAATGTCTTTGTAATTAG |
| CACCGGCCATCGCTGCATATTCATGATACTGTTGAAACATGTATTGAGCGATTTGAGCGGACGAACCTGACGATTCGCCTTTGT |
| CTAAATATTTATTATAAACTTTTTTGTAAGCGTTCCTGCATCCTTCGTCTATTATACTATCGCCATTTTCGGGCCAATAAAAAT |
| TATTTTCTGAAAAACATATATATTGTCGAGCCACCGGATAGGACAAGTACCCATGCGACTGTACAAATCGAAACGAACTTAAAA |
| TTACTATAGCAAAATTAATTAAAATCATATTGTTTATTAATTATGCCAGACTTAATTGAAAACAACGAGGATGATTTTTATATT |
| ATATTGTATGAGTTTATTGAATTAATAATAAATAATATGGACGAGCCCGACACCGACAGCGGTTACGAGAGTACATAAAGAACG |
| ACAAGCCTCAGAGCCCATCATTTCGGTATCGATATGAGAGACGGTTACATACACGACACGATTCACGCCCCTGTTATACCAGAG |
| GGTAAAGCCGTATTATATGTCGCTACTACAAAGACATATGCACAAAATGACCAATACAAAATTGGTTACACCACTCGGATTCAC |
| GGACGTTTATCTTCGTTCAACTGCGGCCGTGCCGAAGAAGACAAAATGTATTACTGTTTATACACTAGACCAATGTATAATTGT |
| GCAAAGTTAAAAAGGCTGTTGAAAAAAAAATTGTCTTCACACCAATGTGGCGGAGATATGTTTAGGTTAAGTTTAGAAGAATTA |
| GAGAATCTTATTGTTAAATGTTGTATTAAATTAAAAAAGGTATTACATTAATGTTTGGTTTTATTTTTATAGTTCATCCTTTAC |
| TACTCTCAATCCCTCATTCATAGCGTTAAGTATGTCGCCATCATCGGCGTCAATTTCCCAAGCAAACAAGCCTCCCAGACCGTG |
| GTCTAAAACATATTTAGCTTTAGCCAAAACCGATTTGCCATCATCGAATGTAATCAACTCTCCGGTTTGCGGCTTGAACGCGTA |
| CGAGGCTTTGGCCACTTTATCGTAATTATATTCGTACGACGGCAAATCGGCTTTAATGTGACGATAATCTTTTACACCGTCCTC |
| CCATGTGCCCGCAATGGGACCATCGGCGATTCCGGTAAAAGGATTTTGGTCGTTGTAATCTTTAACACCTCTCCATCCGCGACC |
| GTACATCGCTACGCCCACAACGATCTTTTCGGGTAAAACTTTTTGTTTTAGCAAAGCGCGCACGGCAAAATCGGTGGTGTAGCG |
| TTCGGTAGGGTTCCAAGTTGGAGCATAAAGATTAGTTTGATATCCAAGATCGTTTAAAGACCAAGCGCCTTTAAAATCGTAATT |
| CATTAAAAAAATGTGATTCAGATATTTTTGAGCTTCTGTGTAATCGACCACGGCGATTTTGTCGTCGCCCGCACTGATGGCACT |
| GGTTAATTCAAAAGTTTTGTTCATTTCATTTCCCAACTGATCTAGCATGTGGCGCAATTCTTTAAGCAACAAAGTATAGGTGAC |
| TTTGTCATTTTCAACATCGCCTACATTTGGGTTGGCCCCTTTGCCGCCAGGAAACTCCCAATCAATATCGACTCCATCGAAAAA |
| CTTCCAAGTCGACAAAAATTCCTTGACAGATTCTACGAACACGGCACGTTTTTTACCATCGTCAAAATGATAAAACGGATCCGA |
| AAGTGTCCATCCGCCGATGGATGGCAAAACTTTTAGATGAGGATACGCTTTTTTAGCCGCCATTATTTGTCCAAAATTACCTTT |
| GAAAGGTTCGTTCCATGCGGTAACTCCACGTTGCGGTTTTTGCACGGCCGCCCAAATGTCGTGGATAGTTACTTTGAAATCTTC |
| CCGTCCGACGCAGGAACGTTGTAACGCTTCGAAACTGCCCGCGATAGTTTTAAGAGAATCGTTTATACCGTCACCGCCACAAAT |
| AGGGATGAATCCGTACAAAAGATGACTAACATTTGGTATAGGAACTTTATCTAGAGGAAATTTTCTATCATAAACGCCCCATTC |
| AACAAAATATGCCGCGACAACTTTGTCGCTCATGGGTAAATTATCAAAGTTTTTGTTATTTTCCTGAAATTCATAAGTTAAAGG |
| GTCCAAATGATCACCGTTAGTATCGGCCACAGTTACGGGCACCGTTTGGCTCGTTGAACAACCGTCAGCGTTGCATAAACGAAC |
| TTTCATTTCAAATTTTCCCCCCTTATCGGTTTGTATGGACGCTCGTTTGGGCTTGGCGTCTCCTCTCCACATTACAGTGTCATT |
| GAAAACGATATAAGCAACATCGCCCGCTTCACCGTTCCACACGTTCCAACTGACCGGAATATCAATAGTTTTGTGAACACGAAC |
| TAATTTTTCGTAGGCGGTGGCGGCGGGGTCGGTTTCTACTAGAGAATATTTACGTTCTGCCCAATCGATTTGCGCTACTCCCGG |
| TATAGCAGCGAAACTTTCTAAAACACAAAATGAAAATATCAAGTAAAATAATGACGCCATTTTTATATTGATCTTACATAAGCT |
| ATTTTAATTTAATGTATTTAAAGATGAAACTTTTATTGTTATTTTTATTAATCGCGGGCACTACTAGTGCAACTACTTTTGATT |
| TATTAAAAGCGCCCGACTATTTCGAAAATTTTATTAGCAAATTCAATAAACACTACCCTGATACAGAAACCCGTAATTATCGTT |
| TTAAAATTTTCAAACAAAATTTGGAGGAAATAAACAACAAAAATAAATTAAACAACTCTGCCGTTTACAGCATTAATAAATTTT |
| CAGATTTGACCAAAAATGAAATTGTATCAAAATACACCGGTCTAACTTCGGCGGTAACCGCTCAAAATTTACAAGTCGGTTCAA |
| ATTTTTGCAAAATAGTTTATTTAGATTCTCCACCGGGCGATAATTTACCCATAAACTTTGATTGGCGCATAAGTAACAAAGTTA |
| CCTCTGTCAAAGACCAAGGGGCTTGTGGCAGCTGTTGGGCATTTTCAGCTTTGGGAAGTTTAGAATCGTTGTACGCGATTAAGC |
| ATAACAAACTCATAAACTTTTCAGAACAACAATTGATCGATTGTGACAGAGTCAACATGGGCTGCGACGGAGGTTTGATGCATG |

TABLE 9-continued

| Nucleotide sequence of the *C. peltastica* NPV genome (SEQ ID NO: 2) |
|---|
| TTGCTTTCGAGCAAATAATGAATGTGGGCGGCGTGATGGAGGAAAACGATTATCCCTACAGAGGAGTAAAATCCAGATGCGCCG |
| CTGATCCCAGTAAATTTGTTGTAAGTCTAAGTTCATGTTCGCGATACATATTTCAAAACGAAGACACTTTGAAAAATGTATTAA |
| TTACTCAGGGTCCTATTGCGATGGCCATTGATGCCACCAGTATTTCTACATACTCGAAAGGAATTATTAAATTCTGTGACAACT |
| TTGGGGTGAATCATGCTGTATTGTTAGTGGGTTACGGAACCGAAAATAATGTAAATTACTGGACATTTAAAAATACATGGGGAA |
| CAGATTGGGGAGAGGATGGATATTTCCGTGTCAAAAGAAACATCAATTCTTGCGGTCTAGTAAACGAGTTAGCGTCCACTGCTT |
| CTATCAAATAAAACAAGTGTTTACTGCAAATATACTTTAATTTTTTCCTTTATTTTTTCACGACATATACAACAATTTTTGCAT |
| CTTTCGGCGCATTGTTCACAAGTAGCAAAGTGGCCGCAGGGGCTAAAGCATATTTCTATCGACTTGTCGAAACATATCTTGCAA |
| GTTTTGTTATCATCGTTTGGCGAAACTGTCGTTGACATCAATTTGTGTTCTTCTTTGAAATTTTGCAAGTCGGGATAAATTTTG |
| TTTGACCAAATAGCTTTATCCTCCATGCAAATTTCGTCGTCAATTTCTTGCAGATCGGGCGCAGACGGCTGGGAACGTTTTACA |
| AAGGAGCAATTTTTTGATGTGCTGTGAATAAACTCTACACTATCGTTTCGATTCAGCTTTACAATCACCAAACCGCAATCGACA |
| CATCTAACTTCGTTGTTACGGCCATAAAAAAAGAATCCATTTTGAGCTAAAAGTTTCGCTTCCATTTTCACTCGTTTACGCGCC |
| GTCTTGAATTTAATAAACGATTCTTTCCTTAAAGTTTCGTTTCGCTTCATTAATCTGATCGATTCGGAACACAGCGAATAGGTA |
| TGATATTTCAAAAGTTTCGAATTCAATTTCGTAATTATGTATGAACAAAAAGCGCATTTAAAAGATTGGTCATCAAAATAAAAT |
| CCGTTGCGTGCCATAAATTTTTTGTCTTGATTCATCAAGTTGGTGATGTCTTTGAAAGTTGCCAGACGATTTTCGTAATCGGTG |
| TAAAAATTTTTAGGAGGCGGCAAACTTTTTAGGAACATTCGTTCCATTTTGTAATATGTTTAATAATTTTTTAAGAGCGCGTTT |
| TTGTTTCAAAGCAAATTTGACAGTGTTTAAAGTAAAATTTTTGTGTTCTTTTCTTTCTGTTAATCGATTTTTGCCAATCAAATA |
| TCGTTCAGAATTAGCGGCTCTCGAATGCAACGGTTTAAACACTGTACAAAATTCAAAGTTGGCTGCGAAATCTTTCAACAAAAT |
| CTTTGTTTCCGAATGAAACGTATCGAATATTTTCAGGACACAATCGCCGCCCGGTTTTAGCGAGTTGAGAATGATCTTACATTC |
| TTGGGCCAGTAGCGGTAACGTCAAAATTTCTTGGTCGTTTTCGTTACCTCTGACATCCGTGGCTCCGTCCGCTACAACCAACTC |
| ACATTTTTTACCACACATTAGGTTTAACTCTAGTATAACAGATTCGTCAAAAATGTCACCGCTATTTTTGTAACCGTATATTTT |
| TTTAAAGTTTTCATGATTATAATTATAATCAAGTTTTCCTCGCAAAGTTACACCGTAACCTTTGCAATCAAAATTTGTAGAATG |
| AATGTAATTGGCAAACTGACCTGGTCCTCCGCATAAGTCCAAAAATACATTTACACGTTTGCATACATTAAACTTTTTGTCGAT |
| ATCTTTGAGTTTGTTAAAGCACCTTTTTTTAACGACCCGTTTTTCCATAGCGTCGCGTGCGCGATGAATCGATTTATCATCGAT |
| GTTATCAAGACTATTTTTGAGGTCATTCAATATTAATCTAAGTTTCGATTCCATAATGGATATAATTAATTGATAACAAAATGA |
| TGATAATGCTGCATATAAAAGCGTACACAATTTGTATTAAAGTTATACCACTCGGTACAGCCGTAAACATAGGTCGATCCAGAG |
| CCCTCCTCAAGGGTTCATTGGTGACTAACAACTGTTTATTTTTAATTTCGTATATCAACGGACGTTTATAATCAAAATTTTCAA |
| AGTTTGCTTTGTTAATTCCAGTCCGAAAAGCTGAATATTTTGGGCTCGCTAGGAGTAAATCTATCATTAGATTTTTGTACGCCC |
| GTTCACGAAACTCTGGCGAAACTTCGATTCTGTCAGCATTCAGGACACGCCACTTGACATCATCCAACATGTCTGATCACAAGA |
| GAATATCTGCCGGGCTCGAAGATGTTCTGAACGACGTCGATATGGAGTACCAAGGGACAGAGCACCGTAATAAAAAAAGATCGT |
| CTAGCAGTGGTAGATCATCGAAAAGATCTATCAAAGAAGACAACTACGAGCACGAATCGAAACGGTCCCGTAAGCGAAGGAGTG |
| AAGAAGAAACTAAAGATATGGAACCGGAACAAACGACCTGTCCAAATAAACTTACCTATTGGGAAAAGAAAAGATTGTCGAATA |
| AAACATCTTTAGCTTTGGCAACGCCCAGGATGTCCAGCGAATCGGTAACAGACCAGCCGTCTACTTCAAGCGGAGTACCACAAA |
| CAAAACTACGCACTGTAAGTGTGAATGGTGAGCTGATTAGCAAGTTGCCAATCTCAATTAATAACAAATCATACTACATATTAA |
| AGTTTTTGTGCGACCAAGAAACGAAAGAGTTCTATGGCAGTTCTGTTCACTTCACTGAAATAGTTAAAAATAACATGTACAAAT |
| TAGAGGTGTCTCAAACACCCAGATTTTCGTACATTGAAAATTACCAGATTTTGAACAGTGTGAAACCCACAATGAAAGTGAAGA |
| AAGCTCTAGATAACAGCGATTTTGACGATCAAGATGTTGTGTCGGTGATCGCTCGCATAGAAGGCATCTTTCAAAACTTTACAA |
| ATGAATCTTACAAACTGGTTTTGTCTGTAAACTATGGATCGCGCGCGGTACAAATTGAGTGTTCAAGTAATGGTCAATCTTTGA |
| TAGAGGCTCTAAAATGCGATGATGTCTTAACAATTAAAGATGTGTTGCATTTTTTCAATAATAACATTGGTCGCGAAATACAAT |
| TGATCAGAGTCAAATGTCAGCAAATCAATAACGATTTAAAAAATTTAGTACTGACAAACATATCGTCTATAGAATTGACCAACG |

TABLE 9-continued

| Nucleotide sequence of the *C. peltastica* NPV genome (SEQ ID NO: 2) |
|---|
| AACGTCCCGTAATAATGGACGCGTCTGAGGACATCAAAGTTAACTTGAGCCGTAAGCAAAAATTGATTCATAGAGGCACTTTGC |
| TTTCTTTAAACATTGAAGTGCGCCCGTTTAAAAAAAGTCAGAGAATTATTTTTGATTTTGAACTTAAAGAGGATCCAGGTCATA |
| CACAAAATGCGTCATTCTTTTGTAATGACAGCATGAACGAGGACGAAATTTCCATATTAATGATGAACTTAAATCATTTAAAGA |
| CCATGGTGAACGATATGGAAGTTCACATTTATGAGTTGGGGGACGGGAAAATGTCGACTATTTTAGGCATAACTTGTAAAGTTT |
| TAAATTGTGATGACTATTATTGCATCGATTGTAAAGCGCCTGAAATGTAAAAAAATTTAATCAAGTTTTTTAATAAATATTATA |
| CACTATATTTTGTTTTATTCAACAGGTACATTGGCCGGATTGGTCTTTAATTTACGATAAGCCCGAGTTCTAGAATAGGTTTCT |
| ACTTCTTTATATATTTTATTAAACGTCGTTATAGTATCATAGGCAGTATCTTTAATAGGCTCAAATTCATTAATAAGTTCTTGC |
| TGTTGTTGTTTAATTAAATTAATATTGTCGTTTATGAAATTTTTATATTCTAAATTTTCTTTAATAGTTTGTTCTAATTTATTT |
| CTATCGTGTTGTTCGCTTTGAGCGTTTAATGAGGAAATGTTTGCTGGCGACAACGGCAACTGATCAGACAAAATATCTATTTTA |
| TATCCTAAGTTTTCAATTTCATGTTGTAGTCTGACAATATCCTGGTCCTTTGATGATTGCATCTCTGCATTTTGTACACCTGTC |
| GGAACAGGAACAACTGCAAAGTTAAAACTGTTTGTCGGGTCTACAAATACATTGGGATCTGTTACAGGATAATTATCATCACGT |
| CTTATTCTATTTGCATGTTCGACCTCAGAATTTAATTTTCTATTAATTGCTTTTAATTCTTCGTTTTCAAACTTTAAACTATTT |
| ATTTCTTCATTATAATTATTTGGTATCGACGGTAGCGCGGGCGGTGTATATGCCATTTCAATAGCTCGCATATCTGTTGATCGA |
| TCTTCGGAAGATTCTATAACTAAATTTTCTCTATTAGCTTCTATTTCTCTTAATTGTTCTGATAATACTCTATGTTGGTTAGTC |
| ATTGTAGCAATATTTTTCATCAAAATTGGAAATAAATTACTTTCTTGTATATTTTCTAATGGTATATTAAAGTAAGTAATTAAT |
| ATATAACGCAGATTGTATAACATTTGATTATACGAAGTTGTAAGTTGGGATGTTTTGTCGAACTTGAATAGACTAATTTCTTTG |
| CTTGAAATTTGTTGATTTAAGCTGGTTATTTGTTGATTCAAATTGTCTATTTTTTGCTCTTTTGATTTAAGTTCCAGTTCTTTC |
| ATTTGGAGATCACTCTTGTGTTTTTGTTTTAACCGTGTGATGTCATGTTCAAAAGTATTAATTTTATCTTTCTGATTTACAACC |
| AACATATCATTTATAGAGCTGGTTGTAGTTTCTTTAATACTCTGATTTAATTTATTTAACTTCAAATCATTATTTTCTCTTTCT |
| AAACTATCATTTTTAATTTGAAGTTTAGTGTTATTACTTTCTAGAGTATTATAATTCTTTGTAAGTTGATCATAACTAGATTTT |
| AAACTGTTATATTTAATTTGAAGATTATTACTACCCATAGGTACTATCTGTGTTTGTAATTTAGTATAGTCTTTTTTAAGTTGA |
| TCGTACTTGGATTTGTAATCTTCATCGGGTTTTTTGTTTCTGTAATTTTCCAATTCTGTCAAGGCGCTTGTTGTCGATTCTGTT |
| ATTTTTATTATATCGCTTTGTAAAGATGTAAAAATGAATTTTTTATCAAACTTGAGAGCAATACTTTTAAAACTGTTTAATAAT |
| AAAACTATAAACGGACACAAATCCGGTCCCAATGGCATGATTATATCGGTTTTATTTTTAATGCACCTCAATAAAGCTTGAATA |
| TCGTTGTCGTCGTCTTTGTTCGTATTGACATTGTTACCGATTGGCTGAGAGCAAGAATCGTAAAATTGCTTTAATTTTTCAAAC |
| ACTAAAACTAAATTAGAACTAACAAAATATTTAACGTTAATATTTTTTAGTAAATTAATAAAGATAGTAAAATTATTTACATTA |
| GGAGTTAGATTGTTTGTTAATGCATTTGACAGCTCTGATTCTTCCCGCTCATCTAAAGCAATTGGTCGTGTATAGTTATTTTGA |
| ACAGGAAGTTGTTGTTGATTGTTATAATTTTGCGGTGGCATATTTTGTTGAGGAGGCATCATTTGTTGCGGCGGTTGCGGGCTA |
| CCAAAAGCGTCCATGCCACCTTGATTATAGTTGCTGTTATAATCGTACTTGTAATTGTAATTATGAGTAATCTGATTAGGAAAT |
| GTTATTGGTATAAGGGCTTCTTGAACCAATTCGGGTATCTGCAAATCTAATCTCATTTGCAGGTGTGGCCTGTGTTGGCATATA |
| ATAGATCTGACACGTTCGAGCATCTCGTCATTCGATCCTTGGGCTTGACATCGTCTGTTTAGAGCGCTTATTGTTTTCAATAAA |
| GCCTTTGTTGTAGGGTCTTTGTTAAATTGTAGATACGACATGGCAGGAGATATTGCAATTAATCTTATGAAATGGAGAACGTTA |
| GTTAACGGACTAGAACAGACCAAATACAGAAATTTTGCTATAACTACACAAGATGTGTTTCGAATTACTAAAATGATTTACCAA |
| GATAATCATTTGATAGTATTTTTGACGGGCTACCTACTGCAGGAACCAGAGCGGTGTGTGCAATTTTATGTGAAAGGTAAATGT |
| GACGTGTATTCATATAAAATGTGCTACGAAACACATGCCAATGACGAGTGTTATCGTAACTGTGTGCCTTACAAAACTATGGTG |
| ATGCCGGGGCTGAGGCAAGTTTACAACGACAAAATTAATGTCATTAAATACAGAAGAACTAATGATGAAAACAAATATTGTTTG |
| GACAATTTTATGAGAGACATTAATAGAGTTCATATGCAAACAAACATGATGGAGGGTACATACGTGAGATTCACCAAAGAACAG |
| GTATGTGTAAATCAGTGTGTTCAATGTGACATAGAAAACATTGAACAATTTGAAAAACTGATTCAAAAAGTTAATATAGAAACA |
| TTGAACAAAGAAATCGTTCCCGTTGTCGCGTGTTATGACATAGAGACAAACTCAAACGGACAAAGAAAGTCCAATCCTTTGATC |

TABLE 9-continued

| Nucleotide sequence of the *C. peltastica* NPV genome (SEQ ID NO: 2) |
|---|
| GATAACATCATATCCGTTTCAATTGTTGTTCGTCGCAACGAGAAAAAAACTAATATTTGCCTGTATTACATAGAAGACGGCAAT |
| GATGACGATTTAATCTGTAATGATGTTTTCAATGAAGACGAAACGGTAAAAGCTGTTAAATTTCATAATGAATTGGCAATGATT |
| GCAGCATTTTTTAAATTGTTGCCCCTCATAAATCCAGACTATGTACTGGATTACAACGGAGACTTTTTCGACTTGAAATACATT |
| TACGACAGAATGAATGTATTGGCGGAGGAACTGGAAGACTCCACTAATTTAAAGCGAAAAATAATGCAAATTCAACGTTACGAT |
| TTAGAACCTGTTGACATTGAGCGTAGAGAACTGACGGATAAGTTTCAAAACAAAGCCGACAGTCATTATTTCACCTATTACATT |
| CACATTGACCTGTACAGGTTTCTAACCATCGAAAAAAACGATGCCGAAAACTACCAACTCAACACTGTATCTGAACATTATTTA |
| AAGATGAATAAAGTGGACATGGACAATACCAGGATGGTCAAATTGTATAGCGAAAATCGCATGGTAGAGATCATCAAATATAAC |
| GTTCAGGACTGTGTTTTACCCATAGAGTTGTTTCTAAAACTCGAAATTTTAGATTTCCTTTATACTCAGTGCGAATTATTATAC |
| TTGTGCACCGAAGACGCTTTAAGCAATATATCGCACAAAGTTAATGTGGTAAATTTCCATAAAGCTCTAAATAACACGCGCACG |
| GACGAGTTTGGAAACGAACATCCGGACCCGTATTTTTTCAACAAATTTGATTTAAGCGTGACATCAGGCCGCGATAATTTGTAC |
| CGTACACCCGCGACCAATACCGGCAAAGGTAATAAAAGTTTGGTAGATTTGACTCGCCTGAAACGTACACCCGTTTCGGCTGAG |
| CATTTGAAACATATCCCCCATGTAAAACTGTGTGCTCAAAAGCAGATATGCCTGTATAGGGGCGGTAAAGTGTTAAATCCCAAA |
| CCTGGTATGAAAAAGTGGGTCGCTATTTTAGATTTCAACTCACTGTACCCCACAATAATGATGTCTGAGGGAGTTTGCCTGTCT |
| AATGTATTTTTGTGCGATGATGGCAACGTTTATTTGCACAAAAATATAAACGCTATCAATCCCAAGCTGTTACAACAGCTGCTA |
| AATCTCAGAGTCATTTATAAAAACAAGCGCAACAATTATGTCAAAGACAGTTTCCAATACAATCTAAATGACCGTCTTCAAAAT |
| GCTGTCAAACTTATAGCAAATAGTATTTACGGTTACTTTGGCATATTTTTTAAACCGCTGGCCAACTACATCACCAAAATCGGT |
| AGGGGAAAGTTAGGGGAAGCCATAAAAAGAATCGAAGCCAAAAGCAACGACAAAGAGATTCTTAGGAAATTTGAGCTTAGTAGA |
| ATCGAATTTAATGTCATTTATGGTGACACCGACTCCTCGTTTATTCAAGTCGATTTTGACGAGTCGGAAATTGAGGAGGAAAAG |
| TGCCATGACACAATCAAAGACATAATTAGTAACTATGTCATGCGCGACTTGAACGCGTCGTGGTCGGGTTATAAAATGGGCCTC |
| GAAAATATCATCAGCGACATGATTTTGCTAAAAAAGAAAAAGTATTGCTATATTAATAGCGAACGCGAAGTTAAATACAAAGGT |
| TGGCTCGTGAAAAAAGATATGCCAATGTTTATGAGAATAACTTTTAGGGAAGTTGTGGATTCCTATTTGAATCGACACACGGTA |
| GCGTGCGGCCTCAAACTCATGTATAAATTGATGCGAGCTCATTATGATAATTTTGACAAATCCGACAAACTTTTAGATTACAGT |
| TTTAGTATGACCTATAACGAATCCACTGGCACGGGCGCGACCAAAAATAAAGACGGCACATCTCGCAAAAAAGTCATTACTGTG |
| GCCAAAAAGTGCCGAGAGTTTTTGGTGGCGGCCGGTGCCGATTTCATACCGGGCAATGGCGATAGAATCCCTTATTTGCTCACC |
| GACATTGACGGTAAAGTGACTGAAAAGGCCTTTCCTTTGAAATTGTTTCCAACCAGCGATAAAAACATCAGTTGGCTCAAACAC |
| ATGAATATTTTGTGCACTTTTATGAATGAGCTAATTCAGGTATTTGGCGACGACCCGAGTTTCGAGTATTACTTCGTAAAGATC |
| TACAATTATTATACTCAAAAACAAAAATATGATGTTAAACATCCCACTTTGGTTGAAACGATTGTAAAAAAAACCGCTTCAAAG |
| GGCCAAAAAAATAGTTCTTCTGATGAAGACGACGAAGAATCGGGTACAGATAATGATGAGGCGGACGCGGGTGTTAAGCTTAAG |
| CAGTTTAAGATGTATTGTAAAAAACCCAAAAATGTAAAACACTACAAAGGTTCGCTGTGCACCAAGTGTTTTAAAATTTGTTAA |
| TAAATAAAACCGTTTTCATAATTTTGTGTTTAATTTATTTTTATAATAGCATTATTAACCTCCACCACTAAAAACTCTGATAGA |
| TCCCTAATCATATAGTCGGATAGACATTTCTTTTTTACAAAAGACTTCAAAATATCTACAATATTTTGGTTAGAAAGAGTTTGG |
| TAGTATAGATATTCCACTTGACTGTCGCTCAATTGTAAGCCGTTCGTGGCGTCCACAATTGTACATAAATCATATGTGTCGATA |
| CGTTTGTTAAGAAACATATCGATGACGTTCAGCAATTTGTCAAAAAACATTTCATCTCTCTCCAAATCATCATGGTAGTTTTTG |
| ATGAATGTGCTAACCGTGGCGATTTTAGTAGCTAGCGGCATGCCGTTGTAGACCACTTGAGAGAAGAAATTTTTAACAAAATCC |
| ATGATTAGTCTGTAGAACTTGTGTTCTTATTTAAAATTGCGTCGAACGCTTTTTCTAAATCTCTCTTCTTTTTTATACTCTTAG |
| CTTTACCGGTTTGTAAATCGGCAGCCGTGGACTCTGGTTTAATGTAGTAGACCTGTAGCATTATTATAAATATAATGCAAACTA |
| GAAACAGGAAAAATACAAAGTTAGAAAATCCTTCGTTTTTATCAAACAAAAATCCTAGCACGATTAACAACAAAAACGTTGTAT |
| AGATAAACATTTTGACACTTATAAAATAATTTCAGTATTAAAGTAACAAACTAAACACCTTATTAACTGCTGCTATCGCTGGGT |
| GTGGTGGTAGATGTTTCTTGGTAAACATCGTCCTCGTCTTCTTCATCATCGGTTTCGTTTATGCCGACATTAAACTTATTAATA |

TABLE 9-continued

Nucleotide sequence of the *C. peltastica* NPV genome (SEQ ID NO: 2)

TAGTGTTTGGTGCTGTTAAACGAATCATGGTTCATTAGTTTCGCCACTCGTTGCAATGGCACACCGCTGTTATACAGGTTACTA

CTCAAATAATGCCTGATCATATTGGAGCGTGGCCTATCCATATCTACGCCCGCCTCTTCAAAGAGTCTTTTAAAATCTTTAAAC

GGCGTCGATGTATTTTTTGAAATTTGCAAAATAGTAGGGTGCTTGATATAAATTTCCCTAGCCAACTCTAGCGGTTTTGTTTTA

ATAGTATTAAGTGAATTTGTCCTCGCATGTTTCCTTTTCAAGTTTATAGTAGTACGAATTTTGCCCTTTTTTATAAGGACGGTC

AAATCTTCTACGGAAAGATGACGAGCTTCATTTATACGCATACCGGTTCCTAACATGATACAAAAAACTATAGCGCCCCTGATC

AGGCCTCGGTCATGGGCGTAATCACCGTTAAGATACTTAATTTTTTTTCTATACAATCTATAACATTGTCGATAATTTCCTTT

AAAACGATATTTTTTCTTTAGTTTTAATATTTTTAAGCTCTTTGTCACGAGGCAGCATAACCTGTTTGGGAATTTTGTATTCC

GGTAGACCCATTGTGTTTGAATAAAAATTAATGGTCAGCTGTAAAGTTTCCTTGGTGACGGAACGCAATTCCAACATGCGACGG

CAAAGTTCTTCGGGATCTATTAATGTTTTTTGATAGTATATTGAATCAAATTCCGTATTCAAATCGTGAGTGTCAATTTCGTCT

AAATGATCGTAATCGATTAAACAAAAAATTAATTTAATTAATCTTGACTTGTAACTTTTTAAAGTTGTCGGCGCAAAAGGTTTT

GGAAACATGTATTGGGACCATAAGCTATTATTTTTAACTTCATCGGGCGTGCAACGTTGTCTGTCTGTGGCCAATTCAAAAATT

TCATCGAAACGATCGTGACTCTGAATTTTTGACTTCCAATTATTAAACGTGTGTTCGTTTCTTAACGATGACATCGCTTTATCC

GACTTGATTATAAATGATTTTTGGCTGATTATGATCAGTGTAAATAATATTTCTTCTTAATATTACAAAATAATAAATTGCATA

CAAAAGTAGCATAACGCATACCAAAGAAACTAATCCGATAAACAAAATGTTTACAGAGTTAGACTTTTCAAAATCATTTTCATA

ATTGTTATAATTGGTCAATAATTTTTTTTCAGATTCATAGCTTACGTTCTCGTCAGTTATATCATTGAGAGCTAACTTTAGCGG

TATATAGTCAACTTTGGTGCCTATACCCAACTTTTCGTAGGGAATATCAAAATTCATGTTATTGGATATCCGATTGATTATTTT

GTTTATAACTTAACTGTTGAAATATAAAACGTCTCAGTGCTTCGTTTTGAAATGCCAACTCTGTCAAACTTTGTTGGCACGAAG

TTTTATTTTGAGTAGATGATGCAGCAGCGCCCGCGGACGACGAAGTTCCCGTCATGAATGTCGCCGATTGAAACAAGGTAGGTT

TTCGGCCTGCGCGAGTCGCCAAGTCGGCAACATATTGAAAAATGTCCGTGGAAGCGGCCAGCGGTGCCAAAAATCCAATGTTTT

CTTTTAGGCTAACGATTCTAGCGCGATTTTTTCGTTTAAAACATACAAATAGTATTCGCCACCGCCCGCGAAAATATCATCAA

TAACATTATTGATAATATCGTTAATCATATTGAGGCCGGCGTACTTGCGGCTTTCCACGGCGCCCTGAATGTTCATAGGAATGT

TTGCACGCTGCAATAAAAGTGTCATGTAGCTATTTGTCAATTGCTGGCTAAATGGGAGCGGAATAGGCACATTTGTAGCCACGG

CTTCCGCCACTTGATATTGGATCGCCAGTCCAAGTTGGCGAGCGGCTTGACTCACGCTGTTGGCATTAATATTTTCGGCGTTGT

TGTTGTAAAATTTTTGTGCGTACGATGGAAGTACGCTGTAAACAAAAGATGGTTGGAAAATGTTATCCGTCACCACCGAATGAC

CGAGTTCTTTGCGCAGACGCGTGTAGTGTTTTATTAAATTCTCGTCGTTATCAAAACGTTTGACAACATTTACATTGATAGGAT

TGGAATCGATACAAATGTCGCGAATCGTGTTGACCAGCGCCAGCATCTGAGGCGTGAGCTGTGACATGTCGTTCGTGCGGTAAT

ATCGAATGATTTTTCCTACATAGTCCACACATTTGTTAAGCCACGCTTCATTGCTTGTGGTCGTCATAGTTTTTAATTTTTGTT

ATGTGAGAGCAAAGTATAATTTGAGGATCGCTTATCATATAATTATTGTTAATGTACAAAAGAAACATAAAAAATATGACGAAA

AAAATATTATAGTACGAAAATTTTAACATGTTTATCATAATAACAAACAAAGCTAAAGCAATAATTATAGTTTGCATACTTTTA

CGCTTGCACAGAATGGTTTCGCAATTTTTAAATGCCACGTTAAAATCGTTTTCGCCCTCAATAAAATTTTTAAGTTCGTTTTTG

CAACATTCATTACACAAAACCATTACTGATATTACATGACCGTATGAATGTATCTGCTGAAAAGTGCGAGGCTGACTTCCCGGA

TGAAATTCGAAAGCATAATTATTATACATATTTACTTGCGCGTAATAATGAGCCAATATGGCGCCGCAACTTTTAGTGACTTTA

ACTTTACAAATTTTTATGATATTAACTAAATTCGTGTATTGGTTGTCATCAAAAAGTTCGGCGTTATTAATATCGCCGTTTTCT

TTTATGTTTTGAAACTCGTCAAACAAATAATGAATCAACAGTTCGGGGTCGTATTTTATTCTATTAAACCTCATCAAGTTTTTG

TCTCTTAGGCGGTCTAGCCAAACAGGATTCGTCGTTTTCGCTGTCGTTTTCACTGCCGGTTTCGGTACCGTAGGACTGTTCGGT

GGATCGTCGTTGATCGGAGGAGTAGTCATCTTTAACAAGATTTTCAACAATCTTATTATTCATATATTTGATTTAAATATACA

ACAATTTTTTTTCAGCACCAAAGGTTTTATATTAAACAAAATCGTGTTGAGGTTATTTTCTTCGTTGAAATTATGGCTTACAAC

ATAATCACCGCAAGTTACGGTCTGATAATTAACTAAATTTTCTGTTAAAGGCGCTAACAATTGTGTGTCCAAAATTTTCAAATG

GTACGCACCGACAGGTAGTTTTTTTAAGTGATATTCATCTTGAACAATAAAAGATAAAATATTTTCGTGGTCTGTTTTATCAAG

TABLE 9-continued

| Nucleotide sequence of the *C. peltastica* NPV genome (SEQ ID NO: 2) |
| --- |
| ACTGACATAACAAGCGATGTCCATAGTACCATTATTATTATGCGCCATTATATTGATGATAATGTTTTCTATTTTATACTTAAT |
| ATTATACAATGATTTTAATGAAAACGAATTTAACAAAAGGCTTAGTGTTTTGCTGGAATATATGCGGCGTACCAATTCCGAATT |
| ACCTACGCCGGAACAACTAAGTTACGTATCTCACGTCGATCAAAACTTTTACACAATCACCCAATTCTCCACGAGCGATTTAAA |
| CATTACAAAGCAAACATTACACGATGATCGTATCGAAATTTTCGATTTCCTCTCTCAAAAATTTCAACCGATCCAACATAACGA |
| AGAGGCGCGAGTAAAAGCTCATAGCAAATATCATTCTAAATTTATGGTGAGAGGAGACGACGGATGGATGGACGTTGACTGTCC |
| ATTAAACGAAATTTTTGATGAAAGTATCATGCGATGTGTTCCTACTCCAATATGTGACCAAAAATTGCCAGGCAATTATGGACT |
| CACAGAAAATATGATCGATAAACTAGTTCTCAATCACGCTATTATTCGCGAAAACGTAGATGAAAATTTGTTCCATCCCACAAT |
| GTACTTGCAATGTTTTGATGGCGGATCTCACGCGGTCATGGAATGTCCAAACGACCACATTTTTAATGCCACTACTAAAGTTTG |
| CGAGTTAATAAATGAATGCGAAAATCGTCCCGACGATTTCATACTTACACGATTTCCGGATTATTTAAATATTAACGAATATAT |
| GATATGCAAAAATGGCGAAACTAAGATCGTGTCGTGTCCGAACGGTAAAATTTTCGACCGAAATCAACTAAAATGTGTGTTAGG |
| AAACGCGTGCGAAATTAACGGCGTCGGTTTCACTTATATTACAGACGAAATTGGCGATTCGCAGTTTTTTAAATGTATAAACGA |
| ATCCGAAGCCGAATTAGTTACGTGTATTAACAGAATTTTTCGAAATGACCAATACGAATGTACCGGCGATGTTCAATGTGCCAA |
| TTTCGTTAACGGTTCGGGTACGCAAATAAAAATGTTTGAAGACGATACTTGGATGTTTGCAAACGGAATTTTGATATGCGAAAA |
| TTTTCAAGTCCAAAAAAATATAGATTGCGATTCCACTAATTTATTGCAAGACAAATTGTTCAACGAAAAGTTCAAAGTCAATTT |
| GAATATACCTGCAGAAATATTTGATACCGACTCGGGAATGTGCGTACCCTTCACAAAAAATTTAATCAAAATTAAGAATGAAAT |
| TTTCCCCATCGAAAATATTAATAATGATTACAACATAAATTTTGAAACAGCCATGGTGGGTCGAACCGACGCGGTGGAAACTTT |
| ACTCGAAACTTCCAGTTTGGAATCGTGCGTGTCATTGGCTCGCGATATCGGCGCGGTCGGAATCAATCCTTTAAATGGAGATTC |
| GATAAATTGTTTCGGCGAAAACCTCTATGACATTTTCACCGGAGATAAACTTAACATTTGTGATGATAATCAGCTAGTGAAAAG |
| TGTCGATCTAAACTACGATTTTTATTTTCAGCCAAAAACGTCCAAAGTAGGTCGAGACGATGATTATGAGCGTTTTTGTGGGCA |
| AAAAACTACAAACGCTCAAAAAATCGTAGAAAACGACCTTTTTTCGGCCCGTATATTTGCCCATATACTACGATCTGATGTTTG |
| CGGACTACTTATGGCACAAATATACCATTCATATACTACGATGAACCGAAAATATACTACAATATACGTTCAATATACGTACGA |
| TATCGAAAAGAGCCCGAAAAATATAGTAGTATATGAGTCAAATATACAAAATAAAAACGCTACGATGCAAAAACGAGGGTCGAC |
| AGCAAATGATATTTTTGTAAATCGAGAAATCGTTGATGGGGAAAACGATGTAATCAAACCGCTTTTCGACCCATTTGAGAGATC |
| AGAAATTCAACCTATATTTAATCCATTTGATGTCGCGATTCGTCCGCCGTTATCGTGGTTTCCGGAGTCTGAGCCCGATATTGA |
| ACCTGAACCCGAACCCGAGCCTGAGCCTGTACCAGAATTGATCTTAGCCGACAAGTTATTGGATTATTCTTGTTTCTATTCATT |
| GCCCACATACAAATTTAGTGAATGTGAAATTGCCAACGATTTTATCGTTGATAAAATTAAAGAACTTCGCAACAATATAACAGT |
| CGATCCTGAATGTGAAAACGCGAGAGGATTGTCTAATGTGTTTAATTCATATGTGTATCTGGGTAATGGAATTGGATGCAAATG |
| TCGCTACGATGATGAGAAAGGAATTATCGTTGAGAAAATTTTGGACGGACCCAGATATCTAAATGTTGAAACTCAATCTAACGA |
| CGGAGTAAAATATAATCAGTGGGTACATAAAAATGGAAACACATTTATTGCATGCCCCCAAGAACTTCTCAATGATAATTTCGA |
| TTGTGCCGTTCATTCCGACAAATTTTACTATCTAGAGGATTTGCATGAATAAATAACAAATTTCATTTAAACATTTATTATTTA |
| TAAACCAACATTTATTATTATAAAAACCGACCCCATTACAATAATCTTAAGATTAAAATAAACAAAAAAAAATACATGACTTAA |
| ATCTTATTACAATAAAGACTAAAATAAAAATTTATTTTGAAGTCGAAGGTTCGTTCGACGCAGCACGTCCCGACAACGCAATAT |
| TGGCTCGAGTAATACGCAAGTTAAGATCGGTTTGATATTTCAACATGTCTTTTTGAATCATTACTTTATGCTGTAGATCAGTTA |
| TTTCTTCCTTCATAAATTTTTTATACGATTGCAAAACATTCATTTCTTTTTTCATTGCAGCAATTTTCGTCTCGAGTTTTTTGA |
| ATTCCTCTTCTTTAGACTTGCACAACTGAAATTTTTCCATAGCAAGTCTCTTAAAAACAAAATCATATTGTTGTCTCGCCTTTA |
| ATTTTTTTTTCTTTTCCGTTTCTATAGATTCTTTAATTTTAGTTAATTCAAGTTTGTGCTTTATAATCTCACTTGTAAGCGAGT |
| TAATTGTTTGTGATTTAAATTCATTCTTTTTAGTGTTGTTGTTGTTACTATCGATGATATTTTTATCGAACAGTTGTCGTGCTA |
| TAAGAGCAGTATTAAATTTAGGATCCAGAGGAATAATCACATTTTTGATATTTTTAAGGTCAATATCAATGGTAACATAATCTT |
| GCATGTTAACGGAAAAGATGGTGCCCTTTTTAGACGATTGTCGGCAAGTGGGGCATTTTATTTCCGATAGGCGCTGTGTATTTA |

TABLE 9-continued

Nucleotide sequence of the *C. peltastica* NPV genome (SEQ ID NO: 2)

CATTCATTAGTTTGTAAATACACGGCGCACAAAAATTATGACGGCACGGATCCAACCGTATCAGCGGCAAAATACACATGTTGT

CCACACTTACGTCGTAATCGTCTTCCAAGAGATGGCTGCCGGTGCAAATATGGCAGCTAACACGAGCGATATACTTGGTATTCA

TTGTAAAAGCTTGTGTTTGATGCTTACGCAAAGGCAGATCACAATAAACTGATTTATGTATGAAATTGTTTTCTCTTTTATACT

CATGTCACCACCGGTGCGGTCGCAGGTCGATTTACCGGAGCAGCAGGCATTTCCGCGTCTGTGTTAATACTTGTAGACGGAATT

CTATCTGTACTGAATGTATTTGAATTGTAAAATTTACGAAACGGTTTCTCTTTGTTAGTGTACAACGTTTGTTTTCCTAAAATC

AAAGGCACATCAATAGAATAATTGTCGTAACGTGCTAGAGATCTCTGTAAAGCGTTGGCGTTACCCTGAAATTTAAGAACATTT

TCGACGCGCAAAATATTTTCGTTAACATTAACCCTGTGTTTAGGTTTAACGGGATTATACAATGTGACATCTGCAACTAAGCCG

GTTGAATCAATTTTACACGTGGGACAGTTTCTGATACACAAAGTTTCCGTATCGATTTTTATAATCTCTGGAGCGACAGCTTTT

TCTATTAAATTTTTAATAAAATTGGGCAGTTTAATAAAGTTTTGGTCGCCAATATCATTTTCATTTTCGTCCGCGTTGCTGTAT

AGTCGGTTATCGTATGCTACTCTTGAGCAAAAGACAGTAGGATCCGTCATATTGAGTATAGTCATAGTTTTGCTGTATACTTCC

TCTACTATTTTGTATGTTTGCTCCCTATAATTTTCGTTGTACTGAAGTATCTTGCAAATGTTGTCCTGGTTAGTTTTGTCACCA

TAAATGATATATATTATTAGACGTTCTGCCAACGGTAAACCTTCCACATTAAGTACGGTTTCGTAGTTTTTGTGTGAAGGTATT

AAAACACGCGCATTACCCATTTCTTTGTCTCCCACTAAACTTCTGCCTACTGTTCTGTAATAAATGTTATTGTCGGCATCGGGT

ATGGGCAAAACCATTTTTTCGATTTTAAAGTGCACGGATGAATGGTATTCGCAAATAAACCATCCGTCGTCGACGGACGAGTCA

GACGAGCATTGATTCCCATACCGAAAACACGGGTCGAAAGATTGAACAGCACCAAATATACAATAATTTCTAAGTCGATTACTT

GCGAGTCCTGCCGGTACCAGCGCCATTATGGAAACGATCGAAAAGAAATCTCTTATTCAATAAATTTGAGTCAGGATTTGCTC

TATTTAATTTTAGATTCTTATATTTCTAAAAAGTTTGATTTCGTGGGTAAATATTATGATTTTGTGGATACGAATAACGTGCGA

ACACGTTTGGGAGACAACGGAGCGGTGTCGTGTCAAACTAAAAATGTACAAAACATGGAAAAGTTTGTCTTCGCCGATCGAAAC

GTGATCATACCTTTTGTTACAAGAATCAGCAATGAAATCGAAGTTAACATTGAAAATATTAAACCTGAACTCGACAAAATTGTA

GAGTGTCGCGTGTACACCACCAAAAAATACCCAAAAATCGAAATCAAGTTTGAACAGATATATTTCAACAGAAATTTAAGCGAC

CGCTTTGATTCATTGATGGCAAGCAAACAAATTGCTCTGCTAAATCTGCTTCAAAACCGAAACGAAAGCATCGTTAAACAATCG

TATTTGGGGTCTGATGAAATTCTGGCCAATCTTCGCATAGAATACGAGTACGACGACGGGCCGAACATGGAAACAATTAATGCG

ATTGCCGAAATTGTCCGCGAAATGGACGCCATCAGTCACTACCAAAACATAAGTCCCCTAATACCGTACACGACGTTACAAAAC

AATATTATTTACAGAAAATTTGAAGGCGAAAAATTGATATACAATTTGGAGGACTTGACGAACGTGAAAAAATGGGCACTAAAG

TTGGACGGTATCAGAGGTAAAGGATTTTTTACTCGCAACTTTTGCATAATATTTATGGATGATATGCAATTGTTTGCCGGCCAT

TTTCCCACACTGTTCGAAATAAATAATGTGGTGGCTTTTCAATGCGAACTTATAGATGACAAGTTATACATTACAGATTTGTTG

CACGTGTTTAAGTATACGTACAATAATAAAAGCCAATACGAATGTTCGCACGACGGCTACAACATCGATCCCATCACTGCCATT

AACACTATAAATTTTCTTAATGGCAAATATTCGAATACAAGTCTACACATTGAAAACTGCCACCAAAACAAACTAGAAATCAAA

TTTCAAAAATTTTACGATCCACCGCTTCCCACGAGTTTGGGTTACACTACAATCGCCACGGACGGTTTCGTTGTGTTGGATATC

ACTTTACGCTATGTAAAGTATAAACACGTCAAAACTATAGAATTGGAATACAATGGCAAGGAAAACTGCTTTGCTACTTTGGAG

AAGCTATTGACGAATTATAAAATTAACAGCAATATCGAACTGATTCACAACAATATTTACGAAACTGTCATAGTAGATAACGTT

ATTACCGTAATTAAATTTAGACCCGATCGTTTAGTTCCACAAATGATTCATGATGAAACGAAAATGGAATCGTAATATTTAATA

ATCAAATTATAAAGCAACTTACGAAAATTGATACAATTGGACGAAAAGGGAGAAAACTGGTTTCAAGTCAATCCTTTCGCCGAA

GTTTTAAAATATAATAATAATAATCCTAAAGCTATTACAACACGTTAGCAAAGAAATCAAAAAATGTTTGAAGAAATGTGTCT

ACCCGCAGCGGGCAGACCGATGAATCATCACTCCATCCTGCGACGAAGTTTATCAATCGTGTTTGTAGCGAAATTTTCGCTGGC

AGGATGAATCCATTCTAACATCTATAAAAACCTGACGCGCTGTTCGTAGCTCATTATATCGTCAGTCATTGTTTCGTAACAAGT

AAATTTCGTTGCATTTTTTTAAAAATGTCCATTTCTAAAATCGAATTTGTCAACGGACCGATCGAAGTTTTCACTGTGACTGA

CGAAAAGGGAGAAAACTGGTTTCAAGCAAATACGTTTGCAAAAACATTAAATTATAAAAATTGTCCCAACGCAGTTGCTAAATA

CGTTTCTGCTGAAAACCAATGTACTTATGACGTTTTTAAGACAAATAACGGGTCTCCTCAAATCGAGGAGACTCATGAATCATA

TABLE 9-continued

Nucleotide sequence of the *C. peltastica* NPV genome (SEQ ID NO: 2)

CTTGTCTATTCAACCCAAAACCAAGTTCATCAATCGAGCTGGCGTGTTCGAACTTTTATCTGCTAGCGAAATGCCCGCTGCGAA
GAAATTCAAGCAGTGGAACAATAACGATTTGTTGCCGAAATTGTGCGAAGATGGAGAATATAACATGGCTAGAGACGCGCCTAT
TGAAATTAGCGAGGGAATGAACGCTATACATGTAGCTACCGATCAAGACGGAAGAGAAGCTGCTTGGATCGAGGAAGCCAGGAA
GTTTCAAGCCATTATAAAAGCAAAGGAACATAAAATAGAAGAGCTGACAGTACAGTTAAAAGATTCAAACGACAAATTGATAAC
ATTTGCTACTGGTTTAATTCAGGCCAACAATAATTTAAACGAAGCAAATAAAGGTTTGATTAAAGCTAATGAAACTATCGGTCT
AATGGCCAACCGTATGGCCGATATTTCCCAGGACGTGATCGCCAAGCCGTCGGATCCGCAGCTGTTGCATTCGCTCGCCGTGTG
CGCCATCGGAGGGGAGCAATATGCGTTTTTGAGACCGCAGAAGAGGAGTCTACAGAGAAGCTTGAAGAGTCTCGACGTACGTCC
GGACGATATCGTCTACCAGAGTGACTACGTACCCAACGCAGTGAACGTTTTAAACAAAATCAAAGAGAATCTTCCGAAGGACAA
GTTTAAAGCGCGTCACAACAGAATCACTCTGCTGGACGACTTGACTCGCGAGCAATTAATCGGCGTGATCGACTCTACACTAAG
TTCCAGACAGGTGGCTATAGCCAAGCGCAAGGTTGAAGAAAAAATAAATGATGTATTTAAATTTAATAAATATTCATAAACTT
TATTTTTACTTTTTATTTTAATTACTACACTATATTCAACAATGATTTATAGTGTTCCCAGTCCATTTTTTCCAAGTTGGCAGG
CGGCGAGATATTTCGCTGCACGAATCTGTAATCGTTAATGTGATTATGGAACGCCATGCTAGAGTATAGAGTGCCGTACTTCAT
GAGTATATTTTTAGTGACATTGGCAGGGACAATATCGTTTATTAATAGTATTTTGTTGCCAAACTTCTCCTTGTGCATGGCAAT
CTCTATACGTTCCAAAGCGACAATCATGAAACCTTTAACACTAAGATAATGGTCTCTGCACATGGGGCAGTTTAAAACGAAAAA
TAAATTATAATAAATGGCCTTTATTTGTCTGATGTGGTTTATAATTTGATCATGTTTAAGTTTGTCCCTGTTATTAACCATATC
GTCTACCAAAAGACTGAGGAAATGAATAAAGTCCCAGATGCTGGTGAACGTGTAGGTATAATCGTTTGGTTGAAACGCCCTCAA
ATTTAACTCTACCATTTTTTCCTGGAAAATTACTTTCATGTGTTCTAAATCAAAGGCGGCGTCTAGTGAAAGGACCCATTTTTT
TATTTCGTCAATCTCATACTTTTGTATGTCCTTGTATGTTATGATGCACGCCAACTCGTATAAATAAGTTAATTCGGTGCAAAG
TATTTTGGTCAGCTGTTTCGACTTTGATGTTCGAATCCGATCCAAGTGCCGAAAAAGGTGCAGCAAAAAACTGTTTCTGTAACG
CGACAATAACAGCGAGGGCGGAATCATAATGAAAACTATCAACTTATTTTTGCACGATATGCCCCCCGGCGTTCAAAATGACAA
AGAGATCGACGAAAATGTAATATTTTTCGACGGAGTGATCGAATGTGTCGAGGACGATCACACCGACAAATATTGCGCGCTGGC
AGAGTGTGAAAAAATCAATGCCTTACTAATGCAAAAGATCGTCGTGGATTTGCTGGAAAATAGTAACGGAAACTATTGCAAGAA
CCATGTACTCATCGACAGTTTGCTAATGTATAAGACGTATGTAGAATTGGTGGACGAATCGGCGTTTGGTGAAAATTTTCTGGA
GTCGTGTGTCCTACACATTACTAGCATTTTTAAATTGTTTCGTGCTCAAAGCAGAATCGTAGTTCTTTTACCGTCCAACATTAA
TTGGAAACAAGATAATTTAAGTGCACTTTTGAAACATTTATTACAATTATCTTTAATTGAAATTGCCTAAAATGACGACGATAA
TTTTGATTGTAGTGGTACTGGTGGTTTTGTATTTTTTATATGTCAACAATAAATTACCTCTAAACTCTCTCAACGAATCATCGC
CTAGCATTAACCAAAGTAGCGATTCGGTTCAATTAGATCCGGCCACCGGTCAGTACGCGGTAAAACTAAACAACAGTAAAATTA
AATCGTTTAAAATTTTGCACGGCGACAATCATCTAAGTAGATTGTATGTGTCTGAACGGCCGTTAACCTACAACGAAATTATTG
ATGAAGGTAATCGTACCGCTGCAAACTCTTATGTGTTTGTAGGCACAGTATCTGACCCCGCCACTTTGGCGGGCGCAACTTCAA
CCAGTCGCACGACCTTAAATTTCAAAATTGAGCAGTTTAAGAATGTATTCCTAATTTTCAAAAACTTGGACTTTAACAAGATTA
AAGAAAGCGTTAATATGACTAGATATGAATGCGAAGGCATGGTTTATTGCCTAATAGATCCAAACACAAGTACCGTCCCAGATT
TGAGGGATGTTTCCTATCCTATCACCGTTTATACAACCAATGTCAATGCACAATTAAAACTAAAGGAGTGGGATTATGCAGAGG
TGAATGAGGCGGGAACCCTATTCATTAAAAATGAAAAATCATTTAGAATTCAATAAACTTTATTACTCAACACATAAACTGAGG
CCTAACCGTTACAAAATTTTCTTGTCCCTAACCATGGAAATTTTTTCATAAACATTCCTTTTTCGTTGAAAAATTTGGCACA
TTTGTTTTTAAAATCGCCTTGAATCTTTTCTATTTTTTAGGCAGACCCGCCTGGGTTTTACACTTGAGTTGCTCATGAATCAT
GGTCTCCACAATGGGGACCGCTAGCGCAATAAGTGCGTTTACAGTTTCCTCGGCAATGGGTTCTGCGTTCTCGTTTAATTTTAC
ACTCATCACATAGAAAAGAGCCTTCATAATACTATTGTTAATGTCTAAACACTTTAAGTTGTGTAAATGCATGGGGTCGTTTTG
AAGTATGTTCCTGTACAAAACATAGCCATCGTTGTTTCGCCTATACTTCAGTATGTGAGACAAAAACAATTGGGCCCCCTTTCG
ATGATTTTGAATCTGAGATCGAATCAATGGATATTTTTTTCTTTAATGTGCGAATATACCGACCCGCTAAATTGAAGTTCTTC

TABLE 9-continued

| Nucleotide sequence of the *C. peltastica* NPV genome (SEQ ID NO: 2) |
|---|
| CACAAAAGTATGATCGGTGTAAACTATACCGAACCGATTGCGAACTCCGCGATCATAGTCGCTAATAAACAAAGGTTTATTGTT |
| AATAATAAGCATTTTATAATTGGCTTCGTACTTTTGGCTACCCTGATACTTGCGGCATATTACATTACTTTTGGTGGAGTCGGA |
| ATTTGTTTTGAAAAAGGCATCGTTACACACCTTCATTTCGTTAATGACATAAAGTTGAGAAATCAACTTGTCGGCTTCAATGTC |
| ATTGGTTTGCTCTTTGGTCAACTTGTATTTGTCAGAATCATGTTTGTGTACCACAAACATGCTTTCCATGAGTTCAAAGAAACT |
| CGATTTTCCCGATCCTGCCATACCGTTCAAGTAAATGCAAAACTTGTCATAATCTGAGGGGATAGCAAGACTGGTAGCGAAATA |
| AATCATGACTCTGGAGTTGACATGATTGAAGCCCGTTATGTTTCTAAAGTGTATGTACGCCTTCACAATGTTGGCCAGGGCAAT |
| GTTAGAGTAATGTTTGAAATCAAATTTGTTTAATATCAACCTAATATAGAATCGGGCACACCAGTCGTTTAGGTTGTCTCCCTG |
| CCTGGCAATTATCAATTTGTCCCACCAAACATTGTAGCGCTTTATGATGCGTTTAACAAATTTGTAATGTAAATAAAATTTTAC |
| AATAGTGTTGTCCTCCTCTTCGAAATCTTCATCGTTAACAAACGTGCTCTTTTTTTTATTTTCAACATGTGCTACTATATTTTT |
| AATGAAAATATTTGGGTCATTCATTTCATCGATAATGTCAGTGATATAGCGCACATGTTTAAATTTTGTGTATAGAAAATCGAT |
| AATTTCCCTTCGATTTTCGTAAAAGTATGTTCCGTAATTATTAATCAAATCGGAACTTGACACAATCTTTAAAGTTTCAATATA |
| CAAATCAAAGTTGTACAATAGAGACCAAATTAACTCTATAATTTCTTTAGAGACACTAAAAATATTAAATATTACAGCCACCAA |
| AAAAGCGTTACGATTGATTTCAAACGTTGTGTAGCAATCACATACGTTTTCAACGTTAATGACGCATTTTTTACATTTAAAATT |
| TTTAACAATGTCCGATATTTTTTTTTCGTTTACATACATTGACAAAGGAATAAGTTCCTTGTCGTCATAGTTTAAAATCTCAAG |
| AAATAGCTTGTGCAAATTAATTTTTTCACTCATCTCTTGATTAGCGTCATTGAGCGTCATGGCTATAGATATGTTACATTTAAT |
| AATTTTAATGTCTCTACATATTTTTGCTACATGATATATTCTGTATATGTCAACTTCGTATTGGCTGTTGTCTTCCATGTATTT |
| AATAATTTTTTCCGACAAATATTCTGTTTTTTTACGTTTAGTAATGGCTCCTAACAAAGTGTTACCCAAAATAAACGGACAACT |
| ATCGTGATAGGAATTTGTGAGGACATTGAAGACACCTTCCTCAGTGAAATACATGTACTTCCAATTGTTGAATTTTATGGAAGA |
| CATGCTAGATTCGGGCTCTTTAGAAACGAATTTAAAAATTTTGTCATCTTTATGTACGGCGTTGTTATACTTGGTGCCGTTAAA |
| CATAATTATACAGTTTGAAGTCAGAATTTTTTTAAAGTAGCCTCGCGCCAAAAGACTGGGCGAAGCACCGCAATTTAGGGCATT |
| ATCTGCTGTGTACAACCATTGTTTGGAAGTATCTTTTTCTGATTTCAACTTTAAATAAATCATATAGTGTATAGTGTAAAAATT |
| TGCCAAAGCAATTCGAGGGTCTTCCGACGGAAACACTGTCCATTGGTTACATAAACTTTGAAACACCTCTGGGGACAACTCAAA |
| ATAGGGTTCACACTTTGCAACGGCTCGCTCAAACAGAATATTATCGCAAAAAAAATCGTTGTTGAACAACACACGACACACGGT |
| TTCTAAGCAATATCTAATGTTTGTCTTGTTAATTTCCACTTGATCAGACATGGAAATCAGTTTCCAAATTAAAATTAAAAGGTA |
| ATCGAAATTAACAAAGTCACTTTTGTCAAAATATTCCAACAAAACTGACGTCGTTTTTTTCAATTCGTTTTGCATTGTGTCTAA |
| CATTATATTTATGCAACCGTTTACTATTTCGTTAATATAATCTTTATGTTCAGAACTTGAGGTGATGTTGTAAACGATTTTTTT |
| ATATTCAATTTCTTTAGTGTCAACATAAGTTTCAAAGTCCCTATACAATCTTAGATTTTTCAAATCAATATTAATAATGTTTTT |
| GTACTTTTCGGTTACAACACATTGACGCAAAGTAATGTCTTCTCTAATTACATCAAACAATTTTTTGTCGGAAAAAACCAAAAC |
| GGGCAGCACTTTACAATAACCTACAGTACCGTCCGCAGTGATTATTTTGAACAAATCGTCATTTTCTTCTACGAAATCACTATT |
| GCCGTTTACAAATAAAAAACCTCTACCTTCTATATGTAACGACATTTCCACGTTGAGAAAAAATTCAGCGTTAAAAACAAACAA |
| GTTTACATTGCCGAGTTTATGATTATGTATCAGAGGTATGTAGTCCCCAATGTCTATTCCGAAATTCATAAATATGTACTGACG |
| CCAGCCAAAATAAGAAACGTCAATATTGGGCCAGTAATAATAGTCTTTTGATTTGACACACTTGTTCGCGTACTCGTTGTCACC |
| GACACATCGCACAAATTTGCTAAAGTCCACTTTATTTTTGATAATTTCATAGTGTTTTTTGTTAACAAAAGGTTTCACTGTCAC |
| CATGAAATAGTTTCCTTTCACGTACCAATCGTGGGGATCTACAGAAACACTATCTTGACAATAATCCAACTTGCACTGAGTATT |
| CTTATCCGACATTAACTCCAACAGTTTTTTAAAGTTACTGTTAGACTCTACAACCTTTGTTACTCCAGTTTTGGAGTTTTTTAA |
| CACCAGGTTGTCAACAGTATCAAAATTTTTCATAATATTTTCATCACTGGTTTCGGCGTGAAAAATGGTATCAAAAATATGGTC |
| CACATTTCTAATCGGTTCGGTGTCCATTGTGTTAATGTTACTGTTAATGGTTGTGATTTTTCTTTTAAACCCTATAAATGTAGC |
| TGCTGATAACGTTATAGCTAGTCATGCAGATAGTTTGCACTTTGGGTCTTACGTTGAAGTTTTCGATTTGAGTTTTAATAATAA |
| TGTAGAACGTTTGTTTCTCGTCAATCCTGAAAACATTGTGATTTATAATAATAACGGGTTAATATTTTATTATTTGGATTCGTC |

TABLE 9-continued

| Nucleotide sequence of the *C. peltastica* NPV genome (SEQ ID NO: 2) |
|---|
| CAGCGTATTATGTCCTCACGAGTTTTCTTTGCTACGTCTTTCAAAATCCGACATCAAATCTATAAACGAAAGCGGTATATTTCC |
| GACAGTTTGCACTAATGTTAACGCCCTTTCATTGCTCGAGCATTTTTTAACACTAAAAAATAATGTTCCCGATCATAGAATCGT |
| GTTAGCTGTAAACGAAATTAGCTACACCATTTTAGATATAATAAATATGCTAATTTATTCGGGATACGTTTATTTAGAATAAAC |
| GTTTTCGTAGTTAATAATGTTGGACATAATTGTTTCGTGCCAATATTTCCAATCGTTTATAGGTTCTTTGCATCGTTTCAGATT |
| AACGAAATAGTCGTAGGAATGATCGTTATAAATCAAATCGTCCACCAAAGTAATGGTTTTTATATAATTAACGCCGAGTTTACG |
| AAGATACCAAAGCGGAATTCGTGGTGACTTTGGAATTCTTTCTCTGGACGAATAATCATTATCCAAATAAAAAGGTCTTTCTAC |
| ATATACAATTTTCGATTTGGCATCAACTATGGTGCGCTTTGACGGTTCTGTCGATTTGTATCCGCCACACAGCACAATATCAAA |
| GAAACCGTTCAATTCAGTTTCGTCCATAGAACGCGAGACGTGTTCTCGACTACCGTACGACCATAATATCAATATACAGCCAAA |
| TTTTTTTAATCCTTCCAAGCTTTCATAAACGAATTCGTCTCTGATTCTAACGCGGTCTTCGCTCGTGATCAAGGTTTCGTCCAT |
| GTCAAAAACTATAACATGCGGTATTTCCCACACATATTTTTGAGGCTCCATTTGGAAAACTTCCAAGTAATTTTGAACGTACCA |
| TTCTTTTAAAAAACTATACATGGGCTTGCGTTCATTTATAACATACACATGACCGAGTGATAACGTTTCAAAAGTCATTTTTAA |
| ATGTTCTCGTAATTCCTTCATATTATCACGACATTTAATCAGTCGGACTATGTAATTGTCGGTGTCACATTTGTTGCTTTTGTC |
| AAAAGCAAACACTACATACTCGAAAACATTCAAATGTTTGAACCCGACAATGTTAAGGTCGGTATATTCGGCAATGACAAGAAT |
| ATGCCGCTTCATCAAAGGATTCATGTGCCTCAAAACTGTCCAAACAGCGGATTGTTCCATTGTTACCACTTATTTTTAATGTTC |
| AAAGAGTTTCGAAAAAATCAAAATTACGAAGAACTCATACAATTTCTCAACAAAAACTTTCCCGCTAATGTTAAAAATAAAACA |
| TTTGACTTTTTGAACACGGGACACATGTTTCATTCCCTGTACGCTTACGTGCCATCGATTAACAATCAACAAAAAGAACGAAAG |
| CAAATTAGACTCTCTGAAGAATGTATTAAAAAATTATTTGAAAATACAAAGAATGACATCGAAATGTACCAAGAAATATTCGAT |
| TTGATGCATCAAACAAACTCTGAGTTCGAGTGTCCTTGCGAGCTGCTGATGAAGCGCCGCGAAGAAATCAAAGCGTACGTGGGC |
| ACGTTAGAGCAAAAGGTGTTTGATACTAAACCCGTTAAATTAAAGAAGGAACAAATCGATGCAATTATGAGCAAATACTCGTTG |
| GATTGGAAGAGTATATTAATCAAAAAAAAGGGTAATGAAGTTACCAAAAAAGGTGTTAAAAAGAAACGTAAAATAAAAAAACGT |
| ACTATAATGAACGACGAACAAATTTATTTAAAAATTAATGTCGAAAACAAACTTGGATTAATAAACGGTATGTCTTTAAGCAAA |
| TGCAGTCACGAATATGTTGTCGAGGAAAGGCAGATGCGCGCCGGTGATGAAATTGTATCTTTTGTCAAGTTATGTCGATTGTGT |
| GGTCGGCAAAAGTTTGTTTAATAACGACGATTTCGGTATCTGTATGTTCCGCTACTGCGACGACGAGATGATCGGCGACGTCCT |
| CCGCTCCTGCGTCGTCCTCCACTCGAGCGACGCCTGCCTACAGAACGGCGGCGAGATGTACGTCTTCCACGAGGACGGCCCGGC |
| CGCCGCCGACTTCCGCCGCTGCTAGTACTACTACGTCTTCTGCCTCCATAACTTCTGCGTCTACCGCCTGTCGATCTTCGTCTA |
| TAAACCATTATAATATATAATATATAGTAACCGAATTTTTATTTGCACCTTATAAAATCCATTTATTAATTGTACTTTTTACGT |
| TTAGCTCCTTTGTCCGCTCCCAAATAGACATTCAAACTATCGGACATTTCTAAATGTTTTAACGTGAGCGCATCACTCTCTTTG |
| GTGCACTCCATGATTGTGAAAATGTTGTTATAGTCATTCACATCGAATTTACAATTAGCAACCGCATAGTTTTCCATGCTGCTG |
| TAAAATATACTGTTAGCGGCGTTGTAAAACATTCGAGGAATAGGAAAATCGGTAATCATATCAAACAGATCAGTAATAAATTCT |
| GTATCATCGCAATATGGAATTTTACTGCTGTTTAAATCGTTGATACATTGGTTAGAATCGAGATTTTTAATAGACTCTGAACGC |
| TCAATAATTAAATCGTGTAAAGTGCAGCGTTTGTCTTTGGTCAAGTTGGTGTTTTGAAGCACCATGATGCGAGGGAAGCGGGCC |
| AACGGGTATTTCATCGTTTTTATCATTGTGCTTCTCAACAGCTTCACGGTGTTCATGTCAATTGTCGAACCGGGCATTTCCATT |
| AACAAACGTAGTAAATTTACAATGTTGTACTGTTGATCAGGCGTCACGTAAGGAGAACATTCCACATCGTCGTCCGCCAGGAAG |
| GTTCCTTCTAAATACGCATACAGCGGTCTATACTTTGGTATTCTTGATAAATATATCATGCAGCAAATCAGATCGCTAATTTTA |
| AACTCCACAGACGTGGTACTAGTTAGTGTATAATACTGTAACAATCGCACGCATCGTTTTCTATATTCGTTCAAGTCTTCTATC |
| AAATTATCAGACTTCTCTGTTTGTTGCCGTTGTGAAAACAAATTTAGCAAATTGCGCCGCTGCGGTGCCGATGGCGGTGTAGGC |
| TCGGGCGCAGGCGCGAGTCCCGTAGCCAAAACGGTACTGTTAACATCGGCATTCAAAACAGACTGCCTGGCTACGGTTTCTAAG |
| AAATCCATAAACTCGTTTAGGGAAATATTGAGTGTACTGTTGGAGTTGGATAAAAGCGGAAAAAATTTAGGCCATATTTCCATT |
| TGCATCTGTCGATCGACTTTATTTTTGAGTGTTTCGATTTCCAAAAAAAGCATCACTCCGCTCATGTTGAATGATTTTAATGCT |

TABLE 9-continued

| Nucleotide sequence of the *C. peltastica* NPV genome (SEQ ID NO: 2) |
|---|
| GTTTACTTAATAAGCCTTTTACTCGGTAATATTGTTATCGTAAATATCACTTAGCAACTTTAACGTGTTTATTGTATTGAGGGT |
| ATTCAATTGTATGACGCTTTGTTCGTTTTGAATGGCTGTTAAAATTAACTTTGCCGTTGCCGATCTTTTACTCAAATCTTTGAA |
| AGAAACAACTTTGTTTTCTGACGTATCCGCCATAATTCGCTTGGCAGCAGTTTCTAACACGCTCAGACCGTCCAAAATGTTTTG |
| TTCGTCAAGAGCGTCGCGCACTTGCTCGTCCTCCGAAGGATCGAATTTGCGATTGCGTTTTTTATTTTTATGTCCGCTCGTCAA |
| ATCGTCATCGGACGCCAAAGTTGCAATTAAATCTTCTGTACTAATCATTTTGTAACAACAAGGCAAAATCCTCGTCGATTTTAT |
| GCTTGTTCATTAATTTTCTTATATGTTCTTCGGTAACGATATACTGTTCAATATTTAAATCTTCTTTTATACTTGCCAACTTCA |
| TCATAAAAGTTTCAAATTTCTCATCGTTGTATTTGTTCATAATGAAGCGGCAGACGTTTCGAATTTCCATTTCGAACGGTGTCA |
| TTAATTTAAAATTATTAAAGCAAACATTGTTCTGGTAACCCAGTTTAGCGACCGACGCTTCCATGTATAATCTCAAGTAAAAAC |
| CGGTGAAAACGACCGAAGCAATTTTGTTTATCTTTGAATTTTTTATTTTAGTTTTCAAACACAATTGTAACATGAACTTTTTAA |
| AAGGAGCAAACAGAGGAATATCTAGCGTATGTTGTCCTTTAAGAATGACCAATAACATTTCCAGATTTTTTACATTCATGCCCA |
| AAGTGGCGCGTTTACATTCGTCAATCAACGGTTGTACAGTTTTTCGATCAGTAAACTCTGACGTTTTATCACACAAAATATTTC |
| TGAGGAAATTGACAAAGCAATTTGTGATTAGATCCTCAGACGTGAAAAATTTATTTTCATAGTCGGTTTTTATTAAAACGAATA |
| ACAAAAGCGGTAATCCAAACATGGGCCTCAAAAATATGTCCCATCCTTGCTGTATGGTGGTGTCGAATTGTGTTATGGCGGCGG |
| AAACGTAGTTGGATTTACAAGCGAGGCATGCTAGTTGATTTAGTGAACATATGTTACAAGCCGCGGCGATCGCCGAAATTGATG |
| GGCCGACAATCGGTTTATAGTATTTTTGTAGATAATGCATTATTTCTTTGAAATCACGAACCTGGTTCATAAATTCGTGATTCA |
| GAAACATGGTGAACAGTTTGGTCACATCGCTATTTTGTTGTTTCCTGTTCAAGTTTTGTTTAACAAAATCGATACACTTGCTAA |
| ACTCTGTGTGAAAAGTAAGTCCTTTGACAACGACATACTTTTTTTGGTCAAAGTACTTGGAAAATAGGAACGCTAACGTGTCGA |
| TTTCTTTTTCTAATAAATGAACATTTAAGTTTGCAATTTTAACATCGTTTTCATTTTTGCTGAATTTTAAACTGTAATCAATAA |
| CACCTTTCATTATATTATTTTTCTTTATGGACAGCACCGACCTTATTAGCGATATCAACGATGATGCCCGAGAATACCTTATTA |
| TCAATAATAAATCTATACCGCATAAAATAGTAAAAATCGGTGCTGACGGAGCGTGTCTTTTTAGAGCCATCGCTTTGTTCAAGT |
| ATGGCGATCAAAACATGCATTTAAGAGTTCGTGACGAAATCGTAAAGTATGTTATTGAAAACTGGGACGATTTTTCAAACTATA |
| CATGCGACGAAACTACAAACTGTTACAAATCTATATATGAATACGAAAAATTCATGTCACAACCGCAAACATATGGCAGCACGA |
| CTGAACTTTACGCCGCCAGTATCATTTATGCTATGCGATTTGAAGTTTATAAAGATCAAAAACTTTACGGTAATGGATTTGGAG |
| ACGATTCGTTTCAAATTAAAAGACTTAGGTTTTCCGGCCATAATATGCATGGCCATTTCGATGTATATTTGGCCGACGATAAAT |
| GTGATCCTATACGTGAGCCAGAAAAACAAAATGAAAATAAATTTGTTGATTTGATGTATAATTTGACTAAACGTTCGTACATGA |
| TTAGATTCAACACAGTTCAGGCCATTCACAAATATTTAGTTGAACAAGCGTTGCCTGAACAACAAATGGAATTGGCCGATATCG |
| GGGATAAAATTATTTTTGCCCGAGATCAAATTAACACTGGTAGTTTTGAACTGTTAATATATGAACTTGCAAAAAGATTAAATG |
| AATTATGGTCTGATTTTAGAAGATATTCAATTATAAATAATTTATCGACCAATACCGGCGCTACTGTTTTCGATAGCGTTAAAT |
| TGAGCGATGTTAGCGGCGAAACTAAACGCAAGGAAACACAAAAACGAAAAGTACGTCGACAAAATGATAAACGAGTTATTACAA |
| AAAATAAAAACAAAAATAACACTTTTGAAACCGTATATTCCAATAATGTCCAACCAAGGGACACTGTATACATTCAACCAAGAA |
| ATTTGCCAAATTTAGAAACAATGTTAACAGTCTCAATTTCAGATAGAACAAAGATCGATATAACTATACCAGAACCACTAATGC |
| CGTTCTATATACAAAGTATCGTGGCAAACATACCCACCACCACTACCTACCCATATATTACATATCCTACTAAAAATTTGTCGA |
| TTGTGCCCTCTCGTGAAAATTTCGAAACTAACATTAATATAATAAACGAAATTAATAAATCTATTTTGGATAACAACGTTCATT |
| TTTATGAAATGTTGGAAGCGTTACTTTATTACGGAGGTAACGAAACCGGCCAAGTCAGGGTACTTTGGTTTATTAGTATCGCCG |
| AGGATTATTTCAAAGCGTGCGCCGATCATTTTGATAATTTGAGAGAACAATTTGCTAACGAACCTGATGTTGATCGTTTCATCG |
| TATTTATAATAAAATACAATTTTTTGTGGCATTACAGACAATTCATAAGTACATTAAACTCGTCCATGTTAACTTCGTATCAAA |
| ATCAGAAAATTGTACGGTTTTTGCAATTAACAAACGAATCGGTTCAGAAAAAATTTGACCGAATCAATATTAGATTCGATCTTA |
| ACGTCGTGTATGTCAACAAAGTTCCACAAGTGGTTCAATTGATGATAGGATGTTACTCCAAATTTGGTTAATGATTATCGTTTT |
| CATAGCGGCCCTTGTTATGTTAACTTTGACAAAACTGAATAAGAAAATAATTAATGAAATTGTCTACTTCCAATACAATTTTAT |

TABLE 9-continued

Nucleotide sequence of the *C. peltastica* NPV genome (SEQ ID NO: 2)

TCCGGAACCTCTAATTTCGTTGGTAAACGTTATACGATTAAAATAACTAAGTTAGTTTTACGATGGCTTGCCCTTTTAACATTA
CAGTTTGCATCAGCGAACGTTTCTTTTCTTTTCCCTACGAATATGTGGTACCACAATCTGATGTCGGCGGAGCGCCTGTTGACA
ATTTGGTAATTTACGTTCCAACCGAAGAAGACATACAGTACATTAATACGAGCCAATTAACAAACTTTAAATCCGTACTTGTGT
ACAGGCAAGAGTTTAACAATGTTCGTTCCGAAACACGTCTCGCAAAAAGAATACTAGCGCGACGGTAGTTTACTGGAATCCAA
TTGTGCCGATCGAAGAAATCGGAGTTGGCGAAACTCGCGTTTTTAGTGTCCTTCTAACCAACGATTTGTTCTTTTGTAAAACAA
TTATTGTGGATCATAACACACCAATTTGTCCGATAGAATTTCGTTCGCGTATAGAATACAAAAAATTGTATCCGATAGGTGGAG
AAGTGCCTTTGTTTTACCTCAAAGATTTACTTAACGATAACATCAATGATTTTTTGATTTGTTTCAACCGAGAGACCTCTATAA
TGGTTAAAATTTTAAACATTAAAAGAATCCTCTCTATTTTTGAGTATCGAAAAGTACCTGCGCGCTACGCTATAAATTTACCCG
AACAGGAGGTGGACAATATCTACAACAAATTAACATGGGAAGAACGCGAAGGCTGATGAAAGGAGATGTTAGTAATAAATGTG
TTTATGTCAATCGGCATAGTTTGATGTATGTTAAAAATGCACAAGAAATGTTGGGAATCAAGAATTATTCGCGTTCAATTGTGG
ATTTTGTTAAAATATTTCAACCTCTCATTCAGCCCTACCAAATTGTGCCTGATATAATCATCAAACTAAACACGTTAGAACGTG
CGAAACATGTCAGGTTGTATTGTAGAGGCGATAGTTTCGCTATAACTTCGTACGGTTCTGTGCCGGGCAACATGCCCGACGACA
ATGTCATCCATTTTAATTATACAGACACCAACAATAACAAGAATTTATTCGAAGTTAAGTCTAATTTGTTCGGCAATAACGCTG
TTAATGATTTTACTGTCACAGCTGCTCGATACAACTACTTTTTTTAATAAGTTACAATGCGTCGTACTCAACAAACAACGATAA
CCGCTTTTGATCAATTACAACATTTGATCACAAGAAATCAATCATTTTACAAAGATTTTCTTTTGTTCATTTGTGTCCTAGTAG
TCTTTATAATAATTTTACTCTTTATAATTTTATTATTTGTTCTAACTAAAAACGCATACGAGCGTAGGGAAACTTTTGCTAGTA
ATTTGGATTACAGGAATAGGATGTAAATGAAAATCAAACAGTTTATTAATACATTTATTTTGAATCTGTCGAACCGAAACCGCC
ACAATCCCTTTCGGTAGAAGACAAGGAATCGCTTTCCACCAAAGTCGGAGTGTAGTAACGCTCAAACACAATTTGCGCGACGCT
TTGTCCTCGTTTGAACTGCCGCGTTTTTTTACCGTGATTGAAAAGCAGCACTTTGATTTCGCCTCTGTAGTCGTTGTCGATTAT
GCCGGCGCCCACAACTATTTTGTGATTTGCCGCCAGCCCGCTGCGACTTTCGATCCTTGCATACATATTTGTGGGCATTTCGAT
GGCCAGTCCCATGTTGACGAGGCAGCCGTCACGAGATTTAATAATAAAATCTGTTGGAGTTCTGAGATCGTAGCCCGCCGAACC
TTCCGTCGCCTTTATCGGCATAAAAGCGTTTTTATTTTTTTTAACTTTACAAGAGGTGTTCATGGTTGTGAGTTCCGTTGAACA
ATAAACATGGTTTTTAGTAGTTTTTGTTTTTACAATAACTCGTGTCGCAATCGAAACTGCCACTGATCTTTTTTAAAACATCCA
TGTTCAAATTCAATTTTTTGATGACCGTTAACGATTTGACCTTTCTTTCGGTTTTCAAAGCACACGACGTGCACATGTAACAAT
CGCTAACAAAAATTAAAGCTAAAGGTCCTCTACCTCTGAGACATTTTGCGCCCATGTTGGTGCGGTGTTTTTTGAATCTTTTTT
GTACATTCACTGAAATGCCTGTATAAATGCGATTTTGTACATTTCGAATCAAATATAAAGCCCATAGTTTGGTTGTCATTTTGT
AAGGGCGAATCGCTAATATGTACGCGTATGTTACTTTTGTAATGCTGGGCGACGAATATGTCAAAGGGGCTATCGCGTTGGCTA
AAAGTTTAATTGTGACCGGCACAAAACATGAACTAGTTTGTATGGTCACGAACGATGTTAGCAAATATGCTTTGAAACTACTCT
CGTCTTACTACAAAATCGTAAGTGTAGAGTACATTCATTACAAATGTCCGTCAATGTTGACAAAACGCCAAAACCAACTTTACG
GTACGTGGATAAATTATGCCTTCACCAAATGGACCTGTTTAAAACTGATTCAATACGATAAAATCATCTATTTAGATGCCGACC
ATTTAGTGATTAAAAATATCGATCATATGTTTGATTTAAACGCGCCCGCTATATGTTTCACTGACGAAAGCTATGGGTACTACG
ATAAAATCGTTTACGGTCAAACTATATCGTCGCGCGCTATACAAAAGTTCATGCGCCAAAATAAAGTGCTATGCAAAGGTGGCA
CGGTTCTTTTCGAACCCAATGTTAAACTATTCGAGTTGATAAAGAAGTTGGTCAATAAATCGAATCCATGTTTGACAAGAAACT
ATTACCACAATGGTTTCGATGAACAAGTGTTATTACAAGCCCTCATAAAATTAAACATGCCCATAACGCAGCTATCCATTTTGT
ACGCATGGAACGCAGGCACATACCATCGTTTGAGCAAAAACCACGAACCTTTTGTTATAAATTACTATGGCGATCTTAAACCGT
GGAATTTCGCCGATACAGATGTGATCAATTACATGGATGTGTTTATTTGGAGGTACTTTTCGAATCTAAATCTCTAGTATAAAA
AGCGATTGGCCAGTTTAAATTTCATTCGCTCAACCGACAGCCATCGACGATGTCTCATTATTATTTGATTGAGAAGCTCGACGA
TGCCAGATACAACATCTTCACTTCAGAAGACGAACCTCGAAATCATCGAGGCACCATTATCTACGAAAAGGACCTAAAACGTTT
CGCGCCCATTTATCTTCGATCTCAACTGAAGCACTTGGATAAATATAAAAATGAAAATGACGAGTACGTTTTGGAAAAAGAGCT

TABLE 9-continued

Nucleotide sequence of the *C. peltastica* NPV genome (SEQ ID NO: 2)

```
TGTCGACAAACTAATGTATATGACCGAAATGTATTATAAAAGTATTGAAAGTAGGCTTTAATAAACGTTTTGAAATATATTTTA
TATTTTTTTTGCTAACCTTAACCCAACGAAACTTGAATATGAGTAAAATCTTACTCATATTCAAGTTTCGTTATACTACTAAAA
CGAAACTTGAATATGAGTAAGATTTTACCCCAATTCAGATTTCGATAATATATTTTTTAGTATTCGTTTGTAAATAACGAAACT
TGGATTTGAGTAAAATCCTACTCATATTCAAGTTTCAATTATTGCACCATATTTATGGCATCATCCAATCGAACTTTATCATGA
TAAGATAATCATGTCTCGTGTACAAATTTACAATTTTTTTAAACCATTCTATTGTTGGGTAGCGAGCACGTACGATGGATATG
TGTGTAAAAGAAAACCGACTAAAAACTTTCGAATTATGGCCGGTGAAGTTTTTATCGCCAGAGTTGATGGCTGAAAACGGTTTT
TATTATTTGGGACGCAGTGATGAAGTTCGTTGCGCTTTTTGCAAAGTAGAAATCATGCGTTGGGTGGAAAATGACGATCCCGCT
TTGGACCATCAGAAGTGGGCACCTCAGTGCCCGTTTGTAAGAAAGCAGGTCGACGGTGACGGAAGTTCCGGCGGCCCGGACGAG
TGTGTCGTGAGCTCCTCGCCTAGCATACCCGGCCCTGTACACCCCCGGTACGCCACCGAGCACGCCCGTCTGCAGACCTTTAAG
GATTGGCCCATAAGCATGAAACAAAAACCCCACAAACTTGCCGAAGCGGGTTTCTATTACACCGGTTTGGGCGACAAAACTAAA
TGTTTTTCTGCAATGGTGGCTTAAAAGATTGGGAGGACGATGACGATCCGTGGGAACAGCACGCTAAATGGTATAGCGATTGT
CGTTACGTTATTTTGGTAAAGGGGCAAGATTTTATTCAACGTGTACATTCCGAAGCGGCGGTTGTAAAAAATTATGTTGAAACA
ACCGAAACTGTTGAAGAAATAATTGATGATTCAAAAGTGTGTAAAATTTGCTACAACGCCCCACTTAACGCCGCTTTCAATCCT
TGTGGTCATGTCGTGGCGTGTATCAAATGTTCTGTTTCGGTTAATAAATGTCCTACATGTCGAATGCCTTTTGAAACTATTGTA
AAACTATATTATTCATAATAAAGTTTGTTAATTATTGATGTTTGTTTGAATTTATATTGAATTATGTTTGGATAAAAGCTATAT
ACTAGGTAGGATAAGTAATTTATTAAAATTAACGATCTAACTACAATATAATGTCTGTGTCTATTAAAAAAGTTCAAGACTACG
GCGTGCCGGTGCTGGTCGATCCCGTTACGTGGACGGCCTGGGTCGGCGCGGACGAAGTCCTAAATGTTTTACGTTTGCCATCGT
CGGTGTTACAATCGATTCCGTTGCGCCATAAAAAGTGCTGGTTAGATTTTAGAGGAGGTTTTAATCCAAACAATAATTGTAATG
TTAGTTGCCGGTGGGACACTGGTAAACTTTTCATTGACCTTTACGGTTTAGGATTATTATGTGGTAGAGTAAATTCAAGTTTGT
CTGATTATTTGATGACCCAATTTGTAGGCGAAATTTACAGAGATTATGCGCCTGATGTCTTACCGCAACCTCAACCTCCCTTAC
CGTTCCCCGTACCTCCTCAGCCACCGGTACCGCCGCCGGGCAATTTACCTTTAGAATTACTGGAGCGGCTTAATAGGCAAAGCG
ATTTAATAATTAACGCTTTAAGTCAATTGAGTATCAGTAACTCTAACCAACACTTGGAAATTACAAACCAACTTAACGCTATCC
GATTACAGAACGTGACCATTACCGGTCAGCTAACAAGTATACTTGACATTCTTGAAAATCAATTAGGTAATGTAACTAGCGAAT
TAAACAGGTTGTTGACAGAGTTGGACGGACGTTTCGATAGTTTTGTAAACACGCTGAACAGCGCTCTGTCTGCATTACAAGATA
GTGTTCGAAACGAGTTAACTACAATCAATTCCATACTTAGTAATTTGACTTCGACCGTGACCAATCTGAACTCAACGCTGACCA
ACTTGTTGCAAGCCATCTCCAACTTAAACCTTGGCGATCTTAGCAACGAAATCGAATCCATATCGACTACCGTAGATCAAATAT
TGAGCATTTTAACTCCCGAGATTCAATCGAAAAAAGCTTAAATAAATTACTTAAGACTTAGAATAGGATATAGGATATAGGATA
AGTTTAATTAATTAATAAAAATAGTGTATAAAATTTTTTTATTAAATATTATCATAGGTTTCAACAACTTTATAAATCTTCTC
CACCAAATCATCACAGTATTCGTAGGGTTTCACATCAATAACATTCATGTAATCGTTTCCAATTGTTTCTGATACCATGTCGGC
GGGAGTCGTGGTGATTCCGACCGCTAAACATTGGCCGTGTCTGCTCATAACGGCGTCGATTATATCCAAGTTCATGAGACATTT
TTCGTATATTTCTCGGCCGTTATAATTTTATTGTTAGGTATCGAAAGTACGTATGCAATCAGATTCATTGTAGTACTACATCA
TGAATATTTAAAATCGGTTTATATACTACCATTATTTTTTTTCCAAAATTTACGTAACGCACCTATTGTTATTAAATTATAA
AACTAGTATCTTTTTTAACACTTGAAACGATTTTTGGTTTACTACAAACTTGCCCACTTTTACAGTCTGCCACTCCAATAATAC
CGCAACCTAACCGTCCACCCGAATTGCCCGTAGTTTTGCTAAGAGGATGATCGGTAAGGCCAAGATCGTCACGATTTGTGTGCA
CTACTAAACTGCGGCCCAAAATGCTGTAATTACCATAAAGAGACATGACATTATCGATTATGTCGATTTCGGTGAGCGAATTTG
AGGTTTTCGCTTCAATGTTGCCTAAATCTCCCACGTGTCTTTCCTCTGAGTTGGGCGCGCCGTGATTTTGACCCGTTGGGTTAA
AATGTTCGCCAGCCGACGTACACCCGTTACTTGTATCGCCATATTCGTGCACATGAAATCCGTGCAATCCTTTGGGCAAGTTCA
TAATGTATCCTTGAATTTTTAAAAAGTGCTTTGGTGATTCTTGAATGAAATACACCTCGCCAGTAACGTCACCATCGATTTTAC
AAATGGCTTTCATATCTGCAATCTTATCTAATATGTATAAATTGATGGACGAAAACGCTTTTGGCACATTCGTGTTCAAGCAAG
```

TABLE 9-continued

| Nucleotide sequence of the *C. peltastica* NPV genome (SEQ ID NO: 2) |
|---|
| CGACACAATGGGTCACAATATTGACAGTGTCATTAATCTTGGCGATATGTACTTTTGCGTCCAAGAAAAATACATATTAGTGGA |
| CGAGAAAAAATATTGTTTAGATTGCGCGGCCGATTTCATCATGGAAGATCACATAGTCTGCATCAATCATGGCCCCAAAAACGA |
| TATACAAGATTATTGTTGGAAACTTGAAAATCTATGTTGGAGTTGCGAGAAAAACGTGTATTCGGTTCATCGACTCAAAGATTG |
| CGACAGCTGCACCGAAGTTGTGTTTCAACTTTACGAAAATGTTGTCAATGAAGGCGCCATTTCTGTAACTCTATAGTTTTAAGA |
| ATAAACATTATGAACGAATTTAGTGTTTTTATTTTCGCTGTACTAGTGTCTTTGTTCATAGTTTTCCTTTATTGTGTTAGCACA |
| GTTTCTAAATTAATACAAACAAAAGAAGCCGAATCGTTTTCGCCGGCTTTAGACATAATTTTTGATCGTAACGGCATAGTCGAT |
| TGCAATCTAACCAAACTGCCCTGTGTAACTTCGAGACAATGTTTAGACAATTGTAGCTCTCACAATTTGGTGGGGTCTATTGTG |
| TGCGATGAGGGATTTTGCACTAGTCGCGATTTAAACGTTTCGGGTCGCCCCGATAATTTCGAGTGCGACAGCTCGTTAGGATTG |
| ATTAAAGTTTTTACCGCCAGCGATTTTACCGTGACGAATTTGTGTGTAAGCACATACAGAGACATTATCGACGATTTTGGTAAT |
| AAACGGCCGTATGTATGTGATAATGGCAATCTAACTATCGATCTAACAAATAGGCAATTTAGCGCGGCCGATTGTGTCTGCGAC |
| ACCGGATACACAAGAATGCTATTTAATCAAACGGCCTTAACTCGTTCTGTACCAGTATGTATTCCCGACTCAAACCTAAACATT |
| TACAGCAAAATTTACGATCAAGTATGAAACAAAGTTTCAAGATGAATTACACCGTTGAAGAATACAAACATATTATTTGGGCGT |
| ACGTAATGAACGTTTATGTACAAAACACAAAACTCAGATCGATATGTTTGCGAAAACCCGACGTAAAATATGTAGAAATGGTTG |
| TTAGATTGCTACCCAAAATGGACATGAAAAAATTGTTACCACGGCTGAAAAACATATACGCGCTGCACCGAGTCGACGAATTGT |
| TCAAGGAAACGGACAAAGGAGTTTTAGAATTAATAAATAGTATTAATGAATGTTACAATGAATAAAATGAAGTATTGTTATTTA |
| AGTCTTTTTTTTTACAATGAACGCAGAACATTTGCTCCTTTCCCAGTATGTAAACATACAAAATAGCATAATAGAACTGCAAAA |
| TAACTACCTGGCCAATAGCAAAAACCCCGCGGTTATTGCCGATGTAATTAAAAAGCTTACGAATATTAGAGAGGATAAGTTCCG |
| TACAATAGAATCTAGATTGAATACAATCAATGCTAGCGAGCGAACTGCCACATTTTCACTCATAATTAAAAATGATAAATCGTA |
| TTTGGAAAATTTTTTAAATGTGGTCGATGCAATTTATTATAATACCAATCACGAAATATTTGTTGACGAAAGTTTAGTCGTTAG |
| TCGTGGAGCGTTTTTAGATGACTTGATAAATTATGGCAACATACTCGGCAAGGAAGATTTGATATATTTTAAATATGAAGTCGA |
| GTTGATAGAATTATTGAATAGACCTTTGAAAGAAATAGACTCTGAAATGCTCGAAATCGACCGCATAGATTGCGCATCCATTAT |
| TGTCAAGGCATTTTTTCTAAACAATATTCCAAATGTGAGTTTTGAGTTTTTAAAACAAAATATAGACAACGATATAATAAAAAA |
| GAAACTTTCGGCGATACTTTCCTATATTGCGGGAGTATGTAAAAGAATTCGCGAATGTAAAAATAACGAAAAGGCTATTTTCAC |
| TACATTTAAAATATTTTACACAGAGCAGAATGAAATCAATGACAATTTGACCGTTTATGGTACGTTTGAAAGAAACAAAATTGA |
| TGTAAATATGATTAGTCCTTTGAAATTTAGAGGGGCAACATCACCTGAAAATTTATACGATTTCGTGTTAATGTATACAGAAGG |
| TTTTGGTTCTGTCGAACCTTTCAATGACACTATTAATTTTGAATCCCTTATGTATTTGACGTATCCAGAATTGTTTGCTATGCC |
| GTATTTGTTTAGAAACAGCACTGATAGCGAACATCGTTTTTACAATTTTCAAAATCTTGCAAAATCCAACACGATAGAAGTGGC |
| GAGCAATGGTGGTATAATAATAGAGGAAAACGATCTGGTAAATGTCGACTCTGTCCTGTATGTGAACATCGCATTAATATTTTA |
| CAAGTTTAGGCCTGAATCTCCGCCCGGCACCAAAAGTTTTCTAGACCGACATTTGAATAAAATAAAAACATGTTTATATGAATA |
| CGCCAAAGTGGACGATACTATTACGGTCTATTTAAATCCTAACACTGCAAATTACCACAACGAAGAATATCAATTTTTAATCGA |
| AATGTTGGCCGTGTTACAATTAGGTTTTTTCATTTCTTACAACGCTTTAACAGAGGAAATACGAAGTAACATTAACGACACATT |
| AAACCTAATACCAGACCATTCTCCGCTAACACATATATACGATAAACTTGTCAATTATAACTTTAACATTAGTGGGGATTCTAA |
| CATGGAAAGTGAAACAGATTCTTTTTTATAACAGTTTAATAATATTTATTCGTAACAAAATTTGCCGGGCCTTTTTAACAATTA |
| CAAAAACTGGCCGTGCGCACAAAACATTGTTCACCCAAACACAATCGTCTATTTGCTCGAACTCGTACCGCTCAAAATCGTAGC |
| GATTGTTGACATAAAAATAGTATTCACCATTTCGACGGCGGTAATCGATAGTTTCTTCTCGAACGTGCAGCTCTTGAAACATAT |
| TGTTGACAACGATCTTTACGTGGTCTTTCATAATAAGTGCGTAGTCCAAAATGGATCTGAACATAGATATCGACGACTTTACCA |
| GACTGTTGATCGCTGACAAATGTAACGCATTAATTGCTGCGGAGCGGATGTTGCCCGAAAACATCCTGGCGATAGTCAAAAGCG |
| CCCGCGATAATTATTTTGACGACCCGTCTCCAAAAAATTACGAAAACATCAAGAAACTTTTTAGTCAAACCAAATACGTAGACG |
| ACGCGGTTGATTACAAGGATTTTAACCGTAGAATCATGTTGATCGCTTTCAAATTCGCTTTGAACAAATCGAAAGAATATTTTA |

TABLE 9-continued

| Nucleotide sequence of the *C. peltastica* NPV genome (SEQ ID NO: 2) |
|---|
| AAAACTACAAGTCGGTGTTGGAGGTAGCGCTCAAACGACTCGACGGTATAAATCCCGACTTGAAAAGTTCACCGCGCGCCATGT |
| TACAACATTACAACGAGTGTTTAGAAAACTTGGACAATCCGCGTAACGACGAACATCACCTGGTCACTTTTGCCAAAGAAATTG |
| CTACAAAAATTTTTATTGAGACCATCGATTTGTACAGTTACAATAATAAAAGTCCATTCGAAAACGGCAACGCAACATTGACAG |
| GTTCCGATTCTGAGTTGCTGGCCGTAGCCGCGGCGAGCCGAAAACGGAAAAAAAATAGCATTTTGACCTACAAAATTGTCGATC |
| CCATTTTCGTTTTGTAGAGTTTAGTTTAAAAATATTTTTTTGCGCTCCAAAATTAACGAACGACACATAACACATTGATCGACT |
| TTGGATGCGCAATTTTCGCAACATACTAAATGACGACACGGTTCAAACAGAATACTTTTTTTGCCGACCATGCAAACTACGCAC |
| ACGAAATCATATTTGGGTGTTTCGGTTGGAACAAAATCGGGCCGCGTTTCTTCGTCAAGTTTTGAGAGAACATATTTACACTTG |
| GGCGAATATTTAATGTGTTCTATCAAATAATCACTTTCAATTTCGGTCCAGTTAAAAATTCCATATTGCAATCTTTGCATTTAA |
| TTTTGTTTTGGTTACAGTAGACGAACCCAGCATTTTCGATTTTATCCATTACGTGTAATCATTGTAAATAATTTAGTATAAAAG |
| AGGAGACAGGTCCTTATAATAAATAAAACACATTTTTGTTATAACTGTTTTTTATTAAAACATATCATTTTCATACTTGAACTT |
| GATTCCGCATGCGTGAGCAAACACCGTGTCTTTGTTTGTCGTACCATTATGATTGTCTCCGCAAAAAAAACTGTTTTTACAATC |
| GATCGAGGGATTCATTTGCAAAAGTTTTTCAAAGAATCCCGTCGATGGAAGCTTGTATTGAATAGTATGAGACATCATAACAAA |
| CATGGGCACGGCAATTTGCTTACACACATCCTCAATTTCACGATCCTTACTAAAATTAGACACGAGAACAATAGTAAAGTCTTG |
| GTTAATTAAATTCGTAAATTTGTAGACTATGTTGTCGTACTTAAACTGCCAATTATTATTAACTTTAAGCATTATAGTTTCGTT |
| TAAATCAAAAATGGCTACTTTATTTTTCAGTATAGGCAAGCGGTGGTGATAAATACTCAAAGAATTAGTAATTTCCCACCGAAA |
| GATTATTTTCAAAATGTAGTTGATTATTTCTTCCTGTTGTTCATCTAGAGAAACCTTAGTGTCCACGATTATTTCGTCGTAATT |
| CATCACTCTGCGCCAGCAATCAAACTTTTCGTTCTGCTTGGTAACATAATCCGCTTCGTGTATGTCCAGACCATTGTTGCGTTT |
| CTTCATCATTTTAACAATCTCGTTTTCACTTCCTTGTTTTACGCGTAAAATTAAAGACTTCCAACCGTCACAAAGCCCCATATT |
| CTTGCAAATTTCAAAGGCTTGTTCCGATTCTTGTTCGGGCATGTCTTGGAACACTGCCGAATACACCAACGCCTCCATGGGTTG |
| ACGATCGAAAATGTGAAAACGAGAATGGTCACGCTTGTATGTTTCAGCGCTCTTGCTGCGATACGCCGCGAAAAGCATACCGCC |
| CACATTGCTGGGGTAATTATACTTGTCGTGTAATTCTTTGTAATCCTCTAAGTGGACACGAGCGTGAGGGATTCTATCTTCCAA |
| CCTTTTAAGGATGGTAGTTTTTGTGGTGCAAGCTACACCTCCCAAAGCGAATAAGTACGACATGATGTGACGGTAATAATGTTT |
| GAAAAGAAATCCGTTATTCTTTATATAGTGTATTAATTATCTATAGTAGATTAATTATATATAGTAGATTAATTATCTATAGTG |
| TCGTCTGAAAGTCAAAGTCATCAAACGAAAATAAGATATGAGTAAATTTTTACCCCAATTCAAAGTTCATATACTATTAAAAAC |
| GAAACTCGAATATGAGTAAGATTTTACTCAAATTCGAGTTTCGACAAACGAAATTTATATATGAGTAAAATCCTACTCATATTC |
| CAGTTTCGTTGTTGATATCCACCAGAGCGAACGTGCGTTATTTTATATTATAATGGATTATAGTGCAAACTTGATTATAGACGG |
| CATATATCTAGGGGAATATGCTTTAGAACTAAACTATATGCGCAAATTTATCCATGACAACGACATCACCAGCGTCCTGTCCGT |
| CTTTGATAGCCCGCCCATTGAAAACATTGCACCAAATTATCTCTACGTTTATTGCGAAGACGATGAAAACGACGAAAACATGGA |
| ATCGCGTTTGGACGACATGTACGAATTTTTAGAGAAAGCCGTTCAGAGGCGCGAAAAAATACTGGTTCACTGCCACGCTGGAAT |
| ATCAAGATCGGCCACCGTGGTCATTTACTACATTATGAAGACCTATCGGAAAAGTTTTAAAGACGCTTTCAACATGGTCAATGA |
| GAAACGGTCCATATGGCCCAATGATCATTTTAAACGCATCTTGAAGAAAAAAATTAACAAATAAACAATTATTATTTGTAACAA |
| ATGTTTTTTATTTAATGAAATGATATTAGCGTATCAATTTTTGTATTCATTTCGTCAATTTTTTTACTATTATTCGTAACTAGT |
| TGAATCGTTTCCATTGTGGTGTTGTGGATTTGGTTTAGGAAAAACATGGTCTCGTTGCGCATGTGTTTTATTTCTCGAGTCATG |
| GTATAGAACTTTGTCTCGATCATTTCGTATGTGTCAGAGAGCAATTCTTTGATGGCGTTTATTTCCTCCATGAGCGAACCCGCA |
| TGCCACAAGTATGCCAACAACAAAACCAACGCCACACACGAATAGTTCATTTTGATTTTTGAATGGGTCCTCTTATTTTTTACG |
| AACAATCATGTCTTTTAGCGATTTAAAGTTATCAAGCATAGTATCATTGCTGTACGCTAGTTTGTTTGTTAAATCGATTTGTAA |
| CGATTTTATATTTTCCAAAGCCAGATTAAAATTACTTAACAGAGTGTTGTGCTCGTTTCTTAGCAAATCACGTAGAGAGTCGGT |
| CCAACTGCTCGAAGAATCATACACGGTTGGTTGATATATCGAATCTGGCGAGTCCGATTTGGGCGCGCCGTTGGTTAGGCAATC |
| TTTAATGTGACAAATTTGACTCTTGATATCCGACAGAGGGTCCACCACTTGACTCTGCACACCCATCATCAAATCGCAAACGAT |

TABLE 9-continued

Nucleotide sequence of the *C. peltastica* NPV genome (SEQ ID NO: 2)

```
TCTTTTGATTAGGCTCAACTGTTGAGTGTTAATTGATGAAGCTAAATTTAACGTGGCCAAATATTTACACAGCGTGAAAACATG
AACGTAGTTTTTGTTATTTCTAGTGAGACGCTGCGAAGGAATTACATTTGCCCAAAGCACGGCTTTGTTAAATCCCCTAATAGT
GACAATGTGTGCGAGTAAATCTGCCGCAGCGCCTAATTCTATGTAACCGTCCCTGTCATCTTCGCCGTTTTCAATTATTACCAC
TTCGATACTTTCATCGTTGTAATGAAACCGAGTCGCCTCAGAATTATGAACGGGTGTATTTTTATACATGTCGGTAATGTCTTA
TATTTGTACCGGACCATAAGCTAAGTTAATTTGATTTTTTGAATTAATTATTTCATCATGAATTACAACCATCGCGACGTATAT
CGTCGCCGCTACGATAGACTTAGCGAAAAATACAATGCCGTGCTACATCAGCACGAAAACTTAAAATCCGACTTGCGCCATTTA
AAAATGCAGATTCATGAGGTTTGTCGCAATTCTGTTGGCGCGGATAACGTTATATGTGAGCGTATACTAAACAATACACCCTTG
TTAGATAATACTATCCACCCTCGAAACGACTATACAACAGCATTAGTCAAGGACAAGACGCCTCAACGTAAGCACATGTACAAT
GACGGAAAGCCGTTGGTTAGTGTGGAACCCTTCGATTAAAGCATCACAAATTGACCACGATGCCATGTATCTAATTTCCATGGA
AGACTTTGATGTAGAAGTTTCGCCGTACACCGTGTTTGAGCCTTGCGGTTCAATGAAAGTGTTCATCACGGGTTGTAAACTTTA
TGATATGATTAAAGTTTCTTTAGAGAACGAGCACAAAGTCATGTTGAAACGGTCATCTTCCAACGGCGAAGACAGACTTAACAA
CAAGTTTATGAAAAAAAGTCATCGAAACGTTTGTTTCAATCGGGTGACTGATAGAGCCAGCATTATAGGATTATTGAAAATATC
ATTGAAAATGCCCGAATGTATGGAGAATATTTTTGTGTCTTTGATAGAGTCGCCGAGAGGAGGCAAGCACTACACACGTTTTGT
TTTCAATTGCTATGTTTGTAACCTGTTAACTTGCACAAAGTGTAACAAGCGTTGTTTGGCTTCCGCTTTGTGTACTTTATATCA
TAATGACGATAAATGTGTTAACGAAGTGGAAAGCGCGCTTTTTAAAAAAGAAACCATCTACAAGCCACCCAACTGTGACAATAT
GAAAAGGAAAAAGTTATGTTCGCCTTCTAAGCAGTGTTATGTTAAGAACCCTTTATGTATGTTTAATAAAAATATAAGCACAT
CTTTTTTGTTTTATTTAAGAGTATAAATAAAAATGTCTTTTGACGAACGAATTATTAGCCTGTGTTCGAAGGAAAAAGATCTG
CGATCACAATATGAATCCAAAGTGAATTCGTTTTTTAAAAATAAAGGTATGAAAAAATCTGTAGACATATTGCAAAACGAATTA
CACCAGTTGGATGCCCTCATATTTGGTTACGAAGAACAGATTCATTTCCTGAGCACGAACAATAATGTCGCTCGCCAAGAAATG
GTGGACAACGTTAACGATTTGGATCATTTGGGTATAGACAAAAACTTCATTGAAAGAATGATCGTGGACAAATTAGATGATTCT
TTATTTGAAATATACAATACAGAAATTCTCAACGAAAATATAATTAAAACCTTTAGAAAACATAGTAATAAATTTGTTAAAGTT
TTGTGTCAATTTGACGACAAACGAAAAGCTTACAGTAAAAAGAGTTTAATAGAGAAAAAAACAAGAAAAATATTGATGAAAAC
AACAATTTATTAGTAGAATTAATTTTATTAAAATCAAACTTGGTGTTTCATTTATGTACAATGGAAAAAATTCTCGTGAACAGC
GCTAACAAAAACATAATCAAAAAAATTGCATAATATTCATGATTTTTGATTTCATGTTTTCAATCTCGTTAATGTCTCCGTATT
CTTGTATAGTTGTTATGTTTCCATGTGTTCTTTGCAAAATATATCATAGTTTTTAAAGTTGACAAATCCATTGTCATCCAACGA
AAAACAATCTTCGCACACGGCCAGGGACACGTTGGCACCGTGCACAACAAACAAGGGACAAAGTGATTCTTCAAAATCGTGTC
TGCTAAAATCGCATTGTGACCCGGCAGCTGCGTCTTGATTTCCAGTATATATGCGGCGATCTGCATGATTATTGTGACTGAAGG
AAAACTTCGCTTTCACTTTCGTTATATATTTTTTTGAAATCAAATAAATCATTAAGAATGTATCTACTGTTATTATTGTTAAC
CCTGCTATTTTTGTCTCTCCTCTATAAACCGCTGTACGATGCCTACACTAAAATTAAAGAAACCCAAACACACTACAATGCTAC
GGTCGATGATCGCATCGATTACATGGAGACCGTTTTAAAACATCGTCGTTTCGTGCCTCTGCATGTTTTACCAAACGTAATTTT
CAACACTAATTTGGGTACGCTTAACGAAGGCGATGTCAAATGTTTATCGGTCCCAATGTACGTTGGCATTTACGATACTCCCAA
TTTTGATTGTACAGCTTTATGTGACAATCCGTCGGCAGTTTATTTTTACGTAAACGAATATGACAAATTCGTTATCAACGGAGA
TTTATTACCAAGAGGCGGTTATTGTACCACTAGTAGCGTGCCTCGCAATTGTAACAGGGAAACTAGCGTAATTTTGCACAGTTT
AAATCAATGGTCTTGTATAGCCGAAGATCCTCGCTACTTTGCCGGTCCCCAAAATATGACCCAAGTCGCCGGTCGCCAGCATGC
GGACAAAATATTACCGGGACAAGTCGATAAAAATGTGCTAACAGATCGGCTTTTAGGAACCGAAGTTGACGTTTCCAAAAACAC
TTTTAGGTCGCATTGGGACGAGCTATTAGACGACGGCACGAGGCGTTTCGAAATGCGCTGCAACGCCAAAGACAATCATAACAA
TCAAATGTTTCTCAACCCGTTCAATCTCATCGAGTGTCTGCCCAACGTGTGCACAAATGTCAATAACGTTCACCCCAGTGTCAG
ACCCATATTCGAAACTGGCGAATGCGATTGTGGAGATTCTAACATCACCCGTCTAACACACATAATTCCCGGTGACCGCACGTC
CATGTGCGCATCCGTAGTCGATGGTTTCAATCGAGATTCGATGTCGCATCAATTTAGAGTTGAATGCGTGAACATGGACATGCT
```

TABLE 9-continued

| Nucleotide sequence of the *C. peltastica* NPV genome (SEQ ID NO: 2) |
|---|
| GTTATCGGAATTCAGCAGTACTAAACCCCTTTGTCCCCCTGATACTTTTACCCAAAACACAGACAACGCATTTTTGTTCGAATT |
| GCCAGGTTCTTTTCCTTTTTCGGGCAACGGTATCGACGAGCCCACTTATAGAGTGTACATGGAAACTAGGAACAGGATAAATTA |
| TAACACAACAAGAAGTATACCAAATTAATTTATTTTTTTAATAGTAAAGTTTAAATGAAACAATCGATTTAATTCTTGCAAGTA |
| AATTTTCCAACACTTTGAAAAATATCCTTGTTCTTTAACATACGGGAAGTTTATCTGGTGGGTGATGTCCGTTATGCTGTTTCG |
| AAATCGGCCGGCGAAATATAATTCAATAACGAGGCGTGCCCCAAGCCGCGGGTTAGTTTTGTAAAACAGCGTTTTTACGTTCCT |
| GATGTTGATCATGTTTTTGTCTCGCTTTATGTTTGCATATTTTTGTAATTGCTTTTCTGTGGTCGGCATGTTGTACGACCGCAA |
| CAGGTCCTTCAAAATCTCCAATCGGTTTTGGATTGAAGGCACGCGATTAAATACATCAAACAACAAGCATTCCAGTTGATCGGC |
| GATAGTGAGATTGATATTTACCACACAAACATATGTGTCGAACTTTTCGACCAAATTGTACAAATTTATTTTTTCATAACTATT |
| CTTTATAACTAAATCCAGAAAGTAAACATCGAACGGAAAGTAAACGTACGTGTTAACCGAATTGTCAGATTTGTAGTTCCAAAT |
| TGGAGATGCGCTTTTCATGTGTACATTAAACGAAAACCGTACCAGCAAAAACTCGTCGTTCACCCACGAAGAAGTGGTTTTGAA |
| CGGAGCATTGCGATTGATTTCAAAGTAAACATCGTTCACAGAATCGATTTTAATCGCTTCGTTTACGTACGATTTGAAGAACAC |
| GAGTCCATTATTAAATTCTTGATCGAACTTGCTACCGTCAATTTGGTTCAGCATAAATTTCATGTCAATCATTTTTAATGTTTG |
| TTCGACTTTTATGATGTCGTCTCGAAATTCATTTGAAATGGCATTTTCGAATAAGGCTATTGGTAACGTTTCTAATGCGTTTTT |
| TCCCTCATTGATATTGTCCAAGTAAATTTCAATGTTTAGATTGTTCGTCAGCTTGTAGGGTTTGATGGTTCGGTAATAGTCCGT |
| GTAGCTATCGATAGCAAACGTGCCTTTGATTATGGAGAATTGATCTTCGAAAACGTTTCTAAAAGTTTTGTATAGTTTACAAAA |
| AAAGTTTTTGTCGAACCGGTCTAAAACATCGCTGCAAAGTTGATCATTTATATTTTTTTTTGAAATATAAGGTATGGTTTTTAA |
| ATAAAACAATTGTTGACGCAGGGATTCCATAATGAACAAGGCGGCGTTAACTTCGCGACGTCTTAATAATGCACAAAATATTTT |
| GGCCACTATTGTGGATATCAATTCTCTTCTTAACGTAACGGACACCAGAAACAAAAGATTGTTTTACAATTTGTGCTCGCGCTA |
| TATAAATCAAACACTATTTCAATTTACGAAAGGAAATATGGCGCTAGCCACCGTTCAGACGGTTTTGGATAGCGTCATATCTGC |
| AGAACGTATGTTTTTCTCAAAAAGCAATGTGCTAAATATCATTGTAAACTTTCTGACCGCGCACAGCGACGGTGATAACCTACA |
| GTGTATGATTAATTTAAAACTCCTAGACTATTTTTTACACAAGTATTATTAAATAAAAATACACATGAAAAAGTTTGATTGTTA |
| TTTATTAAAATCTTACACATGAAATTATACAAGGTAAAATACACATGAAAAGTTTGATTATACAATTGATATTTATAAAAATCT |
| TAATATATACATGATTGTTATTTATTAAAAATCTTCCATAATCTCAAATTTGTCATCTCCGGCCCCGAACCGCTTGTACTCGCC |
| AACTCGCCTTTCGAAAAAATTCGTTTTGCCTTCCAACGAAATGTTGTTCATGAAGTCAAATGGATTGGTCGCGTGAAAGTACTT |
| TTCTTGATTTAGCGCCACCAAAAGACGATCCGCAACAAACTCAATATATTGACACATTGATTTTGAGTTCATGCCCAGCATATC |
| GCAAGGAATGGCAGTAGTGAAAAATTCCTTTTCAATTTCCACAGCTTCTTTAAACATACTCAATATTTCCGACGAAGTCAGTTT |
| GTCATTCTCAGCAATGTAATTGTTATAGTATAAACAAGCAAAGTCGGTATGCAAACCTTCGTCTCTGCTGATTAATTCATTGCT |
| AAACGTCAGACCCGGCATGACTCCTTTGGTTTTTAAAAAAAATATAGCCGCGAAACTGCCAGAGAAAAATACGCCCTCCACTAT |
| AGCAAACGCGACCATACGTCGAGCCAGTCTGCTTCCTTGCGAAACTTTTGTGGGAGTTTTCTTGAAATAATTATACACTTGCTG |
| TACGGGATATACGATGAATCTATCCCACAGAGTTTGTTTCTCTTTGTTATCGTCTTCAATCCATTTCATGGCCCAGCGCGCTTT |
| GTTTCTCACACAATCGACATCATCGAAAGCATTGAGTAACATGTCACGTTCGGTTTCGTTTGAAATGTACTCAAAAATCAGCAA |
| ATTGTACATTTCTGTGTGTACATTCTCAATGAGTATTTGCTGGTCGTAAAAGTAGCGGGCTTCCAGCTCTGACACAGCGTCTCG |
| CACATATTCTATGAGGTTGATGTTGACGATGCTGTCGGCGGCAGCAAAGAAGGCCAGAACATGTTTCAAAAAGTGCCTTTCGTT |
| GTCATTGAGCTTTGCCATGTAGTCGTCGTAATCTTTTGACAGATCGACTTCCTCGACTTTCCACATACAATCGAGTGCCTTTTT |
| GTAAGCCTCCCATAGTTTGAAATGTTGAATGGGCAAAAGTACCTTGCGTGTGTTGGACATGTTGAAGAATAATAATAAATTGAG |
| GCTGCGACGCCTTTTATACCAATCAGGAGTAGTACCTCTCACCTACGTCATCGCCTACTCTCGCCTTTGTGCCGGATAGCGTCC |
| ACAGTAGTATTCGTTGATATTTTGATATTACAATATTTATAAAACGGGTCACATACGGATTTTTTTTCAGTTAAAATGGAGACT |
| CTGTCGCCCGAGCAATTAATTGTGTACAATAAATTTATGTACAGTAATTATGTAACAAATTTGACATGTCCAACTTCAAGACTA |
| GACACTGAAACCATTTTAAAAGTGGAAAAACTGACGAGGGGACAATCCGATAATGCGCTATGGGTTTTGCTGCGAATGGACAGA |

TABLE 9-continued

Nucleotide sequence of the *C. peltastica* NPV genome (SEQ ID NO: 2)

CATACGGCTTCGGGCTCGCCTTTGTCCTACAGCACATCGCCGACGTTGGCCATGACGTTTGGCCACAATCAAGAGCGTTTGGTC
AAAACGAAACACGCTCTGTTGGATTTGCTCGAAAACACCATTGAAACCGCGCTAGGATGCAGCGTGGTGGAGCGCGTTCTCGAT
TGTGGCATGTTTTTTTCATCAATGGGTTTGTTTTCGGCGTCGCCCGACGCTTACTTCGCCACCAACAAGGGCCAGTACATTCCG
ATTGAAATAAAGTGTCCTTACACGTATAAAGATGTGACTATTGACGAAATCAGAAACGAAATGAAAACGCGCAAAAGTCGCTAT
CGTGTTAAGCACACTGCGTTTTCGTTAAACAAACCGGACCGCCGATTTTCAGTGTAGAAAAACGGATCCTCATTACAGACAA
ATGCAGAGACAAATGTATGTTATGCGTGCCCCTATTTGCATATACGTAGTAAGTTTCAAGGACCATTTCGTGGCAAGCACAGTT
GAACGTGACGATGAATTCTATTTGTCAGAGTACAAAAAAGAAAAGAACATTTTTGATATGTTTGTCCGGTCAAATGGGCTTGCG
AAACGCATGAAAAACCAACGAAATCGGATTGCTACTTTTCAAAATACTAATAAATTTAGAAAAGAAGATGTACTGAAGTTGACA
CGAAGAGGTTTGTACTTGAAAAACGGCGAAATTATTTGCGCAATTTGCGCGACAAAGTCCGACAGCGACATTGATATATCAACG
GTCCTAGATTTACACGAGCAGTGCATGGATCATAAAGACAACGAGAACATTATTGAATGTAAACATCAAAAATTTTTCAATCAT
TCCACCAGGATGAAGTCACTGATTGCGGCGAACGTGGACTCTTCACATGCCAAATGGGGTTTATTTCACGAAGACGGTTTGTTT
AAAACCTTTTGTTGTGACATGATCGTTACAGATTTTGTGCCAAACCACGCTACTGATTGTGATTTTGCTCAGATTAGATTATTT
AGATAAAGTTAATCTTTTTATTGATAAGTTTACTATATAAATCGACTAATGTCCCATCGTTTCATCATTCTTATTGGTCTCCTT
TAAAGGAATTAATAACATTTGGAATCTTTGAATTAATAACATTTGGTAAGTTTCTCTCTCTATAATTATATAATTAATTTAG
AAGATGTAATTGTTAGTATGTTTATTCATTTTCTTTTATTGTTTTCAGGTAACATGTCTCTTCCTCTCAAAAATCCCTGCAG
CTTATATTCTCTTTCTATTAAAGAAATAAAGAAGCGAATATTAGATGAAAATAGTTTTAAGGATTGTCACTTCCTAAAGTTAT
TATTTCCGATTTGGAAACTTTGTATGCTGAGATGCCTCCAGGATGGTATTATTGTCCGAGAAGATTAATATGTGTTGTCGATAA
AGATCTTTTTGATTTTAATATTCACAAAGAAATTTGTGAGTATTACAAACAAAAAAATCTTGTTGATTTCTATGAATGTATAAA
TACGTATGTTTACTGGCGGTGTTCTGATGAAATTCCTCCAGAAAACGATCTTCATTTGCAAATTGATTTGCTTCAAAATTTCAT
AATGAGATTCTTTCGTTTAGGTGATGGAATGTTTATAAAACCTTGGATGGGAGGCGCACTTGAATTGTCAAATAATCGTAATAC
TAAACTCATTAAATATGTAGAAGTAGATGATGATGATGATTATAAAGAAACGCCTCCTTCTTGGTTGAAGCTTGTTAAATTTAA
CGATGTAGATCAAAAATGCTGTTAAAATAAACACAAATGAAACATGTAATAATTATTAAATAAAATTTATTATATTCAAATGA
GTGTATTTATTTAATTAAGTATTTTTTAATAGAAAGGTATGAAATTTTTAATCGCGCTTTTAGCCGTTGGCTTGGCAAAGGCGG
CACCGTCGGGCGGTTTACCGTTGTTGGCAGAGACAGAAACTCTCATTCAAATATTCGTCAACCACCAATATTTAACTGGGTCAA
AGAATGGCACAGTGTCAGGTGGTCAGGATAAAAGTTTGAAAGGCACATATTGGCGAAGAAGTAACGAAAACGGAAAACAGATTT
TGCTTAGAAACGCCGCATACTGTTATTATTTGTGTATAAACGAGTGCGGTTATTATTATACAGCGAAAGAGCCCAATTCAGAAT
GTTTATTGGGAGAATCTTTCACAGACTTTGCTTATACACAGATGTTCAAAGATCACGGTAAAAAGAAGGCTTATGTGGCTTTGA
GCCAGTCGGGAAAGATTAGAAGACTAATGAGTAAAAAACTATCAAACAGCAAACTGTTAAACGCGTCAAAAATGACCATTATTA
GAGATACTGTCGAATACACGTTTGAGTGTAACAAAATTCTCAAAACAAAATTGAAATTTGTGCCGGTAAAAACTTGTGTGAATC
CACCCAAAAGGATGAACCACAAGAACGAAGCCGCCGACGATGATTATGATGATGAATCTGTGGAGACTGTTCAAAATTACTACC
ACTTTGGTGAAGACGAGATCCATTTTAATCTGTTGACAACAGATCCCATAACCACAACAACGACCGAATCGTCAAAAAATTCAT
CTTTAGATCGTGTAATCGACAAGCTAATAAATATTGATGTGGTGGCGGATCTACCGTCCGAACATTTTGTTATAAACAATCTAG
TTGTAAATCAAATGTGTAAAATTTAACTACTTTTTCAATAAAACAAATTTTTTAAAGTCTGTTTATTTGTTTCAATTTTAGCA
TGTAACTCTATAATTGAATCCAAACATTGATCCATCAATTGTTGGTTCTTTACTTCACCCCTCTCTATGTAGTCTAACGCTTTT
TCGTAACATATCAGCGATCTTTTATAATATCCAATCTTTTCAAACAAACGTGCTAACGTGAGACTTTCATTTAGGTTTTCGATA
TCGTTTTCCATGTTAATTTACAGAGTAATTTGAATAAGTATTCAACACTTCGGCTAGTCCCGTTGGATTGTTGGTGTTGACTCT
ATTTCCTTGAACCAAAGCCACAACGCTATAGTCGCGTATATTGGGTAAAATTGCAAACAAAACGTTGATTCGTAACGCCACGGG
ATATATGTTATTTCGATATCGGGTCGCTGGACTCCATATACGCAACAAAGTTCCGTTCCTACTTAAAAAGCACCACGAATTAGT
AAAAGTTTCCGCGGTCCAAACTTGCGCATTGCCATGGCGTCTTATACAATCATTATGGTTTGCCGTTATACATCTGCCCTCCTC

TABLE 9-continued

Nucleotide sequence of the *C. peltastica* NPV genome (SEQ ID NO: 2)

```
GCCGGGATATAAACATGGCGATGAAGTTCTCGCCGACAATTGAATGTACCTATCAAATAAACTTTGATGGCTAATGTCAGTAAC
GTTTTGGTCAAGCAAATGTTCGTTTCGGGCGTGTAGGCCGTGGAAAACTTTAGTATCATAAAACCTGTATGGCTAATATCGGG
ATGGTTGGTCAAGTACGGGTAGAGAATTGAGGCGTAACGTTCGTGGCTAAGTTGATTCACTCTAACCATTGCTACAACATCATC
GTCTGACCGCGTCGTGTCCGATTGTGCCCAGAAAAACTTGTAGTCTAATTTTCTTAAAAACAATAACGATTGGTTAAACGGACG
AATACATGCGTTGGAAACATTGGCGCTAGATTGACCAATCATTGTTTCATTAGTGGGACTGTAAACAGCAAACAAAGCGTCAAC
CACGGGACAACTACAATATTTGTATTCAATGTTGGAGTTTTCATTTTTGTAATACATTAGTTTTCCTAAAGTGCGCTGACCGCT
AATGGGATCTATCGAGCAGGGATCCGCCACGCAAATATCATTTAGTCTGAGTTCTTGACGATAGCGTTCGTGAAGCGCTGGATG
ATCCAATCTAACGAAACCCGCTTCGCAAGGTGCGCGATGAAAAAATCGTTGATCGTAAATCACGTCTCGCACCGTCAACGGTCG
GCAAAACGGCGTTTCTGTTTCTGAATTGAAATCAGACACGTAACCTTCGTTACACTGACAACGTAGCGGGCGTTCGTGTAAATC
TACTATTGAGCCGTTGGGTTGACAGCCGACACTGACATTGCAATCTTCGTACATATTTAGCTGTGTAACCAAACCTGGTGTAAT
GCATGAACATAACAATGAAAATCCCGTCGAACTTTCGGCCAACAACCAAATTCCTGTGTTGGGATTGCACGAACGTGCTCTGTT
TCGATCGAGAGCCATGCAATACGATTCGCCCGCCTCGATGACTTTTTCGATTTCGTTGCCGTCCGTGTCGTGCATCGTAATTAC
TGTACGATCGTCAAATTGCTGGCAATTTGCCAAACCCTCTCGGCAAATATCGCAATCCATATGTGTGTTGCACGGTGTAAGAGT
TTTATGACATTCGTGCGAATTGCCTTCGATAATAATTTCAGAGGGAGGTTCAATTAAAGGAGTTTCAGAATTGTCAAAACGAAG
TAACACGGTTTGAGCGGGTTCATAATCAGTTTTTAATAATATTATCAAAGTGGCTAGGATGATTACAATAATAATGAAACATAC
GATTATTACAATCATTGTAAAACTTACATTTTATTTTTATAAAAGTTAGATTCTTCCTTTTCGTTGTCGTCGTCAAATTTGTTT
ACAGGCTTACCGTTTTTATTTAATAATTTCATCATAAAACTAGGTTGGTTATCCTCAACGTAATGAAGTTGATTGTTAACCCGA
ATTACCGATGGCTTGTCCGATTTGCAACATTCAAACAATTTGCTGATCGTCCCCGCACAACAGCAGTTGTATATTTTGAAAATT
AGCAAGAAAGCAAACGCTAAAATTATACATACAATAATCGTTTCGGCTGTTCTACATTTGAGACCAAACCAGCTGGCGAACCAG
CACATCCAACTTTCCGCCGTGGCTTGATCCGTTTCTTCAACCATGGTGTTATTGTTCATACGATGTCTCAAATCTATCAGGCGT
TCGGTCATGCCTTTCAAATTGGTATGGTCGAGATCGCTGTTAGAGTTTATCGCCAACACATTTAGTTTGTCGATATCGTTTATA
GCCGCCGTTAAATTAAAGGTCGAACTAATGGGCACTGTTATCATCGTCTTTAGAGCTACTGTGTTTTTAATTTTTCTCAAACTC
AAAATCACCTTTTTGGTATTCATTACACAATTCTTTGTACCATCTCCTCGAATAATACCCGTGCCCGCCTTGAGGTGATACTCA
AGCACGGTGCATCCAAACAAAAGATCGGTGTCCTTTTCGAGAACATACAACCAGTTGTTGTAGTCTGAAATGGGGTAAAAAATT
TCACTATCGAATTTGCCCACACGAACATCGCAATCCTTTTCAAAATCAATATTTTCAACATCATTATTGAGTAGTATTTTTATG
TCGCACAATTTGGCTTGGTTAGATTCGTATATGATTTGCGGTTTGGAGCAAAACATTCTGTCGTGTAAAGTTTGACAATACGGA
CTATCATCTAAACGCACATAGTTGCGGCGATCTTTTGACAATCCAATGTATTTGCTGTTGGGCAAAACTATGGCACATTTGTGT
TCGCCATTTTTGGCCCGACACATTGGTATAGGAATGACTTGAAACAGATTATATTCCACGTTGTTAATGAGGGGAATTTCGACA
ATAAAAATAATTTTTCTCATGTTAGTAATGAAAACGTGGCTTTTAACAAAGTTGTCTATCAAAATGTTCATACCGTTCATGTCA
GATGAAACGGGCCACGCTAAGTTTGCGGGCAAATGTATATTTATAATTTCGTTAAGCAATCGTTTGGGCGTTAGAACTAAAGAA
TTTAAATGGTTTTGTTTTGCATCGTCCACCGACTTTTCCAAGTTTTCATACAAAAATTCAATTTGATTTAGCTGCTCTTGAATC
AAATCGAACTTGGCCACGATATAACTGCAATATTCTGATCGTTTCTCATCGATGCATTTTTATGTTCTTCGAACGAAGCCATT
TTTATTAATTCGTCTGTTAGCGATTTTACTTGTTCGTTAAGGGCGTTATTGTTTTGGCAAGTTCATTGAGTCGCTCAGCGTCA
TTACTGTCCATAACTCCGAAAAGATACTTGTCAACATTGCCCACAAAATTGAACAGTCCTCTTTTTTTACGAGTGTGTAGACTC
AAATCTTTGTGATCTTCAAAACTGCCAGCTTTTTGAATTTTCGAATCCAGAGTATTATGATTGTTAACCAAATCTTTGATGCGT
TTCATAATGATATTTTTATGCCCATACTAACTAGATTGGATTGAACGCAACTACTAGACGCGTTTGTGGCGGTTTCGATTTCG
CTCAACAACTTCAACGACTCTTCGTGTAGAGCGTTGAGTTCTTGAAAAACTTTGCTGTGATCCATTTCGATTACAAAATTCCAT
ATGTTTTCTATGAATTGCATTCTGTTAGTTGGTTGGTAATAAAGTCCCGAAGTGTTAGGTAGTCGCTCTACGGTTATCAAGTTT
TCAACACGAATTTCGCTCGTAACTACTAATCCTGCCATTGAGGCCGTTAATAAAACACACAAAAGTGTCGTGGTCATTTTGAAA
```

TABLE 9-continued

Nucleotide sequence of the *C. peltastica* NPV genome (SEQ ID NO: 2)

AATATAATAGCTCGTTGATACCCTTATTAAACTTTTATTTTTGATAATTATTCACAACTCGTCAATATGCGAAACGTGTCGAAT
CTATTGTTCTCGTTTTTAAATATTATCGTTTTTAAAAAAATTTGTGCTCATAATAATGAAATTAGTAAAATCGATTCGTTAGTC
GAATCATGCATCGATGTCAAGTTTAGTTCTGGTGAGTGTGAAAATAAATCCCTAATGGAAAAGTTCGATAAACAAACGTTTGAC
TTTGGCACCGCAAACGGCGTGAAACACTATACTTCGTGGCTATGTTTAATGAATAACATGGAATATTTTTCGCCGTACGATAAA
CCTCGATTGTTCAAAATTATGGCGCGCCACAATAACGCCATTGCAAAAATCGACGGTAAAAACATAACTAATGAAATGCGCCGA
GTAAGTTCCGAAATGTTTCGATGGACATCCGACACGCTGACCAGATACCACGATCTGCAAATTATCTATGATACTTTCGATTCG
TTTTATAATATGTTTAACACGTTCGTTTTATGGACGGGGCCGGGCAGTTTGTACCACTTTAACACGATTCTCTACGCGTACAAA
AACGTGAGACATGCGAAATGTGCCAGGAAAATTGACGAAGCTGCCAAAGCGGCGGCAAAAATTGCCCTCTATTATCCCCTGTCC
ACTATGAACAAAACTGAAGTTCTCCAACAATTTTTCATCAATTACGTTTCAAAACTAAAAATGTCTGATAGAAAAATGTTTGGG
GGTTTGTACAGCTACGTAAGTCAGACGAACGTTTTGCCGTTTTTGTTGACCATACAAGTGGGCTCGTACACTTTTAATTTGCAT
CATTACGAAACTGACAAGTCCAGAATTGATGCTATAAAAAATGAAACAAGATTTGTGCACGAGAATTTCAAGCGTTTCTACAAA
AATTTAAATGTAAATTACGTGTACTACCAAATTGTGATTAACGGTTTCATTCATCCGACCAAACGAGCCTACACCCATTTTGGT
TCGATGTGGGACATTAGCACGGACAACGGTGGATACACGCACATGACACAAAAATTGCAAATAGAATTTCATGTGTATTACAAA
AACAAAGATGATTCTTTGCCGTGGAATTACGGCCACGAAATGCACCACAGCATGTTATACGCCGTAGATGCGGTGAACATAATG
CCCGCTTGGTATGTCGAAGGTAGCGCAAACAGGATCGGTAACCGGCCGTGTTACGAATACGATCACGAATTGTTAAAAATTTAC
ACCAACAAAACTATAAAAGAAATAATCGACGCTACCTATTCGTCGCCCTTCCTTTATGGAATGGGCAGTGTGCTGGTCCAATAT
TTGTACGAAAATCGACCTGCCGATTTCAGACACATGATAGAATCAAAGAATTACTCCGTTAGCGAAACTTACGAAACGGATTTT
GATGTGTTCAAATTAAATTTAATCGGTAGATGTGAAGCTGTGAAGAGAAATCAAACTGAACACAAGTTTGATAGCCAGCTGGCG
TACAAAAATTTAATAGACTCGAGCACGTTTGCCTCTTGTAAAAATTACATTCGATTCGATTTTGACGATATTATTTTCGTGTTA
ACACCGGACCGATTGATAAAACGAAACAAAAACGGGCAGCCCATGCTCGAATATACTCAATATTTGATCGGTCAAACTCATTTT
GATGAAATCAACGAGTACACCTTTGCTTGGTTCATGGCGGGATTGGTTAAAAAGGCGGTTCAGTACTTATCAGACAATGTAAAT
TTTTATTACAAATATCAGTCTAGCTATACGTATGATTCGACGGTCAAATGTCAGTATATCGACGAGTCTGCCAAAGATGCCATT
ATAAATATGGCGTTTAAATATAAAAACATCGCCGATATGGTCACGTTTCCCGTCGATCAAGCAAAGGAATACATACGCCAAAAA
GACAAGGCGATTGAAATGTGTGAAATGTACATGCCGCCCGTACTGCTTAATACGGCCGGGCCTGCCAAAGTATTCATCGATAGT
TTGGCAAGTCCCAATTTAGTGATCCCGAGAAAAGAAACATATTATATGCGCATCGATTTAAAAGGGAACACAGTAATTCATTAT
GCTGCCATGTACAAAATAAATGCCTACGAAAAAATCAAACTGGCAAACAGGACAGCCGTAGATATGGCGCCTCTCAATGCCGAC
GGAAAATCGGCCGAGCAATTGTACGAATATAGTTTAAAGTTTTACAAAAAGTACAACCAAAGTAATCCTTTATATTGCTTTAAA
TATATGGAAGATACAGAAAGTATCACAGAAATTATTGAAGAGGAGGTGGTGGAAAAGGAATATGAAGGAAACAATACAGTTTTA
TCAAACAACCCTTTATTAAGTAAAAGCACATCAGTTATAACAGAGAAAAGCATTATTATAACAGAGATTACTACAACAGAGAAA
AGCCTTATTATAACAGAGAAAAACATTATTTCAACAGACAATAACTTTAGCATTACATTTAGTTTCAAAAATTGTATAATTTTC
ATACTTGTATTATTAATATCATTTATAGTTATAATACTGTTAAACGCATTGGTAACTTTAATAATAACAAAAAAAATCACTAAG
CAAAAACAAAAAGTGCAACAAAAAGTTGAATATAACAAAGATAAATTTTATACTAACGACGAATGTACAATTAATTTATTTGAT
TAAATACTGTTAAGGAACCATCGTTTTTTATTTATATTCAAAAACAATATCTATAGTTAGTAGTAAAGGACCCGTTTTTGAATT
CACAGGGGCCCATTGAGTCGTATTGGCAAGATTACGGACGTTTAGTTCGCACTCGTTTCTTTCCACATCCTCTTCGTTGATTTT
GGACAACAAATAGTTGTCGTAAACTTGTCCATCGACACTGTCCTCTTGTTTGCGATGATTGAACCATAATTTATTGTACCACTT
CACATCAGATACCATAATAGCCTCATTTATGTATACTGTTAAAATTGTCTTGTCTCCCATTGCTCGCGCCATTCCCTTGACCGA
AATCAAATTGTGATTTTCCTTTAGCGATTTTATCTTGCTCAATATAAATGGTGTGGTTTTAGCTTCATCTTCGCGACTCGAAAA
CCCATCAAAGTAGATACATTCTTTCGGCGATTGAGCGTTCACTATACTTATGTGTTCTTTTAAATATTTAAAAGTGGCCTGGAT
GTAGCTGTTACTAGAGTCAATTTCCACTTTTACCGTTTTGGATTTATTGTCCTCTATTAAATATTTATATGTTATTTTGTTAAG

TABLE 9-continued

Nucleotide sequence of the *C. peltastica* NPV genome (SEQ ID NO: 2)

```
AAGTCTGTCCGCGCTAACCGATGCATGCTCATTTTTTATGTCGTCCAAATACAGAGTAACAGGATATTTGCATAGTTTAAACAT
TTTTAAATATGCGTATTATTTCCTGTGCAAAAGCCTCCGCCTCCTGGTAATGATGAAATTTTATTCTTGTCGGGGTAATATCTA
CGCGCGTACCAAACTTAGCTTCTGCCAAATTTGCACAGATTACGCGTGCTTCGCTCGGATCATCACTTACTCTGTACGCTAAAA
TCCTGCATTCCTTAGTGATCTCACTGATTTTGTGTAAAATCTAATATAATTTAACTCTTTCACAATATAAACATAATTTTTTA
CCTTTGACTGAAGTTGTTTTATTTTTGTGTCTTTTCTTCGTATAGTATTCTTTAATTTTTCTGTCGATATTTCAAACTCGTGCT
TGTCGCGTTTGTTTTTTTCACACATTTTTTGGTATGCTTGTTTTAAAAGCTCAAGTGCACGAGCAATTTTTTTCAAGTCTTTAA
CAGTAACAAAACGAAACATTTCACCACTTTCAATATTAGCAGCGGTCAAACTACGGACTAGACTTTTGTTTCGTAGAGTAGACA
TGTTTCGCGACGGTCGAACACCGAATGAAATTTGAAAGGCGAACGCGAACGTCGTCATATTTATCATCTGACGACCACGCAAAG
ACACGCGATAGCTATTCCTGGAAACGAGGAAAAAAAAATACAAACATGGTAAAAACAACATTTATTATGCGTAAATCATTTTTA
ACAAATTTTTAAACTGATTCATAATTGTGTAGGTGACAAACTCAATAATCATATTAGTCATGTAATACTCATTGTAATCAACAT
TGGCCGCCTTTGTTTTGAAAATATTCTTGCTGTTTTTTAAATTGATTACGTAATCGGTGTACCAAACGGCCTTCCGGATAGGTG
TGATCGGTTGATGACGAATATTATGTCGCAATTCTAGTATGTTTTTGCGATACAACGGATCATTGATGACAGTTTTGATCGCTT
CCGTTAACTGGTTGGAGTCCACGGTGGCGGTGTCGAGTGCCAGCCCAATGCCCAATTCTACATACTTGTCGGTGTTAAACGACT
GATCGCCCATCATCGGCAAACCTACCATCGGTACACCGGCGTCGATAGCTTCGTCCGTGGATTGAACCCCTCCTTGTGTCACAA
ACGCTACAACATTTTTATGTTTTAGCACTTCCGGTTGGTTGAACCAAGTTTGCACCAAAACGTTGTAAGGTAATTGAGAGTTAA
GTTCTTCGTCGTCCGTTTCAAACTTGAATAAAATTTTGTAGGGTAGCGCTTTAAAAGTTTGTAATAGCATATATTTAAAATCAG
CATCGGTGTCTTTGGTGTTTATGCTCGAGCCGAAACTAACGTAAACCGCTCCTTGAGTGGCGCCGTCCAAGTAACGCTTCATGA
AATCGTCCAGCGGCACGGGCTCGTTTCTATGCAAATGAATTCCACCCAAGTATTGAACACTAGGCGGAACCGGCCTGTTATTGT
CAAAAACAGAGTGTGTATTAACAAATAACATCTGGACACGATTGCGCAGTTCCTTGATAGACGGCGATTTTCGACCGAATTGCG
AGCGTATTAATTTATTCTGCTCGTCCACCAATTTTGAAAACTCATTTTGTAGCGTCAACTCCATGTAAATTTCGTTGATAGTTT
CCCATACCGTTAAATCCCTGAACCGATCGCGCCACATGTTCGGATAGTATTTCGGGTGGCGGCTAACTGCACCCATAGTTTCAA
AATTTTCTGCCAGTCCGTAGCCCGATGAAATTTGAATTACGGGCAGGTCACCGAACAGATGAGAAAATATTAGCGAGTAGTCCA
TAAAAGCCTCGCAAATTAGCAAATCGAAATGCTCATTCTTTCGATTATTGATTAGCCTCTTGACGGCCGGCAAGTCAAATTGAT
CTCTAATCATGCGCACTAAACCCATGTAGTTGTGCGCCGTGACGGTAGTACTGTCCGATATTATTCCCCTTTTTCGGAATACGC
TAGATTGTTTAACCAGGTTTTTAAAGTAATTTTCGGCAAGGGTGGCATCGACTTCTGTCACATTTCGGGTAGCGTAATTGACTT
TGGTAGTGGGTTTTATCACGACAATTTCGTGGCCTCTTTCCGCCAAAGCTTGTATGTAAACTTTGAACACACTCTGGTGGCTGT
AGGCGGGTGTTGGTAAAACTGCGAGAATTCTCGCTCCATTTACTGCAGAAATGGCACACAAAAATAGAATATGGAAGTGCATGA
CGAACAATATTCGGAATAATTTGTGTCAGTAGGCCAACGGTTTATATACTTTTATTGTGTTTCAACGAAAGTGATTCTGGAATG
TTGGTCATTTTATTAAAATTATAATTTAGCTCGTTAATCTGTATAGTTTCCAGTTGCTCCTTTTCGTTGCTCTTTTTGCGTTTA
CAACACATTGAATATTTGTAAAATTTAATTTTTATCAAAAGAACCGAAATTAGCACTAATAATATCAAAACGATTTTTGTATAA
TTAACATCGTTTACTTCGTTTTTCTGAATGTCGGTGAGTTCATCGACAATAATATCGAGAATTTTATCTAGCTCGTCTTGCTCA
CTGCCAACGGTTACGTTGATGAAATCGTCCGAACTGTTTTCGCTGTACGTAGTACTGATAAAAATAGATATGATAAAGAAAATC
TGAGTAATCGTCATATTTAATTTTTTTCTTAGTCACTACTTGATATTTCCAGAGTCAACATCATGTCTCGGCGTTTCGCGATAT
ACACCAGCGAAAAGGCGAAGATGGTTTGGGACTCGGTAGCATTCAATAATAGTCGCCAATTTGCCTTTTTCGATGGCACACACT
GGTATCATCCCCAAAATCATTTTGCAGACTTTGATGAGTTTTTCAACTACTTGAATGAAAACAATATCAAAGATGTGCATGTAA
AAGCGCTCGAGGACAACGGAGGACGCGAGTGGGTTATCGATGTGGATTTCATCGAAACTGGAAAAATATTGGAGTTTAAAATTG
AAACTGCCAAAAAGATTTTCATCAATTTTTACAAGGAAAACATTGCACGGATAATGCACTCCGGGAATCGAGGACTACATGTCT
GGTTGCGCATAGATAGATTTTTAATGTCGTCAAAGAAAAGTTTGCGCACCAGCTACTACTCGATATTTGTGCAACCCGAAACTG
TGATTTTAGACGAAATCGTGCCCGGTAGTTTCATTCATGCTGTGAAAACCGCAGTTGAAGAAGAAACCGTTGCTCAAAAGATCG
```

TABLE 9-continued

| Nucleotide sequence of the *C. peltastica* NPV genome (SEQ ID NO: 2) |
|---|
| AAGAATATTTTAAGGTGAAAACTTTGGAGCAAAGAATATTAGCCGTTTGGCCCCAAGTGGACTCACACGTGTTTTGTAACTTAA |
| ACCAAATTCGTGCTCCGTTTAGTTTTAATTCTAAGGGTCGTGATTTCTCCAAACAATTGTACTAGTAATGTTAATAAAGATGTT |
| AAGCAAAATATTTTCGTTTGTTTTCAATAATAAAAATGACGAGGAGAACATCGAACATGAAGAGGAAGACACCGATCGGCCGCG |
| CCGTCTGCCCGCCGTAGGTTTTTCGTATCTGTTTCAGAAAAAAAATTTCATTTTCGATGAAAACATATCGTTTTTATTACGATA |
| CTTGTATGACAAAGACGAAGTTTGGATTTTGTATTTCGATCTGTCCGACGGGGTGGGTCTGCCAGAAGACGCCCGTGACTCTAT |
| TAGTTATCAGAATATCAAAACTGTCAATGAACTTTTGCCCAAACAGTCTTCGCAAATTAGCAGAGTGGAATGTATTAACAAGCA |
| TGGCATGTTGGAGGCGCTAGAATCGATTAGCTTTAAATCCAAGGCACAATTAGTGACAAAGCTGTTGGATATGTTTGCGGAATT |
| GGAATCGAAATCGACGCCGCTATCTAAAATGGACCATAAATTTGACGTCCTATTAAAGGCTATACAAGAAGTCAAAAATGACAA |
| TGCCAATTTGTTTAAAATACAATTGGATCGATGTCAAGATTTCGAGCGCAAAATAACAGAACTGGACAAAAAGATTAGCTTGTA |
| TGAAAATATCGATCATCTTTACGAGCGGCTGCGTGAACGGCACAAAGCGACGGCATCGGACAGACACATGTTTCTAGATGACAA |
| TAACGAAATGACCATTAAGCTACCAAAAGATGTATCGAAACATCCTCGAATAGCAGTGTTTATGAAACCCTCACAAGCTGGAAC |
| AAAAGTTGCATTCGTCTCTGGCCAAAAGAAGTATTTGCAAAAAGGGAAACGAAAATTTCAAGATATGGAGTTGGTGTACGACGG |
| GGTTCATCCGAATCCCCAGATGGCTGTAAATTGTATAGCCGAGGAACTAGACTTTAAAAATTTTGATTATATTAAAAAGGCTCG |
| TTTGTATTATTTAAACTGTAACTTGGAAACGGCAAAGTCGTTTATAAAAGAAAATTTGTAATAAATAAATTTGAATATACACTT |
| TTGTTATCAGTTACGCCTCCGTTTTTTATCTATTCCTCCCTATAAAAGAACAGATTTTCAAAATAAAATCACAGTACAGCAACA |
| TGTTTGTGGTTAAACGTAACGGTCGTAAACAACCCGTCCTCATGGACAAAATCACTAAAAGGCTTGAAAAGTTATGTTTTGGAC |
| TAAACATCAAAGCCGTTTTAGTGGCGATGGAAGTGGTCAATTTTATTTACGAAAATGTAACCACCGAAGAATTGGACATGCAAG |
| CGGCAAAGGTTGCTGCAAACAAATCATATTTGCACAATGATTACGCCTTATTGGCAGGCAGAATCATGATTAGCAACCTGTCGA |
| AAAAAATCAAGTCTGATTTTTCTGAAGTTATCGAAAGATTGTACAAATACAAATTGGTTACTAAATTTTTGTACGATGTAGTAT |
| GTGCCAACAAAAAAGTTCTCAACGAATGTATACTTTACGAGAACGATTACGATTACAAGTACTTTGGTTTTAAAACCTTAGAAA |
| ACGGGTACTTGTTTAAAATCGATGAGCAGACCGCTGAATTACCGCAGCAAATGCTGATGAGAGTTTCGCTCGGAATTCACGGCG |
| ACAACATTGAAGATGCCATTGAAACATACAAACTGCTGTCTGAAAAAAAATTCATTCACGCCAGTCCCACACTATTTGCGGCCG |
| GAACAAACTTGCCCCAATTATCATCGTGTTTTTTGGTGAGCATGAAAGAAGACAGCATAGCCGGCATATACAACACGCTAACCA |
| CTTGCGCGTTAATTTCGAAACATGGCGGCGGAATAGGACTGAACGTACACGAAATTCGCGCTCGTAACAGTCCCATCAAAGCGA |
| CCAACGGAACTTCGAGCGGACTAGAGTCTATGCTTCGCGTATTCAATAATATGGTACGACACGTTGATCAGGGCGGCAAAAGAA |
| AAGGCGCCATGGCAATTTACTTGGAACCGTGGCACGCCGACATTTATGATTTTTTAAATCTAAAAAGAAACATGGGCGCCGAAG |
| ACAAAAAGGCCCGTGATCTTTTGTACGCTCTATGGGTACCTGATTTATTTATGAAACGTGTAGAAAATGGCGAAATGTGGTCAC |
| TCATGTGTCCCGACGCTTGCAAGGGATTGGATCGAATTTATGGAAAAGAATTTGAAGAGTTATATTCGCGTTATGAATCAGAAA |
| AGAAATACGTGAAGCAAGTGAACGCGCGCGATCTTTTCAGATTCATAATTGAAACCCAAGTCGAAACCGGTACACCGTACATGC |
| TGTACAAAGATGCTTGTAACGGTAAAAGTAATCAAAAAAACTTGGGCACAATAAAATGTAGTAATCTTTGTGCCGAAATAGTAC |
| AATTCAACAGTGGTGACGAAACAGGCGTTTGCAATTTGGCATCTATTTCGGTCAACAAGTTTGTTTGCGATAATTTCGAGTACG |
| ATTTCAAGTCGTTAAAAAAGGTGACCAAAGTGATTGTGAAAAACCTCAACAAAATAATCGATGTCAATTTTTATCCAGTAAATT |
| GTGCCCGCGATTCGAATTTCAAACATCGACCTATCGGCGTGGGTATTCAGGGGCTGGCCGATACTTTTGTAATGCTCAGACTGC |
| CGTATGAAAGTGACAAGGCCAAGTTGCTAAACAAACAAATAGCAGAAACCATTTATTATGCCGCGCTGGAAGCTAGCTGCGAGC |
| TCGCAAAAACTGACGGGCCATATTCGTCATACAAAGGCAGTCCGGCCAGCGAAGGTTTGTTACAATACGATTTGTGGAATGTGA |
| CTCCTACAAAACTTTGGGACTGGAAAGTTTTGAAAGAGAACATTAAATTGTACGGACTCCGCAATTCTTTGCTGGTAGCGTACA |
| TGCCTACCGCTACGACGGCTCAAATACTCGGCAACAACGAATCTTTCGAACCTTTCACTAACAACTTGTATGTGCGCCGAGTGC |
| TGGCGGGCGATTTTCAAGTTGTAAACCAATATTTGGTGGATGATTTGTTGCGTCTCAATTTGTATAATGATAATATGCTCAACA |
| AAATTATCGCCAACAACGGCAGTATTCAAGCCATCGAAGGTATACCTGCCGATATCAAAGAGTTGTATAAAACCGTGTGGGAAA |

TABLE 9-continued

| Nucleotide sequence of the *C. peltastica* NPV genome (SEQ ID NO: 2) |
|---|
| TGAAGCAAAAAAATTTGATTGACATGGCCGCCGATCGCGCAGCGTTCATAGACCAGAGTCAATCATTTAATGTTTTCGTTGCCA |
| ATCCCACTTATTCTCTGATGACATCGATTCATACTTACGCTTGGAAAAAAGGATTGAAAACGGGAATGTATTATTTGCGCACCA |
| AGCCTGCCGCGGATCCTATCAAGTTTACTGTGGACGCCACATGTTCTAAAGTGAACGGTCAATGTATGGGATGTGATGCTTAAT |
| AAAATTTGTAATAAAAATTTTCATTGTTTTATTTTTTTTATTGTAAAAATGAAGAAATATTTTTCGTGTCTTTCTTCATTTTTA |
| CAAGCAAATAAGTATTTTTCTCCTTTCGTAAAACATTGTGAAAAATCAAATATA |

The invention claimed is:

1. A biopesticidal composition for use in controlling insect populations, the composition comprising:
a homogenized mixture of:
   larvae infected with a nucleopolyhedrovirus (NPV) having a genome sequence with at least 98% sequence identity to SEQ ID NO: 2;
   an artificial larval diet on which the larvae were reared; and
   occlusion bodies of the NPV from the infected larvae;
   water; and
   an additive which improves the stability or maintains the activity of the virus in the composition;
wherein prior to being homogenized, the larvae have been cultivated, fed on the artificial diet, inoculated with an inoculum of the NPV, maintained on the artificial diet to allow the virus to replicate within the larvae, and harvested.

2. A biopesticidal composition as claimed in claim 1, in which the NPV has a polyhedrin gene with more than 95% sequence identity to SEQ ID NO: 1.

3. A biopesticidal composition as claimed in claim 1, in which the NPV is an isolate or genotype of an NPV whose genome sequence is represented by SEQ ID NO: 2.

4. A biopesticidal composition as claimed in claim 1, in which the NPV has a virulence host range comprising the Grapholitini tribe of the lepidopteran family, Tortricidae.

5. A biopesticidal composition as claimed in claim 1, further comprising one or more additional biopesticide.

6. A biopesticidal composition as claimed in claim 5, wherein the additional biopesticide is selected from the group consisting of a *Cryptophlebia leucotreta* granulovirus, a *Lydia pomonella* granulovirus, a *Cryptophlebia batracopa* granulovirus, and a *Grapholita molesta* granulovirus.

7. A biopesticidal composition as claimed in claim 1, further comprising a feeding stimulant, a mineral oil, and/or a UV protectant.

8. A method of controlling insect populations, the method comprising applying to the insects or their locus an insecticidally effective amount of a biopesticidal composition comprising:
   a homogenized mixture of:
      larvae infected with a nucleopolyhedrovirus (NPV) having a genome sequence with at least 98% sequence identity to SEQ ID NO: 2;
      an artificial larval diet on which the larvae were reared; and
      occlusion bodies of the NPV from the infected larvae;
   water; and
   an additive which improves the stability or maintains the activity of the virus in the composition;
   wherein prior to being homogenized, the larvae have been cultivated, fed on the artificial diet, inoculated with an inoculum of the NPV, maintained on the artificial diet to allow the virus to replicate within the larvae, and harvested.

9. A method as claimed in claim 8, which comprises simultaneously or sequentially applying, in addition to the biopesticidal composition, at least one additional biopesticide to the insects or their locus.

10. A method of treating or preventing insect infestations on plants or fruit, the method comprising applying to the plants or fruit an insecticidally effective amount of a biopesticidal composition comprising:
   a homogenized mixture of:
      larvae infected with a nucleopolyhedrovirus (NPV) having a genome sequence with at least 98% sequence identity to SEQ ID NO: 2;
      an artificial larval diet on which the larvae were reared; and
      occlusion bodies of the NPV from the infected larvae;
   water; and
   an additive which improves the stability or maintains the activity of the virus in the composition;
   wherein prior to being homogenized, the larvae have been cultivated, fed on the artificial diet, inoculated with an inoculum of the NPV, maintained on the artificial diet to allow the virus to replicate within the larvae, and harvested.

11. A biopesticidal composition as claimed in claim 1, wherein the additive which improves the stability or maintains the activity of the virus in the composition is glycerol.

12. A biopesticidal composition as claimed in claim 1, wherein the NPV has a genome sequence with at least 99% sequence identity to SEQ ID NO: 1.

13. A biopesticidal composition as claimed in claim 1, which has a concentration of NPV of at least $1\times10^3$ viral occlusion bodies/mL.

14. A method according to claim 8, wherein the additive which improves the stability or maintains the activity of the virus in the composition is glycerol.

15. A method as claimed in claim 8, wherein the composition has a concentration of NPV of at least $1\times10^3$ viral occlusion bodies/mL.

16. A method according to claim 10, wherein the additive which improves the stability or maintains the activity of the virus in the composition is glycerol.

17. A method according to claim 10, wherein the NPV has a genome sequence with at least 99% sequence identity to SEQ ID NO: 1.

18. A method as claimed in claim 10, wherein the composition has a concentration of NPV of at least $1\times10^3$ viral occlusion bodies/mL.

19. A method as claimed in claim 10, wherein the insects are selected from the tribe Grapholitini.

20. A method as claimed in claim 10, wherein the insects are selected from the larvae of the group consisting of *Cryptophlebia peltastica*, *Thaumatotibia leucotreta*, *Lydia pomonella*, *Grapholita molesta*, and *Thaumatotibia batracopa*.

\* \* \* \* \*

SEQUENCE LISTING

<160> NUMBER OF SEQ ID NOS: 4

<210> SEQ ID NO 1
<211> LENGTH: 521
<212> TYPE: DNA
<213> ORGANISM: Cryptophlebia peltastica nuclear polyhedrosis virus
<220> FEATURE:
<221> NAME/KEY: Polyhedrin gene
<222> LOCATION: (1)..(521)

<400> SEQUENCE: 1
acttactttg tttaaagaaa tccgtagcgt taagcccgac acaatgaaac tagttgttaa 60
ttggagcggt aaagagtttt tgagggaaac ttggactcgt ttcatggagg acagctttcc 120
cattgtaaac gaccaagaaa ttatggatgt tttcctagta gttaacatgc gcccgactag 180
acctaaccgt tgctacaagt tcttggctca acacgctctt cgttgcgacc cagactatgt 240
gcctcacgaa gtaattagaa tagttgagcc gtcatgggtg ggaagcaaca acgagtaccg 300
tattagtctg gccaagcgcg gcggcggatg tccagtgatg aatctgcatg ctgagtacac 360
caactcgttt gaagagttca ttaacagagt catttgggaa aacttctaca agcccattgt 420
gtacattggt accgactctg ctgaggaaga ggaaattcta atggaagttt ccctggtgtt 480
caaagtaaag gatttcgccc cgggccatac ctgtttttcg g 521

<210> SEQ ID NO 2
<211> LENGTH: 116646
<212> TYPE: DNA
<213> ORGANISM: Cryptophlebia peltastica nuclear polyhedrosis virus
<220> FEATURE:
<221> NAME/KEY: Genome sequence
<222> LOCATION: (1)..(116646)

<400> SEQUENCE: 2
atgtatacgc gttacagtta taacccatct ttgggtcgta cgtatgttta tgacaacaag 60
tattacaaaa acctcggctc agtaatcaaa aacgccaaac gtaagcgcca cctactcgag 120
catgaaatcg aggaacgtaa tttggacccc ctagataatt atctggtcgc cgaggatcct 180
ttcctgggac ccggcaaaaa ccagaaactt actttgttta aagaaatccg tagcgttaag 240
cccgacacaa tgaaactagt tgttaattgg agcggtaaag agtttttgag ggaaacttgg 300
actcgtttca tggaggacag ctttcccatt gtaaacgacc aagaaattat ggatgttttc 360
ctagtagtta acatgcgccc gactagacct aaccgttgct acaagttctt ggctcaacac 420
gctcttcgtt gcgacccaga ctatgtgcct cacgaagtaa ttagaatagt tgagccgtca 480
tgggtgggaa gcaacaacga gtaccgtatt agtctggcca agcgcggcgg cggatgtcca 540
gtgatgaatc tgcatgctga gtacaccaac tcgtttgaag agttcattaa cagagtcatt 600

```
tgggaaaact tctacaagcc cattgtgtac attggtaccg actctgctga ggaagaggaa    660
attctaatgg aagtttccct ggtgttcaaa gtaaaggagt ttgctcctga tgctcctttg    720
tacaccggac cagcgtatta acaatagat  tgcgcaggtt tcataatttt caatagtctt    780
tgctgtagtt gaagcaaagg tgccgaagcg ggtttcgctt gtaaagcctt gttgataaaa    840
tccatagcat tttgatattt ctcgtgtaaa attatgaatt ttacttccct aagaaattgg    900
gcttcgtttt cgttatataa atttgtggtg ctcggagttt ggttttctaa gatattaata    960 tttttagtc  ttttaacaat cgaattaata atttcgtctg ccgaatttaa attttgctcg   1020
ttttcgtacg gaatattgat taaacgactc gcttcggaga tttcgttagc aaaactatta   1080
tcgctaattt ctgttaatat tactaatttt gaggctagcg cattctttct atcccggtac   1140
tctgttttat catcatcgtc ccactcatcg ttagtcgtgt tttcgttttc ggaagccgta   1200
ctaacaggtt ctaaggctat acgtctactc ataatttgag cgacatgttc gatacctttt   1260 gtttcttta  gaggttcttt ttctatttca acctttttca atgtaggtct tttcttaata   1320
gcctctaata gggcgcttct ggggtctact gtagtttcag gttaggtgg  ggtagaacgt   1380 tctgcggcag atttaatgc  tggcctagat cttatttgtt ccattagttt actagggtct   1440
aaaggcgatt cggaaggttt tggaggagac ggtgtcgatg tttctaaacc cgacattggc   1500
ggagcaggcg gtgcctcgct agctgtgggc ataggcggtg ggggcggagg accaaaatct   1560
gaagccatcg gcggaggcgg aggaggaaca aaatctgaaa ccatcggcgg aggcggaggc   1620
ggcggtggtg gtatgctcgt ttctagctct ttcataggag gcggcggagg tatgtttgta   1680
ataggttcag gaggcggcgg aggcggcggt ggcatgaaag gttcaactat tttatcgttt   1740
accgtagata taaaatcgtt ggatgtaagt agaatgtctt ccacacgttt aactaactca   1800
ccatagtttt gatcgggaat aacagtttta atgttttgat catcagtttc gttcgaaaca   1860
attggtgcta ctatcgtttc cctgttcaaa cttttgtcgg cgccttttgt ggcgatatca   1920
tccaacgaaa ctatatcatt gagaatgcta tcgatctttt cggtgtcctt ttgaatcttt   1980
tggttgtgat cgtgtaaata ttttttatac acgacaaaaa attgtttata gttatcttct   2040
acgtttgttt cattttgaat ttcgtcaatt atcgaaagta gcaatgattt attttcatcg   2100
ttgtcgtcta ctttctggc  aatgtttatt aaaattttga ctttattatc aaccgattta   2160
actatgggca acgtcgtttc tgtttctaca tgacttaccc tttcctgctc ataaattatg   2220
gcagtgttat tgtaaatatc attggcaagt tgaatcaatt ctaacgactc tgctaaagta   2280
agtttcagca gttcgttttt gggagtagca aaaactttac gtttcagttt atttatttgg   2340
ggacttttga tcatatgcat taatttgata ggttcaatta aagattcatg tataaaataa   2400
tctctggcgg attgtatgtc agttcggtct agtcttttct caaacatgga cattgtggtt   2460
gacgatttag acgagtttaa acaaaattta actctagaaa aaatattaa  acttataaat   2520 ggaaaatttg gcaaagtgtc cgtgtggcgc cacgagccca ctaaaaaact atttttactg   2580
aagcaaataa ctcatggtta taatgaaatc gaacctatga ttcattattt gatgaaaaaa   2640
aacaagtact tttaaatct  ttactactct gtcaattcgc caactactaa tatacttatt   2700
atggactaca tcgccgatgg tgacctgttt gatcttctgc gccgcgagtc ccgcttgccc   2760
gaacccgaag tccgcagcat tattttacag ctagtcgacg ctctacaagc cctacataaa   2820
aacttcatta tacataacga tgtcaagctg gaaaatgttt tgtaccatag aaagagacaa   2880
atttatttgt gtgactatgg actctgccgc atagtcggag tcaagtcttg ccaagacggc   2940
actttagatt atttctcacc cgaaaaaatc atgggaagaa actatgactt tggatttgac   3000
```

```
tggtggtcag tcggtgttct aacctacgag ctaatcacag gaacccatcc atacaaattt    3060
gatccggacg aagacctcac tacaaatgtt ctgcagcgaa ggcagcaaag aaaacttgaa    3120
tttaaaccta gcgtgtctat agctgctcag tcttttattg aaaaattact gttttataat    3180
attaactata gattaactag tggtgatgaa ataaaattaa acaagttttt gcaataaaaa    3240
aatttatttc atttataact atagtaccct atacaaaata ctagagaata caggttatta    3300 atactaaatac tatgctaagt ttatacaata aatgcttaaa tgttagtaca cttaaatttt    3360
ttgtcgtgtt ccgtatgaat atgattaaca atgatatctg acatgcaatc tgtatttaac    3420
aatttgtggg acacatttga caaaaatatg ttacgttttt taagttcctg aaacttttgt    3480
ttaacaattt catcgttagt tttatataaa acttgccgct ggttacaaat ttgctgcggc    3540
ttaggcatag gatcagcact gacaatgatg acatcatcat cgtcgtcatc attgtcagcc    3600
acattaataa ctttaaccga ttcgtcaatt acttcaacgt cctcatcggg ttcttttttta   3660 attataggct cgttatcttg aactatggca gaaattacaa aaggttcgtc atcagcgggc    3720
tcggttttaa ttacgcgcga agttgacatt gtagttatta aatcggaaat gtcagctgtc    3780
ttatgtgact tatgtgattt agatttgcgc gattttgact ttttagtttt ctctggcagc    3840
ggctcgggcg ccaatatgtg gttacggtct aaattctggt ctaaaatcag gttctccaca    3900
gccgctgcgg tagaatcatc aaactgagct aaaacgtctt caaagttaat aataggtata    3960
gcgggattgt tagaatcaaa tatgtatgat tcctctggtt cgcgaaccga agccggctcg    4020
tttttcataa tatatatttt gttatttttc tcaaagtatt tgaccccatt gtgtattatt    4080
tcttgcgcct cactgacaaa atctgttaga tttttacctc taatcgcgtc agacctatca    4140
attgccgggg ccggttggtc accaagaatt tgttccaatt cttgggcagg ttgttcaccg    4200
agaattagtt ctaattgttt ttcttgctcc agaatagcct gcctttctct ttcacacttg    4260
tttatttttt tttgaagctc gataatggcg gcttcattgt cggtgttaga tgtacgaatc    4320
acactacggc tacgatcagt attagcgact tttacctttta atccttttttt aggttttctg    4380 ttacggctgc ggctgcgtct ttcatggaca acgcggggc tgtaaggttc attttgtcgc    4440
tcagatcgag cggggctgag gctttgctga ggttggtcgg gactagggct acggcggctg    4500
aaggtaggac tgggggctgcg gtggttggca gggctggggc tgcggcgggt tgcggctgaa    4560
tgctggctga aggcggggct aggcgtgcgc tcgttcgaac caaaacgatg tccgacacaa    4620
ggactcggag ttctggttct gtcattgcgg gcaggggtcg ggtccctgct taaagcggga    4680
ctcggagttc tggtacggtc gccattgcgt gacccgctct ggctgcgaga gcagatctg    4740 cttttgcgct cactagattg gctgcgggaa cggcttctac acgtttcgct cgattggctg    4800
cgggaacggt cgctgtcgtc agcgacggaa cgctggccag aagtggaccg gcgactttta    4860
cgaatagaaa cggaccggga tcggtctgat gtctcgctgc cggaaggact tgaagatcgg    4920
gttcggttgc catggttaat aatatcgctt tggtcgcttt cgtgtgaact gttactataa    4980
ctacgtttac tgacacgact atcggtacgg tttaacgcgg gcttcttttt tccttttttt    5040
agaattacat tatctttaag gcctcgcgaa atggcaatgg cttcggccac ttcaaatggg    5100
gtttcttcgc gttatagtt acattaata cacgcgcctc tctgataact ttcaatgaaa    5160
caatcgctgc acaatttatg ttcgcagttt ttgtaaaagc ttctaataaa agatttttta    5220
cacgcctcgc atattatagt ttgcaattct ttattaccgt tacattgact gattatttca    5280
gaactgattt taattttaac taaattatta attttattga taagatcttt ccgaagattt    5340
```

```
tcaatggcag tgaggccaca tttgtccata atcctaatat gttctcgaat ttcataggtc   5400
gcgcctatgt tacgcaagtt tttaggaacg tgttgaatct gttcgtaaaa aaactcgcta   5460
gaagcaataa agtcgtgttt agacccattg acatctcca acaatacgtt atggaccgtg   5520
ccgaaagcgc tgttattatc tcctaaagtg ggatagtaat gattgtaaaa ggctccataa   5580
cacagtctga gatgaatcaa aacatcaaac tgagtcagac acgtcagtaa agtttgtaag   5640
tcttttttta cttggaggtt aggcgattct ataatgtaat tatagatgtt ttcatagttt   5700
cgtgtcagta aattacgatt tttaaaggta atacccataa atttaaacgt attagtatta   5760
gtgtagtcta aaaaggcgac ctttttttc ccggcttgaa attcaagata gaaataaagc   5820
ctgccctcag gtttattatt aaccatttgc aacttttgt acgagttctg aaaataaagg   5880
aaaaaactta gagtttgtca ctctaaaaaa aaaaacaca aaattattta caagtccaaa   5940
aatgggaaac ataaaaaac actgttactc acatcaagta gacggctcat cctgtgcact   6000
tcactggact ttgcagggag aagaggtgtt gcgtgttcga agctcgaaac gaaactgaat   6060
ccaagtttcg ctaccaaggc ttatataccc tggctggcga ccttgtgggc gtaatcagtc   6120
acgcggctgc gggcgtaaac aaagtcagtc acgtacgccc tgacctccag acgaacggaa   6180
caaacaacct aatcagcagc gcttatcggc gcatgaccgg agattgttat ccggtcacgt   6240
aggcgctcgt tgtcacgta ggcgcttgtt tgtcacgtac gccaggaagg tgataagcag   6300 tttttgctc tacaaaaaag gacctaaaat cgtagtatat tgggagcata ttgtacagtg   6360
tagactatta tagtaaaata gtctacgata tgaaatattc cactgtatat tagctgtaag   6420
gacttaagta acttttttgc actgcaaaaa aatgaccttt cgattctgga ctagtcgtgc   6480
ttgattagat taggtttcgt ataaaaggcc tgacaaattg aacacgaatc atactttcgt   6540
acggagccct acataccaac agataaccgg ccgtagcatc atgaacaaag tgagtattct   6600
tgtgtattat ttttgtgcat atcctgtcag acatagtttg ttcgttttat ttattttgtt   6660
ttttgtttca gatcgacaaa aaatctgtta ccaaaatcga attatttaaa cctactattt   6720
acagcctgag aaaaaataac aaagattttg tccatcacac cgaatttact aacctcatgt   6780
tcaataattt aattcgtcag tataaaattt ctgaaaaaga aactggcgac gcaaaaaaat   6840
tacgccaaat agatgctttt aatttttgtc gttacatcca aaattactac gaatttaaca   6900
cagatcaaag ttcttttat ttgtataata tcagaactgc cgttattaaa tatgatttga   6960
ttttaaggat ggaaaagttt aaaaaatttg ttaaaaggcg ctacttcaaa gaacatggcg   7020
tacgtatgca tcaggataaa gttatgtgtc ctgacaaaca ttacgtggac atttacaaac   7080
ctaaacttac aaaaattcac ctcacaagta aagaagaaaa atattcggac gactctgatc   7140
tggacagctc ggaggatgaa ggcttcggag gactacgcca gcgacctcgg tctcctatta   7200
ggtttaggat tgtaaataac acgagagtaa tgtcgcgtta ctatcctcag tattaattat   7260
aacagtattt tatagtatta cagtattata tagtattcaa taaacattat tatggtatttt   7320 tttgtttcaa ttatctcgcc ataggttcta gaggtttggt taacaattgt ttaaaaataa   7380
aaatgccaat ggcaagcata attaataaac ccctaccaa catgattaaa ggcaaaagtt   7440
tttctcccaa acttttactt ttattcatgg atttgttaac cagaccttct tctccgagca   7500
aatgatctag acctaaatct cctatcagat ctcctaaatt gtagggttct atacattgga   7560
tagtttggcc gacagacaaa tcagaaatgt caacatactg aggtgactct gggtcggcat   7620
taggatcgct agctctacaa actgtctgtt ctgtttcgta attaaccccc tgcaaagtt   7680 ccagcagctc ttgctcattc gaaattagcg ggtcgaattc gcataaaact actctgtcca   7740
```

```
ttgcgtccgc attcagctga caggttctgt gtctgagcat acaaacagtc atatcatcgc   7800
ctccgttaaa acccacataa aaatagctac cgccagtgtt attcaatgca ttgattatgt   7860
cctgaattaa gctagcggtg ctaaatgcca aatatacacc cgtaccgatg agagctgtaa   7920
cgcctgcaag ttttaaattt tctaagtatg tgcgcaaacg aggctgttga gtaagcacag   7980
tttccacacc gtttgcgttt cgtgtgtttg tagacggata gttttgttta accgcatttt   8040
tacgcaaatt aatggaatgt aaattagcat cgggaacatt gtctatacgg cgtaaagatc   8100
ctaaagaatt taactggccg ttagttgcgt cgggaaacat ggttcgtaag tttgtactgt   8160
cattattgcg cataaatcga ttcatgtcag cgacactaac aaaatcattg tttctgacca   8220
aataacctgg catgtacatg tcattgttta ggtttcgaaa acttgaagac gaaaaaacgt   8280
tttgaaaacc agcaggggag gagttgacga catttaaatt gtctacatta agaaattgat   8340
tagggttatt ataaacttta ttaactctac gcaatgaggt aaagaaactc attttttcctt  8400 atttacttt taggcttagt tctacgcgtt tcaggcgtag gttcaggctc gggctccggt    8460
tctggctcag gttccggctc tggctcaggt tcgggctccg gctctgggtc gagatcagga   8520
ttaagagttt catcaatttt atctacggta gtttggatag tttgtagagt ctctgactga   8580
gcctgcagtg cctcattaat ttcggacaca tctggcagat tggctctgat gtcttgcacc   8640
gatgcctgta gcgccgcgac tttagtgtcc acggctttaa tatcggatcg aatcaaaacc   8700
aaaatatttt gggacatgat tatttaatat acaaatgatt atgtattata acttattaac   8760
ggcccgtcaa acctcacccct gtcaatttcg tattcaccct ctgataaagt tataacaatt   8820
tcgtggtcgt tataaaaaac attaatattt ctgggcaaat ctcgatacgt attttttatt   8880
tgatcaacag ttaacgcata cctttttgagc atgaaactag aatcgccaac gtacggcaat   8940
tgttttgtac catcacgga cataccttgc aaaaattat ggaacgaaac agatttatca     9000
aagttcattt gaccggacac taatttctcg gacgtatgc ccgttatagg aaaaatgacc     9060
aggccgtttt tatagtcatt gtgacgacaa gtaattactg aaattagtcg attttctcta    9120
aaaacgggcg cgcccaagta aattttgttt gccagactaa aatcagtgag tgcaaacgca    9180
tacatttgac cataaattaa cctttgtttg tggatatgaa aatttgcata cacacgatcc    9240
accgtaaaac tagccagatc gccgttattt aacaaaacat ctaacgcgga attgttcgat    9300
actttaggga acacaatatt gctcgctacg ccgggaaatt ggtgcagcag accatattcc    9360
tcgtcgtgta cacggctcat gggcgctatg attttaataa acgattcttg cccgtcaact    9420
tttgttattg taacagtctt ttttagctcg ttttttttcat agttaacatt attaatttct    9480 aaatttgac cgtttctgat acagagcaat agcaataaca aaaatgtcat tgtccttttt     9540
ataatcatat cttattagtt ctttaacctt tgataaaaat tactatataa ttgtctcgtt    9600
tctcgagatg aatcacagaa tcacacagca tcttaagata tatccatcat catgccggtt    9660
acaaaatgca agcaaatacc cgcctaccag tttattcaaa aactcaattc attgctacgc    9720
aacattagtt ctgtggaaaa acggatcgat cattggaaga gaattaaacg gattacaaag    9780
gataaacgag aactcatcga aatagattgt atgctggcaa aaatggatgc tgaacttaga    9840
tcactaagaa acgatgtatt ggttttaaac agtaaataaa ataaaatatt tttataaatt    9900 gtatttatt caatatcatc ttcacaaact tccacatcaa ttatagatcc attttcgtac    9960
caatcttcat ccacgttttc gctagttcc accgctgcag gcgttttctc cggtattttg   10020
actcgatgcc gattattatg aaatccgttt ctaaccaaat agcatttaaa aggttcacca  10080
```

```
ctgggccagt aaacacgccg gttcacattc aacaagcggt tagccgtata gcggcaatgt    10140
agtattaatt ttttgcgcgt acaggaatcc cagtcaatat cgagcctacc gccgcaaaca   10200
tggttaagaa actctttggt gaaccttttg gcatagttgg taccgttaat gtgaaatatg   10260
tacattttta atcggtttgc tcgatattga aaaatatcat aggtttgatg gccaacgagt   10320
atgttttctc ttggtacttc ttattgttaa cactttccaa cgtagtttcg ttcttactct   10380
gcttgaatcc ctcaattata gcgcccatat acagatccac ttcttgagag ggctgtgctt   10440
gttctccgcc ttcttgttgg aacgcgaata aatcgttgta acgttccacg gtaaatggct   10500
cacacacaac gcttttgacc aagtctcctg tgctataaac ggtctcgttg ctgtgctgct   10560
ttatatcata aaattttcgc acaaacgaga tcttacccgg gttattttca tcgggcgcgt   10620
ttattatgga acagtcttgc aattttattt ggtcctcttt gaaatattgt gacatgatgt   10680
tggaatagat catattatgc cgattgatat tggaccagcg cagaataaag aactcaccaa   10740
aagtactttt gtagcgcttc attttcaccg tatcgaaaaa ataaaacggt atagctcctc   10800
ctttgacatg ataacccacg ttgtacacca ctctaggcgc tttaggggtt tctatggtga   10860
tcttgtcatc gatctttgga tacaaacggc tttcccatcg agaaaagttg ttgcacgttt   10920
ccaaaaatcc tagcgccgtt tccaattgat tctgattaaa ctctgtctgg caattaacca   10980
ccgtgatgtt cttgcccttg gccaaattgt gtatcatttt ttcgacccat gtcatggcac   11040
gcgtctcttc acgattttta aaaatgcaaa tcaacttatc gttagcgtca tattccactt   11100
cggttttgta aatgtccaaa ctatcgcagc ttttttttgga caccgacata ccgtccgagg   11160
aatcgcttga tctacgcttg gtagccatta ttaaaataat gttgcactta atttaaggtt   11220
actatttata ctatggaacc gtttaccacc gatgaactac tcttcgaaat tacccttaa   11280 attttctcaa tacattgata tattaaattt aaccaaggt gttatatcca aaaacatttt   11340
gccatgtttt attaacgaac tcaacaaaat cccccgaatc gatttggatc ccgacacacg   11400
tttcataaaa aacgctttcg attacaatta ttacatcaag gaaaatgaca tttccaagat   11460
ttatgtagtc gatgccgaaa caaaagtgtg tatttctcaa attacagtag caatggttga   11520
cgaaaattgc attaaactgt ttgtagacct agtataaatt ttggaaccac ggcacctcgc   11580
caatctcgtc ggtcaaagat cgcatagtca aaaatatttt aaacgaatct tcgaaaaaca   11640
tgtacattcc tatgagtaaa aatatcacga aaaacacaat aacgttttca gtgtgcggca   11700
aaaaataaat aatcagagcg ctcgcaaacc acaaatatgc caagttttta tggccacttt   11760
cgtggtacaa aatattattg tgtcgttctg tgtagagcat aaattctagc cgcgaataca   11820
tagaactcga agctaaaacg ctaccaacca aagttacttc gtcaaaatcg tcgataactt   11880
tactgtcttc aaaattcaaa agctgaccat tggaatttac ttccaacgca gacacgtaat   11940
ctaaaatata aaacaatgaa tcgaacatgg cctcgtcatc ttcctcaatt aaatcatcaa   12000
aaaactccgg caaaaactca atcatgtccc gcgtttctcc catcgactcg aaataagcgc   12060
tcaaaaacga ccgcgacata tcgtcgggaa attcacgagg aaacatgttg ctatagccga   12120
acgggtccca cagcatgagc accagatcag ttatggttag tagaattaac agaatgccta   12180
ccaccgatgc agctttgatg gcaattttgg tcatggcttt agccactgca gaaatagttt   12240
taatagcgat acggttgaaa gaatgaacga ttgccgcttt gtaggtttcg cccaataatt   12300
ttaccgttac ttgtttagac gaagttagca aaactctttt caataatggt attaagaac   12360 tattaatttt ctttaacata gctttaagtt gatcgaaaac gacatcgaaa cctatgctag   12420
tgagaatgcc aaacaaaaac gcgtgatcct ccaaaaactg ggaaattatc tcgtccaatg   12480
```

```
tagcgttgtc aatttcgtta gtaagcggta cgaaaccgga ttcgccaagt ttaatacgtt  12540
cctcaattat tcgtttcgaa atagattctt tagaaaaacc attttgagcg cggtaaatca  12600
atttaacgtt ttcgtttata cccaaatctg acaacgtttc aaagttgacc atgtcaattt  12660
ctctttccaa gtccacaaaa gaatctcgct gatttagcca agagtctagt acgtgagcag  12720
agttcgcggc cggtttcgtg ggcaattcgg gcgatggacg cgtgtagtca aagtgtctca  12780
gttcgctaaa aatattatta gccataagct tgaaagtgac atagatagta tcgcctaaca  12840
caaaacctat taagctttcc caccatcgca acgagcatcc gccgttgatg agctcgcgtc  12900
caaatcggcg gcaataagcc tcgttgaatt cgcctttgaa catttcggga aacaacggat  12960
catcactggg cgttacattg aagcccggca catcgtcgac accctgaatc aaatgttcgt  13020
cggtacgcaa gtacggcgaa ttcatgtaca tttttgacaa agtgtctacc aaaatacatt  13080
tattaccgtt ttcaatgtac ctcaattctg gcgattgaac ttcgttttcg gctccttctc  13140
gtgtggccat tgcccggtca agattgtaac atgcgggctg ggcataaccg acggccacat  13200
cagacgtttg agtataacca aagggtgtcg cgtaatccgc cgggccggtt tcatgaaacg  13260
gatagcaaga catactctcg caaccgactt tactaaattt taggctaacg gcgatggcgc  13320
gttcggctag tttgggcggc acataatagt cgtcattgtt ggccggtcga atttcatagt  13380
caacaaatat gtggggaaat ttggttctcc aacgtggtat gaaattcagg cggtgcatgt  13440
gtgtcgcata gcgagaagcg ttggtcaaat ctagaatcgt taaacttgtc atagtaattt  13500
ttacttatga tttcgtgtat aaacgaaact agaatttgag taaaatctta ctcatattca  13560
agtttcgttg atatatattt ttactagtct tttgtgaaac aacgaaatta gaatatgagt  13620
aagatcctac tcatatccaa gtttcgttta tttccataca atgaaattta gattcgagta  13680
agatcctacc ccaattcaga tttcgatggt taggtgtaaa aaaaacaaga attatttact  13740
cataccatat tttaatatac aatatacatc gcattttttca caagtattgt ctttttagatg  13800 attacatata acaaaacatt tacccaaaca ttcatcggta caataaagtt ctcgcatgta  13860
cacgctgcga cctaatcgcg aagtcgattt tctgcatttc gtgcacacca tagtttgaac  13920
ggcattatca aaatacggac tcaacatggt tttactgatc gtgttaatga acaacatatc  13980
gatcaaagtt ttgggcaaaa agcactttga aataaacgcc tctaaacggg tatccaattc  14040
gagtacgggc ataattttttt ttccctcagt aatttcgccg ctaagtttgt tcaaacacaa  14100
attaaccaaa ctgcgaggag tcttgtgcca ttcgtttact cttcgaacga tattttcata  14160
gacatcttct aatcgttcat actgcttcaa gtctacattt atgtcatagt tgtaacagcg  14220
caacaaacgc tcttcgtttt ccaccaaaac tgcggggcaa gtttttataga acattcggcc  14280 ctttaattct ttgtagcgtt tgttcaacaa attatatggt cgtatgtcga aattatcatc  14340
gtaacatttg tctacatggg tgtaaaacga acccagacgg gcaaagttcg tttcatattt  14400
cgtccacagg atggatacag aatgtgtcga agagcaatat ttttgtattt tttgagaaaa  14460
actcaacttt tcattgtaag aatcgacacg gtccaaattt ataactatta tagacgtcat  14520
gttcacacaa ttttaacatg ataactgtcg aaacttggat atgggtaaaa tcttactcat  14580
attctagttt cgttcaagag aatatataaa gttattaatt aattatgact atcattattt  14640
ttaaagcact catcatggca caagtgaaaa tcggtcaatt caaattcggc gaggacctgt  14700
tcaacctgcg gtacgtgctg gatcaaaatc agcaagtaaa atttgtggcc aaagacatcg  14760
cgaataaatt aaattattta gatactaaaa aagctgtgaa agaccacgtt gacgaaaaat  14820
```

```
ataaatgtaa gttcgagcag gggggcgat ttgtcgcccc tgcctccgac agcgtagcca    14880
agaggggtga cccgttgtat ttacaaccac atactgtact catcagtaag gaaggcgtca    14940
tccagcttat tatgaagagc aaactgcctt acgccgtgga actgcaagcg tggctgttgg    15000
aagaagtgat tccgcaggtg ctatgcacgg gcaaatacga cccggcttta aaacagcaac    15060
aagaggaaaa caagcagctg gtaaccaaac taatagcgac attcaccgaa cacactaacg    15120
agctacagaa acaactagtg aaaaaacaag agtttattga gcatgtcgtc gctatgaaag    15180
acaaacaaat cgaagcaaag gacaagcagg tgatgcgcgt gatgaccgat ctaaaccgca    15240
tgtacaccgg attccaggaa accatgcagc gcaaagatga gttgttgcaa actaaagatg    15300
agcaagttag cgaacttgtt aacaaaataa tggacctatc ggatcgtgcg gtgcagtacc    15360
cagcggacga gcgcaagcac ccggtcctgt gcgtggcgcg cgacggtacc acctttacgg    15420
ccatcgccgg gcaaaaatcc tatgtgcaca accaaaaaca aaaacgcaac attgatgagg    15480
acaacatcgt ggtcgaaacg aggcggccca atcccaccgt ggactggaac aacgcgacgg    15540
agcaagtttc gatgccggcc aaaaaaagca gacggtccat tagtttcgac tcgccggagg    15600
acgcccagca gttcgaagat cagatcaaac aattgatgaa caaataaatt ttaaaatgaa    15660
ccaaattctt ttatttcata caacgaaact cgaatatggg taagatttta ctcttaaatg    15720
tatagcatca tattcgagtt tcgttttgag caagtctaaa cttgtctaga tgatgtcatg    15780
tggatgggtg acctaatggg tcggtctgct caaatagaaa tttcgcatgt gagtatgttt    15840
gaaacgatct tttgggatgg gtgagtaaat ctcatatgta gttttgtatt tgtcaacatg    15900
atgttatgta gtgtgtaatc atacatccgt ttgcgtaaac aacggatgta tgagatcatc    15960
ggtatgagat catcgaatga ataaaaaaaa tatttcacaa caacagtttt tatttcacaa    16020
tcatttcaca gcaattttct taaactctgt taaatcataa tacaacaagc tacctaaaat    16080
ccgtttcttc attttaacac acagtttata gtaatcaatc ttggaaatgt caattttgtt    16140
aatgaaatac cacggatttg taaatccaca gtacacacag taaagaatca aattattctt    16200
gtacatcttt ccgcggcact tttcgcattc aactttata caaggcaaag caaaaaatgc    16260
ggtataatca aaattagtat tgtaaacttt gcgatgcacc acataatagt atgttagatt    16320
caagtgagta tgcccgttga cgaacttcag aatgttactt tcttcgggca cgactctgat    16380
caaaccgtcc tctatttcat gcttgcgagc cgaaaactcg tcgagatttt tttgcaaaaa    16440
aaatctgttg gccgattctg acaccaatgt tttctccaga gtgcaaatat ccacgcttat    16500
aatttgttcg tttgccttct tggcgtccac tatagatttg aaaaattcat acacgttttc    16560
gtgggtttct ttcacggtat tttaacaat tttgtggctc agatccacgg gaaacaaata    16620
gcggttgacg aagcgaagtt cgcacaactt ttccaccaca tcgagataca atcgaggaaa    16680
cagttcgtaa aaatcgtaat tggaatcgaa ttgattgctc aaataacaat caaaacagtt    16740
cattttgaac ttttccatag cagtttgggg tgtagtaata tcgatacttt tgtcgcttct    16800
cacatataat tttctagatt gagacccgga aaacggctcg cgacatagat cgcaaaaagt    16860
tgacaccacc acgtcccgat tgttgtggcg caaacaatcc atgagatttt tgttggtcac    16920
aaaatatctg ccctgtatgt actcgttggc gaattgaagg acgagcaca ttaaataata    16980
gttttggtta gacaaaaatc gccatcgcaa gtccttgcga agcgtggcgc gcggtgcggg    17040
cacgggagtc gtcattatta tgtggaggaa acttcaacga aatgttggct tatatcatgt    17100
attttgagtt cataattcgg tctcatctca attatttaaa ttcgtttccg gcgcacttcc    17160
ttctcctacc acgccgttgg ggtctatata agttctgttg acaaaaattc gatgacagtt    17220
```

```
ttgtggtatc cacaatggat tacaccatct ctaataacac aatggaagct gacagcgagt   17280
cctccacgca cttttgcaat atgggcgagg attttttcaa agaggtaata ctaaagttta   17340
tattttctaa ccactacaaa cccactttac ctttgaatcc caaacaacaa cacgaactca   17400
gattggcagc attcgatatc gttaacaaaa tgtttcttca aatgtacaac gaaccgattc   17460
cgcccctgtt aatgtttcgc gaagttgacg atgaaatttt attgtcgaaa gagcggtgtt   17520
ctcatcactt gatcgagacc attgccaaag tttgcgccgc gattaaccaa ctcaagagca   17580
tgcccaaata taaacaccaa atttttattt tccttcctta cttgaaacag ttaaaaacta   17640
ttttgtcttg ttttgtcaac gattattgct gcggaaagat cgttaataaa accctaaaaa   17700
atttaaccac actgatagac accggacaaa gttctcttga aactatcaaa acacttttcg   17760
agcgtgtgca agtgatgaac gtgtttcgcg acgacattca tttatatcaa tgtaatattt   17820
gccacgaaac ttcggctgag agccatttcc ttaaacctaa tgaatgttgc ggctacaaaa   17880
tttgccaggc gtgttacgcg aacctttgga aatttagcaa tctgtatccc gtgtgtcccg   17940
tgtgtaaaca gagttttaaa aaatccagca gcggcaaata gacgattgtt ttgtggtagt   18000
ttttattatt aagtatgaat tcgttacaca gtctagaaga gagacaatat aaattttgt    18060 ttctagccag ttactttaat ctcaacgatt atgatcactt gcaaacggac agcaaaccgt   18120
tcatcggcga atatttaaaa aacaactttg ccaatttgaa cgaggaaagt ttattgtcat   18180
acattgatta tttacattcc atcaacctaa agttttaat cgccgatcgt accacggacg     18240
ttttcaaata tatcaaaccc cagttcaagt ttaaatgtat caaaaataat attgatattt   18300
tggagtttga caacaaaacc tacatccaac ctaacacggc catttacgcc accaattttt   18360
ttgtaaaaga tccgaaagat tttcgattgc tcatgtatca gcaattttct caggtgttta   18420
gcgacaggca ttttgttagt aacggagaaa actattgttt aatgaacgga aacgtcgggt   18480
acattttcga agactcgtac ttggattggt gcggcgcgcg catgtgtagc gtgccaagaa   18540
tagaggaaac gtttcatccc tttcgtttgt atttgatcgg cgacgaaatg gcccaccatt   18600
ttatcgttaa taacatcgct tttgataaaa gcaacatgtg gattttttaaa aattttcata   18660 aaggtttgcc actatttaaa accaactatc ggctcataaa ctctaaaaaa tttcaaacta   18720
aaaaacctaa tgaacttttc aatgaaatga acaagagtt ggatcgtacc gaatacatta    18780
agtttatcca acgagattat atttacgatg ccaacttccc cgaagatttg ctcgaggaac   18840
tcaacgagta catgagcaaa acagccattt acaagtttat taccaaattt atagaaccgc   18900
atgaacgtat gtccaatttt tactctgaaa ttattgtgga cagatatgcg ataaataagt   18960
accgcaaatt aaatataaaa attgaaccgt ccacgctctt tccatctttg cgaattaacg   19020
atccttcata tattttgta cgacccgaca taattcaaat caaaggcact ctgaacgcgt     19080
tttacgtacc caaagaaaaa ctgtttgcta ttttggcgag caacagtttg ttcggttcca   19140
ccgaactttt gcatttcgac atcagattaa ttccctacaa acagagttcg cctccaaaac   19200
ggttggaact cgaaactttc atagtaaaca aacaacaaaa actatatttg actaaattta   19260
ttttcggtaa caggatccct gcatatcttt taataagagg tgattacgaa agttcattta   19320
aaactttgga tcatttaaaa aatccttggg tagagaacac gcttcttaag ttgttaaaca   19380
cacctattcg cgcataaaat ggaagatttg agaagtcccg cgggcggtgt aggtggccgt   19440
tttggctcgt ttttcaatcc tagcgtcctt atgacggtgt taatttttct tgtgattatc   19500
attcttatga tcatgctttt ccagtctagt agcagcggtg gtaacaacag tagttctccc   19560
```

```
gcgcaaggtg ccacaacaac atataccaat cctttgaacg caacaatgag agccaatcct   19620
tttattaact ctccccaacg cctataatct aagtgaaatt cttaaactgt aacacgatga   19680
aacgattcaa atgtcaaact cctaaagtta ggaccgtcac tgaaattatt cacagtgacg   19740
aaaggttaaa aaaagaatat gatatggcag aattcgatgc caaaaatctc aacagtctgg   19800
aagggtttaa cgctgttcgc attaaaatga ttatagtcaa gtacatggcc atgttgaaca   19860
ccctagattt gagtcagcct ctcttaacga ttttcgcga tcgcaacgcc actgttgaca   19920
taacaaaaat tattatcggt tctttggggt atgttcatag gcgggtgaat cctttagtca   19980
cgaatttcga gggcagaatg gaaacggtca ttatcgaaaa tccccaacat agcatcgcgg   20040
gtgaacccat ttattttacg gaaaccgaaa aaggcgacat tcgttgccat attgaccgtg   20100
tcagtatcgt tcgtatgttg gaacgccatt acgatatgga cgttaagata acgattcgc   20160 ctctcaacca aaataaacta agttaatgc aagcgctaac attgagcggg agtagcaagc   20220
gtagaagaag ccacgatact tcccgatacg atttgcaatt gacagaagtc gagtgcaccc   20280
gctacctaac tctactgtta ataatcgagc atgcctattg tcactatgtt atccttaaaa   20340
ctttcgacac gtacaattat gtcaaatcgc tgttagacca ttcgttgttt gctcacaagt   20400
gccgccccgg tgtcaacatg aacttgtcaa gtttactttt aagtaaattt aaatttactg   20460
tagaagaatt tgatccgaac aaaagtagca ataaaaattt gggcatacta aactataagt   20520
cgtaatgtgg cttatgctag cctttttat catagtaaaa ctgttggtat ttcacaaact   20580
acaaaaaatg cacctcgaca tgcacgttgc taaaatttgc cctaacggtt tccacggact   20640 cgccccgat cctttcgatt gctccagcta ctatttgtgt ccgcaatcga ttcaaatgtt   20700
ttgcaccgaa ataccccaat ttgatctgga aacgaattcg tgtgtgccac aatcgtttga   20760
gagcggctgt ctcggtagat tgtataaaaa tttgttaatt taatcgcaca caattcttac   20820
cgggtcgttt ttggttttaa tatttcgcca catgtgtgtc acgatttcaa agttttttc   20880 atgtgaaatc ggctttgaca atattgaaat aaagttagcc ggcacatttc cagtaaccgc   20940
gatcaattct ttttgatga atacatctcg gccgttttcg tctaccaagt ttacgccttt   21000 aattttttt gtcgaaagta actcggtttt tcgtcggacg gagaatatgt gccaaacttg   21060
atcttccgtt ttcgatgtca tcacaactaa cgaaagcggc gtagtaaaat attcattaaa   21120
aattagtttc gaataaatgt acggcaaacg aacacagctc acaacgaagc cgtctttaaa   21180 cttttttcatg tcaatttcgt ttaaaatatc taaaacgaca tgcacttttc gttttggtgt   21240
attttcgtag ccgctaacca atttggtact aataacttcg tctttatcat ccttttctgt   21300
gtcgtcacaa acaaaacaa tattaaatcc gtttatcgaa gtaggacaga cgaatgtgat   21360
aatgctgtta tcgtatgtgg gtcggtataa atggaccttc attttttatt tggtttcagt   21420
atacgatcaa cgttgccgag ttcgatcaac tacttacaat gaagaaccaa gctagcaaca   21480
tgccctgctt ggacagaaac gtttcacctt atgtaagttt tgaaaaaaca ccacacaggg   21540
aagacattcg caacgagtct cctgagccgc caagcgccga tatagatact ttaatgaaaa   21600
cggtcaacga gatcgtggaa actatggagc agggaacttc ggcggcaacg acaccgatta   21660
acgtcacacc gcctaccatg ccgattggta aaaaacaaat ttctttaaa agaagccata   21720 gcaaaagtga tgacatgaaa agtagcaaga aaaacgtcc cactttgaca gatttggcta   21780
aaactgatat tcatgaagaa acagaaaaag aaaagcaaaa aaaagttca gtcgccaaga   21840 ttcgcggacc gtaccgcaaa ctaaaaatcg acaaggctgt gcctattacg caccatatca   21900
agcaggtgac ttttgaacag caaaaccaaa ttattaacag tgccaccgac ttgattaggg   21960
```

```
aaaatacaag ccagatcaac gagctatacg gaaaccaata tacagacgac cgccgattta   22020
ccgattgtat cagtagtacg tattactaca tgtttattgt gtgcgaagac aataacaatg   22080
gtaatgttta caaaattcat tatgtgaatt gtgtggctag ggttaccgta gagtatgctg   22140
ctcgttacag ttgcattgat aattatgtga tggtagtttc cattaacaat cacagattca   22200
tgatttcgta taatctgttg aaaaaattaa acgttaaaat ccccaaatcg gaagatttta   22260
acgaatcttc caaaaacaaa aataaatgtc agtttaacga agtaaagat atcgatttca    22320 tggccacatt gattaacatg tttcacttag atatttgtta tgttcagtcg aacatgatgt   22380
taatgttggc ggcgctaggt ccgagcaaag cgcctttcat agccgaccgg ttgtattaca   22440
tgatcaacca gtctgtaata tttaatttac ccatcaattt ggccattaaa gagagtcagt   22500
ctacggaaaa tgtggacgat atttctgcct atgtgcagga aattatgaag tattcagcaa   22560
aggccaagtt tgaaactctt aaacatggcg aaatcggtat ggacaagatt gtaaaacatg   22620
tcgacatgtg gttaacaac aaaaaagata aaacctggcc tttctttttt acttacaaat    22680
acggtagcgt agtgagaatt ttttacaaca aaaacgatga tagtttcaac aaattgttga   22740
aggttaaaaa ccgaaaggaa aacaatggtg ttaatttgat tgagacatat ttaaattcta   22800
gcgtaaattc tgacacttcc gaaaatttca ttttgattaa cgtgaaagcc gacgagcgca   22860
ttacgattat aaaaaaggga aaaaaatatg tctggatcag caccgtgtgc aaggaaatta   22920 acgtttaga cattatttca aagtttagac gcttcaggca ccatatttc gatgtaagct      22980 gcgttgctcg caaagagctc aataatacgc acaacgccat gatcactttg ccagtttct    23040 atgtaaagaa tgttatcagt agcaaacagg ccgaggagat tgcctcgcaa aagtttaacg   23100
tcaaatacag gtctaaaaat tatgagtaaa tattgtgtaa atagtttaag ccttttatt    23160 atagttttaa gccttttat attaccctat gagattatta tgtgtttatt ttaaataaat    23220
tttttaaaaa taaattttg tttatccttc atcctcatca cccacatcca tactttgaat    23280
gtttgcctgg tcgacatcat cggcaacatt gtggccgtaa taggttagca attctttgag   23340
actggaaaag ccggtcaaat ctctaagtag aatttgagca ttcgctttcc aaaactccaa   23400
gctcagatag gtgtagtaca gctcaataaa actaatgatg cccatttcgc tgttgagaaa   23460
ttcaatgtat tcttcataat tttcctttc gttttagta aaaatatact ttttgtgaaa     23520
atcacagcgg gtctgatcat tgcgatggta acatagtcga cagtgttcaa acttctcggt   23580
ctgtaacgcg tttagatagt ctctcgtctc gtcggacact tctaaaacga cttttatatc   23640
gaaattatca tccttttttcc tttgcaacaa caaaccgtgc gccccaaat actgaaccac    23700 atcgcccaac ttagagtcgg gattgacggg acagtctttg gttatggtag cggtcagctt   23760
tttaagatcg cgcctaaaat cattcattct tataagagtg agaattcata atgcagattt   23820
ttgtaaaaac tctaacgggt aaaactatta ccttagaagt ggaatcagcg gacacgatag   23880
aaattatcaa acaaaaaatt gccgaaaaag aaggcattcc gcccgaccag cagagattaa   23940
tttttgccgg caagcaattg gaggatagta ggacaataag tgattacaac atacaaaaag   24000
aatctacgct acacttggta ttaagactca ggggtggctg aaaaaaatgg gtggataata   24060
taaagaaaca aaaaaaattt ttttttacat ttttatttat ttcaaaatac atctattcgg   24120
acatttgact atcttcaaaa gtgtcattac tcattacaaa ttctgtcttt ttaacacgct   24180
tgctagtggt gttggatttg acagagtctt ttgtattttt ccttttttcgt acaggggcag  24240 gaacgacgtc ggttggagtt gatgaatggc tcgtattcct cttcttgtac agtactttga   24300
```

```
caaaagttttt tagagggttt tggattttttg aactgttcaa ttttttcattg ttcacagtgt    24360 acgcataaaa gggatcatct ataggagcgt gtaaattttc agagtccagt gtgtgcgtaa    24420
gcagacgata aaattgttca taaataacat ttcgtttcgc gttgataatt tcgtgtttct    24480
tggtttcttc gttttcattc gtaacttcaa tagatttgcc cagttttttcc acaaagtcga    24540 acagattgat aaaatctgct gattctgtct tcatcaagtt ccacatgtca cagctgctgg    24600
gataccactc ttttttgatg ctgtgatacc aactattaaa aagaatatat ttattgttgc    24660
tgatgatctt tttgctgcgt ttaatgttct tcttttcgtc cccgtaaacc ggcaccacct    24720
gcagtacata aggcattttt ttcttttcgc acaagctaat gttctgtcct agaaaatcat    24780
ttttagtctt gttatacacg ctttgttcac tcttgttgat gatttctgcg agtgtttgag    24840
gcgccattgt atcttgagga ggatcgcttg tattcagtga ataaatcagt gtttaaatta    24900
aacacgtttt ctatacgttt gtggtgcgac actaaacgct tgcgattctg gctacagtcc    24960
gcaattacaa aggcgctttt tagattatcc cttatatact tcatttgcgt ttcaaatgcc    25020
tcttcgaaaa tgtgagcgca aactccagtg taatcgcctg aatgttttct cttgtttatc    25080
acttctctaa caagcgcgta aatttcgctg cgggtcacgc aagattcatc aaattttcca    25140
attccgtttt tgctaaagcc gaaatctttt tgcgttttg ttgacatgtc ggtgtttgcc    25200
gctggtaaat gtctagtttt aacgacagca aaaaaaattc atttaaagaa ccgtaatcaa    25260 atttttttt aatggttttc acaaagtcaa aaattccaa ataattgctc gaatcgtaag    25320
tgaaaagttg cttttcgttc atgtactgga ataatcatc gagcggcaga atatataggt    25380
tgcgttgaat ttcgttgttg tatcggcgag tttcaatgtt aattttgtaa tcgttgggac    25440
gaaacagtct cagcttgaca caaaaagtgt tgggctcttg cggaatgctt tgcaacggac    25500
cgttcaaaat gccaatgtaa atggcatact tgtacgtcac accacagtca ttccactgta    25560
gcacaaaagg acttttgtaa acatgggcgc tttcgaaaaa agtgcccgtt tcttcgataa    25620
actctctgat ggcagtttcg taatcaaata tgtcctgtcc gtcgcgctta ccgcgcggta    25680
tggatatttt ttctaggaat gttatagcgt tgttggtgtt gaaggcggca ttgtacgcgc    25740
gtcgagccct caaagcacg gcgcggttat ggtccattat catgaaaaga ccggcacact    25800
tcatgcctca agtaaataat aacactactg ttataaatat gacgtgtatt tttattatat    25860
atcaacatat ttaacttatt atgaacaatt acatttggaa cagctatgac attggcacaa    25920
acgtttcatt tacaattgaa caattcggtg actgtaatga gtgcccgttt ttattcgttt    25980 tccctttaatg aaatcgattt taatttcatt gttattttgc acaactctag attgagcggc    26040
cgatcttttt atagagttca atctacgcgt ggacaattcc agcggattat acaacaaaga    26100 ttttttccagc gtaaaggaat ttaagtgccc accattgtgc cactccaacg aaattatcat    26160
attcaacaag aaaattattt cagagtctct tttttcaaac acaaacttat tttgcaaaca    26220
ataatagtac agttttaagg aattatacaa ataaacatg taattgttag ttttataata    26280
atgatccaca tcggtcacga acagcacatt gatgatcttg tcctggatga gttggctaaa    26340
ctttaataaa tactgcatgg aattttttgtc gtcgtcaata caaatcgcac acacgttttt    26400
cagatagacg ttttcgatca ccacaaattg attgttaaca aaaagttctt tgaggttttc    26460
gttgtaatca ttggcaagtt cgagcactat gtattttttg gcacatcggt gccgcttgat    26520
cacgtccgaa atcgaagcga tggacgagag aaacttttca aaatacttat cgttttttcca    26580 gcctctagcg ccgatcgttt tgcgcggatc gtcgttattc tgatgtttga aatccaaacc    26640
actttgtata agtttggtgg tgatgcgaat gctcaattgc tgacccaagg tataattatt    26700
```

| | | | | | |
|---|---|---|---|---|---|
| ttcatatcca | cgttcccaca | taacgttaca | agcgaacgct | atcaaatcgg | ctacgtcgtt | 26760 |
| ttgctttaac | attttatgca | atctatcaaa | gtcacccttg | taccaacgat | ctcgcgccat | 26820 |
| caactttagc | atattttat | cgtgctcgtt | taacgatttt | cgactcacgt | caatgtattg | 26880 |
| gtcgatttgg | tcgggcttgc | tgctcctcaa | gcacgccatg | tcgaacacaa | ctactttct | 26940 |
| gtgtagagtg | ataaaatttt | catcgtcaac | atcaatactt | tcccacaaaa | tatgctttga | 27000 |
| cgttttcggt | ggcatgcctt | gcaaatgtaa | caaataattg | ccgatgggat | cggcaaggta | 27060 |
| cttgcagcat | tgcggcaaac | gttgcgtgga | agttttgtag | tagatagcaa | acattgtgac | 27120 |
| gcccgccata | caaatgatat | cacatatctt | gtctgcatat | atatagcccg | tcatttcgat | 27180 |
| aaaagtttta | gtttatgttc | aacaccagca | gcataatgaa | tagcaagtat | catttcaatc | 27240 |
| ctgcgaaact | ggagattatg | gctaaaatgt | cgttggacaa | caacgtggca | gtgtctaaat | 27300 |
| ttttgccaaa | acatcttgcc | atgcaatttc | aattttgcct | gaggtgtaac | attactactg | 27360 |
| tagaaaaaag | ctttaatagg | atctcctatt | gctacgactg | cggttccaag | tgccaacact | 27420 |
| gtgacaagcc | tggcagagtt | cgccggctgg | aaacgttaca | cggatggacc | acggacatgg | 27480 |
| agtcgttgga | acgacatttc | aacattcgat | tgaaagatgt | catgacggtc | cgccggagga | 27540 |
| ctcacatgca | atattacgat | aattacatat | ttaataatgt | tgcatacaaa | attttatgct | 27600 |
| cagattgcaa | gtacaatttt | tgcgcactgt | gcaaggcaga | gatgcccgaa | aatgaaatgg | 27660 |
| tcaagatcgg | agtaagttcc | ggtaccctgg | aaatgaccca | tgcgttttgc | tgtaaagaat | 27720 |
| gcgtgttaca | ttgcaagtgt | gtagagtgtc | ggcgtaccat | tagcttagag | aacgttttag | 27780 |
| agtttgaaaa | tagcacggcc | gaaataattt | ttggtgtgta | tggttattct | tacgtgttga | 27840 |
| tttgctttaa | ccacactcat | acagtgaccg | cttgcaacga | gtgtacatct | tggcaattta | 27900 |
| acaatgtatg | tgaaacatgt | gaaattgaag | gaaacaatag | ggagtacata | cacaatcatc | 27960 |
| aaacgtttaa | taatcaaaac | gttacagttt | gtgatgagaa | cgaagcagta | ataaaaatgc | 28020 |
| tatgtcaaat | cgataatagg | caagtgcttt | ttaattgtat | tcaatctgtg | tctgaacaat | 28080 |
| tattctatcc | catttctttc | gacacagccg | tagggtacat | agaaagaggc | atgcttaact | 28140 |
| tgggtcgtaa | ggaagtgata | gagctgatta | tttacgcgat | tgtttcaaga | aaacgcgaga | 28200 |
| ctatagttag | cttttacgac | caaacaggca | taccgtggta | tacgtataac | aaggaaattt | 28260 |
| gtcccgattg | tgaagatagg | gaaaacatgt | gtgtctctcg | taataaacca | aggaatttgt | 28320 |
| accatacagc | tatgtatgat | actcagtgct | gcaacaccac | taaatgtaaa | gtgtattccg | 28380 |
| aagatgacga | tatttctgat | gtgtttttaa | atgaatataa | ttattgtgaa | aaatgtttaa | 28440 |
| aaccttgtt | tgaaattatg | gatgtacaat | tcgattcaga | ttttgtttgc | actaaccaag | 28500 |
| aatctcttga | atattgctaa | gttttaata | aacctgttta | ataaacctgt | tatatattcg | 28560 |
| aaatctgcct | gttatttatt | attccctaac | tcaccatgcc | aaagttagga | tctacggtaa | 28620 |
| cgataattga | tcgttgcgct | tttgaagagc | gattaaatca | tgtaaagttt | tttgtgcaac | 28680 |
| taatgaatgt | tgtaatatgt | gaaatgatcg | cttcgcacga | aatcaccaaa | gcagaaggcg | 28740 |
| cgtcgttgtg | tttagccgac | gatacggccg | cctggatttg | cggacgcatt | tccgattgca | 28800 |
| actttgtcac | tttccgtgtg | aaagttttat | catttaacaa | aatacaaagt | aaatatattaa | 28860 |
| agaaaaaata | caactttgaa | gaaacttacg | aacagcaact | attgggaaac | gagtggcaat | 28920 |
| acctaattta | cataaaccgc | acgttcaaac | aggtagctat | caaattgatt | gtggtcagag | 28980 |
| aggacgtgcc | catgatttat | tcgaacccgt | acataaaact | ttcgtatttc | atcaaattgc | 29040 |

| | |
|---|---|
| aagatttgaa cgtgagcact ctggactgcg attgtggcaa cgacaacgac gacctacagt | 29100 |
| ggtgtaacga gatggaccat tatcaccgtt cgcttgctgt acaagcagac ttgtgtgagg | 29160 |
| ataatcacaa cgaaaatatt attagtttag tgtgttttg taaaaataaa gtatattatt | 29220 |
| aagttaacaa gatggttatt atctattgga ttgtgttaat agccgtgatc gttttatt | 29280 |
| ttttgtatgt aacgtggtca gaagaagcgg caccatcccc tagcccgcct cctagtcctc | 29340 |
| caataataat aataaacaat gaactaaaag actttgagta ttatttcgtt gaaacttac | 29400 |
| ccgtatattt tagtcgcaaa gctgaaaaaa ttgcaaatcc cactagacaa tggagttcta | 29460 |
| gtagcggttt tgtcggttta gacccatgga caagtactgt cgattttggt acttttgtc | 29520 |
| acaccatgat aggttatgcc gttaactttg tggacaaaaa tagtaaccaa tattacgatg | 29580 |
| aacaaatcgg ttataatttg ttgatgtgcc ttcgtcttct ctctcatcat ctacccgaca | 29640 |
| cgccgcccgt tcaaaacgcg ccttggggac ccgtggcgga ttggtatcac ttctcaatta | 29700 |
| ccatgcccga gtttacatg acggtaactt gcgttttaaa agatacaatt tattatgaaa | 29760 |
| ccgccgcaga gttaacaaaa actacgttat cgaagtactt gcccaccgcc acaacgtctt | 29820 |
| tgggatgggt gagaacggcg ggcaacgcga tgcgcatggg cgtgccgtat gtttattctc | 29880 |
| aattgcttaa aggtttcaac attagccaaa tacgaatgca ggattctgta caagacgtgc | 29940 |
| tcaaaattat tagctttccg tttgtaaccg aaggcaacgg attgcacata gactcaattt | 30000 |
| acatagatca tattgatgtg agggcttacg atatttgat taattccttc tttacattcg | 30060 |
| gttactacat gtggttcttt ggttcagatg tcattaatca ctacgggcta accaaatcga | 30120 |
| tattgaacgt ttcctcccca gaaggaatag taaacccggc agtcatgtcg agacagggca | 30180 |
| ctatgttttc caatgtcatt ggaaactttg tcgattataa aatcgccgtt cattctgccg | 30240 |
| atgtgagtaa agtgctaacg aaattaacaa acaaatatta cgggtgctgt gtgggataca | 30300 |
| ctaccaaact ggcatattac gaagctgacc cgaccaactt taatcacgca cctttgtggg | 30360 |
| ctatgaaccg ccgattgtgg cggcgagatt atcccataat aaaattacaca cccgaaacgg | 30420 |
| tcggttttga atctggcgtg cttttgcaag acttgagcgg ccgatggccc gtgccgtcca | 30480 |
| cgaccacctc gacacaatcg tttagacctg tcatggccaa aaccgccgtt gtgaaaaacg | 30540 |
| aaactctcgg cgcaatgtta gggtacgcaa aaataaaaga attaaacgat ttagagtttt | 30600 |
| attcgtgtac ggtttattat gaaacgggca tggtacaact ttattacaac atgaaaattc | 30660 |
| cagtagatac tttgtccatt aatcctcgaa tggttatttt gaccaaacct gtgatcgacc | 30720 |
| aatcgaccaa ctggagtaca tcaaacagct tcaacactgc cacattcaat ggcgtaactt | 30780 |
| gccaccatgt caatataatc aatttagcag gtttagcaaa ctacgtgtat agacaagtta | 30840 |
| atgccgttga aaatattgaa caaattatag caagatcggt tttagaagaa ggcatgggga | 30900 |
| tgtcatgtta caaactaacc gtgaccgaaa ctaatgacag cgtcaccgtt actaacaatt | 30960 |
| caaaatacaa taatttcact gtaaacatac cgaatgaggg aattttata ttttatttc | 31020 |
| catatttagc actgtacgac gacaatcagt taataatttc aaacgctgac gaggacaatg | 31080 |
| aaataccaaa aatgatagta gatagtttca tataccaatt cgatatacaa gccgatatgg | 31140 |
| aaccttcaa ttgtgtccta atcaatgact tttaccgaat atttaccgac gaatacagtt | 31200 |
| ttatttttaa taagctctcc taaacatgaa tatcaacagg tacactagtt gttttttgtg | 31260 |
| caacgaaatt gtttatagtt ttcgtcaata cagcaataaa tcctcagact tctttttaa | 31320 |
| caaacacaga tctgtttgta aaagttctgt gtattttgt ttaaagtgct acagagatct | 31380 |
| ttacgtgaaa aaggttgtaa aactaaaaaa ttttacaatc cctaaccgtt tatttagtaa | 31440 |

```
ataaaacaca cagagaaaat tttgttttt ttttattgaa taattgtatt gttacaatga   31500
agcaaactca gcatgacgtt gtattcgcca ctgttatcgg gcaaattaga actgcccttg   31560
acgcactgca aactctccgt ccaacggttg cctgcaaacg actggtttat ggtccattga   31620
tctagccgag ttccttccac tttttcgtgg ccggtatggt tgatttttat aaactcttta   31680
aatatgttgt ctggcgtgtt attgaaaagc atgtacggaa tgttgaaaat aggatatcgc   31740
ttggcgtttg gattgttaaa atcgcctcct ctcaccacat attttacttc gacgtcctcg   31800
aaattagatt ggcgagaaag atacgaaatg ggcgacaaac atatttgcgc gcaagtcccg   31860
tcttctgcga tccactcggt caaatcttcg gcgccgttta tgactccttt ctggccatga   31920
ataccgcata ttttgatgcc ttccagatcg tcggttgaag ttatcgtaac caactttatg   31980
tacactgtat cgttaaaaat agtaatgatg gtgtcgattt tattgatcgc ttggtttttt   32040
atttgcctca gatacaggta aatcttgaaa acgaaaaagt ttttgttttt gcacgcttca   32100
attttatatt ttttaccgtc gtaaatccaa ccgatcttta cgttggaaac aacggttccc   32160
gcgatatgca acaaatttcc accttccacc gccacacaat tgttttctgg cggaggttta   32220
atcaacttta ctacgggagt ttcgttttta gtgtaaatca ttttccttt tagtttgtta    32280 attttattat tgtatagtcg aatgggcaat ttgatgtcag cgatgtaagg atcctcagcc   32340
gtcataagtt tactgtcacg cacaatcgtc cataatttga acattttgtt gttaagtttg   32400
atctccggct tgacagcgac gcaattgcca acggtagcg tgtccaaaaa agtttcatcg    32460
gtttcactgc tggacaaaat cggcatggca ttttcaagt tagttaaaga tacaatcaat    32520
ttgggcgtcg gaatggtgct gtagattttt aaaaaattat tgtaataata ttgaaccaac   32580
tttgacatga gacaatcaac gctgtcgttt tccataatga tccccacgtc ggtagtgctg   32640
tttaagatag aatggctgtt gtggtattcg tatggagtta acagcgtggc gatagttgcc   32700
tggtcgttta ccttcactgt tcgtttaata caaatcatac cttcgtgatg attgataaat   32760
aaaattccgt tggacatttt catctccacg ggcgtcatgc cccgtttaaa ttcgtaaaaa   32820
attttgtaca aatctgctcg ctgacaataa aaaacggtcg gacgatcgtt gaaagttagc   32880
cacaaagttt tcgaatccgc gttagaatta aaaacatggg tatcattttc gtcgatcatt   32940
ttagttatta attttgttc aattaatcta ttgaacttt cacggaccat ttcataatcc     33000
acggtcggta gacgaacgtt gcggcataag aaaaattttt tacccgccac cgtcatttcg   33060
ccgtggaaaa aactgtccac gaacttgaca aagtcatctt tctgcatcaa catgtcttgg   33120
cgcattgtgt cattggtgat cctgaccact tcgttgccga tgcgatattt caagtgtggc   33180
ggtgttattt caatgttatt gttgctacta ttgtcctgat aatttatgaa attctttctt   33240
tgcttgctaa aagttttga aacgctgtaa atcagttttc cgttgacgat agtgtccacg     33300 attttttgc tatctttggg atacaaaatg gtttgcattt tcttacgctt tgtactttca    33360
cggttaagtc cgttggatat caaagttttg taattattta gcacgggact gtagatcagc   33420
tccagcagat aaacgtgttt gtatataatt ttgttggcca aactgtcgat ggaataattg   33480
atgccggctt tcatgatttt cttgatttgt tccaccagcg tcttgctctg cacggttcg    33540 tattcgaaaa tatcgttgag aggtttccat tttccgctgt tttttaaata gatgccgaga   33600
atcgcgttca aatcctcgga cacgacatag tcacttgcgt acacgtctct agcgaataaa   33660
acgtcctcgt tgttatcgta caccaattgt atggctctat tgattttttt ctcttcgtcc   33720
acgttaccgt aaagaaacat gcgtttgcaa cttttggagt agagtttgtc ataaaaattg    33780
```

```
tgaatcagaa tattgttatt catcattatg ttggggaaac tgagattacg accatcgatc    33840
ataaaagtgc catcgaaatt gcaacttttg tttgtgtcgt ttttttctaaa tatatgatcg    33900 agccaagtgc cgaaaatcac cacgacacat tgtgaagca cacaccggtt taaattgtcg     33960
acggcgcagc aaaagtatga ttttctttcc agcaaaaatt tgatcgtgca atgatttacg    34020
ttcttttcgt tgcaattcag gtaaaacgac aaaccgtaat tgtttttaa attatcatat    34080 aagttgttaa aatcgttaat aacatcagtc ataatggaaa ctaacaaagc aactgaattt   34140
accgaagcga atgataacaa tgacccatcg gaacgtatga tatatactaa aagaattcat   34200
gagggaagaa aacgaaaatc attgaatccc atcaccacca accccgcaa aattattaga    34260 gttagtaaaa gaagatttga atatgagagc aatgaatttc accctgataa tttgagatat   34320
gtggattttt acacattttt agatgtcgat tttaaaaatt ataatctaaa tgatgtttta   34380
gcaaaaatta aaagtaaata tgaaacattg aaaaatatac actttaattc agaatatttc   34440
gaagatactt taattttcat taaatttgta aatcaagtat ttaaaaatga agacgcgtta   34500
tcagaatata atacaacaac tataccagtt ttaaattttt tagaacttgt aaataaaata   34560
aatgaattta aaaatttcct cgatgtggtc aacgaaaaaa ttaatgggtc gaacattcaa   34620
atggaaaata gactaaattt aaaaatagta ccacgaaaca ctaaaactaa cagagctttg   34680
atcacatggg atgttcaccc gaataacgtt aacaacgaaa acatcaatat tgaaagtatt   34740
attgcacatt tcagtatttta tggtgaaata taggagggg taatgtgtga aaataaacaa    34800
ggttgtgctg ttttagaatt tgctttattg gatgatatgt tgaaagcaat aaatagggaa   34860
caaatgtacc gtgtttcaga ctacacggaa aatgaaatag taaaaattcg ctcagacaca   34920
ataaccaact taaagaaca gttacaaaat atacgatccc agattgtttg aatcgatttc    34980
ataagtatgc ctttaataat agtcgttata acaaaaaata aaaaatggtt taaaagtaca   35040
aaacggcgag ccgttaaacg atatacacaa aagtctctat caaaacttgt aaaacgaaaa   35100
tatattgaat tccgagaaac ttggatatga gtaaaaataa actcgaatat aattttcgaa   35160
tggatctcat tcaatgaaac ttggatatga gtaaaaataa actcatatcc aagtttcgat   35220
ttaaacctgt cgagacttgt cggcataatt atggtgcaat aattaaatga tgtcacgacg   35280
gcgtccaaca ggttgtgacc ggttagatcg aaactggaat atgagtaaaa tcatactcac   35340
attgaaaaat atacacttta attcagaata tttcgaagat actttaattt tcattaaatt   35400
tgtaaatcaa gtatttaaaa atgaagacgc gttatcagaa tataatacaa caactatacc   35460
agttttaaat tttttagaac ttgtaaataa aataaatgaa tttaaaaatt tcctcgatgt   35520
ggtcaacgaa aaaattaatg ggtcgaacat tcaaatggaa aatagactaa atttaaaaat   35580
agtaccacga acactaaaa ctaacagagc tttgatcaca tgggatgttc acccgaataa    35640
cgttaacaac gaaaacatca atattgaaag tatcattgca catttcagta tttatggtga   35700
aataatagga ggggtaatgt gtgaaaataa acaaggttgt gctgttttag aatttgcttt   35760
attggatgat atgttgaaag caataaatag ggaacaaatg taccgtgttt cagactacac   35820
ggaaaatgaa atagtaaaaa ttcgctcaga cacaataacc aacttaaaag aacagttaca   35880
aaatatacga tcccagattg tttgaatcga tttcataagt atgcctttaa taatagtcgt   35940
tataacaaaa aataaaaaat ggtttaaaag tacaaaacgg cgagccgtta acgatatac    36000 acaaagtct ctatcaaaac ttgtaaaacg aaaatatatt gaattctgag aaacttggat    36060
atgagtaaaa ataaactcga atataatttt cgaatggatc tcattcaatg aaacttggat   36120
atgagtaaaa ataaactcat atccaagttt cgatttaaac ctgtcgagac ttgtcggcat   36180
```

```
aattatggtg caataattaa atgatgtcac gatggcgtcc aacaggttgt gaccggttag   36240
atcgaaactg gaatatgagt aaaatcatac tcatattcca gtttcgtttt ctttataaaa   36300
gagtagtaaa aaatttataa acaaactttg aatttgagta aaatcctact catattccag   36360
tttcgttgtt ttataaaata gtagtaaaaa atttataaac gaactttgat ttggagtagg   36420
atcttactca tattccagtt tcgttttctt tataaacgaa ctttgaattg gagtaagatt   36480
ttactcatat tccagtttcg tatatacaaa taaaattgaa acaacagatt gttttcaaat   36540
gtagtttatt tgaaataaag ggaacaaaca tcttcgacaa aaagatcat aattaaattt    36600 cttggttact aattcgctat cactaacaca tgattcacat tgcaaacatt gttcgatatc   36660
aactttgtaa attttgtcgt gggtttcgtg taaggtccat gccatttta ctcgcgcgtt    36720 ccacactgtg taatcgtttt cagacacctc atgcatgttc atttcccagt aacacacgct   36780
cagcaaacag tacattgaaa attccttgtc cgttttagt atgcacacgg aaacaggca    36840 attttacac agctccgttc cactgttgtc ggtgaaacaa taatcgcaaa ccgaaacggc    36900
gcatgaagat tgtctcataa acggttcttt aaagcttgcc aaccgttcat tacattggtc   36960
gaaaaattga gttctcacag tgggatctgt aagttttttg tataattttg agtatttaat   37020
aaaaggctca attaaattca tgattaacgt ttaaccctga tgagttgtga ataagtaata   37080
acatgctatt gataattaat ttacaggata aatctgattt cctgtttaga tcgtttatca   37140
aactgtggaa agatacgttt gtcgagtgcc aaatttgtta cgaaaaaatc gaaaatgacg   37200
gcgaagtcgc catcactgat aacggctcga tcaatttaga aaaaatgttt cattcaaaat   37260
gcataacacg ctggagactt gaaaacacta gggatccttt taatcgcaac gttaagtttt   37320
ggtttaactt tccgcctaaa aaccaagcag agtgtagcgc gctggtaaat cagattaaaa   37380
aattcattgg tgataatgaa accgacaaaa aatacggcgc ggaatttaaa agagtcaatg   37440
aagaatcgtg tatagatgtg gacattgact ttactaattt attacattat tgaagttcaa   37500
cgtggtcttt tgcacaatta caaccacttt aatatgatcg atcatgtttt ctttcttaac   37560
ttttaacgtt ttaatattgt taacatcgtt gtcattagtg tatttgtaat aaacattatt   37620
atgtattcga gacaacacat ggttaatttt tttcgttaat atattttgat tgatgtgaac   37680
ttttgattga aaacgtatgg gtacattcat ttcctcgttc ggtttagtca cttgcgcttt   37740 caaaacctt ctcaacatat tgatggctaa attatttaca acgccacaaa ttaacaacga    37800
aatgttggtt ttgttatgag tgtaattgac gttaattaaa attggcacga tattttctat   37860
gttatccagt aaactatagt aatatttaaa aattagctca ctcattttg aataatttcg    37920 tgcgtttata tcgtatttgc caaaattaga catgatatct tcgtacaaaa ttttatttga   37980
taacttcgat gtaagtttaa gtatcttctc taattttacg aacagttcga agttcaggta   38040
tgttattaaa acgttaaagc cgttttgaat agattctata ttttcatgta cgataggcat   38100
cattaacggt ttgatttgta ttattttttg tctatattct attatttcgg ctgcggtttc   38160
gtttggatcg gggttatttt cggaatcatt attattatct tgatatataa tatcataatc   38220
aggtatatct ttgttcgcca tacttaaatt atacttaata aactattatt tgataatcag   38280
tataatcatt tatagtttct tttcttcaa agtgcgaat aactttttct tccaaaacat     38340
cataataatg aattgatccg tcggcattat aggacatggt tttaaaacga ttcaatttat   38400
taaattcatt ataagtaact agttttactt tcgcatcatc aaatatgtct tttctgttat   38460
cggaatcgga cgccataata aaaaatattc taaaaaacaa cctcgaatta atcgatgata   38520
```

```
cttatattat tttaaatgtc atcgaaaacg acgaaagtgg caacgcccag attcaaccaa   38580
tgtgtatcgg agaaattaat tcctttcaaa ccgatcaaat tacctcagac tcaatgtccc   38640
tatcatcctc tacgagcgaa ttgccgactg atcaaaccat gtgaccgata cgaccgagaa   38700
gaagatgccg gcaaacacgt tacggtttta caagctgcca ccggcatcaa ttataacctg   38760
cagccgtatt acatgtgcct tttagacgac gctgaactgc gtggctacag tatgaacgca   38820
aacgaatttt ttggccatgt ccagttgaac aaactagata atgacgaaga atttttggt   38880 atagacgctg ccggagaaaa aaatatggga actataaaaa tggtaatcaa aagtattatg   38940
gacagtttcg caacatgtga aaattattac attttgatga ttgacgaact tcaactcgat   39000
ctattgtttt ccatgttcag atcgataatt ttacctcaaa gaatggtatc tattcacaaa   39060
aacaattttg tgaccgacga tgtttatttt aaacttttct ctgtacccgt aaccgacgaa   39120
tcggatcagt cgcaacaaat ttaccgcacc tttttgatgt ataacaccgt gttaactatg   39180
atactcaaac agcctaatcc tttcaatgac gctagaaaaa acatttcggt gattttcaga   39240
agtctggggc gatgtccgaa caataaagaa agagttaaat gttgcgattt agcctatggc   39300
ggtaacgcgc cgaatcatgt aatgtgtcct ccccgcgaaa tggtcaaaag agtttttccat  39360 tacgctaaat ggtcgcgcac gcccaataac tacaaaagat actacgaaaa aattaccaac   39420
aaaattgatg attcaagaaa cgatcaaagt tcattatcaa aatatgcgct attgacgtta   39480
gattggtaca attttataga agattttcgt acatactttg gagtctgatg gcaaaatgcc   39540
caaagttgac ctatttaaac gttgcgcatg tcctatttt atttattaaa cgaattgaac   39600
ttttatcaga aggaggatcg gacgcgaaaa aatggacat caattttaag ctgaaagaaa    39660
taataaacac taccgtggat aacaaatatg gagaaaaaag caccaaaatt tccttggccg   39720
atttttataa gaaacatcaa gaagacattg cgtgcgtcgg aaaaagcacc acatacaact   39780
gtaccggcaa acgtgactac gaaaaacacc taagcgacaa aaaatacaaa ttctaatgga   39840
ccggcgagtg gatgaaactg accaagtgat tcggtgtgcg cactgcttgt ttgttgctcc   39900
aatatcatta agttatgaag aatatcaata tttacacagg gtctataata atttgttatg   39960
ccaagattgt tttgcaagta accctttcat gtcaacaaca gaattggatc caaccactaa   40020
gttggatgaa gtttcttgat ggattgtttt gtttacccaa atagtttgcc agttttccaa   40080
taaacaattt aatagaacta caccagcctt tcattatgtc taccttaacg ccgctccata   40140
taaacgacga acattgcttc gatagtttag ttcgattcgc aatggctacc aatatgagcg   40200
cgcgcttctt ggagtttgaa gaagtgtgta ttgatcttag aaatgtacac tttagttttg   40260
accaggacca tcaaagtaac aataaaacat tcataatatt tatgaacgtg aagcaagctt   40320
tttattcaaa tttcaaaata aaaacggatt tgtcacttga aactttgaca tattacatat   40380
atcagcactg tttatgtact gtggaagaca ccgttttacc tatattccgg cgtttcgacc   40440
aattcatctt taatgaaaac gataaatgta aatccattat cattcagctg catcggcgcg   40500
cccgtgtcat tgtggctgaa tgtatacgcg agaacgaata ttaccattcg gatgtgagtg   40560
gttacattga ttttgaaaac cggcacacta gattaccgct ttcgctgagc gaagaggaaa   40620
gatcgaaaat aaaccgagag gcacaattaa aactactgga aacgacctaa aatctttgag   40680
aagaggtctc gatgtaatct tcgtcatcgg cgtcgtcatc ggtttcgtcg tcatcgtcgt   40740
cgtggtagtg acgttgtgtg gtattggcgg tagtgttatt gttagcgtta atgtcatcat   40800
catattcata ttcgtcctcg tcttcatcgt aatctaagtc attgtaagaa aggtgactag   40860
ctgtgtgagg cgcattagca ggcgcactgg tagattcatc ctcgctgtcg taaatgtcgt   40920
```

```
gccgtacaat gtgttcagcg gcaaccttag gaatccacat gttatttaat tttacataat    40980
tacgttcaat agcctttcta gccatgtgca gtgccacgtc ttcgttggcg ctatctaatt    41040
tatgatattt attaaaagtg tcttaaaaa gttttttgc tttagcggga agctcctctt      41100
ggtagtatgc gtcggttaga tgaaacattt tattataccc ttacaattac tctgtatcgt    41160
agtcgtcgtt ttcagtgtcg gtggtgtcaa aatcgttgtc atttgtataa gctaaccatc    41220
tgtaattttt cttgtaatat tttcttttaa ccgccgacca cgctatacta ttggccgaca    41280
cttttgattt gtaatttttg tatgcacgat taaaaaattt catgtatatt ctacgaccat    41340
tgtaaggaag ccgttttaca gcggaaggta actctgatat gctgtcatac attgtattct    41400
taataaatat attaaaaaaa aattgtttca ttaattttat ttttcctaaa ctacaaaaat    41460
cagatccatt ttatgagatt caacaaataa tcacaaccat ttaacgggca taaaattatt    41520
gcctgcaagt catattaaat tagattcggc actgtccaaa ctatcaaacg acacacgttt    41580
ggcctttact agcaattcat gaatgtcgtt ttcgttttta acaatatgca cagtacttct    41640
gtctgttttg cgagccatca cgccgttttt acacaaactt acatatttgt agtgaggcaa    41700
aagagcgtcg cgagttttct ttaggagatt tttgtgttcc aaagatgcgg ctacaaaaat    41760
tttaacaggc ccgtcataat ttatgtttaa atcgtaattt ttgattctga tttcacgcga    41820
ccggttttgc cactctcgag ctgtggcagc atccgtcaaa tgaactacga tatgattttt    41880
ttcgtaatcg tttcaatta cttgtttcaa atctagtttt aaaagagagc atatttttt     41940 aatgtaattt agccggattt ttttgttagt caggcgtttg tcgtgaatac cgtaaatttc    42000
cacgctgtcg tttagattga ttatttctaa tttcttaagt ttttcattta attcgttaac    42060
attgcggtca atttcgcgtt taattaaagt ttgtaaaatc ggcacgttta tcaagctgtc    42120
ggcttccatg atgttggcaa gaatgtttaa atccgaaata ccctcttatt aataattcaa    42180
actctgttgt taatttcagt cgctattatg gagcacgacg cgcaaacacc caaaatcaat    42240
tttgttgaga aaagtcccgc tgtttttcg atactcacca atcccgatca aattaagaat     42300 gtgttttca ttaaaattaa caaatttaga tcgtttttaa aaatttttt ggcggatcta      42360 aaaaaggtta aaataaactt tttcaacagc ctgatcgaac agttgatatc cgtttacacg    42420
gaaaacaatg tgagaaacga gcacaccgaa actctcgtta aaataatcaa cgctacaact    42480
attgtcatta ccgacttgcc gtccaatgtg tttttgaaaa aacttaaaac taacaagttt    42540
acagacacaa tcgattatct tatccttcct aatttcatat tgtgggatca caactttata    42600 attttttga acaaagcttt caattcgaaa cacgaaaacg gtctcgtgga catttccgga     42660
gccatacaaa agattaaatt aacacacggt gttatcaaag accaattgca aagcaaaaat    42720
ggttacgctg gccaattttt atattctact ttcctaaaca cggcatcgtt ctacgccaat    42780
gtccaatgtt taacggcgt caacgaaatt atccctccga aagcgagcat taaacgctat     42840 tacgccgag acgttaagaa cgttcgcgca tggaccactc gccatcccaa catttcgcaa    42900
ttgagcacac aaatttcaga tgttcatcaa ccaaaggaat ataccgattg gaacgttaaa    42960
gtgggcctag gaatattcac cggtgcaaac acagattgtg acggtgacaa aaagtaatt     43020 acttttctac ctcaaccgaa ttcgttaatc gacttggaat gtttgttgta cggagacccg    43080
agatacaatt ttatttgttt tgacaagaat cgtctgtctt ttgtgtctca acaaatatat    43140
tatctctata aaaacaggaa aaatatagaa gtgatttaa acactatgcc tatgttaaaa     43200
acggtatggc aaacatacgg cgatagaaag ttttccacca aacttgatat gctgctgcgg    43260
```

```
gattgtgcat tattattgag ctcaaattgt agttatttac tgtttaaaga attaacaaac   43320
ctaattgacg aagaagaaat ggtttgcggt gaagaggaaa tattcgaatt taaaggaata   43380
tttaacgatg tgatcgacag cggagccaaa ggaagttacg acctgataaa aagtactaaa   43440
atttacaagg aaaccagctt caaagacatt gaaaccgtat cacagcgagc aattaatagt   43500
ttaaacaatt acatttcgtc gcataatcgt gtcaaggtgg gcggaggcga tatttaccac   43560
aataccacag tcttacaaaa catttattta aaaaacaata aaatttgtta caaaagtgac   43620
tttagacaaa ttggcgatat ttgtaccttg ccttcggaat tttattttcc cgaacatttg   43680
cttgacacct ttctatgtta acgatgtaaa cagaacccga atgctgccga acaagcaccg   43740
ctacaacatt gatcgtttcg attacagttt cgtccggtct caacacacgc cattgcatag   43800
gcgacacatg ccatcaaaat tattaatgta gttttaaac gcattttgat taaaactta   43860
tataaactta tgtttaaaac tcatagtgtg tacggtcgaa aacgacatcg gcacaattgt   43920
agaaccttc gccggccgga tcgtttcttt gccaacgcac atacaataaa aatgggtttt   43980
ttctgaaagg aacgttacg ggtatagtgt agacaaaatc cgaattacaa agtttgtcat   44040
gtggatacga aactaaattt gatccgtcgc cgccgattag ttcgagatcg tcccacaaca   44100
agtgatgttt acgattccag ttttctttag taatataaac ttcaaagtaa ctcggctcat   44160
gaattgcggt gggacagaat ctaatcaaag ttggcgaaac gtcttttgat atagtcgtaa   44220
gttgccaatt cgtaaaaggt tcgtccatac cgcttttgtc gccaaaaact gcgcggctat   44280
cattggctcc cgcgccgcat agtgtgtggg gaacgacatt ggtcttgata tgttcaatgt   44340
ctttgtaatt agcaccggcc atcgctgcat attcatgata ctgttgaaac atgtattgag   44400
cgatttgagc ggacgaacct gacgattcgc ctttgtctaa atatttatta taaactttt   44460
tgtaagcgtt cctgcatcct tcgtctatta tactatcgcc attttcgggc caataaaaat   44520
tattttctga aaacatata tattgtcgag ccaccggata ggacaagtac ccatgcgact   44580
gtacaaatcg aaacgaactt aaaattacta tagcaaaatt aattaaaatc atattgttta   44640
ttaattatgc cagacttaat tgaaaacaac gaggatgatt tttatattat attgtatgag   44700
tttattgaat taataataaa taatatggac gagcccgaca ccgacagcgg ttacgagagt   44760
acataaagaa cgacaagcct cagagcccat catttcggta tcgatatgag agacggttac   44820
atacacgaca cgattcacgc ccctgttata ccagagggta aagccgtatt atatgtcgct   44880
actacaaaga catatgcaca aaatgaccaa tacaaaattg gttacaccac tcggattcac   44940
ggacgtttat cttcgttcaa ctgcggccgt gccgaagaag acaaaatgta ttactgttta   45000
tacactagac caatgtataa ttgtgcaaag ttaaaaaggc tgttgaaaaa aaaattgtct   45060
tcacaccaat gtggcggaga tatgtttagg ttaagtttag aagaattaga gaatcttatt   45120
gttaaatgtt gtattaaatt aaaaaaggta ttacattaat gtttggtttt atttttatag   45180
ttcatccttt actactctca atccctcatt catagcgtta agtatgtcgc catcatcggc   45240
gtcaatttcc caagcaaaca agcctcccag accgtggtct aaaacatatt tagctttagc   45300
caaaaccgat ttgccatcat cgaatgtaat caactctccg gtttgcggct tgaacgcgta   45360
cgaggctttg gccactttat cgtaattata ttcgtacgac ggcaaatcgg ctttaatgtg   45420
acgataatct tttacaccgt cctcccatgt gcccgcaatg ggaccatcgg cgattccggt   45480
aaaaggattt tggtcgttgt aatctttaac acctctccat ccgcgaccgt acatcgctac   45540
gcccacaacg atcttttcgg gtaaaacttt ttgtttagc aaagcgcgca cggcaaaatc   45600
ggtggtgtag cgttcggtag ggttccaagt tggagcataa agattagttt gatatccaag   45660
```

```
atcgtttaaa gaccaagcgc ctttaaaatc gtaattcatt aaaaaaatgt gattcagata   45720 ttttttgagct tctgtgtaat cgaccacggc gattttgtcg tcgcccgcac tgatggcact   45780
ggttaattca aaagttttgt tcatttcatt tcccaactga tctagcatgt ggcgcaattc   45840
tttaagcaac aaagtatagg tgactttgtc attttcaaca tcgcctacat ttgggttggc   45900
ccctttgccg ccaggaaact cccaatcaat atcgactcca tcgaaaaact tccaagtcga   45960
caaaaattcc ttgacagatt ctacgaacac ggcacgtttt ttaccatcgt caaaatgata   46020
aaacggatcc gaaagtgtcc atccgccgat ggatggcaaa acttttagat gaggatacgc   46080 tttttttagcc gccattattt gtccaaaatt acctttgaaa ggttcgttcc atgcggtaac   46140
tccacgttgc ggttttttgca cggccgccca aatgtcgtgg atagttactt tgaaatcttc   46200
ccgtccgacg caggaacgtt gtaacgcttc gaaactgccc gcgatagttt taagagaatc   46260
gtttataccg tcaccgccac aaatagggat gaatccgtac aaaagatgac taacatttgg   46320
tataggaact ttatctagag gaaattttct atcataaacg ccccattcaa caaaatatgc   46380
cgcgacaact ttgtcgctca tgggtaaatt atcaaagttt ttgttatttt cctgaaattc   46440
ataagttaaa gggtccaaat gatcaccgtt agtatcggcc acagttacgg gcaccgtttg   46500
gctcgttgaa caaccgtcag cgttgcataa acgaactttc atttcaaatt ttcccccctt   46560
atcggtttgt atggacgctc gtttgggctt ggcgtctcct ctccacatta cagtgtcatt   46620
gaaaacgata taagcaacat cgcccgcttc accgttccac acgttccaac tgaccggaat   46680
atcaatagtt ttgtgaacac gaactaattt tcgtaggcg gtggcggcgg ggtcggtttc    46740
tactagagaa tatttacgtt ctgcccaatc gatttgcgct actcccggta tagcagcgaa   46800
actttctaaa acacaaaatg aaaatatcaa gtaaaataat gacgccattt ttatattgat   46860
cttacataag ctatttttaat ttaatgtatt taaagatgaa actttattg ttattttttat   46920 taatcgcggg cactactagt gcaactactt ttgatttatt aaaagcgccc gactatttcg   46980
aaaattttat tagcaaattc aataaacact accctgatac agaaacccgt aattatcgtt   47040
ttaaattttt caaacaaaat ttggaggaaa taaacaacaa aaataaatta aacaactctg   47100
ccgtttacag cattaataaa ttttcagatt tgaccaaaaa tgaaattgta tcaaaataca   47160
ccggtctaac ttcggcggta accgctcaaa atttacaagt cggttcaaat ttttgcaaaa   47220
tagtttattt agattctcca ccgggcgata atttacccat aaactttgat tggcgcataa   47280
gtaacaaagt tacctctgtc aaagaccaag gggcttgtgg cagctgttgg gcattttcag   47340
ctttgggaag tttagaatcg ttgtacgcga ttaagcataa caaactcata aacttttcag   47400
aacaacaatt gatcgattgt gacagagtca acatgggctg cgacggaggt ttgatgcatg   47460
ttgctttcga gcaaataatg aatgtgggcg gcgtgatgga ggaaaacgat tatccctaca   47520
gaggagtaaa atccagatgc gccgctgatc ccagtaaatt tgttgtaagt ctaagttcat   47580
gttcgcgata catatttcaa aacgaagaca ctttgaaaaa tgtattaatt actcagggtc   47640
ctattgcgat ggccattgat gccaccagta tttctacata ctcgaaagga attattaaat   47700
tctgtgacaa ctttggggtg aatcatgctg tattgttagt gggttacgga accgaaaata   47760
atgtaaatta ctggacattt aaaaatacat ggggaacaga ttggggagag gatggatatt   47820
tccgtgtcaa aagaaacatc aattcttgcg gtctagtaaa cgagttagcg tccactgctt   47880
ctatcaaata aaacaagtgt ttactgcaaa tatactttaa tttttttcctt tatttttttca   47940 cgacatatac aacaattttt gcatctttcg gcgcattgtt cacaagtagc aaagtggccg   48000
```

```
caggggctaa agcatatttc tatcgacttg tcgaaacata tcttgcaagt tttgttatca    48060
tcgtttggcg aaactgtcgt tgacatcaat ttgtgttctt ctttgaaatt ttgcaagtcg    48120
ggataaattt tgtttgacca aatagcttta tcctccatgc aaatttcgtc gtcaatttct    48180
tgcagatcgg gcgcagacgg ctgggaacgt tttacaaagg agcaattttt tgatgtgctg    48240
tgaataaact ctacactatc gtttcgattc agctttacaa tcaccaaacc gcaatcgaca    48300
catctaactt cgttgttacg gccataaaaa aagaatccat tttgagctaa agtttcgct    48360
tccattttca ctcgtttacg cgccgtcttg aatttaataa acgattcttt ccttaaagtt    48420
tcgtttcgct tcattaatct gatcgattcg gaacacagcg aataggtatg atatttcaaa    48480
agtttcgaat tcaatttcgt aattatgtat gaacaaaaag cgcatttaaa agattggtca    48540
tcaaaataaa atccgttgcg tgccataaat ttttgtctt gattcatcaa gttggtgatg    48600
tctttgaaag ttgccagacg attttcgtaa tcggtgtaaa aattttagg aggcggcaaa    48660
ctttttagga acattcgttc cattttgtaa tatgtttaat aatttttaa gagcgcgttt    48720
ttgtttcaaa gcaaatttga cagtgtttaa agtaaaattt ttgtgttctt ttctttctgt    48780
taatcgattt ttgccaatca aatatcgttc agaattagcg gctctcgaat gcaacggttt    48840
aaacactgta caaaattcaa agttggctgc gaaatctttc aacaaaatct ttgtttccga    48900
atgaaacgta tcgaatattt tcaggacaca atcgccgccc ggttttagcg agttgagaat    48960
gatcttacat tcttgggcca gtagcggtaa cgtcaaaatt tcttggtcgt tttcgttacc    49020
tctgacatcc gtggctccgt ccgctacaac caactcacat ttttaccac acattaggtt    49080
taactctagt ataacagatt cgtcaaaaat gtcaccgcta tttttgtaac cgtatatttt    49140
tttaaagttt tcatgattat aattataatc aagttttcct cgcaaagtta caccgtaacc    49200
tttgcaatca aaatttgtag aatgaatgta attggcaaac tgacctggtc ctccgcataa    49260
gtccaaaaat acatttacac gtttgcatac attaaacttt ttgtcgatat ctttgagttt    49320
gttaaagcac ctttttttaa cgacccgttt ttccatagcg tcgcgtgcgc gatgaatcga    49380
tttatcatcg atgttatcaa gactattttt gaggtcattc aatattaatc taagtttcga    49440
ttccataatg gatataatta attgataaca aaatgatgat aatgctgcat ataaaagcgt    49500
acacaatttg tattaaagtt ataccactcg gtacagccgt aaacataggt cgatccagag    49560
ccctcctcaa gggttcattg gtgactaaca actgtttatt tttaatttcg tatatcaacg    49620
gacgtttata atcaaaattt tcaaagtttg ctttgttaat tccagtccga aaagctgaat    49680
attttgggct cgctaggagt aaatctatca ttagattttt gtacgcccgt tcacgaaact    49740
ctggcgaaac ttcgattctg tcagcattca ggacacgcca cttgacatca tccaacatgt    49800
ctgatcacaa gagaatatct gccgggctcg aagatgttct gaacgacgtc gatatggagt    49860
accaagggac agagcaccgt aataaaaaaa gatcgtctag cagtggtaga tcatcgaaaa    49920
gatctatcaa agaagacaac tacgagcacg aatcgaaacg gtcccgtaag cgaaggagtg    49980
aagaagaaac taaagatatg gaaccggaac aaacgacctg tccaaataaa cttacctatt    50040
gggaaaagaa aagattgtcg aataaaacat ctttagcttt ggcaacgccc aggatgtcca    50100
gcgaatcggc aacagaccag ccgtctactt caagcggagt accacaaaca aaactacgca    50160
ctgtaagtgt gaatggtgag ctgattagca gttgccaat ctcaattaat aacaaatcat    50220
actacatatt aaagttttg tgcgaccaag aaacgaaaga gttctatggc agttctgttc    50280
acttcactga aatagttaaa aataacatgt acaaattaga ggtgtctcaa acacccagat    50340
tttcgtacat tgaaaattac cagattttga acagtgtgaa acccacaatg aaagtgaaga    50400
```

```
aagctctaga taacagcgat tttgacgatc aagatgttgt gtcggtgatc gctcgcatag   50460
aaggcatctt tcaaaacttt acaaatgaat cttacaaact ggttttgtct gtaaactatg   50520
gatcgcgcgc ggtacaaatt gagtgttcaa gtaatggtca atctttgata gaggctctaa   50580
aatgcgatga tgtcttaaca attaaagatg tgttgcattt tttcaataat aacattggtc   50640
gcgaaataca attgatcaga gtcaaatgtc agcaaatcaa taacgattta aaaaatttag   50700
tactgacaaa catatcgtct atagaattga ccaacgaacg tcccgtaata atggacgcgt   50760
ctgaggacat caaagttaac ttgagccgta agcaaaaatt gattcataga ggcactttgc   50820
tttctttaaa cattgaagtg cgcccgttta aaaaaagtca gagaattatt tttgattttg   50880
aacttaaaga ggatccaggt catacacaaa atgcgtcatt cttttgtaat gacagcatga   50940
acgaggacga aatttccata ttaatgatga acttaaatca tttaaagacc atggtgaacg   51000
atatggaagt tcacatttat gagttggggg acgggaaaat gtcgactatt ttaggcataa   51060
cttgtaaagt tttaaattgt gatgactatt attgcatcga ttgtaaagcg cctgaaatgt   51120
aaaaaaattt aatcaagttt tttaataaat attatacact atattttgtt ttattcaaca   51180
ggtacattgg ccggattggt ctttaattta cgataagccc gagttctaga ataggtttct   51240
acttctttat atattttatt aaacgtcgtt atagtatcat aggcagtatc tttaataggc   51300
tcaaattcat taataagttc ttgctgttgt tgtttaatta aattaatatt gtcgtttatg   51360 aaattttat attctaaatt ttctttaata gtttgttcta atttatttct atcgtgttgt   51420
tcgctttgag cgtttaatga ggaaatgttt gctggcgaca acggcaactg atcagacaaa   51480
atatctattt tatatcctaa gttttcaatt tcatgttgta gtctgacaat atcctggtcc   51540
tttgatgatt gcatctctgc attttgtaca cctgtcggaa caggaacaac tgcaaagtta   51600
aaactgtttg tcgggtctac aaatacattg ggatctgtta caggataatt atcatcacgt   51660
cttattctat ttgcatgttc gacctcagaa tttaattttc tattaattgc ttttaattct   51720
tcgttttcaa actttaaact atttatttct tcattataat tatttggtat cgacggtagc   51780
gcgggcggtg tatatgccat ttcaatagct cgcatatctg ttgatcgatc ttcggaagat   51840
tctataacta aattttctct attagcttct atttctctta attgttctga taatactcta   51900
tgttggttag tcattgtagc aatattttc atcaaaattg gaaataaatt actttcttgt   51960
atattttcta atggtatatt aaagtaagta attaatatat aacgcagatt gtataacatt   52020
tgattatacg aagttgtaag ttgggatgtt ttgtcgaact tgaatagact aatttctttg   52080
cttgaaattt gttgatttaa gctggttatt tgttgattca aattgtctat ttttgctct   52140 tttgatttaa gttccagttc tttcatttgg agatcactct tgtgttttg ttttaaccgt   52200 gtgatgtcat gttcaaaagt attaattta tctttctgat ttacaaccaa catatcattt   52260
atagagctgg ttgtagtttc tttaatactc tgatttaatt tatttaactt caaatcatta   52320
ttttctcttt ctaaactatc attttttaatt tgaagtttag tgttattact ttctagagta   52380
ttataattct ttgtaagttg atcataacta gattttaaac tgttatattt aatttgaaga   52440
ttattactac ccataggtac tatctgtgtt tgtaatttag tatagtcttt tttaagttga   52500
tcgtacttgg atttgtaatc ttcatcgggt ttttgtttc tgtaattttc caattctgtc   52560
aaggcgcttg ttgtcgattc tgttattttt attatatcgc tttgtaaaga tgtaaaaatg   52620
aattttttat caaacttgag agcaatactt ttaaaactgt ttaataataa aactataaac   52680
ggacacaaat ccggtcccaa tggcatgatt atatcggttt tattttaat gcacctcaat   52740
```

```
aaagcttgaa tatcgttgtc gtcgtctttg ttcgtattga cattgttacc gattggctga   52800
gagcaagaat cgtaaaattg ctttaatttt tcaaacacta aaactaaatt agaactaaca   52860
aaatatttaa cgttaatatt ttttagtaaa ttaataaaga tagtaaaatt atttacatta   52920
ggagttagat tgtttgttaa tgcatttgac agctctgatt cttcccgctc atctaaagca   52980
attggtcgtg tatagttatt ttgaacagga agttgttgtt gattgttata attttgcggt   53040
ggcatatttt gttgaggagg catcatttgt tgcggcggtt gcgggctacc aaaagcgtcc   53100
atgccacctt gattatagtt gctgttataa tcgtacttgt aattgtaatt atgagtaatc   53160
tgattaggaa atgttattgg tataagggct tcttgaacca attcgggtat ctgcaaatct   53220
aatctcattt gcaggtgtgg cctgtgttgg catataatag atctgacacg ttcgagcatc   53280
tcgtcattcg atccttgggc ttgacatcgt ctgtttagag cgcttattgt tttcaataaa   53340 gccttgtgg tagggtcttt gttaaattgt agatacgaca tggcaggaga tattgcaatt   53400
aatcttatga aatggagaac gttagttaac ggactagaac agaccaaata cagaaatttt   53460
gctataacta cacaagatgt gtttcgaatt actaaaatga tttaccaaga taatcatttg   53520
atagtatttt tgacgggcta cctactgcag gaaccagagc ggtgtgtgca attttatgtg   53580
aaaggtaaat gtgacgtgta ttcatataaa atgtgctacg aaacacatgc caatgacgag   53640
tgttatcgta actgtgtgcc ttacaaaact atggtgatgc cggggctgag gcaagtttac   53700
aacgacaaaa ttaatgtcat taaatacaga agaactaatg atgaaaacaa atattgtttg   53760
gacaatttta tgagagacat taatagagtt catatgcaaa caaacatgat ggagggtaca   53820
tacgtgagat tcaccaaaga acaggtatgt gtaaatcagt gtgttcaatg tgacatagaa   53880
aacattgaac aatttgaaaa actgattcaa aaagttaata tagaaacatt gaacaaagaa   53940
atcgttcccg ttgtcgcgtg ttatgacata gagacaaact caaacggaca agaaagtcc   54000 aatcctttga tcgataacat catatccgtt tcaattgttg ttcgtcgcaa cgagaaaaaa   54060
actaatattt gcctgtatta catagaagac ggcaatgatg acgatttaat ctgtaatgat   54120
gttttcaatg aagacgaaac ggtaaaagct gttaaatttc ataatgaatt ggcaatgatt   54180
gcagcatttt ttaaattgtt gcccctcata aatccagact atgtactgga ttacaacgga   54240 gacttttcg acttgaaata catttacgac agaatgaatg tattggcgga ggaactggaa   54300
gactccacta atttaaagcg aaaaataatg caaattcaac gttacgattt agaacctgtt   54360
gacattgagc gtagagaact gacggataag tttcaaaaca aagccgacag tcattatttc   54420
acctattaca ttcacattga cctgtacagg tttctaacca tcgaaaaaaa cgatgccgaa   54480
aactaccaac tcaacactgt atctgaacat tatttaaaga tgaataaagt ggacatggac   54540
aataccagga tggtcaaatt gtatagcgaa aatcgcatgg tagagatcat caaatataac   54600
gttcaggact gtgttttacc catagagttg tttctaaaac tcgaaatttt agatttcctt   54660
tatactcagt gcgaattatt atacttgtgc accgaagacg cttttaagcaa tatatcgcac   54720 aaagttaatg tggtaaattt ccataaagct ctaaataaca cgcgcacgga cgagtttgga   54780
aacgaacatc cggacccgta tttttcaac aaatttgatt taagcgtgac atcaggccgc   54840
gataatttgt accgtacacc cgcgaccaat accggcaaag gtaataaaag tttggtagat   54900
ttgactcgcc tgaaacgtac acccgtttcg gctgagcatt tgaaacatat ccccccatgta   54960 aaactgtgtg ctcaaaagca gatatgcctg tatagggggcg gtaaagtgtt aaatcccaaa   55020
cctggtatga aaaagtgggt cgctattta gatttcaact cactgtaccc cacaataatg   55080
atgtctgagg gagtttgcct gtctaatgta ttttgtgcg atgatggcaa cgttatttg   55140
```

```
cacaaaaata taaacgctat caatcccaag ctgttacaac agctgctaaa tctcagagtc  55200
atttataaaa acaagcgcaa caattatgtc aaagacagtt tccaatacaa tctaaatgac  55260
cgtcttcaaa atgctgtcaa acttatagca aatagtattt acggttactt tggcatattt  55320
tttaaaccgc tggccaacta catcaccaaa atcggtaggg gaaagttagg ggaagccata  55380
aaaagaatcg aagccaaaag caacgacaaa gagattctta ggaaatttga gcttagtaga  55440
atcgaattta atgtcattta tggtgacacc gactcctcgt ttattcaagt cgattttgac  55500
gagtcggaaa ttgaggagga aaagtgccat gacacaatca aagacataat tagtaactat  55560
gtcatgcgcg acttgaacgc gtcgtggtcg ggttataaaa tgggcctcga aaatatcatc  55620
agcgacatga ttttgctaaa aaagaaaaag tattgctata ttaatagcga acgcgaagtt  55680
aaatacaaag gttggctcgt gaaaaaagat atgccaatgt ttatgagaat aacttttagg  55740
gaagttgtgg attcctattt gaatcgacac acggtagcgt gcggcctcaa actcatgtat  55800
aaattgatgc gagctcatta tgataatttt gacaaatccg acaaactttt agattacagt  55860
tttagtatga cctataacga atccactggc acgggcgcga ccaaaaataa agacggcaca  55920
tctcgcaaaa aagtcattac tgtggccaaa aagtgccgag agttttggt ggcggccggt  55980 gccgatttca taccgggcaa tggcgataga atcccttatt tgctcaccga cattgacggt  56040
aaagtgactg aaaaggcctt tcctttgaaa ttgtttccaa ccagcgataa aaacatcagt  56100
tggctcaaac acatgaatat tttgtgcact tttatgaatg agctaattca ggtatttggc  56160
gacgacccga gtttcgagta ttacttcgta aagatctaca attattatac tcaaaaacaa  56220
aaatatgatg ttaaacatcc cactttggtt gaaacgattg taaaaaaaac cgcttcaaag  56280
ggccaaaaaa atagttcttc tgatgaagac gacgaagaat cgggtacaga taatgatgag  56340
gcggacgcgg gtgttaagct taagcagttt aagatgtatt gtaaaaaacc caaaaatgta  56400
aaacactaca aaggttcgct gtgcaccaag tgttttaaaa tttgttaata aataaaaccg  56460
ttttcataat tttgtgttta atttattttt ataatagcat tattaacctc caccactaaa  56520
aactctgata gatccctaat catatagtcg gatagacatt tcttttttac aaaagacttc  56580
aaaatatcta caatattttg gttagaaaga gtttggtagt atagatattc cacttgactg  56640
tcgctcaatt gtaagccgtt cgtggcgtcc acaattgtac ataaatcata tgtgtcgata  56700
cgtttgttaa gaaacatatc gatgacgttc agcaatttgt caaaaaacat ttcatctctc  56760
tccaaatcat catggtagtt tttgatgaat gtgctaaccg tggcgatttt agtagctagc  56820
ggcatgccgt tgtagaccac ttgagagaag aaattttaa caaatccat gattagtctg  56880 tagaacttgt gttcttattt aaaattgcgt cgaacgcttt ttctaaatct ctcttctttt  56940
ttatactctt agctttaccg gtttgtaaat cggcagccgt ggactctggt ttaatgtagt  57000
agacctgtag cattattata aatataatgc aaactagaaa caggaaaaat acaaagttag  57060
aaaatccttc gttttatca aacaaaaatc ctagcacgat taacaacaaa aacgttgtat  57120
agataaacat tttgacactt ataaaataat ttcagtatta aagtaacaaa ctaaacacct  57180
tattaactgc tgctatcgct gggtgtggtg gtagatgttt cttggtaaac atcgtcctcg  57240
tcttcttcat catcggtttc gtttatgccg acattaaact tattaatata gtgtttggtg  57300
ctgttaaacg aatcatggtt cattagtttc gccactcgtt gcaatggcac accgctgtta  57360
tacaggttac tactcaaata atgcctgatc atattggagc gtggcctatc catatctacg  57420
cccgcctctt caaagagtct tttaaaatct ttaaacggcg tcgatgtatt ttttgaaatt  57480
```

```
tgcaaaatag tagggtgctt gatataaatt tccctagcca actctagcgg tttgttttta      57540
atagtattaa gtgaatttgt cctcgcatgt ttccttttca agtttatagt agtacgaatt      57600 ttgcccttt  ttataaggac ggtcaaatct tctacggaaa gatgacgagc ttcatttata      57660
cgcataccgg ttcctaacat gatacaaaaa actatagcgc ccctgatcag gcctcggtca      57720
tgggcgtaat caccgttaag atacttaatt ttttttttcta tacaatctat aacattgtcg     57780
ataatttcct ttaaaacgat attttttttct ttagttttaa tatttttaag ctctttgtca    57840
cgaggcagca taacctgttt gggaattttg tattccggta gacccattgt gtttgaataa      57900
aaattaatgg tcagctgtaa agtttccttg gtgacggaac gcaattccaa catgcgacgg      57960
caaagttctt cgggatctat taatgttttt tgatagtata ttgaatcaaa ttccgtattc      58020
aaatcgtgag tgtcaatttc gtctaaatga tcgtaatcga ttaaacaaaa aattaattta      58080
attaatcttg acttgtaact ttttaaagtt gtcggcgcaa aaggttttgg aaacatgtat      58140
tgggaccata agctattatt tttaacttca tcgggcgtgc aacgttgtct gtctgtggcc      58200
aattcaaaaa tttcatcgaa acgatcgtga ctctgaattt ttgacttcca attattaaac      58260
gtgtgttcgt ttcttaacga tgacatcgct ttatccgact tgattataaa tgattttttgg    58320 ctgattatga tcagtgtaaa taatatttct tcttaatatt acaaaataat aaattgcata      58380
caaaagtagc ataacgcata ccaaagaaac taatccgata aacaaaatgt ttacagagtt      58440
agacttttca aaatcatttt cataattgtt ataattggtc aataattttt tttcagattc      58500
atagcttacg ttctcgtcag ttatatcatt gagagctaac tttagcggta tatagtcaac      58560
tttggtgcct atacccaact tttcgtaggg aatatcaaaa ttcatgttat tggatatccg      58620
attgattatt ttgtttataa cttaactgtt gaaatataaa acgtctcagt gcttcgtttt      58680
gaaatgccaa ctctgtcaaa ctttgttggc acgaagtttt attttgagta gatgatgcag      58740
cagcgcccgc ggacgacgaa gttcccgtca tgaatgtcgc cgattgaaac aaggtaggtt      58800
ttcggcctgc gcgagtcgcc aagtcggcaa catattgaaa aatgtccgtg gaagcggcca      58860
gcggtgccaa aaatccaatg ttttctttta ggctaacgat tctagcgcga ttttttttcgt    58920 ttaaaacata caaatagtat tcgccaccgc ccgcgaaaat atcatcaata acattattga      58980
taatatcgtt aatcatattg aggccggcgt acttgcggct ttccacggcg ccctgaatgt      59040
tcataggaat gtttgcacgc tgcaataaaa gtgtcatgta gctatttgtc aattgctggc      59100
taaatgggag cggaataggc acatttgtag ccacggcttc cgccacttga tattggatcg      59160
ccagtccaag ttggcgagcg gcttgactca cgctgttggc attaatattt tcggcgttgt      59220
tgttgtaaaa ttttttgtgcg tacgatggaa gtacgctgta aacaaaagat ggttggaaaa     59280
tgttatccgt caccaccgaa tgaccgagtt ctttgcgcag acgcgtgtag tgttttatta      59340
aattctcgtc gttatcaaaa cgtttgacaa catttacatt gataggattg gaatcgatac      59400
aaatgtcgcg aatcgtgttg accagcgcca gcatctgagg cgtgagctgt gacatgtcgt      59460
tcgtgcggta atatcgaatg attttttccta catagtccac acatttgtta agccacgctt     59520
cattgcttgt ggtcgtcata gttttttaatt tttgttatgt gagagcaaag tataatttga    59580
ggatcgctta tcatataatt attgttaatg tacaaaagaa acataaaaaa tatgacgaaa      59640
aaaatattat agtacgaaaa ttttaacatg tttatcataa taacaaacaa agctaaagca      59700
ataattatag tttgcatact tttacgcttg cacagaatgg tttcgcaatt tttaaatgcc      59760
acgttaaaat cgttttcgcc ctcaataaaa tttttaagtt cgttttttgca acattcatta    59820 cacaaaacca ttactgatat tacatgaccg tatgaatgta tctgctgaaa agtgcgaggc      59880
```

```
tgacttcccg gatgaaattc gaaagcataa ttattataca tatttacttg cgcgtaataa   59940
tgagccaata tggcgccgca acttttagtg actttaactt tacaaatttt tatgatatta   60000
actaaattcg tgtattggtt gtcatcaaaa agttcggcgt tattaatatc gccgttttct   60060
tttatgtttt gaaactcgtc aaacaaataa tgaatcaaca gttcggggtc gtattttatt   60120
ctattaaacc tcatcaagtt tttgtctctt aggcggtcta gccaaacagg attcgtcgtt   60180
ttcgctgtcg ttttcactgc cggtttcggt accgtaggac tgttcggtgg atcgtcgttg   60240
atcggaggag tagtcatctt taacaagatt ttcaacaatc ttattattca tatatttgat   60300
tttaaatata caacaatttt ttttcagcac caaaggtttt atattaaaca aaatcgtgtt   60360
gaggttattt tcttcgttga aattatggct tacaacataa tcaccgcaag ttacggtctg   60420
ataattaact aaattttctg ttaaaggcgc taacaattgt gtgtccaaaa ttttcaaatg   60480
gtacgcaccg acaggtagtt ttttaagtg atattcatct tgaacaataa aagataaaat   60540 atttcgtgg tctgttttat caagactgac ataacaagcg atgtccatag taccattatt   60600
attatgcgcc attatattga tgataatgtt ttctatttta tacttaatat tatacaatga   60660
ttttaatgaa aacgaattta acaaaaggct tagtgttttg ctggaatata tgcggcgtac   60720
caattccgaa ttacctacgc cggaacaact aagttacgta tctcacgtcg atcaaaactt   60780
ttacacaatc acccaattct ccacgagcga tttaaacatt acaaagcaaa cattacacga   60840
tgatcgtatc gaattttcg atttcctctc tcaaaaattt caaccgatcc aacataacga   60900
agaggcgcga gtaaaagctc atagcaaata tcattctaaa tttatggtga gaggagacga   60960
cggatggatg gacgttgact gtccattaaa cgaaattttt gatgaaagta tcatgcgatg   61020
tgttcctact ccaatatgtg accaaaaatt gccaggcaat tatggactca cagaaaatat   61080
gatcgataaa ctagttctca atcacgctat tattcgcgaa aacgtagatg aaaatttgtt   61140
ccatcccaca atgtacttgc aatgttttga tggcggatct cacgcggtca tggaatgtcc   61200
aaacgaccac attttaatg ccactactaa agtttgcgag ttaataaatg aatgcgaaaa   61260
tcgtcccgac gatttcatac ttacacgatt tccggattat ttaaatatta acgaatatat   61320
gatatgcaaa aatggcgaaa ctaagatcgt gtcgtgtccg aacggtaaaa ttttcgaccg   61380
aaatcaacta aatgtgtgt taggaaacgc gtgcgaaatt aacggcgtcg gtttcactta   61440
tattacagac gaaattggcg attcgcagtt ttttaaatgt ataaacgaat ccgaagccga   61500
attagttacg tgtattaaca gaattttcg aaatgaccaa tacgaatgta ccggcgatgt   61560
tcaatgtgcc aatttcgtta acggttcggg tacgcaaata aaaatgtttg aagacgatac   61620
ttggatgttt gcaaacggaa ttttgatatg cgaaaatttt caagtccaaa aaatataga   61680 ttgcgattcc actaatttat tgcaagacaa attgttcaac gaaaagttca agtcaattt   61740 gaatatacct gcagaaatat ttgataccga ctcgggaatg tgcgtaccct tcacaaaaaa   61800
tttaatcaaa attaagaatg aaattttccc catcgaaaat attaataatg attacaacat   61860
aaattttgaa acagccatgg tgggtcgaac cgacgcggtg gaaactttac tcgaaacttc   61920
cagtttggaa tcgtgcgtgt cattggctcg cgatatcggc gcggtcggaa tcaatccttt   61980
aaatggagat tcgataaatt gtttcggcga aaacctctat gacattttca ccggagataa   62040
acttaacatt tgtgatgata atcagctagt gaaaagtgtc gatctaaact acgatttta   62100 ttttcagcca aaaacgtcca agtaggtcg agacgatgat tatgagcgtt tttgtgggca   62160
aaaaactaca aacgctcaaa aaatcgtaga aaacgacctt ttttcggccc gtatatttgc   62220
```

```
ccatatacta cgatctgatg tttgcggact acttatggca caaatatacc attcatatac    62280
tacgatgaac cgaaaatata ctacaatata cgttcaatat acgtacgata tcgaaaagag    62340
cccgaaaaat atagtagtat atgagtcaaa tatacaaaat aaaaacgcta cgatgcaaaa    62400
acgagggtcg acagcaaatg atattttgt aaatcgagaa atcgttgatg gggaaaacga     62460
tgtaatcaaa ccgcttttcg acccatttga gagatcagaa attcaaccta tatttaatcc    62520
atttgatgtc gcgattcgtc cgccgttatc gtggtttccg gagtctgagc ccgatattga    62580
acctgaaccc gaacccgagc ctgagcctgt accagaattg atcttagccg acaagttatt    62640
ggattattct tgtttctatt cattgcccac atacaaattt agtgaatgtg aaattgccaa    62700
cgattttatc gttgataaaa ttaaagaact tcgcaacaat ataacagtcg atcctgaatg    62760
tgaaaacgcg agaggattgt ctaatgtgtt taattcatat gtgtatctgg gtaatggaat    62820
tggatgcaaa tgtcgctacg atgatgagaa aggaattatc gttgagaaaa ttttggacgg    62880
acccagatat ctaaatgttg aaactcaatc taacgacgga gtaaaatata atcagtgggt    62940
acataaaaat ggaaacacat ttattgcatg cccccaagaa cttctcaatg ataatttcga    63000
ttgtgccgtt cattccgaca aattttacta tctagaggat ttgcatgaat aaataacaaa    63060
tttcatttaa acatttatta tttataaacc aacatttatt attataaaaa ccgacccat    63120 tacaataatc ttaagattaa aataaacaaa aaaaaataca tgacttaaat cttattacaa    63180
taaagactaa aataaaaatt tatttgaag tcgaaggttc gttcgacgca gcacgtcccg     63240
acaacgcaat attggctcga gtaatacgca agttaagatc ggtttgatat ttcaacatgt    63300
ctttttgaat cattacttta tgctgtagat cagttatttc ttccttcata aattttttat    63360
acgattgcaa acattcatt tctttttca ttgcagcaat tttcgtctcg agttttttga      63420
attcctcttc tttagacttg cacaactgaa attttccat agcaagtctc ttaaaaacaa     63480
aatcatattg ttgtctcgcc tttaatttt ttttctttc cgtttctata gattctttaa      63540
ttttagttaa ttcaagtttg tgcttataa tctcacttgt aagcgagtta attgtttgtg     63600
atttaaattc attcttttta gtgttgttgt tgttactatc gatgatattt ttatcgaaca    63660
gttgtcgtgc tataagagca gtattaaatt taggatccag aggaataatc acattttga    63720 tattttaag gtcaatatca atggtaacat aatcttgcat gttaacggaa aagatggtgc     63780
cctttttaga cgattgtcgg caagtggggc attttatttc cgataggcgc tgtgtattta    63840
cattcattag tttgtaaata cacggcgcac aaaaattatg acggcacgga tccaaccgta    63900
tcagcggcaa aatacacatg ttgtccacac ttacgtcgta atcgtcttcc aagagatggc    63960
tgccggtgca aatatggcag ctaacacgag cgatatactt ggtattcatt gtaaaagctt    64020
gtgtttgatg cttacgcaaa ggcagatcac aataaactga tttatgtatg aaattgtttt    64080
ctcttttata ctcatgtcac caccggtgcg gtcgcaggtc gatttaccgg agcagcaggc    64140
atttccgcgt ctgtgttaat acttgtagac ggaattctat ctgtactgaa tgtatttgaa    64200
ttgtaaaatt tacgaaacgg tttctctttg ttagtgtaca acgtttgttt tcctaaaatc    64260
aaaggcacat caatagaata attgtcgtaa cgtgctagag atctctgtaa agcgttggcg    64320
ttaccctgaa atttaagaac attttcgacg cgcaaaatat tttcgttaac attaaccctg    64380
tgtttaggtt taacgggatt atacaatgtg acatctgcaa ctaagccggt tgaatcaatt    64440
ttacacgtgg gacagtttct gatacacaaa gtttccgtat cgatttttat aatctctgga    64500
gcgacagctt tttctattaa attttttaata aaattgggca gtttaataaa gttttggtcg   64560
ccaatatcat tttcattttc gtccgcgttg ctgtatagtc ggttatcgta tgctactctt    64620
```

```
gagcaaaaga cagtaggatc cgtcatattg agtatagtca tagttttgct gtatacttcc    64680
tctactattt tgtatgtttg ctccctataa ttttcgttgt actgaagtat cttgcaaatg    64740
ttgtcctggt tagttttgtc accataaatg atatatatta ttagacgttc tgccaacggt    64800
aaaccttcca cattaagtac ggtttcgtag tttttgtgtg aaggtattaa aacacgcgca    64860
ttacccattt ctttgtctcc cactaaactt ctgcctactg ttctgtaata aatgttattg    64920
tcggcatcgg gtatgggcaa aaccattttt tcgattttaa agtgcacgga tgaatggtat    64980
tcgcaaataa accatccgtc gtcgacggac gagtcagacg agcattgatt cccataccga    65040
aaacacgggt cgaaagattg aacagcacca aatatacaat aatttctaag tcgattactt    65100
gcgagtcctg ccggtaccag cgccattatg gaaacgatcg aaaagaaat ctcttattca     65160 ataaatttga gtcaggattt gctctattta attttagatt cttatatttc taaaagttt     65220 gatttcgtgg gtaaatatta tgattttgtg gatacgaata acgtgcgaac acgtttggga    65280
gacaacggag cggtgtcgtg tcaaactaaa aatgtacaaa acatggaaaa gtttgtcttc    65340
gccgatcgaa acgtgatcat acctttgtt acaagaatca gcaatgaaat cgaagttaac     65400
attgaaaata ttaaacctga actcgacaaa attgtagagt gtcgcgtgta caccaccaaa    65460
aaatacccaa aaatcgaaat caagtttgaa cagatatatt tcaacagaaa tttaagcgac    65520
cgctttgatt cattgatggc aagcaaacaa attgctctgc taaatctgct tcaaaaccga    65580
aacgaaagca tcgttaaaca atcgtatttg gggtctgatg aaattctggc caatcttcgc    65640
atagaatacg agtacgacga cgggccgaac atggaaacaa ttaatgcgat tgccgaaatt    65700
gtccgcgaaa tggacgccat cagtcactac caaaacataa gtcccctaat accgtacacg    65760
acgttacaaa acaatattat ttacagaaaa tttgaaggcg aaaaattgat atacaatttg    65820
gaggacttga cgaacgtgaa aaaatgggca ctaaagttgg acggtatcag aggtaaagga    65880 tttttactc gcaacttttg cataatattt atggatgata tgcaattgtt tgccggccat     65940
tttcccacac tgttcgaaat aaataatgtg gtggcttttc aatgcgaact tatagatgac    66000
aagttataca ttacagattt gttgcacgtg tttaagtata cgtacaataa taaaagccaa    66060
tacgaatgtt cgcacgacgg ctacaacatc gatcccatca ctgccattaa cactataaat    66120
tttcttaatg gcaaatattc gaatacaagt ctacacattg aaaactgcca ccaaaacaaa    66180
ctagaaatca aatttcaaaa attttacgat ccaccgcttc ccacgagttt gggttacact    66240
acaatcgcca cggacggttt cgttgtgttg gatatcactt tacgctatgt aaagtataaa    66300
cacgtcaaaa ctatagaatt ggaatacaat ggcaaggaaa actgctttgc tactttggag    66360
aagctattga cgaattataa aattaacagc aatatcgaac tgattcacaa caatatttac    66420
gaaactgtca tagtagataa cgttattacc gtaattaaat ttagacccga tcgtttagtt    66480
ccacaaatga ttcatgatga aacgaaaatg gaatcgtaat atttaataat caaattataa    66540
agcaacttac gaaaattgat acaattggac gaaaagggag aaaactggtt tcaagtcaat    66600
cctttcgccg aagtttaaa atataataat aataatccta aagctattac aacacgttag     66660
caaagaaaat caaaaaatgt ttgaagaaat gtgtctaccc gcagcgggca gaccgatgaa    66720
tcatcactcc atcctgcgac gaagtttatc aatcgtgttt gtagcgaaat tttcgctggc    66780
aggatgaatc cattctaaca tctataaaaa cctgacgcgc tgttcgtagc tcattatatc    66840
gtcagtcatt gtttcgtaac aagtaaattt cgttgcattt ttttaaaaa tgtccatttc    66900 taaaatcgaa tttgtcaacg gaccgatcga agttttcact gtgactgacg aaaagggaga    66960
```

```
aaactggttt caagcaaata cgtttgcaaa acattaaat tataaaaatt gtcccaacgc   67020
agttgctaaa tacgtttctg ctgaaaacca atgtacttat gacgttttta agacaaataa   67080
cgggtctcct caaatcgagg agactcatga atcatacttg tctattcaac ccaaaaccaa   67140
gttcatcaat cgagctggcg tgttcgaact tttatctgct agcgaaatgc ccgctgcgaa   67200
gaaattcaag cagtggaaca ataacgattt gttgccgaaa ttgtgcgaag atggagaata   67260
taacatggct agagacgcgc ctattgaaat tagcgaggga atgaacgcta tacatgtagc   67320
taccgatcaa gacggaagag aagctgcttg gatcgaggaa gccaggaagt ttcaagccat   67380
tataaaagca aaggaacata aaatagaaga gctgacagta cagttaaaag attcaaacga   67440
caaattgata acatttgcta ctggtttaat tcaggccaac aataatttaa acgaagcaaa   67500
taaaggtttg attaaagcta atgaaactat cggtctaatg gccaaccgta tggccgatat   67560
ttcccaggac gtgatcgcca agccgtcgga tccgcagctg ttgcattcgc tcgccgtgtg   67620
cgccatcgga ggggagcaat atgcgttttt gagaccgcag aagaggagtc tacagagaag   67680
cttgaagagt ctcgacgtac gtccggacga tatcgtctac cagagtgact acgtacccaa   67740
cgcagtgaac gttttaaaca aaatcaaaga gaatcttccg aaggacaagt ttaaagcgcg   67800
tcacaacaga atcactctgc tggacgactt gactcgcgag caattaatcg gcgtgatcga   67860
ctctacacta agttccagac aggtggctat agccaagcgc aaggttgaag aaaaaaataa   67920
atgatgtatt taaatttaat aaatattcat aaactttatt tttactttt attttaatta   67980 ctacactata ttcaacaatg atttatagtg ttcccagtcc attttttcca agttggcagg   68040
cggcgagata tttcgctgca cgaatctgta atcgttaatg tgattatgga acgccatgct   68100
agagtataga gtgccgtact tcatgagtat attttagtg acattggcag ggacaatatc   68160
gtttattaat agtattttgt tgccaaactt ctccttgtgc atggcaatct ctatacgttc   68220
caaagcgaca atcatgaaac ctttaacact aagataatgg tctctgcaca tggggcagtt   68280
taaaacgaaa aataaattat aataaatggc ctttatttgt ctgatgtggt ttataatttg   68340
atcatgttta agtttgtccc tgttattaac catatcgtct accaaaagac tgaggaaatg   68400
aataaagtcc cagatgctgg tgaacgtgta ggtataatcg tttggttgaa acgccctcaa   68460
atttaactct accatttttt cctggaaaat tactttcatg tgttctaaat caaaggcggc   68520
gtctagtgaa aggacccatt tttttatttc gtcaatctca acttttgta tgtccttgta   68580 tgttatgatg cacgccaact cgtataaata agttaattcg gtgcaaagta ttttggtcag   68640
ctgtttcgac tttgatgttc gaatccgatc caagtgccga aaaggtgca gcaaaaaact   68700 gtttctgtaa cgcgacaata acagcgaggg cggaatcata atgaaaacta tcaacttatt   68760
tttgcacgat atgccccccg gcgttcaaaa tgacaaagag atcgacgaaa atgtaatatt   68820
tttcgacgga gtgatcgaat gtgtcgagga cgatcacacc gacaaatatt gcgcgctggc   68880
agagtgtgaa aaaatcaatg ccttactaat gcaaaagatc gtcgtggatt tgctggaaaa   68940
tagtaacgga aactattgca agaaccatgt actcatcgac agtttgctaa tgtataagac   69000
gtatgtagaa ttggtggacg aatcggcgtt tggtgaaaat tttctggagt cgtgtgtcct   69060
acacattact agcatttta aattgtttcg tgctcaaagc agaatcgtag ttcttttacc   69120
gtccaacatt aattggaaac aagataattt aagtgcactt ttgaaacatt tattacaatt   69180
atctttaatt gaaattgcct aaaatgacga cgataatttt gattgtagtg gtactggtgg   69240
ttttgtattt tttatatgtc aacaataaat tacctctaaa ctctctcaac gaatcatcgc   69300
ctagcattaa ccaaagtagc gattcggttc aattagatcc ggccaccggt cagtacgcgg   69360
```

```
taaaactaaa caacagtaaa attaaatcgt ttaaaatttt gcacggcgac aatcatctaa   69420
gtagattgta tgtgtctgaa cggccgttaa cctacaacga aattattgat gaaggtaatc   69480
gtaccgctgc aaactcttat gtgtttgtag gcacagtatc tgaccccgcc actttggcgg   69540
gcgcaacttc aaccagtcgc acgaccttaa atttcaaaat tgagcagttt aagaatgtat   69600
tcctaatttt caaaaacttg gactttaaca agattaaaga aagcgttaat atgactagat   69660
atgaatgcga aggcatggtt tattgcctaa tagatccaaa cacaagtacc gtcccagatt   69720
tgagggatgt ttcctatcct atcaccgttt atacaaccaa tgtcaatgca caattaaaac   69780
taaaggagtg ggattatgca gaggtgaatg aggcgggaac cctattcatt aaaaatgaaa   69840
aatcatttag aattcaataa actttattac tcaacacata aactgaggcc taaccgttac   69900 aaaattttc ttgtccctaa ccatggaaat ttttcataa cacattcctt tttcgttgaa   69960
aaatttggca catttgtttt taaaatcgcc ttgaatcttt tctattttt taggcagacc   70020 cgcctgggtt ttacacttga gttgctcatg aatcatggtc tccacaatgg ggaccgctag   70080
cgcaataagt gcgtttacag tttcctcggc aatgggttct gcgttctcgt ttaatttac   70140 actcatcaca tagaaaagag ccttcataat actattgtta atgtctaaac actttaagtt   70200
gtgtaaatgc atgggtcgt tttgaagtat gttcctgtac aaaacatagc catcgttgtt   70260
tcgcctatac ttcagtatgt gagacaaaaa caattgggcc ccctttcgat gattttgaat   70320
ctgagatcga atcaatggat attttttc tttaatgtgc gaatataccg acccgctaaa   70380
ttgaagttct tccacaaaag tatgatcggt gtaaactata ccgaaccgat gcgaactcc   70440 gcgatcatag tcgctaataa acaaaggttt attgttaata ataagcattt tataattggc   70500
ttcgtacttt tggctaccct gatacttgcg gcatattaca ttactttgg tggagtcgga   70560 atttgttttg aaaaaggcat cgttacacac cttcatttcg ttaatgacat aaagttgaga   70620
aatcaacttg tcggcttcaa tgtcattggt ttgctcttg gtcaacttgt atttgtcaga   70680
atcatgtttg tgtaccacaa acatgctttc catgagttca aagaaactcg attttcccga   70740
tcctgccata ccgttcaagt aaatgcaaaa cttgtcataa tctgagggga tagcaagact   70800
ggtagcgaaa taaatcatga ctctggagtt gacatgattg aagcccgtta tgtttctaaa   70860
gtgtatgtac gccttcacaa tgttggccag ggcaatgtta gagtaatgtt tgaaatcaaa   70920
tttgtttaat atcaacctaa tatagaatcg ggcacaccag tcgttaggt tgtctccctg   70980 cctggcaatt atcaatttgt cccaccaaac attgtagcgc tttatgatgc gtttaacaaa   71040
tttgtaatgt aaataaaatt ttacaatagt gttgtcctcc tcttcgaaat cttcatcgtt   71100
aacaaacgtg ctctttttt tattttcaac atgtgctact atatttttaa tgaaaatatt   71160
tgggtcattc atttcatcga taatgtcagt gatatagcgc acatgtttaa attttgtgta   71220
tagaaaatcg ataatttccc ttcgattttc gtaaaagtat gttccgtaat tattaatcaa   71280
atcggaactt gacacaatct ttaaagtttc aatatacaaa tcaagttgt acaatagaga   71340 ccaaattaac tctataattt ctttagagac actaaaaata ttaaatatta cagccaccaa   71400
aaaagcgtta cgattgattt caaacgttgt gtagcaatca catacgtttt caacgttaat   71460
gacgcatttt ttacatttaa aatttttaac aatgtccgat attttttttt cgtttacata   71520
cattgacaaa ggaataagtt ccttgtcgtc atagtttaaa atctcaagaa atagcttgtg   71580
caaattaatt ttttcactca tctcttgatt agcgtcattg agcgtcatgg ctatagatat   71640
gttacattta ataattttaa tgtctctaca tattttgct acatgatata ttctgtatat   71700
```

```
gtcaacttcg tattggctgt tgtcttccat gtatttaata attttttccg acaaatattc   71760
tgttttttta cgtttagtaa tggctcctaa caaagtgtta cccaaaataa acggacaact   71820
atcgtgatag gaatttgtga ggacattgaa gacaccttcc tcagtgaaat acatgtactt   71880
ccaattgttg aattttatgg aagacatgct agattcgggc tctttagaaa cgaatttaaa   71940
aattttgtca tctttatgta cggcgttgtt atacttggtg ccgttaaaca taattataca   72000
gtttgaagtc agaattttt taaagtagcc tcgcgccaaa agactgggcg aagcaccgca    72060
atttagggca ttatctgctg tgtacaacca ttgtttggaa gtatcttttt ctgatttcaa   72120
ctttaaataa atcatatagt gtatagtgta aaaatttgcc aaagcaattc gagggtcttc   72180
cgacggaaac actgtccatt ggttacataa actttgaaac acctctgggg acaactcaaa   72240
atagggttca cactttgcaa cggctcgctc aaacagaata ttatcgcaaa aaaaatcgtt   72300
gttgaacaac acacgacaca cggtttctaa gcaatatcta atgtttgtct tgttaatttc   72360
cacttgatca gacatggaaa tcagtttcca aattaaaatt aaaaggtaat cgaaattaac   72420
aaagtcactt ttgtcaaaat attccaacaa aactgacgtc gttttttca attcgttttg    72480 cattgtgtct aacattatat ttatgcaacc gtttactatt tcgttaatat aatctttatg   72540
ttcagaactt gaggtgatgt tgtaaacgat ttttttatat tcaatttctt tagtgtcaac   72600
ataagtttca aagtccctat acaatcttag attttttcaaa tcaatattaa taatgttttt   72660
gtacttttcg gttacaacac attgacgcaa agtaatgtct tctctaatta catcaaacaa   72720 tttttgtcg gaaaaaacca aaacgggcag cactttacaa taacctacag taccgtccgc    72780
agtgattatt ttgaacaaat cgtcattttc ttctacgaaa tcactattgc cgtttacaaa   72840
taaaaaacct ctaccttcta tatgtaacga catttccacg ttgagaaaaa attcagcgtt   72900
aaaaacaaac aagtttacat tgccgagttt atgattatgt atcagaggta tgtagtcccc   72960
aatgtctatt ccgaaattca taaatatgta ctgacgccag ccaaaataag aaacgtcaat   73020
attgggccag taataatagt cttttgattt gacacacttg ttcgcgtact cgttgtcacc   73080
gacacatcgc acaaatttgc taaagtccac tttatttttg ataatttcat agtgtttttt   73140
gttaacaaaa ggtttcactg tcaccatgaa atagtttcct ttcacgtacc aatcgtgggg   73200
atctacagaa acactatctt gacaataatc caacttgcac tgagtattct tatccgacat   73260
taactccaac agtttttaa agttactgtt agactctaca acctttgtta ctccagtttt   73320 ggagttttt aacaccaggt tgtcaacagt atcaaaattt ttcataatat tttcatcact   73380
ggtttcggcg tgaaaatgg tatcaaaaat atggtccaca tttctaatcg gttcggtgtc    73440
cattgtgtta atgttactgt taatggttgt gattttctt ttaaaccta taaatgtagc     73500 tgctgataac gttatagcta gtcatgcaga tagtttgcac tttgggtctt acgttgaagt   73560
tttcgatttg agttttaata ataatgtaga acgtttgttt ctcgtcaatc ctgaaaacat   73620
tgtgatttat aataataacg ggttaatatt ttattatttg gattcgtcca gcgtattatg   73680
tcctcacgag ttttctttgc tacgtctttc aaaatccgac atcaaatcta taaacgaaag   73740
cggtatattt ccgacagttt gcactaatgt taacgcccttt tcattgctcg agcattttt    73800 aacactaaaa aataatgttc ccgatcatag aatcgtgtta gctgtaaacg aaattagcta   73860
caccatttta gatataataa atatgctaat ttattcggga tacgtttatt tagaataaac   73920
gttttcgtag ttaataatgt tggacataat tgtttcgtgc caatatttcc aatcgtttat   73980
aggttctttg catcgtttca gattaacgaa atagtcgtag gaatgatcgt tataaatcaa   74040
atcgtccacc aaagtaatgg tttttatata attaacgccg agtttacgaa gataccaaag   74100
```

```
cggaattcgt ggtgactttg gaattctttc tctggacgaa taatcattat ccaaataaaa   74160
aggtctttct acatatacaa ttttcgattt ggcatcaact atggtgcgct ttgacggttc   74220
tgtcgatttg tatccgccac acagcacaat atcaaagaaa ccgttcaatt cagtttcgtc   74280
catagaacgc gagacgtgtt ctcgactacc gtacgaccat aatatcaata tacagccaaa   74340 ttttttttaat ccttccaagc tttcataaac gaattcgtct ctgattctaa cgcggtcttc   74400
gctcgtgatc aaggtttcgt ccatgtcaaa aactataaca tgcggtattt cccacacata   74460
tttttgaggc tccatttgga aaacttccaa gtaattttga acgtaccatt cttttaaaaa   74520
actatacatg ggcttgcgtt catttataac atacacatga ccgagtgata acgtttcaaa   74580
agtcattttt aaatgttctc gtaattcctt catattatca cgacatttaa tcagtcggac   74640
tatgtaattg tcggtgtcac atttgttgct tttgtcaaaa gcaaacacta catactcgaa   74700
aacattcaaa tgtttgaacc cgacaatgtt aaggtcggta tattcggcaa tgacaagaat   74760
atgccgcttc atcaaaggat tcatgtgcct caaaactgtc caaacagcgg attgttccat   74820
tgttaccact tatttttaat gttcaaagag tttcgaaaaa atcaaaatta cgaagaactc   74880
atacaatttc tcaacaaaaa ctttcccgct aatgttaaaa ataaaacatt tgacttttttg   74940 aacacgggac acatgtttca ttccctgtac gcttacgtgc catcgattaa caatcaacaa   75000
aaagaacgaa agcaaattag actctctgaa gaatgtatta aaaaattatt tgaaaataca   75060
aagaatgaca tcgaaatgta ccaagaaata ttcgatttga tgcatcaaac aaactctgag   75120
ttcgagtgtc cttgcgagct gctgatgaag cgccgcgaag aaatcaaagc gtacgtgggc   75180
acgttagagc aaaaggtgtt tgatactaaa cccgttaaat taaagaagga acaaatcgat   75240
gcaattatga gcaaatactc gttggattgg aagagtatat taatcaaaaa aaagggtaat   75300
gaagttacca aaaaaggtgt taaaagaaa cgtaaaataa aaaaacgtac tataatgaac   75360
gacgaacaaa tttatttaaa aattaatgtc gaaaacaaac ttggattaat aaacggtatg   75420
tctttaagca aatgcagtca cgaatatgtt gtcgaggaaa ggcagatgcg cgccggtgat   75480
gaaattgtat cttttgtcaa gttatgtcga ttgtgtggtc ggcaaaagtt tgtttaataa   75540
cgacgatttc ggtatctgta tgttccgcta ctgcgacgac gagatgatcg gcgacgtcct   75600
ccgctcctgc gtcgtcctcc actcgagcga cgcctgccta cagaacggcg gcgagatgta   75660
cgtcttccac gaggacggcc cggccgccgc cgacttccgc cgctgctagt actactacgt   75720
cttctgcctc cataacttct gcgtctaccg cctgtcgatc ttcgtctata aaccattata   75780
atatataata tatagtaacc gaattttttat ttgcaccttta taaaatccat ttattaattg   75840 tacttttttac gtttagctcc tttgtccgct cccaaataga cattcaaact atcggacatt   75900
tctaaatgtt ttaacgtgag cgcatcactc tctttggtgc actccatgat tgtgaaaatg   75960
ttgttatagt cattcacatc gaatttacaa ttagcaaccg catagttttc catgctgctg   76020
taaaatatac tgttagcggc gttgtaaaac attcgaggaa taggaaaatc ggtaatcata   76080
tcaaacagat cagtaataaa ttctgtatca tcgcaatatg gaattttact gctgtttaaa   76140
tcgttgatac attggttaga atcgagattt ttaatagact ctgaacgctc aataattaaa   76200
tcgtgtaaag tgcagcgttt gtctttggtc aagttggtgt tttgaagcac catgatgcga   76260
gggaagcggg ccaacgggta tttcatcgtt tttatcattg tgcttctcaa cagcttcacg   76320
gtgttcatgt caattgtcga accgggcatt tccattaaca aacgtagtaa atttacaatg   76380
ttgtactgtt gatcaggcgt cacgtaagga gaacattcca catcgtcgtc cgccaggaag   76440
```

-continued

```
gttccttcta aatacgcata cagcggtcta tactttggta ttcttgataa atatatcatg   76500
cagcaaatca gatcgctaat tttaaactcc acagacgtgg tactagttag tgtataatac   76560
tgtaacaatc gcacgcatcg ttttctatat tcgttcaagt cttctatcaa attatcagac   76620
ttctctgttt gttgccgttg tgaaaacaaa tttagcaaat tgcgccgctg cggtgccgat   76680
ggcggtgtag gctcgggcgc aggcgcgagt cccgtagcca aaacggtact gttaacatcg   76740
gcattcaaaa cagactgcct ggctacggtt tctaagaaat ccataaactc gtttagggaa   76800
atattgagtg tactgttgga gttggataaa agcggaaaaa atttaggcca tatttccatt   76860
tgcatctgtc gatcgacttt attttgagt gtttcgattt ccaaaaaaag catcactccg    76920
ctcatgttga atgattttaa tgctgtttac ttaataagcc ttttactcgg taatattgtt   76980
atcgtaaata tcacttagca actttaacgt gtttattgta ttgagggtat tcaattgtat   77040
gacgctttgt tcgttttgaa tggctgttaa aattaacttt gccgttgccg atcttttact   77100
caaatctttg aaagaaacaa ctttgttttc tgacgtatcc gccataattc gcttggcagc   77160
agtttctaac acgctcagac cgtccaaaat gttttgttcg tcaagagcgt cgcgcacttg   77220
ctcgtcctcc gaaggatcga atttgcgatt gcgtttttta tttttatgtc cgctcgtcaa   77280
atcgtcatcg gacgccaaag ttgcaattaa atcttctgta ctaatcattt tgtaacaaca   77340
aggcaaaatc ctcgtcgatt ttatgcttgt tcattaattt tcttatatgt tcttcggtaa   77400
cgatatactg ttcaatattt aaatcttctt ttatacttgc caacttcatc ataaaagttt   77460
caaatttctc atcgttgtat ttgttcataa tgaagcggca gacgtttcga atttccattt   77520
cgaacggtgt cattaattta aaattattaa agcaaacatt gttctggtaa cccagtttag   77580
cgaccgacgc ttccatgtat aatctcaagt aaaaaccggt gaaaacgacc gaagcaattt   77640
tgtttatctt tgaatttttt attttagttt tcaaacacaa ttgtaacatg aacttttaa    77700 aaggagcaaa cagaggaata tctagcgtat gttgtccttt aagaatgacc aataacattt   77760
ccagattttt tacattcatg cccaaagtgg cgcgtttaca ttcgtcaatc aacgttgta    77820 cagttttcg atcagtaaac tctgacgttt tatcacacaa aatatttctg aggaaattga    77880
caaagcaatt tgtgattaga tcctcagacg tgaaaaattt attttcatag tcggttttta   77940
ttaaaacgaa taacaaaagc ggtaatccaa acatgggcct caaaaatatg tcccatcctt   78000
gctgtatggt ggtgtcgaat tgtgttatgg cggcggaaac gtagtggat ttacaagcga    78060 ggcatgctag ttgatttagt gaacatatgt tacaagccgc ggcgatcgcc gaaattgatg   78120
ggccgacaat cggttatag tattttgta gataatgcat tatttctttg aaatcacgaa     78180
cctggttcat aaattcgtga ttcagaaaca tggtgaacag tttggtcaca tcgctatttt   78240
gttgtttcct gttcaagttt tgtttaacaa aatcgataca cttgctaaac tctgtgtgaa   78300
aagtaagtcc tttgacaacg acatactttt tttggtcaaa gtacttggaa aataggaacg   78360
ctaacgtgtc gatttctttt tctaataaat gaacatttaa gtttgcaatt ttaacatcgt   78420
tttcattttt gctgaatttt aaactgtaat caataacacc tttcattata ttatttttct   78480
ttatggacag caccgacctt attagcgata tcaacgatga tgcccgagaa taccttatta   78540
tcaataataa atctataccg cataaaatag taaaatcgg tgctgacgga gcgtgtcttt    78600
ttagagccat cgctttgttc aagtatggcg atcaaaacat gcatttaaga gttcgtgacg   78660
aaatcgtaaa gtatgttatt gaaaactggg acgattttc aaactataca tgcgacgaaa    78720
ctacaaactg ttcaaatct atatatgaat acgaaaatt catgtcacaa ccgcaaacat      78780
atggcagcac gactgaactt tacgccgcca gtatcattta tgctatgcga tttgaagttt   78840
```

```
ataaagatca aaaactttac ggtaatggat ttggagacga ttcgtttcaa attaaaagac    78900
ttaggttttc cggccataat atgcatggcc atttcgatgt atatttggcc gacgataaat    78960
gtgatcctat acgtgagcca gaaaaacaaa atgaaaataa atttgttgat ttgatgtata    79020
atttgactaa acgttcgtac atgattagat tcaacacagt tcaggccatt cacaaatatt    79080
tagttgaaca agcgttgcct gaacaacaaa tggaattggc cgatatcggg gataaaatta    79140
tttttgcccg agatcaaatt aacactggta gttttgaact gttaatatat gaacttgcaa    79200
aaagattaaa tgaattatgg tctgatttta gaagatattc aattataaat aatttatcga    79260
ccaataccgg cgctactgtt ttcgatagcg ttaaattgag cgatgttagc ggcgaaacta    79320
aacgcaagga aacacaaaaa cgaaaagtac gtcgacaaaa tgataaacga gttattacaa    79380
aaaataaaaa caaaaataac acttttgaaa ccgtatattc caataatgtc caaccaaggg    79440
acactgtata cattcaacca agaaatttgc caaatttaga aacaatgtta acagtctcaa    79500
tttcagatag aacaaagatc gatataacta taccagaacc actaatgccg ttctatatac    79560
aaagtatcgt ggcaaacata cccaccacca ctacctaccc atatattaca tatcctacta    79620
aaaatttgtc gattgtgccc tctcgtgaaa atttcgaaac taacattaat ataataaacg    79680
aaattaataa atctattttg gataacaacg ttcatttta tgaaatgttg gaagcgttac    79740
tttattacgg aggtaacgaa accggccaag tcagggtact ttggtttatt agtatcgccg    79800
aggattattt caaagcgtgc gccgatcatt ttgataattt gagagaacaa tttgctaacg    79860
aacctgatgt tgatcgtttc atcgtattta taataaaata cattttttg tggcattaca    79920 gacaattcat aagtacatta aactcgtcca tgttaacttc gtatcaaaat cagaaaattg    79980
tacggttttt gcaattaaca aacgaatcgg ttcagaaaaa atttgaccga atcaatatta    80040
gattcgatct taacgtcgtg tatgtcaaca aagttccaca agtggttcaa ttgatgatag    80100
gatgttactc caaatttggt taatgattat cgttttcata gcggcccttg ttatgttaac    80160
tttgacaaaa ctgaataaga aaataattaa tgaaattgtc tacttccaat acaattttat    80220
tccggaacct ctaatttcgt tggtaaacgt tatacgatta aaataactaa gttagtttta    80280
cgatggcttg ccccttttaac attacagttt gcatcagcga acgtttcttt tcttttccct    80340
acgaatatgt ggtaccacaa tctgatgtcg gcggagcgcc tgttgacaat ttggtaattt    80400
acgttccaac cgaagaagac atacagtaca ttaatacgag ccaattaaca aactttaaat    80460
ccgtacttgt gtacaggcaa gagtttaaca atgttcgttc cgaaacacgt ctcgcaaaaa    80520
agaatactag cgcgacggta gtttactgga atccaattgt gccgatcgaa gaaatcggag    80580
ttggcgaaac tcgcgttttt agtgtccttc taaccaacga tttgttcttt tgtaaaacaa    80640
ttattgtgga tcataacaca ccaatttgtc cgatagaatt tcgttcgcgt atagaataca    80700
aaaaattgta tccgataggt ggagaagtgc ctttgtttta cctcaaagat ttacttaacg    80760
ataacatcaa tgatttttg atttgtttca accgagagac ctctataatg gttaaaattt    80820
taaacattaa aagaatcctc tctatttttg agtatcgaaa agtacctgcg cgctacgcta    80880
taaatttacc cgaacaggag gtggacaata tctacaacaa attaacatgg aaagaacgc    80940 gaaggctgat gaaggagat gttagtaata aatgtgttta tgtcaatcgg catagtttga    81000
tgtatgttaa aaatgcacaa gaaatgttgg gaatcaagaa ttattcgcgt tcaattgtgg    81060
attttgttaa aatatttcaa cctctcattc agccctacca aattgtgcct gatataatca    81120
tcaaactaaa cacgttagaa cgtgcgaaac atgtcaggtt gtattgtaga ggcgatagtt    81180
```

```
tcgctataac ttcgtacggt tctgtgccgg gcaacatgcc cgacgacaat gtcatccatt    81240
ttaattatac agacaccaac aataacaaga atttattcga agttaagtct aatttgttcg    81300
gcaataacgc tgttaatgat tttactgtca cagctgctcg atacaactac ttttttttaat   81360
aagttacaat gcgtcgtact caacaaacaa cgataaccgc ttttgatcaa ttacaacatt    81420
tgatcacaag aaatcaatca ttttacaaag attttctttt gttcatttgt gtcctagtag    81480
tctttataat aattttactc tttataattt tattatttgt tctaactaaa aacgcatacg    81540
agcgtaggga aacttttgct agtaatttgg attacaggaa taggatgtaa atgaaaatca    81600
aacagtttat taatacattt attttgaatc tgtcgaaccg aaaccgccac aatcccttc     81660
ggtagaagac aaggaatcgc tttccaccaa agtcggagtg tagtaacgct caaacacaat    81720
ttgcgcgacg ctttgtcctc gtttgaactg ccgcgttttt ttaccgtgat tgaaaagcag    81780
cactttgatt tcgcctctgt agtcgttgtc gattatgccg gcgcccacaa ctattttgtg    81840
atttgccgcc agcccgctgc gactttcgat ccttgcatac atatttgtgg gcatttcgat    81900
ggccagtccc atgttgacga ggcagccgtc acgagattta ataataaaat ctgttggagt    81960
tctgagatcg tagcccgccg aaccttccgt cgcctttatc ggcataaaag cgttttatt    82020
ttttttaact ttacaagagg tgttcatggt tgtgagttcc gttgaacaat aaacatggtt    82080
tttagtagtt tttgttttta caataactcg tgtcgcaatc gaaactgcca ctgatctttt    82140
ttaaaacatc catgttcaaa ttcaattttt tgatgaccgt taacgattttg acctttcttt   82200
cggttttcaa agcacacgac gtgcacatgt aacaatcgct aacaaaaatt aaagctaaag    82260
gtcctctacc tctgagacat tttgcgccca tgttggtgcg gtgttttttg aatcttttt    82320
gtacattcac tgaaatgcct gtataaatgc gattttgtac atttcgaatc aaatataaag   82380
cccatagttt ggttgtcatt ttgtaagggc gaatcgctaa tatgtacgcg tatgttactt   82440
ttgtaatgct gggcgacgaa tatgtcaaag gggctatcgc gttggctaaa agtttaattg    82500
tgaccggcac aaaacatgaa ctagtttgta tggtcacgaa cgatgttagc aaaatatgctt   82560
tgaaactact ctcgtcttac tacaaaatcg taagtgtaga gtacattcat tacaaatgtc    82620
cgtcaatgtt gacaaaacgc caaaaccaac tttacggtac gtggataaat tatgccttca    82680
ccaaatggac ctgtttaaaa ctgattcaat acgataaaat catctattta gatgccgacc    82740
atttagtgat taaaaatatc gatcatatgt ttgatttaaa cgcgcccgct atatgtttca    82800
ctgacgaaag ctatgggtac tacgataaaa tcgtttacgg tcaaactata tcgtcgcgcg    82860
ctatacaaaa gttcatgcgc caaaataaag tgctatgcaa aggtggcacg gttcttttcg    82920
aacccaatgt taaactattc gagttgataa agaagttggt caataaatcg aatccatgtt    82980
tgacaagaaa ctattaccac aatggtttcg atgaacaagt gttattacaa gccctcataa    83040
aattaaacat gcccataacg cagctatcca ttttgtacgc atggaacgca ggcacatacc    83100
atcgtttgag caaaaccac gaaccttttg ttataaatta ctatggcgat cttaaccgt     83160
ggaatttcgc cgatacagat gtgatcaatt acatggatgt gtttatttgg aggtactttt    83220
cgaatctaaa tctctagtat aaaaagcgat tggccagttt aaatttcatt cgctcaaccg    83280
acagccatcg acgatgtctc attattttt gattgagaag ctcgacgatg ccagataaca    83340
catcttcact tcagaagacg aacctcgaaa tcatcgaggc accattatct acgaaagga    83400
cctaaaacgt ttcgcgccca tttatcttcg atctcaactg aagcacttgg ataaatataa    83460
aaatgaaaat gacgagtacg ttttggaaaa agagcttgtc gacaaactaa tgtatatgac    83520
cgaaatgtat tataaaagta ttgaaagtag gctttaataa acgttttgaa atatatttta    83580
```

```
tatttttttt gctaacctta acccaacgaa acttgaatat gagtaaaatc ttactcatat   83640
tcaagtttcg ttatactact aaaacgaaac ttgaatatga gtaagatttt accccaattc   83700
agatttcgat aatatatttt ttagtattcg tttgtaaata acgaaacttg gatttgagta   83760
aaatcctact catattcaag tttcaattat tgcaccatat ttatggcatc atccaatcga   83820
actttatcat gataagataa tcatgtctcg tgtacaaatt tacaattttt tttaaaccat   83880
tctattgttg ggtagcgagc acgtacgatg gatatgtgtg taaaagaaaa ccgactaaaa   83940
actttcgaat tatggccggt gaagttttta tcgccagagt tgatggctga aaacggtttt   84000
tattatttgg gacgcagtga tgaagttcgt tgcgcttttt gcaaagtaga aatcatgcgt   84060
tgggtggaaa atgacgatcc cgctttggac catcagaagt gggcacctca gtgcccgttt   84120
gtaagaaagc aggtcgacgg tgacggaagt tccggcggcc cggacgagtg tgtcgtgagc   84180
tcctcgccta gcatacccgg ccctgtacac ccccggtacg ccaccgagca cgcccgtctg   84240 cagacccttta aggattggcc cataagcatg aaacaaaaac cccacaaact tgccgaagcg   84300
ggtttctatt acaccggttt gggcgacaaa actaaatgtt ttttctgcaa tggtggctta   84360
aaagattggg aggacgatga cgatccgtgg gaacagcacg ctaaatggta tagcgattgt   84420
cgttacgtta ttttggtaaa ggggcaagat tttattcaac gtgtacattc cgaagcggcg   84480
gttgtaaaaa attatgttga aacaaccgaa actgttgaag aataattga tgattcaaaa   84540 gtgtgtaaaa tttgctacaa cgccccactt aacgccgctt tcaatccttg tggtcatgtc   84600
gtggcgtgta tcaaatgttc tgtttcggtt aataaatgtc ctacatgtcg aatgcctttt   84660
gaaactattg taaaactata ttattcataa taaagtttgt taattattga tgtttgtttg   84720
aatttatatt gaattatgtt tggataaaag ctatatacta ggtaggataa gtaatttatt   84780
aaaattaacg atctaactac aatataatgt ctgtgtctat taaaaaagtt caagactacg   84840
gcgtgccggt gctggtcgat cccgttacgt ggacggcctg ggtcggcgcg gacgaagtcc   84900
taaatgtttt acgtttgcca tcgtcggtgt tacaatcgat tccgttgcgc cataaaaagt   84960
gctggttaga ttttagagga ggttttaatc caaacaataa ttgtaatgtt agttgccggt   85020
gggacactgg taaactttc attgaccttt acggtttagg attattatgt ggtagagtaa   85080
attcaagttt gtctgattat ttgatgaccc aatttgtagg cgaaatttac agagattatg   85140
cgcctgatgt cttaccgcaa cctcaacctc ccttaccgtt ccccgtacct cctcagccac   85200
cggtaccgcc gccgggcaat ttacctttag aattactgga gcggcttaat aggcaaagcg   85260
atttaataat taacgcttta agtcaattga gtatcagtaa ctctaaccaa cacttggaaa   85320
ttacaaacca acttaacgct atccgattac agaacgtgac cattaccggt cagctaacaa   85380
gtatacttga cattcttgaa aatcaattag gtaatgtaac tagcgaatta aacaggttgt   85440
tgacagagtt ggacggacgt ttcgatagtt ttgtaaacac gctgaacagc gctctgtctg   85500
cattacaaga tagtgttcga aacgagttaa ctacaatcaa ttccatactt agtaatttga   85560
cttcgaccgt gaccaatctg aactcaacgc tgaccaactt gttgcaagcc atctccaact   85620
taaaccttgg cgatcttagc aacgaaatcg aatccatatc gactaccgta gatcaaaatat   85680 tgagcatttt aactcccgag attcaatcga aaaagcttaa ataaattac ttaagactta   85740 gaataggata taggatatag gataagttta attaattaat aaaaatagtg tataaaattt   85800
tttttattaa atattatcat aggtttcaac aactttataa atcttctcca ccaaatcatc   85860
acagtattcg tagggtttca catcaataac attcatgtaa tcgtttccaa ttgtttctga   85920
```

-continued

```
taccatgtcg gcgggagtcg tggtgattcc gaccgctaaa cattggccgt gtctgctcat   85980
aacggcgtcg attatatcca agttcatgag acattttttcg tatatttctc ggccgttata   86040
attttttattg ttaggtatcg aaagtacgta tgcaatcaga ttcattgtag tactacatca   86100
tgaatatttt aaaatcggtt tatatactac cattattttt ttttccaaaa tttacgtaac   86160
gcacctattg ttattaaatt ataaaactag tatctttttt aacacttgaa acgattttg    86220
gtttactaca aacttgccca cttttacagt ctgccactcc aataataccg caacctaacc   86280
gtccacccga attgcccgta gttttgctaa gaggatgatc ggtaaggcca agatcgtcac   86340
gatttgtgtg cactactaaa ctgcggccca aaatgctgta attaccataa agagacatga   86400
cattatcgat tatgtcgatt tcggtgagcg aatttgaggt tttcgcttca atgttgccta   86460
aatctcccac gtgtctttcc tctgagttgg gcgcgccgtg attttgaccc gttgggttaa   86520
aatgttcgcc agccgacgta caccgttac ttgtatcgcc atattcgtgc acatgaaatc    86580
cgtgcaatcc tttgggcaag ttcataatgt atccttgaat ttttaaaaag tgctttggtg   86640
attcttgaat gaaatacacc tcgccagtaa cgtcaccatc gatttacaa atggctttca    86700
tatctgcaat cttatctaat atgtataaat tgatggacga aaacgctttt ggcacattcg   86760
tgttcaagca agcgacacaa tgggtcacaa tattgacagt gtcattaatc ttggcgatat   86820
gtactttgc gtccaagaaa aatacatatt agtggacgag aaaaaatatt gtttagattg     86880
cgcggccgat ttcatcatgg aagatcacat agtctgcatc aatcatggcc ccaaaaacga   86940
tatacaagat tattgttgga aacttgaaaa tctatgttgg agttgcgaga aaaacgtgta   87000
ttcggttcat cgactcaaag attgcgcacag ctgcaccgaa gttgtgtttc aactttacga   87060
aaatgttgtc aatgaaggcg ccatttctgt aactctatag ttttaagaat aaacattatg    87120
aacgaattta gtgtttttat tttcgctgta ctagtgtctt tgttcatagt tttcctttat   87180
tgtgttagca cagtttctaa attaatacaa acaaaagaag ccgaatcgtt ttcgccggct    87240
ttagacataa ttttttgatcg taacggcata gtcgattgca atctaaccaa actgccctgt   87300
gtaacttcga gacaatgttt agacaattgt agctctcaca atttggtggg gtctattgtg   87360
tgcgatgagg gattttgcac tagtcgcgat ttaaacgttt cgggtcgccc cgataatttc   87420
gagtgcgaca gctcgttagg attgattaaa gttttttaccg ccagcgatt taccgtgacg   87480
aatttgtgtg taagcacata cagagacatt atcgacgatt ttggtaataa acggccgtat   87540
gtatgtgata atggcaatct aactatcgat ctaacaaata ggcaatttag cgcggccgat   87600
tgtgtctgcg acaccggata cacaagaatg ctatttaatc aaacggcctt aactcgttct   87660
gtaccagtat gtattcccga ctcaaaccta acatttaca gcaaaattta cgatcaagta    87720
tgaaacaaag tttcaagatg aattacaccg ttgaagaata caaacatatt atttgggcgt   87780
acgtaatgaa cgtttatgta caaaacacaa aactcagatc gatatgtttg cgaaaacccg   87840
acgtaaaata tgtagaaatg gttgttagat tgctacccaa aatggacatg aaaaaattgt   87900
taccacggct gaaaaacata tacgcgctgc accgagtcga cgaattgttc aaggaaacgg   87960
acaaaggagt tttagaatta ataaatagta ttaatgaatg ttacaatgaa taaaatgaag   88020
tattgttatt taagtctttt tttttacaat gaacgcagaa catttgctcc tttcccagta   88080
tgtaaacata caaaatagca taatagaact gcaaataac tacctggcca atagcaaaaa    88140
ccccgcggtt attgccgatg taattaaaaa gcttacgaat attagagagg ataagttccg   88200
tacaatagaa tctagattga atacaatcaa tgctagcgag cgaactgcca cattttcact   88260
cataattaaa aatgataaat cgtatttgga aaatttttta aatgtggtcg atgcaattta   88320
```

```
ttataatacc aatcacgaaa tatttgttga cgaaagttta gtcgttagtc gtggagcgtt   88380
tttagatgac ttgataaatt atggcaacat actcggcaag gaagatttga tatattttaa   88440
atatgaagtc gagttgatag aattattgaa tagacctttg aaagaaatag actctgaaat   88500
gctcgaaatc gaccgcatag attgcgcatc cattattgtc aaggcatttt ttctaaacaa   88560
tattccaaat gtgagttttg agttttaaaa acaaaatata gacaacgata taataaaaaa   88620
gaaactttcg gcgatacttt cctatattgc gggagtatgt aaaagaattc gcgaatgtaa   88680
aaataacgaa aaggctattt tcactacatt taaaatattt tacacagagc agaatgaaat   88740
caatgacaat ttgaccgttt atggtacgtt tgaaagaaac aaaattgatg taaatatgat   88800
tagtcctttg aaatttagag gggcaacatc acctgaaaat ttatacgatt tcgtgttaat   88860
gtatacagaa ggttttggtt ctgtcgaacc tttcaatgac actattaatt ttgaatccct   88920
tatgtatttg acgtatccag aattgtttgc tatgccgtat ttgtttagaa acagcactga   88980
tagcgaacat cgttttttaca attttcaaaa tcttgcaaaa tccaacacga tagaagtggc   89040
gagcaatggt ggtataataa tagaggaaaa cgatctggta aatgtcgact ctgtcctgta   89100
tgtgaacatc gcattaatat tttacaagtt taggcctgaa tctccgcccg gcaccaaaag   89160
ttttctagac cgacatttga ataaaataaa aacatgttta tatgaatacg ccaaagtgga   89220
cgatactatt acggtctatt taaatcctaa cactgcaaat taccacaacg aagaatatca   89280 attttttaatc gaaatgttgg ccgtgttaca attaggtttt ttcatttctt acaacgcttt   89340
aacagaggaa atacgaagta acattaacga cacattaaac ctaataccag accattctcc   89400
gctaacacat atatacgata aacttgtcaa ttataacttt aacattagtg gggattctaa   89460 catgaaagt gaaacagatt cttttttata acagtttaat aatatttatt cgtaacaaaa   89520
tttgccgggc ctttttaaca attacaaaaa ctggccgtgc gcacaaaaca ttgttcaccc   89580
aaacacaatc gtctatttgc tcgaactcgt accgctcaaa atcgtagcga ttgttgacat   89640
aaaaatagta ttcaccatt cgacggcggt aatcgatagt ttcttctcga acgtgcagct   89700
cttgaaacat attgttgaca acgatcttta cgtggtcttt cataataagt gcgtagtcca   89760
aaatggatct gaacatagat atcgacgact ttaccagact gttgatcgct gacaaatgta   89820
acgcattaat tgctgcggag cggatgttgc ccgaaaacat cctggcgata gtcaaaagcg   89880
cccgcgataa ttattttgac gacccgtctc caaaaaatta cgaaaacatc aagaaacttt   89940
ttagtcaaac caaatacgta gacgacgcgg ttgattacaa ggattttaac cgtagaatca   90000
tgttgatcgc tttcaaattc gctttgaaca aatcgaaaga atattttaaa aactacaagt   90060
cggtgttgga ggtagcgctc aaacgactcg acggtataaa tcccgacttg aaaagttcac   90120
cgcgcgccat gttacaacat tacaacgagt gtttagaaaa cttggacaat ccgcgtaacg   90180
acgaacatca cctggtcact tttgccaaag aaattgctac aaaaattttt attgagacca   90240
tcgatttgta cagttacaat aataaaaagtc cattcgaaaa cggcaacgca acattgcagg   90300
gttccgattc tgagttgctg gccgtagccg cggcgagccg aaaacggaaa aaaaatagca   90360
ttttgaccta caaaattgtc gatcccattt tcgtttttgta gagtttagtt taaaaatatt   90420
tttttgcgct ccaaaattaa cgaacgacac ataaacatt gatcgacttt ggatgcgcaa   90480
ttttcgcaac atactaaatg acgacacggt tcaaacagaa tacttttttt gccgaccatg   90540
caaactacgc acacgaaatc atatttgggt gtttcggttg gaacaaaatc gggccgcgtt   90600
tcttcgtcaa gttttgagag aacatatttta cacttgggcg aatatttaat gtgttctatc   90660
```

```
aataatcac tttcaatttc ggtccagtta aaaattccat attgcaatct ttgcatttaa   90720 tttttgttttg gttacagtag acgaacccag cattttcgat tttatccatt acgtgtaatc   90780
attgtaaata atttagtata aaagaggaga caggtcctta taataaataa aacacatttt   90840
tgttataact gttttttatt aaaacatatc attttcatac ttgaacttga ttccgcatgc   90900
gtgagcaaac accgtgtctt tgtttgtcgt accattatga ttgtctccgc aaaaaaaact   90960 gttttttacaa tcgatcgagg gattcatttg caaaagtttt tcaaagaatc ccgtcgatgg   91020
aagcttgtat tgaatagtat gagacatcat aacaaacatg ggcacggcaa tttgcttaca   91080
cacatcctca atttcacgat ccttactaaa attagacacg agaacaatag taaagtcttg   91140
gttaattaaa ttcgtaaatt tgtagactat gttgtcgtac ttaaactgcc aattattatt   91200
aactttaagc attatagttt cgtttaaatc aaaaatggct actttatttt tcagtatagg   91260
caagcggtgg tgataaatac tcaaagaatt agtaatttcc caccgaaaga ttattttcaa   91320
aatgtagttg attatttctt cctgttgttc atctagagaa accttagtgt ccacgattat   91380
ttcgtcgtaa ttcatcactc tgcgccagca atcaaacttt tcgttctgct tggtaacata   91440
atccgcttcg tgtatgtcca gaccattgtt gcgtttcttc atcattttaa caatctcgtt   91500
ttcacttcct tgttttacgc gtaaaattaa agacttccaa ccgtcacaaa gccccatatt   91560
cttgcaaatt tcaaaggctt gttccgattc ttgttcgggc atgtcttgga acactgccga   91620
atacaccaac gcctccatgg gttgacgatc gaaaatgtga aaacgagaat ggtcacgctt   91680
gtatgtttca gcgctcttgc tgcgatacgc cgcgaaaagc ataccgccca cattgctggg   91740
gtaattatac ttgtcgtgta attctttgta atcctctaag tggacacgag cgtgagggat   91800
tctatcttcc aaccttttaa ggatggtagt ttttgtggtg caagctacac ctcccaaagc   91860
gaataagtac gacatgatgt gacggtaata atgtttgaaa agaaatccgt tattctttat   91920
atagtgtatt aattatctat agtagattaa ttatatatag tagattaatt atctatagtg   91980
tcgtctgaaa gtcaaagtca tcaaacgaaa ataagatatg agtaaatttt taccccaatt   92040
caaagttcat atactattaa aaacgaaact cgaatatgag taagatttta ctcaaattcg   92100
agtttcgaca aacgaaattt atatatgagt aaaatcctac tcatattcca gtttcgttgt   92160
tgatatccac cagagcgaac gtgcgttatt ttatattata atggattata gtgcaaactt   92220
gattatagac ggcatatatc taggggaata tgctttagaa ctaaactata tgcgcaaatt   92280
tatccatgac aacgacatca ccagcgtcct gtccgtcttt gatagcccgc ccattgaaaa   92340
cattgcacca aattatctct acgtttattg cgaagacgat gaaaacgacg aaaacatgga   92400
atcgcgtttg gacgacatgt acgaattttt agagaaagcc gttcagaggc gcgaaaaaat   92460
actggttcac tgccacgctg gaatatcaag atcggccacc gtggtcattt actacattat   92520
gaagacctat cggaaaagtt ttaaagacgc tttcaacatg gtcaatgaga aacggtccat   92580
atggcccaat gatcatttta aacgcatctt gaagaaaaaa attaacaaat aaacaattat   92640
tatttgtaac aaatgttttt tatttaatga aatgatatta gcgtatcaat ttttgtattc   92700
atttcgtcaa ttttttttact attattcgta actagttgaa tcgtttccat tgtggtgttg   92760
tggatttggt ttaggaaaaa catggtctcg ttgcgcatgt gttttatttc tcgagtcatg   92820
gtatagaact ttgtctcgat catttcgtat gtgtcagaga gcaattcttt gatggcgttt   92880
atttcctcca tgagcgaacc cgcatgccac aagtatgcca acaacaaaac caacgccaca   92940
cacgaatagt tcattttgat ttttgaatgg gtcctcttat tttttacgaa caatcatgtc   93000
ttttagcgat ttaaagttat caagcatagt atcattgctg tacgctagtt tgtttgttaa   93060
```

```
atcgatttgt aacgatttta tattttccaa agccagatta aaattactta acagagtgtt    93120
gtgctcgttt cttagcaaat cacgtagaga gtcggtccaa ctgctcgaag aatcatacac    93180
ggttggttga tatatcgaat ctggcgagtc cgatttgggc gcgccgttgg ttaggcaatc    93240
tttaatgtga caaatttgac tcttgatatc cgacagaggg tccaccactt gactctgcac    93300
acccatcatc aaatcgcaaa cgattctttt gattaggctc aactgttgag tgttaattga    93360
tgaagctaaa tttaacgtgg ccaaatattt acacagcgtg aaaacatgaa cgtagttttt    93420
gttatttcta gtgagacgct gcgaaggaat tacatttgcc caaagcacgg ctttgttaaa    93480
tcccctaata gtgacaatgt gtgcgagtaa atctgccgca gcgcctaatt ctatgtaacc    93540
gtccctgtca tcttcgccgt tttcaattat taccacttcg atactttcat cgttgtaatg    93600
aaaccgagtc gcctcagaat tatgaacggg tgtatttta tacatgtcgg taatgtctta    93660
tatttgtacc ggaccataag ctaagttaat ttgattttt gaattaatta tttcatcatg    93720
aattacaacc atcgcgacgt atatcgtcgc cgctacgata gacttagcga aaaatacaat    93780
gccgtgctac atcagcacga aaacttaaaa tccgacttgc gccatttaaa aatgcagatt    93840
catgaggttt gtcgcaattc tgttggcgcg gataacgtta tatgtgagcg tatactaaac    93900
aatacaccct tgttagataa tactatccac cctcgaaacg actatacaac agcattagtc    93960
aaggacaaga cgcctcaacg taagcacatg tacaatgacg gaaagccgtt ggttagtgtg    94020
gaacccttcg attaaagcat cacaaattga ccacgatgcc atgtatctaa tttccatgga    94080
agactttgat gtagaagttt cgccgtacac cgtgtttgag ccttgcggtt caatgaaagt    94140
gttcatcacg ggttgtaaac tttatgatat gattaaagtt tctttagaga acgagcacaa    94200
agtcatgttg aaacggtcat cttccaacgg cgaagacaga cttaacaaca agtttatgaa    94260
aaaaagtcat cgaaacgttt gtttcaatcg ggtgactgat agagccagca ttataggatt    94320
attgaaaata tcattgaaaa tgcccgaatg tatggagaat attttttgtgt ctttgataga    94380
gtcgccgaga ggaggcaagc actacacacg ttttgttttc aattgctatg tttgtaacct    94440
gttaacttgc acaaagtgta acaagcgttg tttggcttcc gctttgtgta ctttatatca    94500
taatgacgat aaatgtgtta acgaagtgga aagcgcgctt tttaaaaaag aaaccatcta    94560
caagccaccc aactgtgaca atatgaaaag gaaaagtta tgttcgcctt ctaagcagtg    94620
ttatgttaag aacccttat gtatgtttta ataaaaatat aagcacatct tttttgtttt    94680
tatttaagag tataaataaa aatgtctttt gacgaacgaa ttattagcct gtgttcgaag    94740
gaaaaagatc tgcgatcaca atatgaatcc aaagtgaatt cgttttttaa aaataaaggt    94800
atgaaaaaat ctgtagacat attgcaaaac gaattacacc agttggatgc cctcatattt    94860
ggttacgaag aacagattca tttcctgagc acgaacaata atgtcgctcg ccaagaaatg    94920
gtggacaacg ttaacgattt ggatcatttg ggtatagaca aaaacttcat tgaaagaatg    94980
atcgtggaca aattagatga ttctttattt gaaatataca atacagaaat tctcaacgaa    95040
aatataatta aaacctttag aaaacatagt aataaatttg ttaaagtttt gtgtcaattt    95100
gacgacaaac gaaaagctta cagtaaaaaa gagtttaata gagaaaaaaa caagaaaaat    95160
attgatgaaa acaacaattt attagtagaa ttaattttat taaaatcaaa cttggtgttt    95220
catttatgta caatggaaaa aattctcgtg aacagcgcta acaaaaacat aatcaaaaaa    95280
attgcataat attcatgatt tttgatttca tgttttcaat ctcgttaatg tctccgtatt    95340
cttgtatagt tgttatgttt ccatgtgttc tttgcaaaat atatcatagt ttttaaagtt    95400
```

```
gacaaatcca ttgtcatcca acgaaaaaca atcttcgcac acggccaggg acacgttggc   95460
accgtgcaca acaaacaagg gacaaaagtg attcttcaaa atcgtgtctg ctaaaatcgc   95520
attgtgaccc ggcagctgcg tcttgatttc cagtatatat gcggcgatct gcatgattat   95580
tgtgactgaa ggaaaacttc gctttcactt tcgttatata ttttttttga aatcaaataa   95640
atcattaaga atgtatctac tgttattatt gttaaccctg ctattttgt  ctctcctcta   95700 taaaccgctg tacgatgcct acactaaaat taaagaaacc caaacacact acaatgctac   95760
ggtcgatgat cgcatcgatt acatggagac cgttttaaaa catcgtcgtt tcgtgcctct   95820
gcatgtttta ccaaacgtaa ttttcaacac taatttgggt acgcttaacg aaggcgatgt   95880
caaatgttta tcggtcccaa tgtacgttgg catttacgat actcccaatt ttgattgtac   95940
agctttatgt gacaatccgt cggcagttta ttttacgta  aacgaatatg acaaattcgt   96000
tatcaacgga gatttattac caagaggcgg ttattgtacc actagtagcg tgcctcgcaa   96060
ttgtaacagg gaaactagcg taattttgca cagtttaaat caatggtctt gtatagccga   96120
agatcctcgc tactttgccg gtccccaaaa tatgacccaa gtcgccggtc gccagcatgc   96180
ggacaaaata ttaccgggac aagtcgataa aaatgtgcta acagatcggc ttttaggaac   96240
cgaagttgac gtttccaaaa acacttttag gtcgcattgg gacgagctat tagacgacgg   96300
cacgaggcgt ttcgaaatgc gctgcaacgc caaagacaat cataacaatc aaatgtttct   96360
caacccgttc aatctcatcg agtgtctgcc caacgtgtgc acaaatgtca ataacgttca   96420
ccccagtgtc agacccatat tcgaaactgg cgaatgcgat tgtggagatt ctaacatcac   96480
ccgtctaaca cacataattc ccggtgaccg cacgtccatg tgcgcatccg tagtcgatgg   96540
tttcaatcga gattcgatgt cgcatcaatt tagagttgaa tgcgtgaaca tggacatgct   96600
gttatcggaa ttcagcagta ctaaaccct  ttgtccccct gatacttta  cccaaaaacac  96660 agacaacgca tttttgttcg aattgccagg ttcttttcct ttttcgggca acggtatcga   96720
cgagcccact tatagagtgt acatggaaac taggaacagg ataaattata acacaacaag   96780
aagtatacca aattaattta ttttttaat  agtaaagttt aaatgaaaca atcgatttaa   96840
ttcttgcaag taaattttcc aacactttga aaaatatcct tgttctttaa catacgggaa   96900
gtttatctgg tgggtgatgt ccgttatgct gtttcgaaat cggccggcga aatataattc   96960
aataacgagg cgtgccccaa gccgcgggtt agttttgtaa aacagcgttt ttacgttcct   97020
gatgttgatc atgttttgt  ctcgctttat gtttgcatat ttttgtaatt gcttttctgt   97080
ggtcggcatg ttgtacgacc gcaacaggtc cttcaaaatc tccaatcggt tttggattga   97140
aggcacgcga ttaaatacat caaacaacaa gcattccagt tgatcggcga tagtgagatt   97200
gatatttacc acacaaacat atgtgtcgaa cttttcgacc aaattgtaca aatttatttt   97260
ttcataacta ttctttataa ctaaatccag aaagtaaaca tcgaacggaa agtaaacgta   97320
cgtgttaacc gaattgtcag atttgtagtt ccaaattgga gatgcgcttt tcatgtgtac   97380
attaaacgaa aaccgtacca gcaaaaactc gtcgttcacc cacgaagaag tggttttgaa   97440
cggagcattg cgattgattt caaagtaaac atcgttcaca gaatcgattt taatcgcttc   97500
gtttacgtac gatttgaaga acacgagtcc attattaaat tcttgatcga acttgctacc   97560
gtcaatttgg ttcagcataa atttcatgtc aatcattttt aatgtttgtt cgacttttat   97620
gatgtcgtct cgaaattcat ttgaaatggc attttcgaat aaggctattg gtaacgtttc   97680
taatgcgttt tttccctcat tgatattgtc caagtaaatt tcaatgttta gattgttcgt   97740
cagcttgtag ggtttgatgg ttcggtaata gtccgtgtag ctatcgatag caaacgtgcc   97800
```

```
tttgattatg gagaattgat cttcgaaaac gtttctaaaa gttttgtata gtttacaaaa   97860
aaagtttttg tcgaaccggt ctaaaacatc gctgcaaagt tgatcattta tattttttt    97920 tgaaatataa ggtatggttt ttaaataaaa caattgttga cgcagggatt ccataatgaa   97980
caaggcggcg ttaacttcgc gacgtcttaa taatgcacaa atatttttgg ccactattgt   98040
ggatatcaat tctcttctta acgtaacgga caccagaaac aaaagattgt tttacaattt   98100
gtgctcgcgc tatataaatc aaacactatt tcaatttacg aaaggaaata tggcgctagc   98160
caccgttcag acggttttgg atagcgtcat atctgcagaa cgtatgtttt tctcaaaaag   98220
caatgtgcta aatatcattg taaactttct gaccgcgcac agcgacggtg ataacctaca   98280
gtgtatgatt aatttaaaac tcctagacta ttttttacac aagtattatt aaataaaaat   98340
acacatgaaa aagtttgatt gttatttatt aaaatcttac acatgaaatt atacaaggta   98400
aaatacacat gaaagtttg attatacaat tgatatttat aaaaatctta atatatacat    98460
gattgttatt tattaaaaat cttccataat ctcaaatttg tcatctccgg ccccgaaccg   98520
cttgtactcg ccaactcgcc tttcgaaaaa attcgttttg ccttccaacg aaatgttgtt   98580
catgaagtca aatggattgg tcgcgtgaaa gtacttttct tgatttagcg ccaccaaaag   98640
acgatccgca acaaactcaa tatattgaca cattgatttt gagttcatgc ccagcatatc   98700
gcaaggaatg gcagtagtga aaaattcctt ttcaatttcc acagcttctt taaacatact   98760
caatatttcc gacgaagtca gtttgtcatt ctcagcaatg taattgttat agtataaaca   98820
agcaaagtcg gtatgcaaac cttcgtctct gctgattaat tcattgctaa acgtcagacc   98880
cggcatgact cctttggttt ttaaaaaaaa tatagccgcg aaactgccag agaaaaatac   98940
gccctccact atagcaaacg cgaccatacg tcgagccagt ctgcttcctt gcgaaacttt   99000
tgtgggagtt ttcttgaaat aattatacac ttgctgtacg ggatatacga tgaatctatc   99060
ccacagagtt tgtttctctt tgttatcgtc ttcaatccat ttcatggccc agcgcgcttt   99120
gtttctcaca caatcgacat catcgaaagc attgagtaac atgtcacgtt cggtttcgtt   99180
tgaaatgtac tcaaaaatca gcaaattgta catttctgtg tgtacattct caatgagtat   99240
ttgctggtcg taaaagtagc gggcttccag ctctgacaca gcgtctcgca catattctat   99300
gaggttgatg ttgacgatgc tgtcggcggc agcaaagaag gccagaacat gtttcaaaaa   99360 gtgccttcg ttgtcattga gctttgccat gtagtcgtcg taatcttttg acagatcgac    99420
ttcctcgact ttccacatac aatcgagtgc ctttttgtaa gcctcccata gtttgaaatg   99480
ttgaatgggc aaaagtacct tgcgtgtgtt ggacatgttg aagaataata ataaattgag   99540
gctgcgacgc cttttatacc aatcaggagt agtacctctc acctacgtca tcgcctactc   99600
tcgcctttgt gccggatagc gtccacagta gtattcgttg atattttgat attacaatat   99660
ttataaaacg ggtcacatac ggatttttttt tcagttaaaa tggagactct gtcgcccgag   99720
caattaattg tgtacaataa atttatgtac agtaattatg taacaaattt gacatgtcca   99780
acttcaagac tagacactga aaccattttta aaagtggaaa aactgacgag gggacaatcc   99840
gataatgcgc tatgggttttt gctgcgaatg gacagacata cggcttcggg ctcgcctttg   99900
tcctacagca catcgccgac gttggccatg acgtttggcc acaatcaaga gcgtttggtc   99960 aaacgaaac acgctctgtt ggatttgctc gaaaacacca ttgaaaccgc gctaggatgc   100020
agcgtggtgg agcgcgttct cgattgtggc atgttttttt catcaatggg tttgttttcg   100080
gcgtcgcccg acgcttactt cgccaccaac aagggccagt acattccgat tgaaataaag  100140
```

```
tgtccttaca cgtataaaga tgtgactatt gacgaaatca gaaacgaaat gaaaacgcgc   100200
aaaagtcgct atcgtgttaa gcacactgcg ttttcgttaa acaaaaccgg accgccgatt   100260
ttcagtgtag aaaaaacgga tcctcattac agacaaatgc agagacaaat gtatgttatg   100320 cgtgcccta tttgcatata cgtagtaagt ttcaaggacc atttcgtggc aagcacagtt   100380
gaacgtgacg atgaattcta tttgtcagag tacaaaaaag aaaagaacat ttttgatatg   100440
tttgtccggt caaatgggct tgcgaaacgc atgaaaaacc aacgaaatcg gattgctact   100500
tttcaaaata ctaataaatt tagaaaagaa gatgtactga agttgacacg aagaggtttg   100560
tacttgaaaa acggcgaaat tatttgcgca atttgcgcga caaagtccga cagcgacatt   100620
gatatatcaa cggtcctaga tttacacgag cagtgcatgg atcataaaga caacgagaac   100680
attattgaat gtaaacatca aaaattttc aatcattcca ccaggatgaa gtcactgatt   100740
gcggcgaacg tggactcttc acatgccaaa tggggtttat ttcacgaaga cggtttgttt   100800 aaaaccttt gttgtgacat gatcgttaca gattttgtgc caaccacgc tactgattgt   100860 gatttgctc agattagatt atttagataa agttaatctt tttattgata gtttactat   100920 ataaatcgac taatgtccca tcgtttcatc attcttattg gtctccttta aaggaattaa   100980
taacatttgg aatctttgaa ttaataacat ttggtaagtt tctctctctc tataattata   101040
taattaattt agaagatgta attgttagta tgttttattc attttctttt tattgttttc   101100
aggtaacatg tctcttcctc tcaaaaatcc ctgcagctta tattctcttt ctattaaaga   101160
aataaagaag cgaatattag atgaaaatag ttttaaggat ttgtcacttc ctaaagttat   101220
tatttccgat ttggaaactt tgtatgctga gatgcctcca ggatggtatt attgtccgag   101280
aagattaata tgtgttgtcg ataaagatct ttttgatttt aatattcaca agaaatttg   101340 tgagtattac aaacaaaaaa atcttgttga tttctatgaa tgtataaata cgtatgttta   101400
ctggcggtgt tctgatgaaa ttcctccaga aaacgatctt catttgcaaa ttgatttgct   101460
tcaaaatttc ataatgagat tctttcgttt aggtgatgga atgtttataa aaccttggat   101520
gggaggcgca cttgaattgt caaataatcg taatactaaa ctcattaaat atgtagaagt   101580
agatgatgat gatgattata agaaacgcc tccttcttgg ttgaagcttg ttaaatttaa   101640
cgatgtagat caaaaaatgc tgttaaaata acacaaatg aaacatgtaa taattattaa   101700
ataaaattta ttatattcaa atgagtgtat ttattaatt aagtattttt taatagaaag   101760
gtatgaaatt tttaatcgcg cttttagccg ttggcttggc aaaggcggca ccgtcgggcg   101820
gtttaccgtt gttggcagag acagaaactc tcattcaaat attcgtcaac caccaatatt   101880
taactgggtc aaagaatggc acagtgtcag gtggtcagga taaaagtttg aaaggcacat   101940
attggcgaag aagtaacgaa aacggaaaac agattttgct tagaaacgcc gcatactgtt   102000
attatttgtg tataaacgag tgcggttatt attatacagc gaaagagccc aattcagaat   102060
gtttattggg agaatctttc acagactttg cttatacaca gatgttcaaa gatcacggta   102120
aaaagaaggc ttatgtggct ttgagccagt cgggaaagat tagaagacta atgagtaaaa   102180
aactatcaaa cagcaaactg ttaaacgcgt caaaaatgac cattattaga gatactgtcg   102240
aatacacgtt tgagtgtaac aaaattctca aacaaaatt gaaatttgtg ccggtaaaaa   102300
cttgtgtgaa tccacccaaa aggatgaacc acaagaacga agccgccgac gatgattatg   102360
atgatgaatc tgtgggagact gttcaaaatt actaccactt tggtgaagac gagatccatt   102420
ttaatctgtt gacaacagat cccataacca caacaacgca cgaatcgtca aaaaattcat   102480
ctttagatcg tgtaatcgac aagctaataa atattgatgt ggtggcggat ctaccgtccg   102540
```

```
aacattttgt tataaacaat ctagttgtaa atcaaatgtg taaaatttaa ctactttttc 102600
aataaaacaa attttttttaa agtctgttta tttgtttcaa ttttagcatg taactctata 102660
attgaatcca acattgatc catcaattgt tggttcttta cttcacccct ctctatgtag 102720
tctaacgctt tttcgtaaca tatcagcgat cttttataat atccaatctt ttcaaacaaa 102780
cgtgctaacg tgagactttc atttaggttt tcgatatcgt tttccatgtt aatttacaga 102840
gtaatttgaa taagtattca acacttcggc tagtcccgtt ggattgttgg tgttgactct 102900
atttccttga accaaagcca caacgctata gtcgcgtata ttgggtaaaa ttgcaaacaa 102960
aacgttgatt cgtaacgcca cgggatatat gttatttcga tatcgggtcg ctggactcca 103020
tatacgcaac aaagttccgt tcctacttaa aaagcaccac gaattagtaa aagtttccgc 103080
ggtccaaact tgcgcattgc catggcgtct tatacaatca ttatggtttg ccgttataca 103140
tctgccctcc tcgccgggat ataaacatgg cgatgaagtt ctcgccgaca attgaatgta 103200
cctatcaaat aaactttgat ggctaatgtc agtaacgttt tggtcaagca aatgttcgtt 103260
tcggggcgtg taggccgtgg aaaactttag tatcataaaa cctgtatggc taatatcggg 103320
atggttggtc aagtacgggt agagaattga ggcgtaacgt tcgtggctaa gttgattcac 103380
tctaaccatt gctacaacat catcgtctga ccgcgtcgtg tccgattgtg cccagaaaaa 103440
cttgtagtct aattttctta aaacaataa cgattggtta aacggacgaa tacatgcgtt 103500
ggaaacattg gcgctagatt gaccaatcat tgtttcatta gtgggactgt aaacagcaaa 103560
caaagcgtca accacgggac aactacaata tttgtattca atgttggagt tttcattttt 103620
gtaatacatt agttttccta aagtgcgctg accgctaatg ggatctatcg agcagggatc 103680
cgccacgcaa atatcattta gtctgagttc ttgacgatag cgttcgtgaa gcgctggatg 103740
atccaatcta acgaaacccg cttcgcaagg tgcgcgatga aaaaatcgtt gatcgtaaat 103800
cacgtctcgc accgtcaacg gtcggcaaaa cggcgtttct gtttctgaat tgaaatcaga 103860
cacgtaacct tcgttacact gacaacgtag cgggcgttcg tgtaaatcta ctattgagcc 103920
gttgggttga cagccgacac tgacattgca atcttcgtac atatttagct gtgtaaccaa 103980
acctggtgta atgcatgaac ataacaatga aaatcccgtc gaactttcgg ccaacaacca 104040
aattcctgtg ttgggattgc acgaacgtgc tctgtttcga tcgagagcca tgcaatacga 104100
ttcgcccgcc tcgatgactt tttcgatttc gttgccgtcc gtgtcgtgca tcgtaattac 104160
tgtacgatcg tcaaattgct ggcaatttgc caaaccctct cggcaaatat cgcaatccat 104220
atgtgtgttg cacggtgtaa gagttttatg acattcgtgc gaattgcctt cgataataat 104280
ttcagaggga ggttcaatta aaggagtttc agaattgtca aaacgaagta acacggtttg 104340
agcgggttca taatcagttt ttaataatat tatcaaagtg gctaggatga ttacaataat 104400
aatgaaacat acgattatta caatcattgt aaaacttaca ttttatttttt ataaaagtta 104460 gattcttcct tttcgttgtc gtcgtcaaat ttgtttacag gcttaccgtt tttatttaat 104520
aatttcatca taaaactagg ttggttatcc tcaacgtaat gaagttgatt gttaacccga 104580
attaccgatg gcttgtccga tttgcaacat tcaaacaatt tgctgatcgt ccccgcacaa 104640
cagcagttgt atattttgaa aattagcaag aaagcaaacg ctaaaattat acatacaata 104700
atcgtttcgg ctgttctaca tttgagacca aaccagctgg cgaaccagca catccaactt 104760
tccgccgtgg cttgatccgt ttcttcaacc atggtgttat tgttcatacg atgtctcaaa 104820
tctatcaggc gttcggtcat gcctttcaaa ttggtatggt cgagatcgct gttagagttt 104880
```

```
atcgccaaca catttagttt gtcgatatcg tttatagccg ccgttaaatt aaaggtcgaa    104940
ctaatgggca ctgttatcat cgtctttaga gctactgtgt ttttaatttt tctcaaactc    105000
aaaatcacct ttttggtatt cattacacaa ttctttgtac catctcctcg aataatacaa    105060
gtgcccgcct tgaggtgata ctcaagcacg gtgcatccaa acaaaagatc ggtgtccttt    105120
tcgagaacat acaaccagtt gttgtagtct gaaatggggt aaaaaatttc actatcgaat    105180
ttgcccacac gaacatcgca atccttttca aaatcaatat tttcaacatc attattgagt    105240 agtatttta tgtcgcacaa tttggcttgg ttagattcgt atatgatttg cggtttggag    105300
caaaacattc tgtcgtgtaa agtttgacaa tacggactat catctaaacg cacatagttg    105360
cggcgatctt ttgacaatcc aatgtatttg ctgttgggca aaactatggc acatttgtgt    105420
tcgccatttt tggcccgaca cattggtata ggaatgactt gaaacagatt atattccacg    105480
ttgttaatga ggggaatttc gacaataaaa ataattttc tcatgttagt aatgaaaacg    105540
tggcttttaa caaagttgtc tatcaaaatg ttcataccgt tcatgtcaga tgaaacgggc    105600
cacgctaagt ttgcgggcaa atgtatattt ataatttcgt taagcaatcg tttgggcgtt    105660
agaactaaag aatttaaatg gttttgtttt gcatcgtcca ccgactttc caagttttca    105720 tacaaaaatt caatttgatt tagctgctct tgaatcaaat cgaacttggc cacgatataa    105780
ctgcaatatt ctgatcgttt ctcatcgatg cattttttat gttcttcgaa cgaagccatt    105840
tttattaatt cgtctgttag cgattttact tgttcgttaa gggcgttatt gttttggca     105900 agttcattga gtcgctcagc gtcattactg tccataactc cgaaaagata cttgtcaaca    105960
ttgcccacaa aattgaacag tcctcttttt ttacgagtgt gtagactcaa atctttgtga    106020
tcttcaaaac tgccagcttt ttgaattttc gaatccagag tattatgatt gttaaccaaa    106080
tctttgatgc gtttcataat gatattttt atgcccatac taactagatt ggattgaacg    106140
caactactag acgcgtttgt ggcggtttcg atttcgctca acaacttcaa cgactcttcg    106200
tgtagagcgt tgagttcttg aaaaactttg ctgtgatcca tttcgattac aaaattccat    106260
atgttttcta tgaattgcat tctgttagtt ggttggtaat aaagtcccga agtgttaggt    106320
agtcgctcta cggttatcaa gttttcaaca cgaatttcgc tcgtaactac taatcctgcc    106380
attgaggccg ttaataaaac acacaaaagt gtcgtggtca ttttgaaaaa tataatagct    106440
cgttgatacc cttattaaac tttatttt gataattatt cacaactcgt caatatgcga     106500
aacgtgtcga atctattgtt ctcgtttta aatattatcg tttttaaaaa aattttgtgct   106560 cataataatg aaattagtaa aatcgattcg ttagtcgaat catgcatcga tgtcaagttt    106620
agttctggtg agtgtgaaaa taaatcccta atggaaaagt tcgataaaca aacgtttgac    106680
tttggcaccg caaacggcgt gaaacactat acttcgtggc tatgtttaat gaataacatg    106740 gaatatttt cgccgtacga taaacctcga ttgttcaaaa ttatggcgcg ccacaataac    106800
gccattgcaa aaatcgacgg taaaaacata actaatgaaa tgcgccgagt aagttccgaa    106860
atgtttcgat ggacatccga cacgctgacc agataccacg atctgcaaat tatctatgat    106920
actttcgatt cgttttataa tatgtttaac acgttcgttt tatggacggg ccgggcagt     106980 ttgtaccact ttaacacgat tctctacgcg tacaaaaacg tgagacatgc gaaatgtgcc    107040
aggaaaattg acgaagctgc caaagcggcg gcaaaaattg ccctctatta tccctgtcc    107100 actatgaaca aaactgaagt tctccaacaa ttttcatca attacgtttc aaaactaaaa    107160
atgtctgata gaaaaatgtt tgggggtttg tacagctacg taagtcagac gaacgtttttg   107220 ccgttttgt tgaccataca agtgggctcg tacactttta atttgcatca ttacgaaact     107280
```

```
gacaagtcca gaattgatgc tataaaaaat gaaacaagat ttgtgcacga gaatttcaag  107340
cgtttctaca aaaatttaaa tgtaaattac gtgtactacc aaattgtgat taacggtttc  107400
attcatccga ccaaacgagc ctacacccat tttggttcga tgtgggacat tagcacggac  107460
aacggtggat acacgcacat gacacaaaaa ttgcaaatag aatttcatgt gtattacaaa  107520
aacaaagatg attctttgcc gtggaattac ggccacgaaa tgcaccacag catgttatac  107580
gccgtagatg cggtgaacat aatgcccgct tggtatgtcg aaggtagcgc aaacaggatc  107640
ggtaaccggc cgtgttacga atacgatcac gaattgttaa aaatttacac caacaaaact  107700 ataaagaaa taatcgacgc tacctattcg tcgcccttcc tttatggaat gggcagtgtg  107760
ctggtccaat atttgtacga aaatcgacct gccgatttca gacacatgat agaatcaaag  107820
aattactccg ttagcgaaac ttacgaaacg gattttgatg tgttcaaatt aaatttaatc  107880
ggtagatgtg aagctgtgaa gagaaatcaa actgaacaca agtttgatag ccagctggcg  107940
tacaaaaatt aatagactc gagcacgttt gcctcttgta aaaattacat tcgattcgat  108000
tttgacgata ttattttcgt gttaacaccg gaccgattga taaaacgaaa caaaaacggg  108060
cagcccatgc tcgaatatac tcaatatttg atcggtcaaa ctcatttga tgaaatcaac  108120 gagtacacct ttgcttggtt catggcggga ttggttaaaa aggcggttca gtacttatca  108180
gacaatgtaa atttttatta caaatatcag tctagctata cgtatgattc gacggtcaaa  108240
tgtcagtata tcgacgagtc tgccaaagat gccattataa atatggcgtt taaatataaa  108300
aacatcgccg atatggtcac gtttcccgtc gatcaagcaa aggaatacat acgccaaaaa  108360
gacaaggcga ttgaaatgtg tgaaatgtac atgccgcccg tactgcttaa tacggccggg  108420
cctgccaaag tattcatcga tagttttggca agtcccaatt tagtgatccc gagaaaagaa  108480
acatattata tgcgcatcga tttaaagggg aacacagtaa ttcattatgc tgccatgtac  108540
aaaataaatg cctacgaaaa aatcaaactg gcaaacagga cagccgtaga tatggcgcct  108600
ctcaatgccg acggaaaatc ggccgagcaa ttgtacgaat atagtttaaa gttttacaaa  108660
aagtacaacc aaagtaatcc tttatattgc tttaaatata tggaagatac agaaagtatc  108720
acagaaatta ttgaagagga ggtggtggaa aaggaatatg aaggaaacaa tacagtttta  108780
tcaaacaacc ctttattaag taaaagcaca tcagttataa cagagaaaag cattattata  108840
acagagatta ctacaacaga gaaagccctt attataacag agaaaacat tatttcaaca  108900 gacaataact ttagcattac atttagtttc aaaaattgta taattttcat acttgtatta  108960
ttaatatcat ttatagttat aatactgtta acgcattgg taactttaat aataacaaaa  109020 aaatcacta agcaaaaaca aaagtgcaa caaaagttg aatataacaa agataaattt  109080
tatactaacg acgaatgtac aattaattta tttgattaaa tactgttaag gaaccatcgt  109140
tttttattta tattcaaaaa caatatctat agttagtagt aaaggacccg tttttgaatt  109200
cacaggggcc cattgagtcg tattggcaag attacggacg tttagttcgc actcgtttct  109260
ttccacatcc tcttcgttga ttttggacaa caaatagttg tcgtaaactt gtccatcgac  109320
actgtcctct tgtttgcgat gattgaacca taatttattg taccacttca catcagatac  109380
cataatagcc tcatttatgt atactgttaa aattgtcttg tctcccattg ctcgcgccat  109440
tcccttgacc gaaatcaaat tgtgattttc ctttagcgat tttatcttgc tcaatataaa  109500
tggtgtggtt ttagcttcat cttcgcgact cgaaaaccca tcaaagtaga tacattcttt  109560
cggcgattga gcgttcacta tacttatgtg ttctttaaa tatttaaaag tggcctggat  109620
```

```
gtagctgtta ctagagtcaa tttccacttt taccgttttg gatttattgt cctctattaa    109680
atatttatat gttattttgt taagaagtct gtccgcgcta accgatgcat gctcatttt     109740
tatgtcgtcc aaatacagag taacaggata tttgcatagt ttaaacattt ttaaatatgc    109800
gtattatttc ctgtgcaaaa gcctccgcct cctggtaatg atgaaatttt attcttgtcg    109860
gggtaatatc tacgcgcgta ccaaacttag cttctgccaa atttgcacag attacgcgtg    109920
cttcgctcgg atcatcactt actctgtacg ctaaaatcct gcattcctta gtgatctcac    109980
tgattttgt gtaaaatcta ataaattta actctttcac aatataaaca taatttttta     110040
cctttgactg aagttgtttt attttgtgt cttttcttcg tatagtattc tttaattttt     110100
ctgtcgatat ttcaaactcg tgcttgtcgc gtttgttttt ttcacacatt ttttggtatg    110160
cttgttttaa aagctcaagt gcacgagcaa ttttttttcaa gtctttaaca gtaacaaaac   110220
gaaacatttc accactttca atattagcag cggtcaaact acggactaga cttttgtttc    110280
gtagagtaga catgtttcgc gacggtcgaa caccgaatga aatttgaaag gcgaacgcga    110340
acgtcgtcat atttatcatc tgacgaccac gcaaagacac gcgatagcta ttcctggaaa    110400
cgaggaaaaa aaaatacaaa catggtaaaa acaacattta ttatgcgtaa atcattttta    110460
acaaatttt aaactgattc ataattgtgt aggtgacaaa ctcaataatc atattagtca     110520
tgtaatactc attgtaatca acattggccg cctttgtttt gaaatattc ttgctgtttt     110580
ttaaattgat tacgtaatcg gtgtaccaaa cggccttccg gataggtgtg atcggttgat    110640
gacgaatatt atgtcgcaat tctagtatgt ttttgcgata caacggatca ttgatgacag    110700
ttttgatcgc ttccgttaac tggttggagt ccacggtggc ggtgtcgagt gccagcccaa    110760
tgcccaattc tacatacttg tcggtgttaa acgactgatc gcccatcatc ggcaaaccta    110820
ccatcggtac accggcgtcg atagcttcgt ccgtggattg aaccctcct tgtgtcacaa     110880
acgctacaac atttttatgt tttagcactt ccggttggtt gaaccaagtt tgcaccaaaa    110940
cgttgtaagg taattgagag ttaagttctt cgtcgtccgt ttcaaacttg aataaaattt    111000
tgtagggtag cgctttaaaa gtttgtaata gcatatattt aaaatcagca tcggtgtctt    111060
tggtgtttat gctcgagccg aaactaacgt aaaccgctcc ttgagtggcg ccgtccaagt    111120
aacgcttcat gaaatcgtcc agcggcacgg gctcgtttct atgcaaatga attccaccca    111180
agtattgaac actaggcgga accggcctgt tattgtcaaa acagagtgt gtattaacaa     111240
ataacatctg gacacgattg cgcagttcct tgatagacgg cgattttcga ccgaattgcg    111300
agcgtattaa tttattctgc tcgtccacca attttgaaaa ctcatttgt agcgtcaact     111360
ccatgtaaat ttcgttgata gtttcccata ccgttaaatc cctgaaccga tcgcgccaca    111420
tgttcggata gtatttcggg tggcggctaa ctgcacccat agtttcaaaa ttttctgcca    111480
gtccgtagcc cgatgaaatt tgaattacgg gcaggtcacc gaacagatga gaaaatatta    111540
gcgagtagtc cataaaagcc tcgcaaatta gcaaatcgaa atgctcattc tttcgattat    111600
tgattagcct cttgacggcc ggcaagtcaa attgatctct aatcatgcgc actaaaccca    111660
tgtagttgtg cgccgtgacg gtagtactgt ccgatattat tccccttttt cggaatacgc    111720
tagattgttt aaccaggttt ttaaagtaat tttcggcaag ggtggcatcg acttctgtca    111780
catttcgggt agcgtaattg actttggtag tgggttttat cacgacaatt tcgtggcctc    111840
tttccgccaa agcttgtatg taaactttga acacactctg gtggctgtag gcgggtgttg    111900
gtaaaactgc gagaattctc gctccattta ctgcagaaat ggcacacaaa aatagaatat    111960
ggaagtgcat gacgaacaat attcggaata atttgtgtca gtaggccaac ggtttatata    112020
```

```
cttttattgt gtttcaacga aagtgattct ggaatgttgg tcattttatt aaaattataa  112080
tttagctcgt taatctgtat agtttccagt tgctcctttt cgttgctctt tttgcgttta  112140
caacacattg aatatttgta aaatttaatt tttatcaaaa gaaccgaaat tagcactaat  112200
aatatcaaaa cgattttgt ataattaaca tcgtttactt cgttttctg aatgtcggtg  112260 agttcatcga caataatatc gagaattta tctagctcgt cttgctcact gccaacggtt  112320
acgttgatga aatcgtccga actgttttcg ctgtacgtag tactgataaa aatagatatg  112380
ataaagaaaa tctgagtaat cgtcatattt aattttttc ttagtcacta cttgatattt  112440
ccagagtcaa catcatgtct cggcgtttcg cgatatacac cagcgaaaag gcgaagatgg  112500
tttgggactc ggtagcattc aataatagtc gccaatttgc cttttcgat ggcacacact  112560 ggtatcatcc ccaaaatcat tttgcagact ttgatgagtt tttcaactac ttgaatgaaa  112620
acaatatcaa agatgtgcat gtaaaagcgc tcgaggacaa cggaggacgc gagtgggtta  112680
tcgatgtgga tttcatcgaa actgaaaaaa tattggagtt taaaattgaa actgccaaaa  112740 agatttcat caattttac aaggaaaaca ttgcacggat aatgcactcc gggaatcgag  112800
gactacatgt ctggttgcgc atagatagat ttttaatgtc gtcaaagaaa agtttgcgca  112860
ccagctacta ctcgatattt gtgcaacccg aaactgtgat tttagacgaa atcgtgcccg  112920
gtagtttcat tcatgctgtg aaaaccgcag ttgaagaaga aaccgttgct caaaagatcg  112980
aagaatattt taaggtgaaa actttggagc aaagaatatt agccgtttgg ccccaagtgg  113040
actcacacgt gttttgtaac ttaaaccaaa ttcgtgctcc gtttagtttt aattctaagg  113100
gtcgtgattt ctccaaacaa ttgtactagt aatgttaata aagatgttaa gcaaaatatt  113160
ttcgtttgtt ttcaataata aaaatgacga ggagaacatc gaacatgaag aggaagacac  113220
cgatcggccg cgccgtctgc ccgccgtagg ttttcgtat ctgtttcaga aaaaaatt  113280 cattttcgat gaaaacatat cgttttatt acgatacttg tatgacaaag acgaagttg  113340 gattttgtat ttcgatctgt ccgacggggt gggtctgcca gaagacgccc gtgactctat  113400
tagttatcag aatatcaaaa ctgtcaatga acttttgccc aaacagtctt cgcaaattag  113460
cagagtggaa tgtattaaca agcatggcat gttggaggcg ctagaatcga ttagctttaa  113520
atccaaggca caattagtga caaagctgtt ggatatgttt gcggaattgg aatcgaaatc  113580
gacgccgcta tctaaaatgg accataaatt tgacgtccta ttaaaggcta tacaagaagt  113640
caaaaatgac aatgccaatt tgtttaaaat acaattggat cgatgtcaag atttcgagcg  113700
caaaataaca gaactggaca aaaagattag cttgtatgaa aatatcgatc atctttacga  113760
gcggctgcgt gaacggcaca aagcgacggc atcggacaga cacatgtttc tagatgacaa  113820
taacgaaatg accattaagc taccaaaaga tgtatcgaaa catcctcgaa tagcagtgtt  113880
tatgaaaccc tcacaagctg gaacaaaagt tgcattcgtc tctggccaaa agaagtattt  113940
gcaaaaaggg aaacgaaaat ttcaagatat ggagttggtg tacgacgggg ttcatccgaa  114000 tcccccagatg gctgtaaatt gtatagccga ggaactagac tttaaaaatt ttgattatat  114060
taaaaaggct cgtttgtatt atttaaactg taacttggaa acggcaaagt cgtttataaa  114120
agaaaatttg taataaataa atttgaatat acacttttgt tatcagttac gcctccgttt  114180
tttatctatt cctccctata aagaacaga ttttcaaaat aaaatcacag tacagcaaca  114240
tgtttgtggt taaacgtaac ggtcgtaaac aacccgtcct catggacaaa atcactaaaa  114300
ggcttgaaaa gttatgtttt ggactaaaca tcaaagccgt tttagtggcg atggaagtgg  114360
```

```
tcaattttat ttacgaaaat gtaaccaccg aagaattgga catgcaagcg gcaaaggttg   114420
ctgcaaacaa atcatatttg cacaatgatt acgccttatt ggcaggcaga atcatgatta   114480
gcaacctgtc gaaaaaaatc aagtctgatt tttctgaagt tatcgaaaga ttgtacaaat   114540
acaaattggt tactaaattt ttgtacgatg tagtatgtgc caacaaaaaa gttctcaacg   114600
aatgtatact ttacgagaac gattacgatt acaagtactt tggttttaaa accttagaaa   114660
acgggtactt gtttaaaatc gatgagcaga ccgctgaatt accgcagcaa atgctgatga   114720
gagtttcgct cggaattcac ggcgacaaca ttgaagatgc cattgaaaca tacaaactgc   114780
tgtctgaaaa aaaattcatt cacgccagtc ccacactatt tgcggccgga acaaacttgc   114840
cccaattatc atcgtgtttt ttggtgagca tgaaagaaga cagcatagcc ggcatataca   114900
acacgctaac cacttgcgcg ttaatttcga acatggcgg cggaatagga ctgaacgtac   114960
acgaaattcg cgctcgtaac agtcccatca aagcgaccaa cggaacttcg agcggactag   115020
agtctatgct tcgcgtattc aataatatgg tacgacacgt tgatcagggc ggcaaaagaa   115080
aaggcgccat ggcaatttac ttggaaccgt ggcacgccga catttatgat ttttaaatc    115140 taaaagaaa catgggcgcc gaagacaaaa aggcccgtga tcttttgtac gctctatggg    115200
tacctgattt atttatgaaa cgtgtagaaa atggcgaaat gtggtcactc atgtgtcccg   115260
acgcttgcaa gggattggat cgaatttatg gaaaagaatt tgaagagtta tattcgcgtt   115320
atgaatcaga aagaaatac gtgaagcaag tgaacgcgcg cgatctttc agattcataa    115380 ttgaacccca agtcgaaacc ggtacaccgt acatgctgta caagatgct tgtaacggta    115440 aaagtaatca aaaaaacttg gcacaataa atgtagtaa tctttgtgcc gaaatagtac    115500
aattcaacag tggtgacgaa acaggcgttt gcaatttggc atctatttcg gtcaacaagt   115560
ttgtttgcga taatttcgag tacgatttca agtcgttaaa aaaggtgacc aaagtgattg   115620 tgaaaaaacct caacaaaata atcgatgtca attttattacc agtaaattgt gcccgcgatt   115680
cgaatttcaa acatcgacct atcggcgtgg gtattcaggg gctggccgat acttttgtaa   115740
tgctcagact gccgtatgaa agtgacaagg ccaagttgct aaacaaacaa atagcagaaa   115800
ccatttatta tgccgcgctg gaagctagct gcgagctcgc aaaaactgac gggccatatt   115860
cgtcatacaa aggcagtccg gccagcgaag gtttgttaca atacgatttg tggaatgtga   115920
ctcctacaaa acttgggac tggaaagttt tgaaagagaa cattaaattg tacggactcc    115980
gcaattcttt gctggtagcg tacatgccta ccgctacgac ggctcaaata ctcggcaaca    116040
acgaatcttt cgaaccttc actaacaact tgtatgtgcg ccgagtgctg gcgggcgatt    116100
ttcaagttgt aaaccaatat ttggtggatg attgttgcg tctcaatttg tataatgata    116160
atatgctcaa caaattatc gccaacaacg gcagtattca agccatcgaa ggtatacctg    116220
ccgatatcaa agagttgtat aaaaccgtgt gggaaatgaa gcaaaaaat ttgattgaca    116280 tggccgccga tcgcgcagcg ttcatagacc agagtcaatc atttaatgtt ttcgttgcca    116340
atcccactta ttctctgatg acatcgattc atacttacgc ttggaaaaaa ggattgaaaa    116400
cgggaatgta ttatttgcgc accaagcctg ccgcggatcc tatcaagttt actgtggacg    116460
ccacatgttc taaagtgaac ggtcaatgta tgggatgtga tgcttaataa aatttgtaat    116520
aaaaattttc attgttttat ttttttttatt gtaaaaatga agaaatattt ttcgtgtctt    116580
tcttcatttt tacaagcaaa taagtatttt tctcctttcg taaaacattg tgaaaaatca    116640
aatata                                                              116646
```

```
<210> SEQ ID NO 3
<211> LENGTH: 33
<212> TYPE: DNA
<213> ORGANISM: Artificial Sequence
<220> FEATURE:
<223> OTHER INFORMATION: PCT Primer for polH/gran gene
<220> FEATURE:
<221> NAME/KEY: misc_feature
<222> LOCATION: (19)..(19)
<223> OTHER INFORMATION: N= C, A, T or G
<220> FEATURE:
<221> NAME/KEY: misc_feature
<222> LOCATION: (20)..(20)
<223> OTHER INFORMATION: R= A or G
<220> FEATURE:
<221> NAME/KEY: misc_feature
<222> LOCATION: (22)..(22)
<223> OTHER INFORMATION: N= C, A, T or G
<220> FEATURE:
<221> NAME/KEY: misc_feature
<222> LOCATION: (25)..(25)
<223> OTHER INFORMATION: R= A or G
<220> FEATURE:
<221> NAME/KEY: misc_feature
<222> LOCATION: (28)..(28)
<223> OTHER INFORMATION: Y= C or T
<220> FEATURE:
<221> NAME/KEY: misc_feature
<222> LOCATION: (31)..(31)
<223> OTHER INFORMATION: N= C, A, T or G

<400> SEQUENCE: 3
tgtaaaacga cggccagtnr cngargaycc ntt                          33

<210> SEQ ID NO 4
<211> LENGTH: 33
<212> TYPE: DNA
<213> ORGANISM: Artificial Sequence
<220> FEATURE:
<223> OTHER INFORMATION: PCT primer for polH/gran gene
<220> FEATURE:
<221> NAME/KEY: misc_feature
<222> LOCATION: (19)..(19)
<223> OTHER INFORMATION: D = A, G or T
<220> FEATURE:
<221> NAME/KEY: misc_feature
<222> LOCATION: (22)..(22)
<223> OTHER INFORMATION: N = C, A, T or G
<220> FEATURE:
<221> NAME/KEY: misc_feature
<222> LOCATION: (25)..(25)
<223> OTHER INFORMATION: R = A or G
<220> FEATURE:
<221> NAME/KEY: misc_feature
<222> LOCATION: (28)..(28)
<223> OTHER INFORMATION: Y = C or T
<220> FEATURE:
<221> NAME/KEY: misc_feature
<222> LOCATION: (31)..(31)
<223> OTHER INFORMATION: Y = C or T

<400> SEQUENCE: 4
caggaaacag ctatgaccdg gngcraaytc ytt                          33
```

UNITED STATES PATENT AND TRADEMARK OFFICE
CERTIFICATE OF CORRECTION

PATENT NO. : 10,779,543 B2
APPLICATION NO. : 16/320890
DATED : September 22, 2020
INVENTOR(S) : Sean Moore et al.

Page 1 of 1

It is certified that error appears in the above-identified patent and that said Letters Patent is hereby corrected as shown below:

In the Claims

In Column 189, Claim 6, Line 15, delete "*Lydia*" and insert in its place --*Cydia*--.

In Column 190, Claim 20, Line 44, delete "*Lydia*" and insert in its place --*Cydia*--.

Signed and Sealed this
Seventeenth Day of November, 2020

Andrei Iancu
*Director of the United States Patent and Trademark Office*